US012622171B2

(12) United States Patent
Yoo et al.

(10) Patent No.: US 12,622,171 B2
(45) Date of Patent: May 5, 2026

(54) ORGANIC COMPOUND AND ORGANIC LIGHT EMITTING ELEMENT COMPRISING THE SAME

(71) Applicant: LG DISPLAY CO., LTD., Seoul (KR)

(72) Inventors: Seonkeun Yoo, Paju-si (KR); Youngjun Yu, Paju-si (KR); Sangbeomj Kim, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 868 days.

(21) Appl. No.: 17/969,847

(22) Filed: Oct. 20, 2022

(65) Prior Publication Data

US 2023/0180603 A1 Jun. 8, 2023

(30) Foreign Application Priority Data

Dec. 6, 2021 (KR) ........................ 10-2021-0173254

(51) Int. Cl.

| | |
|---|---|
| ***H01L 51/50*** | (2006.01) |
| ***C07D 491/16*** | (2006.01) |
| ***C07D 495/16*** | (2006.01) |
| ***C09K 11/06*** | (2006.01) |
| ***H10K 85/60*** | (2023.01) |
| *H10K 50/13* | (2023.01) |

(52) U.S. Cl.

CPC ........ *H10K 85/6572* (2023.02); *C07D 491/16* (2013.01); *C07D 495/16* (2013.01); *C09K 11/06* (2013.01); *H10K 85/615* (2023.02); *H10K 85/657* (2023.02); *H10K 85/6574* (2023.02); *H10K 85/6576* (2023.02); *C09K 2211/1018* (2013.01); *H10K 50/131* (2023.02)

(58) Field of Classification Search

None

See application file for complete search history.

(56) References Cited

U.S. PATENT DOCUMENTS

2020/0227649 A1 7/2020 Yen et al.

FOREIGN PATENT DOCUMENTS

| | | | | |
|---|---|---|---|---|
| KR | 10-2011-0109687 A | 10/2011 | | |
| KR | 10-2011-0110508 A | 10/2011 | | |
| KR | 10-2014-0064612 A | 5/2014 | | |
| KR | 10-2015-0124924 A | 11/2015 | | |
| KR | 10-2015-0130797 A | 11/2015 | | |
| KR | 2015124924 A | * 11/2015 | ............. | H01L 51/50 |

OTHER PUBLICATIONS

Combined Search and Examination Report issued in corresponding GB Patent Application No. 2215893.5, dated Apr. 25, 2023.

Office Action issued on Apr. 14, 2025 for Chinese Patent Application No. 202211380532.3 Note: KR 10-2015-0124924-A cited therein is already of record.

* cited by examiner

*Primary Examiner* — Gregory D Clark

(74) *Attorney, Agent, or Firm* — Morgan, Lewis & Bockius LLP

(57) ABSTRACT

The present disclosure provides an organic compound represented by the Chemical Formula 1 and an organic light emitting element including the same. Specifically, there may be provided an organic light emitting element having high efficiency or long lifespan by including a first electrode, a second electrode, and an organic material layer positioned therebetween, where the organic material layer includes an organic compound represented by the Chemical Formula 1.

16 Claims, 4 Drawing Sheets

ORGANIC COMPOUND AND ORGANIC LIGHT EMITTING ELEMENT COMPRISING THE SAME

CROSS-REFERENCE TO RELATED APPLICATION

This application claims the benefit of and the priority to Korean Patent Application No. 10-2021-0173254, filed on Dec. 6, 2021, which is hereby incorporated by reference for all purposes as if fully set forth herein.

BACKGROUND

Technical Field

The present disclosure relates to an organic compound and an organic light emitting element comprising the organic compound.

Description of the Related Art

In general, an organic light emitting phenomenon refers to the phenomenon of converting electrical energy into light energy by means of an organic material. An organic light emitting element refers to an electric element using the organic light emitting phenomenon.

The organic light emitting element using the organic light emitting phenomenon may be applied to a display device. Since the portable display device is driven by a battery, which is a limited power source, the organic light emitting element used in the portable display device requires excellent light emission efficiency. In addition, since the image should be displayed normally during use of the electronic device, a long life of the organic light emitting element may be also required.

In order to improve efficiency, lifespan and driving voltage in the organic light emitting element, research has been conducted on the organic material included in the organic light emitting element.

SUMMARY

In order for the organic light emitting element to sufficiently exhibit its excellent characteristics, the materials constituting the organic material layer should be stable and have excellent efficiency. Since the phosphorescent organic light emitting element has a greater hole mobility than electron mobility in the light emitting layer and a long triplet state lifespan, excitons formed in the light emitting layer are distributed over a wide area, so that the light emission may be reduced. Accordingly, the inventors of the disclosure have invented an organic compound and an organic light emitting element that may have excellent efficiency or long lifespan.

Accordingly, one or more embodiments of the present disclosure are directed to an organic compound and an organic light emitting element that may have high efficiency or long lifespan.

Additional features and aspects will be set forth in the description that follows, and in part will be apparent from the description, or may be learned by practice of the present disclosure concepts provided herein. Other features and aspects of the present disclosure concepts may be realized and attained by the structure particularly pointed out in the written description, or derivable therefrom, and the claims hereof as well as the appended drawings.

To achieve these and other advantages and in accordance with objects of the disclosure, as described herein, an aspect of the present disclosure is an organic compound represented by Chemical Formula 1 below.

[Chemical Formula 1]

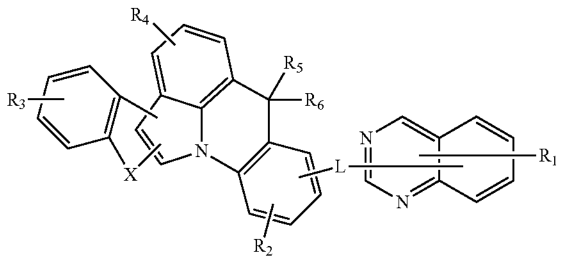

In another aspect of the present disclosure, an organic light emitting element includes a first electrode, a second electrode, and an organic material layer positioned between the first electrode and the second electrode.

The organic material layer includes an organic compound represented by Chemical Formula 1.

According to embodiments of the present disclosure, there may be provided an organic light emitting element having high efficiency or long lifespan.

It is to be understood that both the foregoing general description and the following detailed description of the present disclosure are merely by way of example and are intended to provide further explanation of the inventive concepts as claimed.

BRIEF DESCRIPTION OF THE DRAWINGS

The accompanying drawings, which are included to provide a further understanding of the disclosure and are incorporated in and constitute a part of this application, illustrate embodiments of the disclosure and together with the description serve to explain principles of the disclosure.

DETAILED DESCRIPTION

Figure 1:
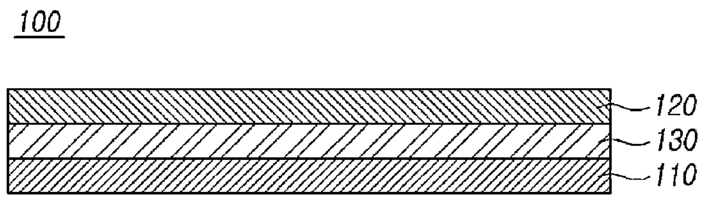
FIGS. 1 to 4 are views schematically illustrating an organic light emitting element according to embodiments of the disclosure.

Reference will now be made in detail to some of the examples and embodiments of the disclosure illustrated in the accompanying drawings. Wherever possible, the same reference numbers will be used throughout the drawings to refer to the same or like parts. Further, in the following description of examples or embodiments of the disclosure, detailed descriptions of well-known functions and components incorporated herein will be omitted when it is determined that the description may make the subject matter in some embodiments of the disclosure rather unclear. The terms such as "including", "having", "containing", "constituting" "make up of", and "formed of" used herein are generally intended to allow other components to be added unless the terms are used with the term "only". As used herein, singular forms are intended to include plural forms unless the context clearly indicates otherwise.

Terms, such as "first", "second", "A", "B", "(A)", or "(B)" may be used herein to describe elements of the disclosure. Each of these terms is not used to define essence, order, sequence, or number of elements etc., but is used merely to distinguish the corresponding element from other elements.

When it is mentioned that a first element "is connected or coupled to", "contacts or overlaps" etc. a second element, it should be interpreted that, not only can the first element "be directly connected or coupled to" or "directly contact or overlap" the second element, but a third element can also be "interposed" between the first and second elements, or the first and second elements can "be connected or coupled to", "contact or overlap", etc. each other via a fourth element. Here, the second element may be included in at least one of two or more elements that "are connected or coupled to", "contact or overlap", etc. each other.

When time relative terms, such as "after," "subsequent to," "next," "before," and the like, are used to describe processes or operations of elements or configurations, or flows or steps in operating, processing, manufacturing methods, these terms may be used to describe non-consecutive or non-sequential processes or operations unless the term "directly" or "immediately" is used together.

In addition, when any dimensions, relative sizes etc. are mentioned, it should be considered that numerical values for an elements or features, or corresponding information (e.g., level, range, etc.) include a tolerance or error range that may be caused by various factors (e.g., process factors, internal or external impact, noise, etc.) even when a relevant description is not specified. Further, the term "may" fully encompasses all the meanings of the term "can".

Hereinafter, various embodiments of the disclosure are described in detail with reference to the accompanying drawings.

As used herein, the term "halo" or "halogen" includes fluorine (F), chlorine (Cl), bromine (Br), and iodine (I), and the like, unless otherwise specified.

As used herein, the term "alkyl" or "alkyl group" may mean a radical of a saturated aliphatic functional group having 1 to 60 carbon atoms linked by a single bond and including a straight chain alkyl group, branched chain alkyl group, cycloalkyl (alicyclic) group, alkyl-substituted cycloalkyl group, or cycloalkyl-substituted alkyl group, unless otherwise specified.

As used herein, the term "haloalkyl group" or "halogen alkyl group" may mean a halogen-substituted alkyl group unless otherwise specified.

As used herein, the term "alkenyl" or "alkynyl" may have a double bond or a triple bond, respectively, and may include a straight or branched chain group and may have 2 to 60 carbon atoms unless otherwise specified.

As used herein, the term "cycloalkyl" may refer to an alkyl forming a ring having 3 to 60 carbon atoms, unless otherwise specified.

As used herein, the term "alkoxy group" or "alkyloxy group" refers to an alkyl group to which an oxygen radical is bonded, and may have 1 to 60 carbon atoms unless otherwise specified.

As used herein, the term "alkenoxyl group", "alkenoxy group", "alkenyloxyl group", or "alkenyloxy group" refers to an alkenyl group to which an oxygen radical is attached, and may have 2 to 60 carbon atoms unless otherwise specified.

As used herein, the terms "aryl group" and "arylene group" each may have 6 to 60 carbon atoms unless otherwise specified, but are not limited thereto. In the disclosure, the aryl group or the arylene group may include a monocyclic type, a ring assembly, a fused polycyclic system, a spiro compound, and the like. For example, the aryl group includes, but is not limited to, phenyl, biphenyl, naphthyl, anthryl, indenyl, phenanthryl, triphenylenyl, pyrenyl, peryleneyl, chrysenyl, naphthacenyl, or fluoranthenyl. The naphthyl may include 1-naphthyl and 2-naphthyl, and the anthryl may include 1-anthryl, 2-anthryl and 9-anthryl.

In the disclosure, the term "fluorenyl group" or "fluorenylene group" may refer to a monovalent or divalent functional group, respectively, of fluorene, unless otherwise specified. The "fluorenyl group" or "fluorenylene group" may mean a substituted fluorenyl group or a substituted fluorenylene group. "Substituted fluorenyl group" or "substituted fluorenylene group" may refer to a monovalent or divalent functional group of substituted fluorene. "Substituted fluorene" may mean that at least one of the following substituents R, R', R" and R"' is a functional group other than hydrogen. It may include a case where R and R' are bonded to each other to form a spiro compound together with the carbon to which they are bonded.

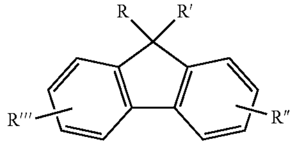

As used herein, the term "spiro compound" has a 'spiro union', and the spiro union means a union formed as two rings share only one atom. In this case, the atom shared by the two rings may be referred to as a 'spiro atom'. The compounds are defined as 'monospiro-', 'dispiro-' or 'trispiro-' depending on the number of spiro atoms in one compound.

As used herein, the term "heterocyclic group" may include not only an aromatic ring, such as a "heteroaryl group" or "heteroarylene group" but also a non-aromatic ring and, unless otherwise specified, means a ring with 2 to 60 carbon atoms and one or more heteroatoms, but is not limited thereto.

As used herein, the term "heteroatom" refers to N, O, S, P or Si unless otherwise specified.

The "heterocyclic group" may mean a monocyclic group containing a heteroatom, a ring assembly, a fused polycyclic system, or a spiro compound.

The "heterocyclic group" may include a ring containing $SO_2$ instead of carbon forming the ring. For example, the "heterocyclic group" may include the following compounds.

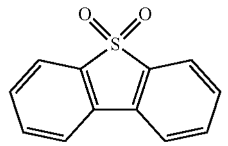 [SMILES: O=S1(=O)c2ccccc2-c2ccccc21]

As used herein, the term "ring" may include monocycles and polycycles, may include hydrocarbon rings as well as heterocycles containing at least one heteroatom, or may include aromatic and non-aromatic rings.

As used herein, the term "polycycle" may include ring assemblies, fused polycyclic systems, and spiro compounds, may include aromatic as well as non-aromatic compounds, or may include heterocycles containing at least one heteroatom as well as hydrocarbon rings.

As used herein, the term "aliphatic ring group" refers to a cyclic hydrocarbon other than the aromatic hydrocarbon, may include a monocyclic type, a ring assembly, a fused polycyclic system, and a spiro compound and, unless otherwise specified, may mean a ring having 3 to 60 carbon atoms. For example, a fusion of benzene, which is an aromatic ring, and cyclohexane, which is a non-aromatic ring, also corresponds to an aliphatic ring.

As used herein, the term "alkyl silyl group" may refer to a monovalent substituent in which three alkyl groups are bonded to a Si atom.

As used herein, the term "aryl silyl group" may refer to a monovalent substituent in which three aryl groups are bonded to a Si atom.

As used herein, the term "alkyl aryl silyl group" may refer to a monovalent substituent in which one alkyl group and two aryl groups are bonded to a Si atom or two alkyl groups and one aryl group are bonded to the Si atom.

As used herein, the term "ring assembly" means that two or more ring systems (single or fused ring systems) are directly connected to each other through single or double bonds. For example, in the case of an aryl group, a biphenyl group or a terphenyl group may be a ring assembly but is not limited thereto.

As used herein, the term "fused polycyclic system" refers to a type of fused rings sharing at least two atoms. For example, in the case of an aryl group, a naphthalenyl group, a phenanthrenyl group, or a fluorenyl group may be a fused polycyclic system, but is not limited thereto.

When prefixes are named successively, it may mean that the substituents are listed in the order specified first. For example, an arylalkoxy group may mean an alkoxy group substituted with an aryl group, an alkoxycarbonyl group may mean a carbonyl group substituted with an alkoxy group, and an arylcarbonylalkenyl group may mean an alkenyl group substituted with an arylcarbonyl group. The arylcarbonyl group may be a carbonyl group substituted with an aryl group.

Unless otherwise explicitly stated, in the term "substituted" or "unsubstituted" as used herein, "substituted" may mean being substituted with one or more substituents selected from the group consisting of halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_8$-$C_{20}$ arylalkenyl group, a silane group, a boron group, a germanium group, and a $C_2$-$C_{20}$ heterocyclic group including at least one heteroatom selected from the group consisting of O, N, S, Si and P, but is not limited to the substituents.

In the disclosure, the 'functional group names' corresponding to the aryl group, arylene group, and heterocyclic group provided as examples of the symbols and their substituents may be described with 'the names of the functional groups reflecting the valence', but may also be described with 'the names of the parent compounds.' For example, in the case of 'phenanthrene', which is a type of aryl group, its name may be specified with its group identified, such as 'phenanthryl (group)' for the monovalent group, and 'phenanthrylene (group)' as the divalent group, but may also be specified as 'phenanthrene', which is the name of the parent compound, regardless of the valence. Similarly, pyrimidine may be specified as 'pyrimidine' regardless of the valence or may also be specified as pyrimidinyl (group) for the monovalence and as pyrimidylene (group) for the divalence. Therefore, in the disclosure, when the type of the substituent is specified with the name of the parent compound, it may mean an n-valent 'group' formed by detachment of the hydrogen atom bonded to a carbon atom and/or a heteroatom of the parent compound.

Further, unless explicitly stated, the formulas used in the disclosure may be applied in the same manner as the definition of the substituent by the following formulas.

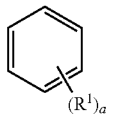

When a is 0, it means that the substituent $R^1$ does not exist, meaning that hydrogen is bonded to each of the carbon atoms forming the benzene ring. In this case, the chemical formula or chemical compound may be specified without expressing the hydrogen bonded to the carbon. Further, when a is 1, one substituent $R^1$ is bonded to any one of the carbon atoms forming the benzene ring, and when a is 2 or 3, it may be bonded as follows. When a is an integer of 4 to 6, it is bonded to the carbon of the benzene ring in a similar manner, and when a is an integer of 2 or more, $R^1$ may be identical or different.

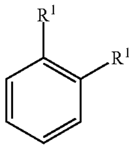

(a = 2)

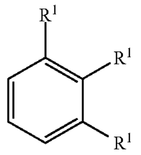

(a = 3)

In the disclosure, when substituents are bonded to each other to form a ring, it may mean that adjacent groups are bonded to each other to form a monocycle or fused polycycle, and the monocycle or fused polycycle may include heterocycles containing at least one heteroatom as well as hydrocarbon rings and may include aromatic and non-aromatic rings.

In the disclosure, organic light emitting element may mean a component(s) between the anode and the cathode or an organic light emitting diode including an anode, a cathode, and component(s) positioned therebetween.

In some cases, in the disclosure, organic light emitting element may mean an organic light emitting diode and a panel including the same, or an electronic device including the panel and circuitry. The electronic device may include, e.g., a display device, a lighting device, a solar cell, a portable or mobile terminal (e.g., a smart phone, a tablet, a PDA, an electronic dictionary, or PMP), a navigation terminal, a game device, various TVs, and various computer monitors but, without limited thereto, may include any type of device including the component(s).

FIG. 1 is a view schematically illustrating an organic light emitting element according to embodiments of the present disclosure.

The organic light emitting element 100 according to embodiments of the present disclosure comprises a first electrode 110, a second electrode 120, and an organic material layer 130 positioned between the first electrode 110 and the second electrode 120.

For example, the first electrode 110 may be an anode electrode, and the second electrode 120 may be a cathode electrode. In another example, the first electrode 110 may be a cathode electrode, and the second electrode 120 may be an anode electrode.

For example, the first electrode 110 may be a transparent electrode, and the second electrode 120 may be a reflective electrode. In another example, the first electrode 110 may be a reflective electrode, and the second electrode 120 may be a transparent electrode.

The organic material layer 130 is a layer positioned between the first electrode 110 and the second electrode 120 and comprising an organic material and may be composed of a plurality of layers.

The organic material layer 130 comprises an organic compound represented by Chemical Formula 1. The organic compound represented by Chemical Formula 1 is described below in detail.

The organic material layer 130 may have a multilayer structure composed of different materials to increase the efficiency and stability of the organic light emitting element 100 and may comprise a light emitting layer. The organic material layer 130 may further comprise at least one of a hole injection layer, a hole transport layer, an electron transport layer, and an electron injection layer.

For example, the organic material layer 130 may comprise a hole injection layer positioned on the first electrode 110, a hole transport layer positioned on the hole injection layer, a light emitting layer positioned on the hole transport layer, an electron transport layer positioned on the light emitting layer, and an electron injection layer positioned on the electron transport layer. In such an example, the first electrode 110 may be the anode electrode, and the second electrode 120 may be the cathode electrode.

The light emitting layer is a layer in which as holes and electrons transferred from the first electrode 110 and the second electrode 120 meet to emit light and may comprise, e.g., a host material and a dopant.

The lifespan and efficiency may be the most important issues with organic light emitting elements. The efficiency, lifespan, and driving voltage are related to each other. If the efficiency is increased, the driving voltage is relatively decreased, so that the crystallization of the organic material by the Joule heating during driving is reduced, leading to an increase in lifespan.

The role of the light emitting layer may be important to enhance the light emitting properties of the organic light emitting element and increase the lifespan. In particular, to have high-efficiency characteristics, the host material of the light emitting layer is required to have a high triplet level, and the stability of the material is needed.

The light emitting layer may comprise the organic compound represented by Chemical Formula 1 described above. The organic compound represented by Chemical Formula 1 may be the host compound of the light emitting layer. For example, the organic compound represented by Chemical Formula 1 may be a phosphorescent host compound of the light emitting layer.

The light emitting layer may further comprise a host compound different from the organic compound represented by Chemical Formula 1 described above. The type of the host compound that may be additionally comprised is not particularly limited, and a known host compound may be used.

Figure 2:
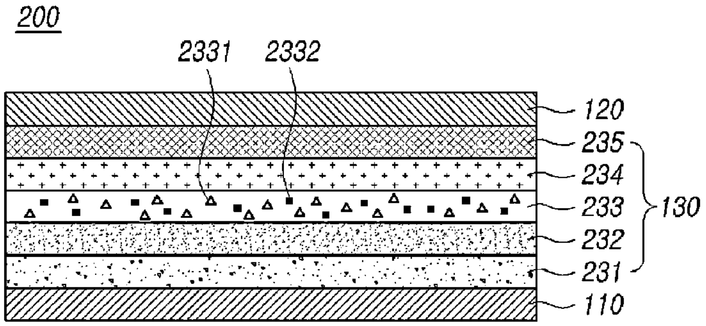

FIG. 2 is a view schematically illustrating an organic light emitting element according to embodiments of the present disclosure.

The organic light emitting element 200 according to embodiments of the present disclosure comprises a first electrode 110, a second electrode 120, and an organic material layer 130 positioned between the first electrode 110 and the second electrode 120.

For example, the first electrode 110 may be an anode electrode, and the second electrode 120 may be a cathode electrode. In another example, the first electrode 110 may be a cathode electrode, and the second electrode 120 may be an anode electrode.

For example, the first electrode 110 may be a transparent electrode, and the second electrode 120 may be a reflective electrode. In another example, the first electrode 110 may be a reflective electrode, and the second electrode 120 may be a transparent electrode.

The organic material layer 130 is a layer positioned between the first electrode 110 and the second electrode 120 and comprising an organic material and may be composed of a plurality of layers.

The organic material layer 130 comprises an organic compound represented by Chemical Formula 1. The organic compound represented by Chemical Formula 1 is described below in detail.

The organic material layer 130 may comprise a hole injection layer 231 positioned on the first electrode 110, a hole transport layer 232 positioned on the hole injection layer 231, a light emitting layer 233 positioned on the hole transport layer 232, an electron transport layer 234 positioned on the light emitting layer 233, and an electron injection layer 235 positioned on the electron transport layer 234. In such an example, the first electrode 110 may be the anode electrode, and the second electrode 120 may be the cathode electrode. The organic material layer 130 may not comprise some of the layers shown in FIG. 2 or may comprise an additional functional layer, such as a light emitting assist layer.

The light emitting layer 233 may comprise the organic compound represented by Chemical Formula 1 described above.

The light emitting layer 233 may comprise a host compound 2331 and a dopant 2332. The host compound 2331 may be an organic compound represented by Chemical Formula 1 described above. The host compound 2331 may further comprise another compound different from the organic compound represented by Chemical Formula 1 described above. For example, the host compound 2331 may comprise an organic compound represented by Chemical Formula 1 and an amine-based compound.

The type of the dopant 2332 is not particularly limited. For example, the dopant 2332 may be a red phosphorescent dopant. For example, the dopant 2332 may be a metal complex, such as of iridium.

Figure 3:
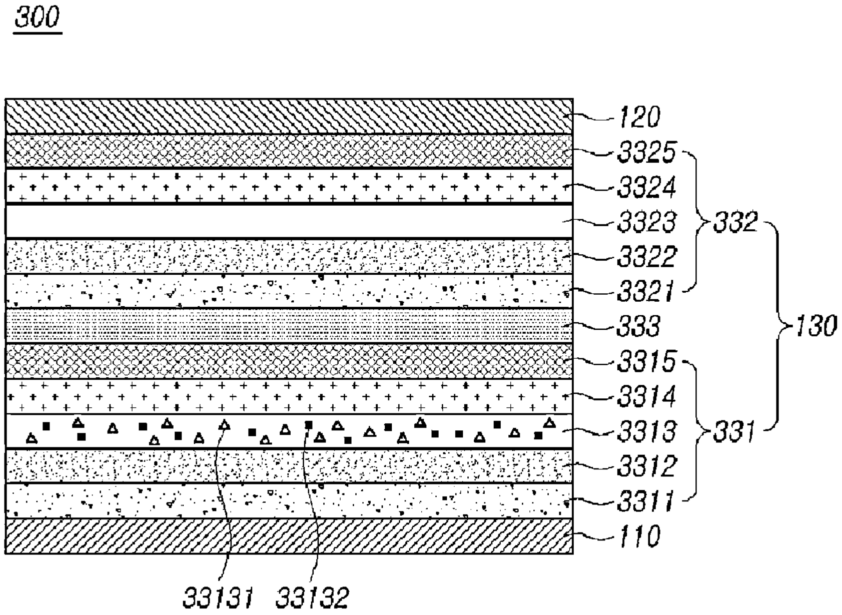

FIG. 3 is a view schematically illustrating an organic light emitting element according to embodiments of the present disclosure.

The organic light emitting element 300 according to embodiments of the present disclosure comprises a first electrode 110, a second electrode 120, and an organic material layer 130 positioned between the first electrode 110 and the second electrode 120.

For example, the first electrode 110 may be an anode electrode, and the second electrode 120 may be a cathode electrode. In another example, the first electrode 110 may be a cathode electrode, and the second electrode 120 may be an anode electrode.

For example, the first electrode 110 may be a transparent electrode, and the second electrode 120 may be a reflective electrode. In another example, the first electrode 110 may be a reflective electrode, and the second electrode 120 may be a transparent electrode.

Referring to FIG. 3, the organic material layer 130 comprises a first stack 331, a second stack 332, and a charge generation layer 333 positioned between the first stack 331 and the second stack 332.

The organic light emitting element 300 may be a tandem-type organic light emitting element comprising a plurality of stacks each comprising a light emitting layer. The plurality of light emitting layers may be formed of the same material or different materials. The first stack 331 may comprise a first light emitting layer 3313. The second stack 332 may comprise a second light emitting layer 3323. The first light emitting layer 3313 and the second light emitting layer 3323 may be formed of the same material or different materials.

The first stack 331 may comprise a first light emitting layer 3313. The first light emitting layer 3313 may comprise, e.g., a first host compound 33131 and a first dopant 33132.

The first stack 331 may further comprise at least one of a hole injection layer, a hole transport layer, an electron transport layer, and an electron injection layer.

For example, the first stack 331 may comprise a first hole injection layer 3311 positioned on the first electrode 110, a first hole transport layer 3312 positioned on the first hole injection layer 3311, a first light emitting layer 3313 positioned on the first hole transport layer 3312, a first electron transport layer 3314 positioned on the first light emitting layer 3313, and a first electron injection layer 3315 positioned on the first electron transport layer 3314. In such an example, the first electrode 110 may be the anode electrode, and the second electrode 120 may be the cathode electrode. The first stack 331 may not comprise some of the layers shown in FIG. 3 or may comprise an additional functional layer, such as a light emitting assist layer.

The first light emitting layer 3313 may comprise the organic compound represented by Chemical Formula 1 described above.

The first light emitting layer 3313 may comprise a first host compound 33131 and a first dopant 33132. The first host compound 33131 may be an organic compound represented by Chemical Formula 1 described above. The first host compound 33131 may further comprise another compound different from the organic compound represented by Chemical Formula 1 described above. For example, the first host compound 33131 may comprise an organic compound represented by Chemical Formula 1 and an amine-based compound.

The type of the first dopant 33132 is not particularly limited. For example, the first dopant 33132 may be a red phosphorescent dopant. For example, the first dopant 33132 may be a metal complex, such as of iridium.

The second stack 332 may comprise a second light emitting layer 3323. The second light emitting layer 3323 may comprise, e.g., a second host compound and a second dopant.

The second stack 332 may further comprise at least one of a hole injection layer, a hole transport layer, an electron transport layer, and an electron injection layer.

For example, the second stack 332 may comprise a second hole injection layer 3321 positioned on the second electrode 110, a second hole transport layer 3322 positioned on the second hole injection layer 3321, a second light emitting layer 3323 positioned on the second hole transport layer 3322, a second electron transport layer 3324 positioned on the second light emitting layer 3323, and a second electron injection layer 3325 positioned on the second electron transport layer 3324. In such an example, the first electrode 110 may be the anode electrode, and the second electrode 120 may be the cathode electrode. The second stack 332 may not comprise some of the layers shown in FIG. 3 or may comprise an additional functional layer, such as a light emitting assist layer.

The second light emitting layer 3323 may emit light of the same color as, or a different color from, the light emitted by the first light emitting layer 3313. In the present disclosure, that the light emitting layers emit light of the same color means that the light emitting layers emit not only light of colors with the same color coordinates but also light of colors similar to each other to be classified as pixels representing the same color in the technical field of the present disclosure.

The second light emitting layer 3323 may comprise a second host compound and a second dopant.

The type of the second host compound is not particularly limited. The second host compound may be the same as, or different from, the first host compound 33131.

The type of the second dopant is not particularly limited. The second dopant may be the same as, or different from, the first dopant 33132.

In embodiments of the present disclosure, the second light emitting layer 3323 may emit light of the same color as the light emitted by the first light emitting layer 3313. In the above-described embodiments, the second light emitting layer 3323 may comprise the organic compound represented by Chemical Formula 1 described above.

In embodiments in which the first light emitting layer 3313 and the second light emitting layer 3323 emit light of the same color, the second host compound may be an organic compound represented by Chemical Formula 1 described above. The second host compound may further comprise another compound different from the organic compound represented by Chemical Formula 1 described above. For example, the second host compound may comprise an organic compound represented by Chemical Formula 1 and an amine-based compound.

In embodiments in which the first light emitting layer 3313 and the second light emitting layer 3323 emit light of the same color, the type of the second dopant is not particularly limited and may be the same as the first dopant 33132. For example, the second dopant may be a red phosphorescent dopant. For example, the second dopant may be a metal complex, such as of iridium.

The charge generation layer 333 may be formed between the plurality of light emitting layers to smoothly distribute charges, thereby increasing the current efficiency of the light emitting layer. Accordingly, the charge generation layer 333 is positioned between the first stack 331 comprising the first light emitting layer 3313 and the second stack 332 comprising the second light emitting layer 3323.

The charge generation layer 333 may comprise a p-type charge generation layer and an n-type charge generation layer to smoothly distribute charges. When the first electrode 110 is the anode electrode, and the second electrode 120 is the cathode electrode, the p-type charge generation layer may be positioned on the side of the cathode electrode, and the n-type charge generation layer may be positioned on the side of the anode electrode.

Although FIG. 3 illustrates a tandem-type organic light emitting element comprising two stacks, embodiments of the present disclosure are not limited thereto but may comprise tandem-type organic light emitting elements comprising two or more stacks. When the organic light emitting element 300 comprises an additional stack, an additional charge generation layer may be positioned between the additional stack and the first stack 331 or second stack 332 adjacent thereto.

Figure 4:
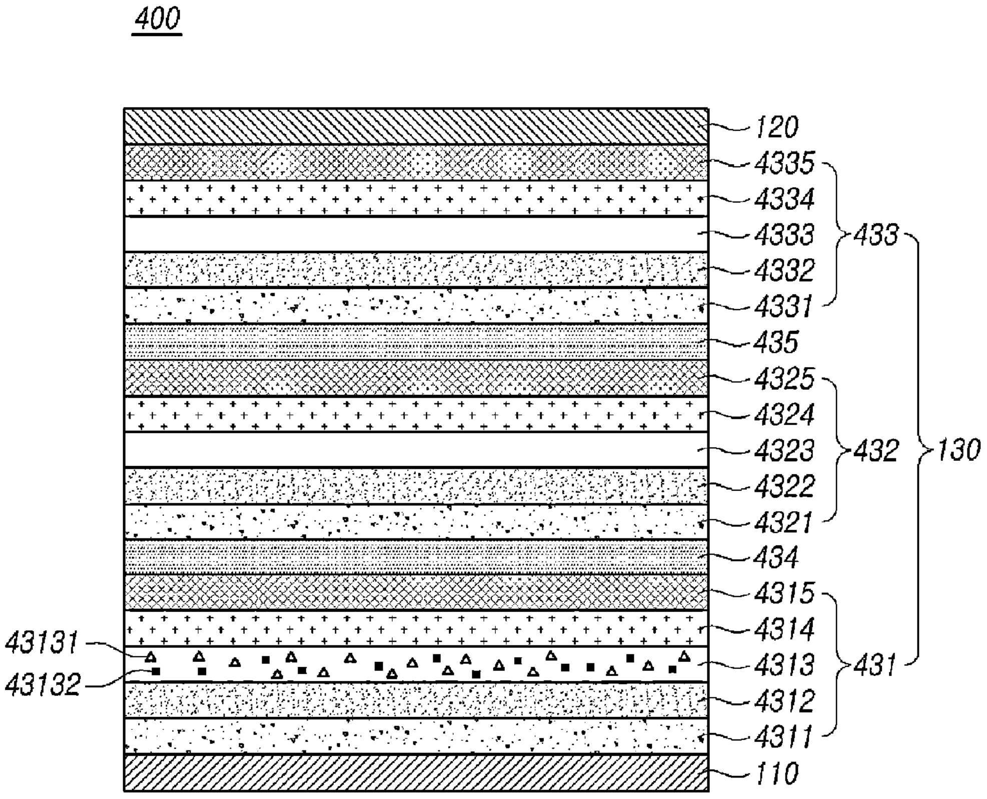

FIG. 4 is a view schematically illustrating an organic light emitting element according to embodiments of the present disclosure.

The organic light emitting element 400 according to embodiments of the present disclosure comprises a first electrode 110, a second electrode 120, and an organic material layer 130 positioned between the first electrode 110 and the second electrode 120.

For example, the first electrode 110 may be an anode electrode, and the second electrode 120 may be a cathode electrode. In another example, the first electrode 110 may be a cathode electrode, and the second electrode 120 may be an anode electrode.

For example, the first electrode 110 may be a transparent electrode, and the second electrode 120 may be a reflective electrode. In another example, the first electrode 110 may be a reflective electrode, and the second electrode 120 may be a transparent electrode.

Referring to FIG. 4, the organic material layer 130 comprises a first stack 431, a second stack 432, a third stack 433, a first charge generation layer 434 positioned between the first stack 431 and the second stack 432, and a second charge generation layer 435 positioned between the second stack 432 and the third stack 433. In the embodiments illustrated in FIG. 4, the second stack 432 is positioned between the first stack 431 and the third stack 433, but embodiments of the present disclosure comprising three stacks are limited to this structure, and the positions of the first stack 431, the second stack 432, and the third stack 433 may be exchanged with each other.

The organic light emitting element 400 may be a tandem-type organic light emitting element comprising a plurality of stacks each comprising a light emitting layer. The plurality of light emitting layers may be formed of the same material or different materials.

The first stack 431 may comprise a first light emitting layer 4313. The first light emitting layer 4313 may comprise, e.g., a first host compound 43131 and a first dopant 43132.

The first stack 431 may further comprise at least one of a hole injection layer, a hole transport layer, an electron transport layer, and an electron injection layer.

For example, the first stack 431 may comprise a first hole injection layer 4311 positioned on the first electrode 110, a first hole transport layer 4312 positioned on the first hole injection layer 4311, a first light emitting layer 4313 positioned on the first hole transport layer 4312, a first electron transport layer 4314 positioned on the first light emitting layer 4313, and a first electron injection layer 4315 positioned on the first electron transport layer 4314. In such an example, the first electrode 110 may be the anode electrode, and the second electrode 120 may be the cathode electrode. The first stack 431 may not comprise some of the layers shown in FIG. 4 or may comprise an additional functional layer, such as a light emitting assist layer.

The first light emitting layer 4313 may comprise the organic compound represented by Chemical Formula 1 described above.

The first light emitting layer 4313 may comprise a first host compound 43131 and a first dopant 43132. The first host compound 43131 may be an organic compound represented by Chemical Formula 1 described above. The first host compound 43131 may further comprise another compound different from the organic compound represented by Chemical Formula 1 described above. For example, the first host compound 43131 may comprise an organic compound represented by Chemical Formula 1 and an amine-based compound.

The type of the first dopant 43132 is not particularly limited. For example, the first dopant 43132 may be a red phosphorescent dopant. For example, the first dopant 43132 may be a metal complex, such as of iridium.

The second stack 432 may comprise a second light emitting layer 4323. The second light emitting layer 4323 may comprise, e.g., a second host compound and a second dopant.

The second stack 432 may further comprise at least one of a hole injection layer, a hole transport layer, an electron transport layer, and an electron injection layer.

For example, the second stack 432 may comprise a second hole injection layer 4321 positioned on the second electrode 110, a second hole transport layer 4322 positioned on the second hole injection layer 4321, a second light emitting layer 4323 positioned on the second hole transport layer 4322, a second electron transport layer 4324 positioned on the second light emitting layer 4323, and a second electron injection layer 4325 positioned on the second electron transport layer 4324. In such an example, the first electrode 110 may be the anode electrode, and the second electrode 120 may be the cathode electrode. The second stack 432 may not comprise some of the layers shown in FIG. 4 or may comprise an additional functional layer, such as a light emitting assist layer.

The second light emitting layer 4323 may emit light of the same color as or a different color from, the light emitted by the first light emitting layer 4313.

The second light emitting layer 4323 may comprise a second host compound and a second dopant.

The type of the second host compound is not particularly limited. The second host compound may be the same as, or different from, the first host compound 43131.

The type of the second dopant is not particularly limited. The second dopant may be the same as, or different from, the first dopant 43132.

In embodiments of the present disclosure, the second light emitting layer 4323 may emit light of the same color as the light emitted by the first light emitting layer 4313. In the above-described embodiments, the second light emitting layer 4323 may comprise the organic compound represented by Chemical Formula 1 described above.

In embodiments in which the first light emitting layer 4313 and the second light emitting layer 4323 emit light of the same color, the second host compound may be an organic compound represented by Chemical Formula 1 described above. The second host compound may further comprise another compound different from the organic compound represented by Chemical Formula 1 described above. For example, the second host compound may comprise an organic compound represented by Chemical Formula 1 and an amine-based compound.

In embodiments in which the first light emitting layer 4313 and the second light emitting layer 4323 emit light of the same color, the type of the second dopant is not particularly limited and may be the same as the first dopant 43132. For example, the second dopant may be a red phosphorescent dopant. For example, the second dopant may be a metal complex, such as of iridium.

The third stack 433 may comprise a third light emitting layer 4333. The third light emitting layer 4333 may comprise, e.g., a third host compound and a third dopant.

The third stack 433 may further comprise at least one of a hole injection layer, a hole transport layer, an electron transport layer, and an electron injection layer.

For example, the third stack 433 may comprise a third hole injection layer 4331 positioned on the third electrode 110, a third hole transport layer 4332 positioned on the third hole injection layer 4331, a third light emitting layer 4333 positioned on the third hole transport layer 4332, a third electron transport layer 4334 positioned on the third light emitting layer 4333, and a third electron injection layer 4335 positioned on the third electron transport layer 4334. In such an example, the first electrode 110 may be the anode electrode, and the second electrode 120 may be the cathode electrode. The third stack 433 may not comprise some of the layers shown in FIG. 4 or may comprise an additional functional layer, such as a light emitting assist layer.

The third light emitting layer 4333 may emit light of the same color or a different color from, the light emitted by the first light emitting layer 4313.

The third light emitting layer 4333 may comprise a third host compound and a third dopant.

The type of the third host compound is not particularly limited. The third host compound may be the same as, or different from, the first host compound 43131.

The type of the third dopant is not particularly limited. The third dopant may be the same as, or different from, the first dopant 43132.

In embodiments of the present disclosure, the third light emitting layer 4333 may emit light of the same color as the light emitted by the first light emitting layer 4313. In the above-described embodiments, the third light emitting layer 4333 may comprise the organic compound represented by Chemical Formula 1 described above.

In embodiments in which the first light emitting layer 4313 and the third light emitting layer 4333 emit light of the same color, the third host compound may be an organic compound represented by Chemical Formula 1 described above. The third host compound may further comprise another compound different from the organic compound represented by Chemical Formula 1 described above. For example, the third host compound may comprise an organic compound represented by Chemical Formula 1 and an amine-based compound.

In embodiments in which the first light emitting layer 4313 and the third light emitting layer 4333 emit light of the same color, the type of the third dopant is not particularly limited and may be the same as the first dopant 43132. For example, the third dopant may be a red phosphorescent dopant. For example, the third dopant may be a metal complex, such as of iridium.

Accordingly, one of the first host compound 43131, the second host compound, and the third host compound may comprise an organic compound represented by Chemical Formula 1 described above. Two of the first host compound 43131, the second host compound, and the third host compound may comprise an organic compound represented by Chemical Formula 1 described above. All of the first host compound 43131, the second host compound, and the third host compound may comprise an organic compound represented by Chemical Formula 1 described above. When there are two or more light emitting layers containing a host compound comprising the organic compound represented by Chemical Formula 1, the two or more light emitting layers may emit light of the same color.

The first dopant 33132, the second dopant, and the third dopant may be the same as or different from each other.

As the first stack 431, the second stack 432, and the third stack 433 are configured as described above, the holes and electrons transferred from the first electrode 110 and the second electrode 120 meet at the first light emitting layer 4313, the second light emitting layer 4323, and the third light emitting layer 4333, emitting light.

The first charge generation layer 434 and second charge generation layer 435 may be formed between the plurality of light emitting layers to smoothly distribute charges, thereby increasing the current efficiency of the light emitting layer. Accordingly, the first charge generation layer 434 may be positioned between the first stack 431 comprising the first light emitting layer 4313 and the second stack 432 comprising the second light emitting layer 4323, and the second charge generation layer 435 may be positioned between the second stack 432 comprising the second light emitting layer 433 and the third stack 433 comprising the third light emitting layer 4333.

The first charge generation layer 434 and second charge generation layer 435 may comprise a p-type charge generation layer and an n-type charge generation layer to smoothly distribute charges. When the first electrode 110 is the anode electrode, and the second electrode 120 is the cathode electrode, the p-type charge generation layer may be positioned on the side of the cathode electrode, and the n-type charge generation layer may be positioned on the side of the anode electrode.

The first charge generation layer 434 and the second charge generation layer 435 may be the same as or different from each other. The first charge generation layer 434 and the second charge generation layer 435 may be formed of the same material or different materials.

The organic compound represented by Chemical Formula 1 described above is described below.

The organic compound represented by Chemical Formula 1 described above may be represented by Chemical Formula 1 as follows.

[Chemical Formula 1]

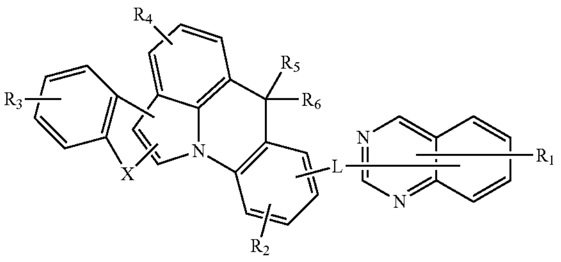

In Chemical Formula 1, X may be O or S.

$R_1$ to $R_6$ may be each independently selected from the group consisting of a hydrogen; a halogen; a cyano group; a nitro group; a $C_6$-$C_{60}$ aryl group; a fluorenyl group; a $C_2$-$C_{60}$ heterocyclic group containing at least one heteroatom selected from the group consisting of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group.

When one or more of $R_1$ and $R_6$ are aryl groups, the aryl groups may be a $C_6$-$C_{30}$ aryl group, a $C_6$-$C_{20}$ aryl group, or a $C_6$-$C_{12}$ aryl group.

When one or more of $R_1$ and $R_6$ are heterocyclic groups, the heterocyclic groups may be a $C_2$-$C_{30}$ heterocyclic group, a $C_2$-$C_{20}$ heterocyclic group, or a $C_2$-$C_{12}$ heterocyclic group.

L may be selected from the group consisting of a single bond; a $C_6$-$C_{60}$ arylene group; a fluorenylene group; a $C_2$-$C_{60}$ heterocyclic group containing at least one heteroatom selected from the group consisting of O, N, S, Si, and P; and a fused ring group of a $C_3$-$C_{60}$ aliphatic ring and a $C_6$-$C_{60}$ aromatic ring.

When L is an arylene group, the arylene group may be a $C_6$-$C_{30}$ arylene group, a $C_6$-$C_{20}$ arylene group, or a $C_6$-$C_{12}$ arylene group.

When one or more of L is heterocyclic groups, the heterocyclic groups may be a $C_2$-$C_{30}$ heterocyclic group, a $C_2$-$C_{20}$ heterocyclic group, or a $C_2$-$C_{12}$ heterocyclic group.

The aryl group, the fluorenyl group, the heterocyclic group, the fused ring group, the alkyl group, the alkenyl group, the alkynyl group, the alkoxy group, the aryloxy group, the arylene group and the fluorenylene group may be each further substituted with one or more substituents selected from the group consisting of a nitro group; a cyano group; a halogen; an amino group; a $C_1$-$C_{20}$ alkoxyl group; a $C_1$-$C_{20}$ alkylthio group; a $C_1$-$C_{20}$ alkyl group; a $C_2$-$C_{20}$ alkenyl group; a $C_2$-$C_{20}$ alkynyl group; a $C_6$-$C_{20}$ aryl group; a fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group.

One or more of the hydrogen atoms contained in the organic compound represented by Chemical Formula 1 may be substituted with deuterium or tritium.

By comprising the organic compound represented by Chemical Formula 1 described above, the organic light emitting elements may have high efficiency or long lifespan.

The organic compound represented by the Chemical Formula 1 may be represented by any one of the Chemical Formulas 2-1 to 2-4 below.

[Chemical Formula 2-1]

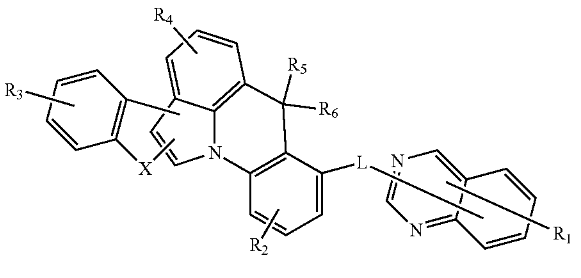

[Chemical Formula 2-2]

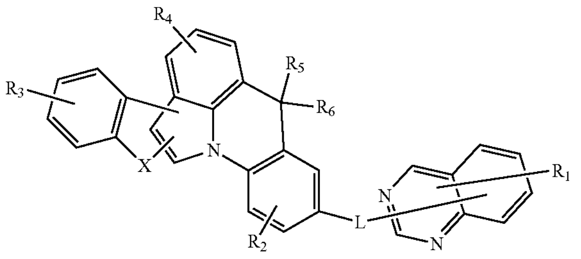

-continued

[Chemical Formula 2-3]

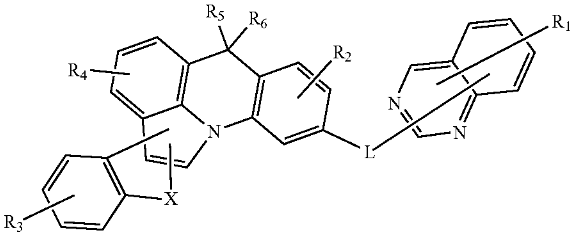

[Chemical Formula 2-4]

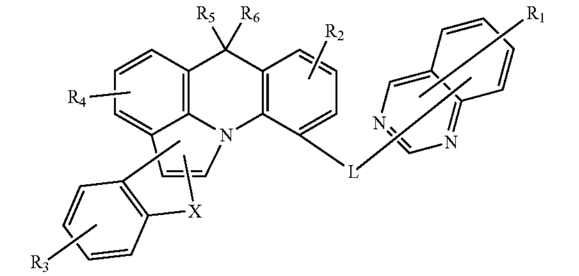

In Chemical Formulas 2-1 to 2-4, X, $R_1$ to $R_6$, and L may be the same as defined in Chemical Formula 1.

One or more of the hydrogen atoms contained in the organic compound represented by Chemical Formulas 2-1 to 2-4 may be substituted with deuterium or tritium.

The organic compound represented by the Chemical Formula 1 may be represented by any one of the Chemical Formulas 3-1 to 3-8 below.

[Chemical Formula 3-1]

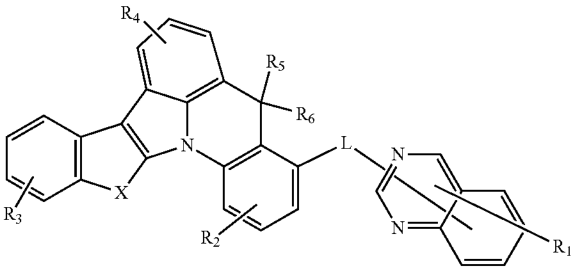

[Chemical Formula 3-2]

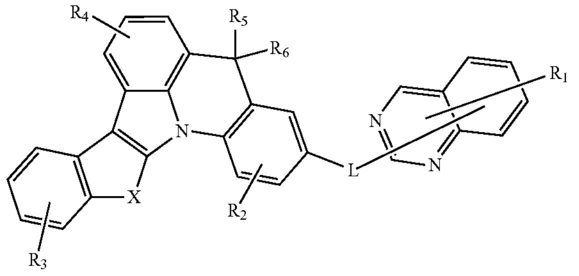

-continued

[Chemical Formula 3-3]

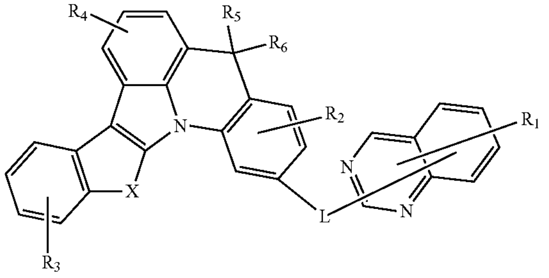

[Chemical Formula 3-4]

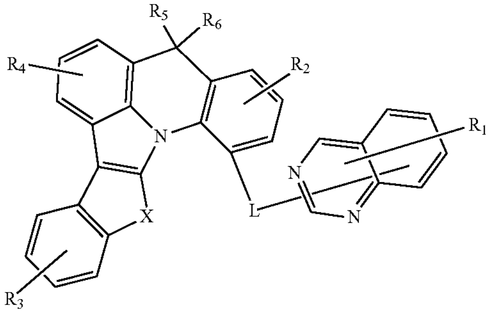

[Chemical Formula 3-5]

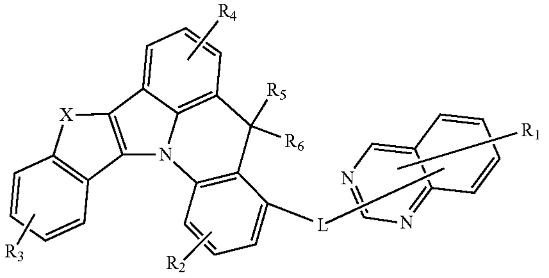

[Chemical Formula 3-6]

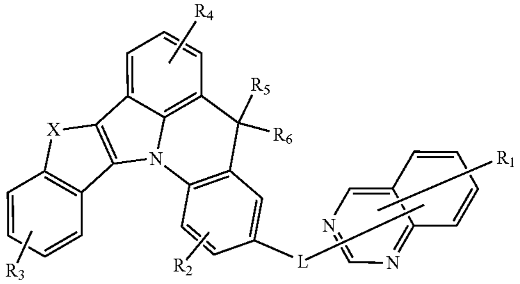

[Chemical Formula 3-7]

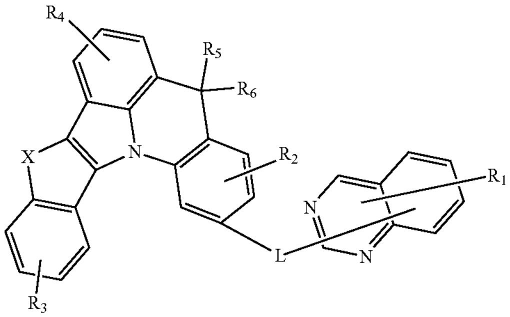

-continued

[Chemical Formula 3-8]

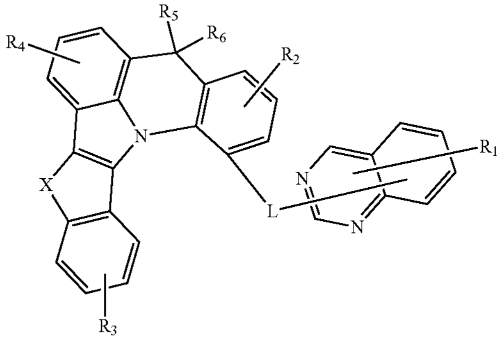

In Chemical Formulas 3-1 to 3-8, X, $R_1$ to $R_6$, and L may be the same as defined in Chemical Formula 1.

One or more of the hydrogen atoms contained in the organic compound represented by Chemical Formulas 3-1 to 3-8 may be substituted with deuterium or tritium.

The organic compound represented by the Chemical Formula 1 is one or more of the following organic compounds below.

HAC1

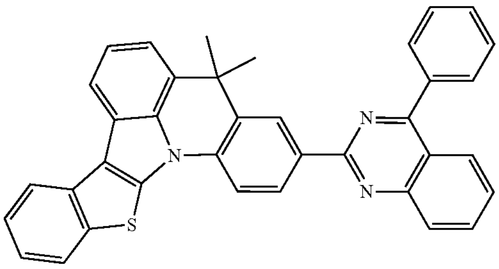

HAC2

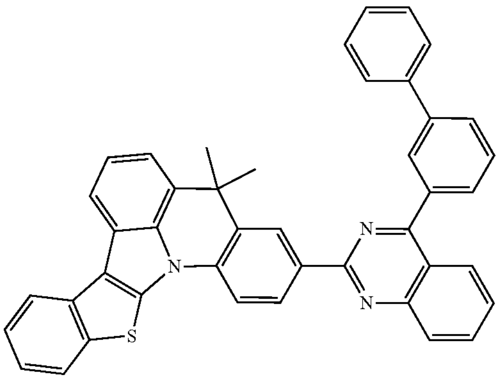

-continued
HAC3
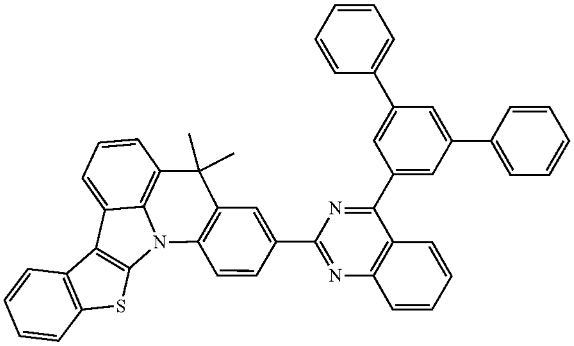
HAC4
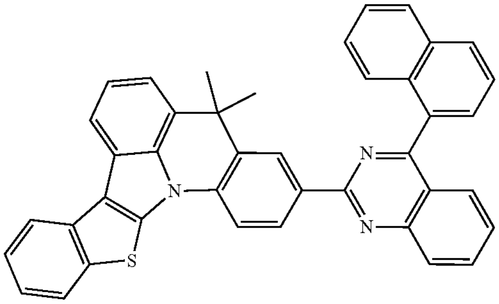
HAC5
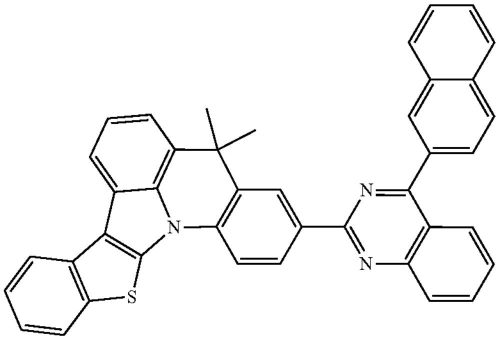
HAC6
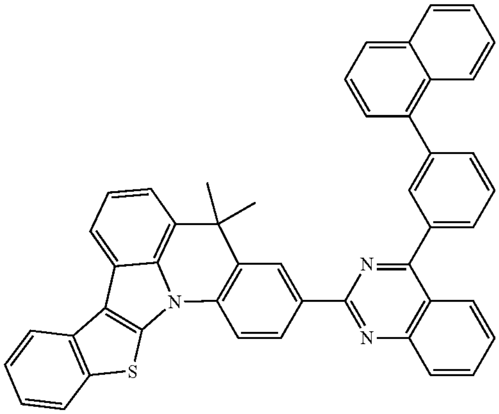
-continued
HAC7
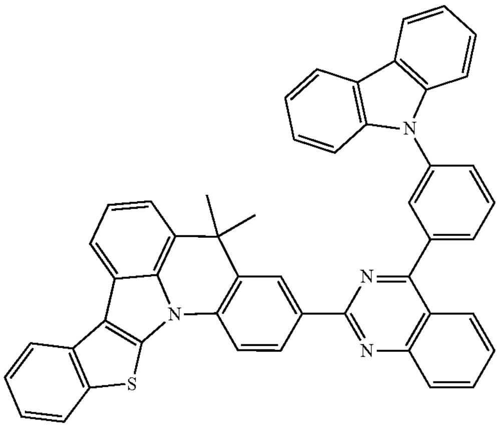
HAC8
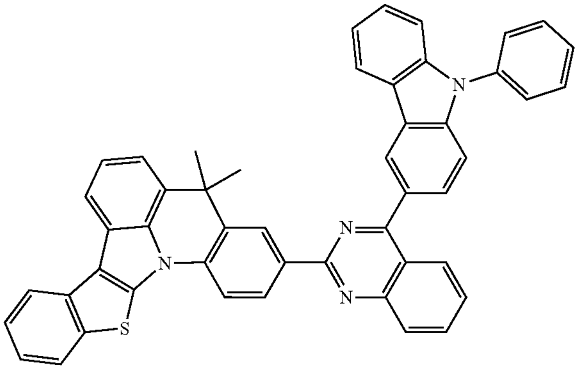
HAC9
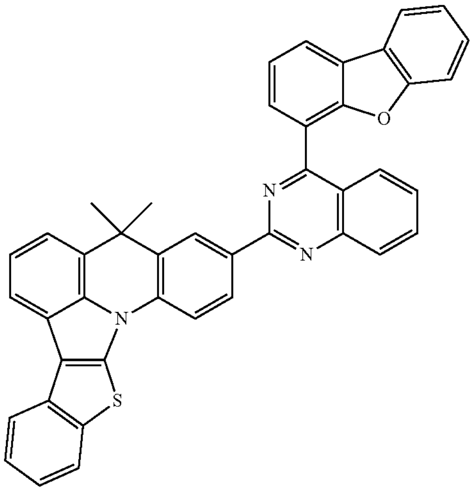

-continued
HAC10
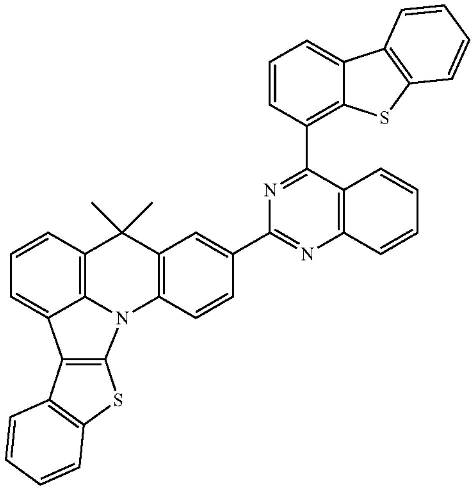
HAC11
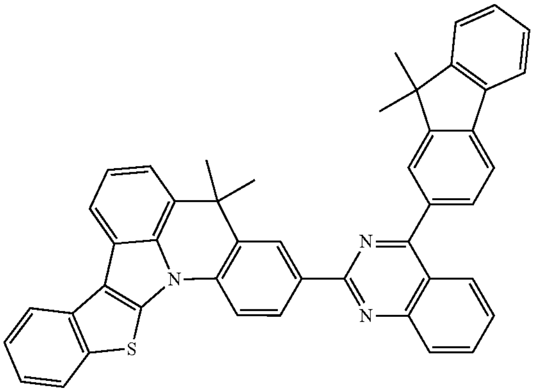
HAC12
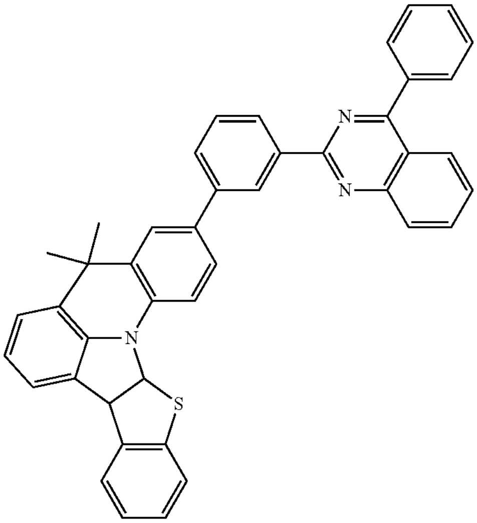
-continued
HAC13
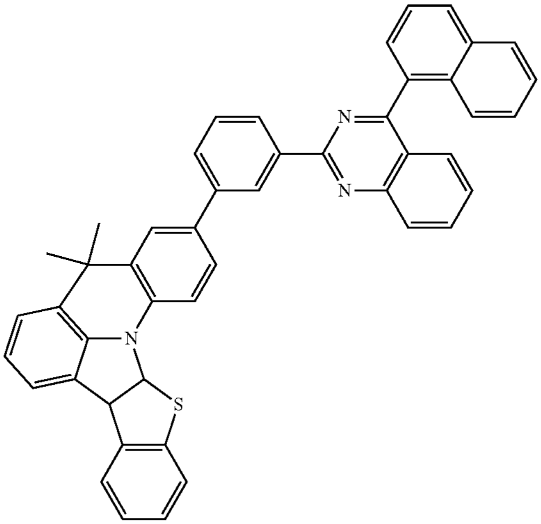
HAC14
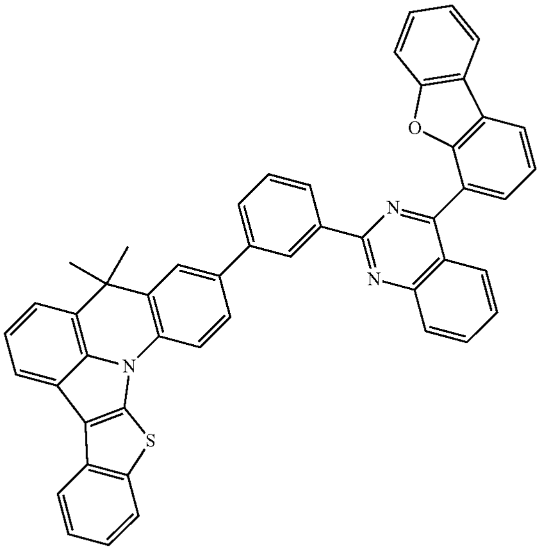

-continued
HAC15
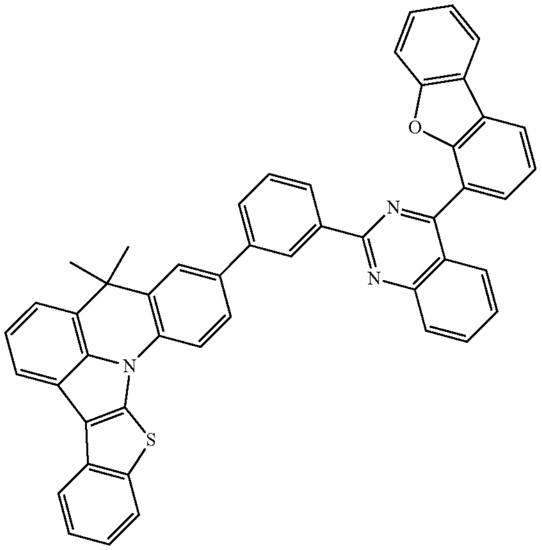
HAC16
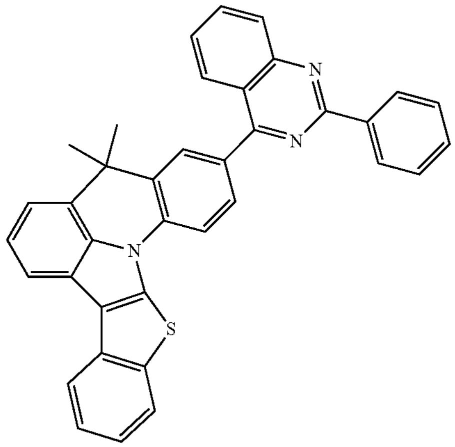
HAC17
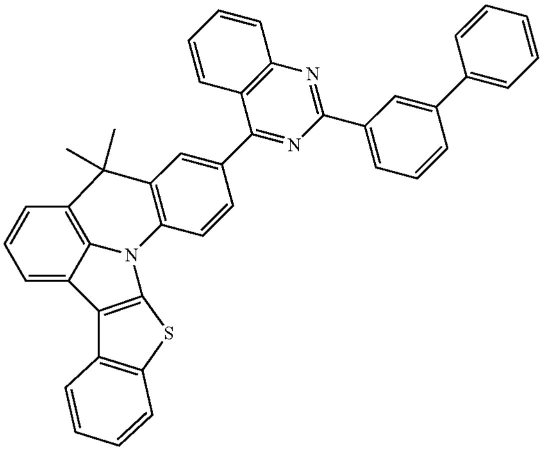
-continued
HAC18
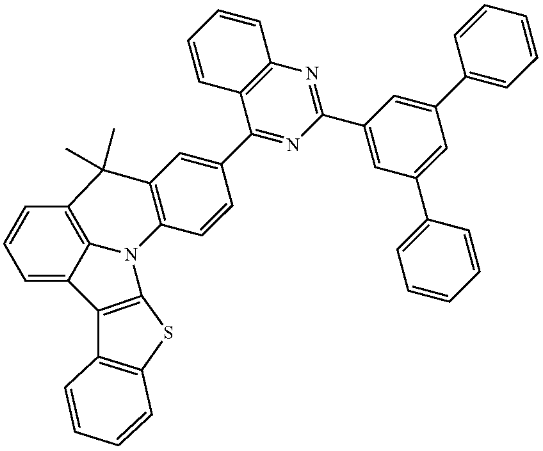
HAC19
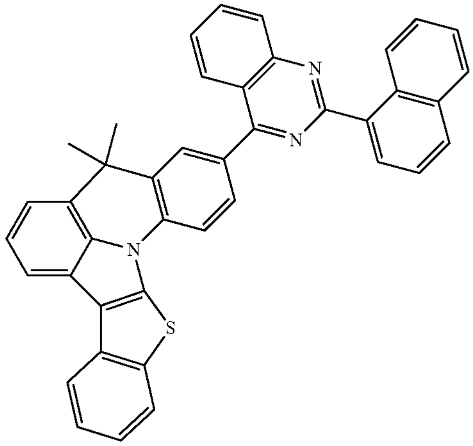
HAC20
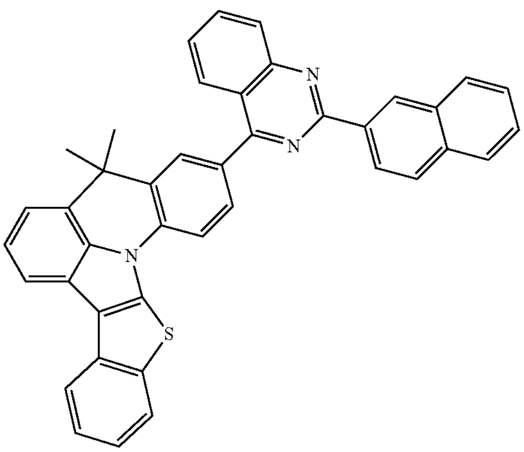

-continued
HAC21
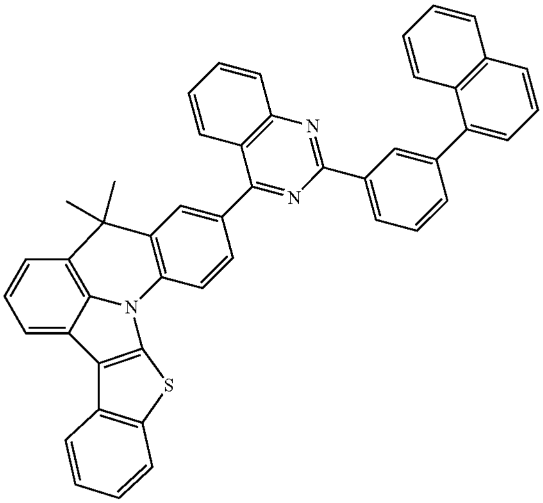
HAC22
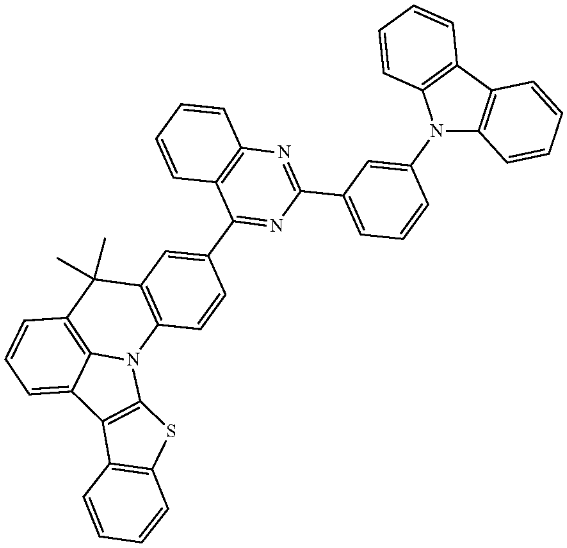
HAC23
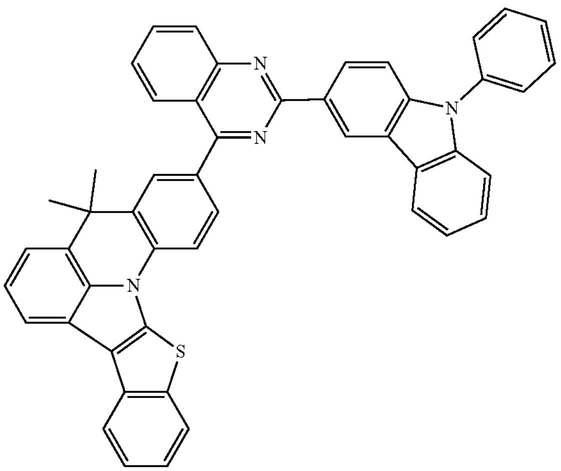
-continued
HAC24
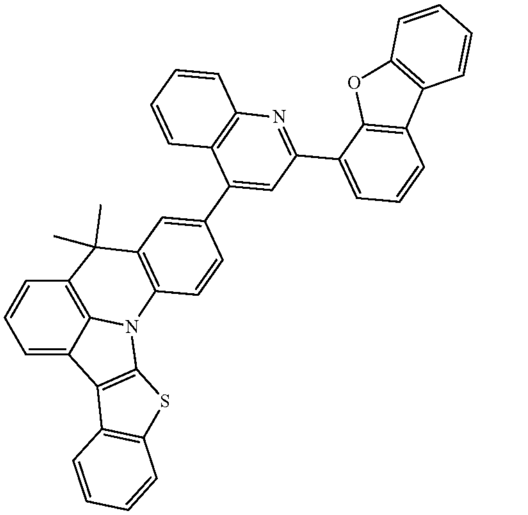
HAC25
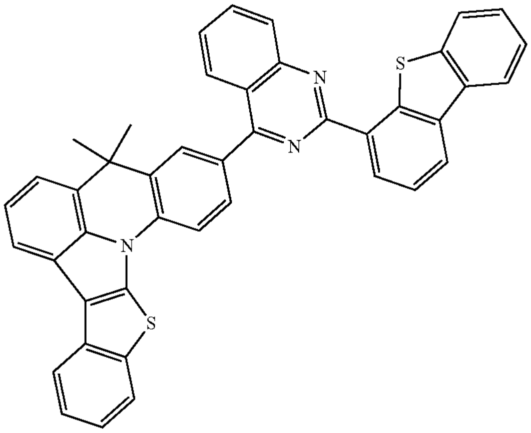
HAC26
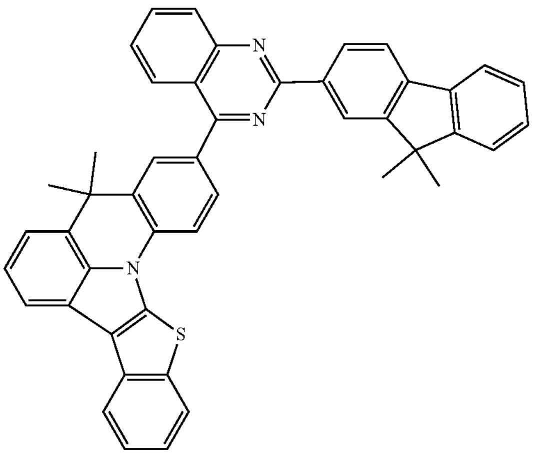

-continued
HAC27
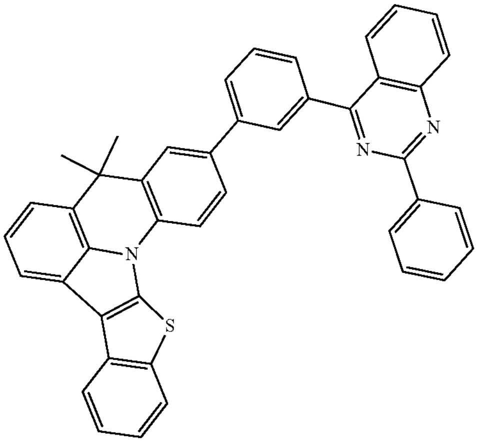
HAC28
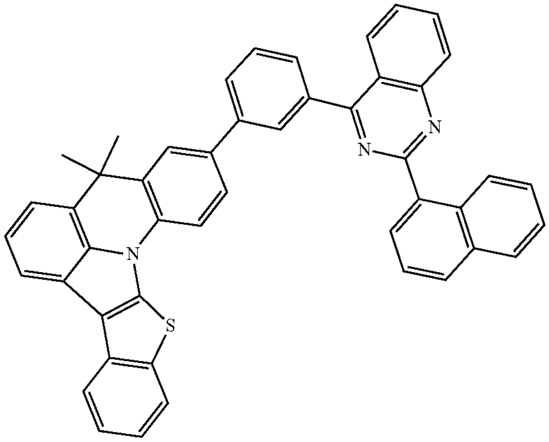
HAC29
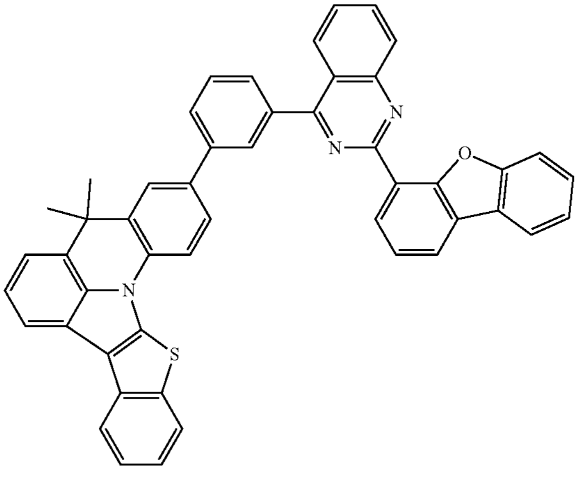
-continued
HAC30
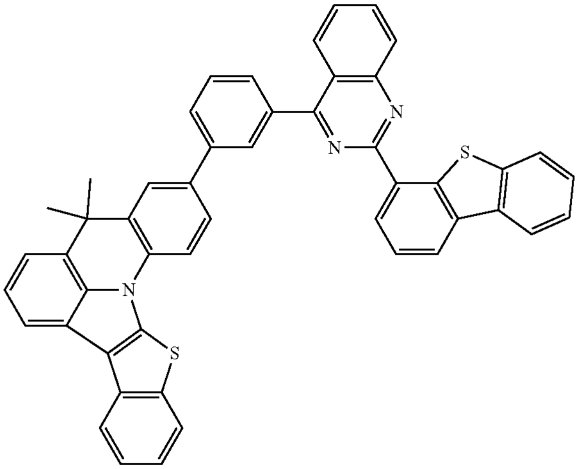
HAC31
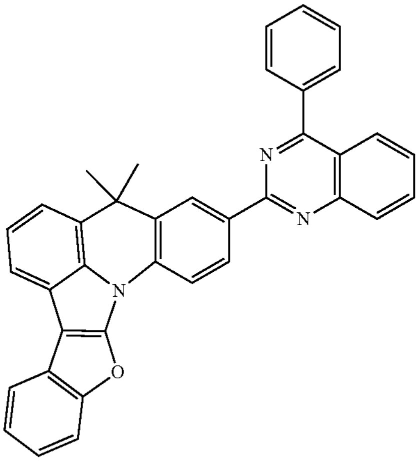
HAC32
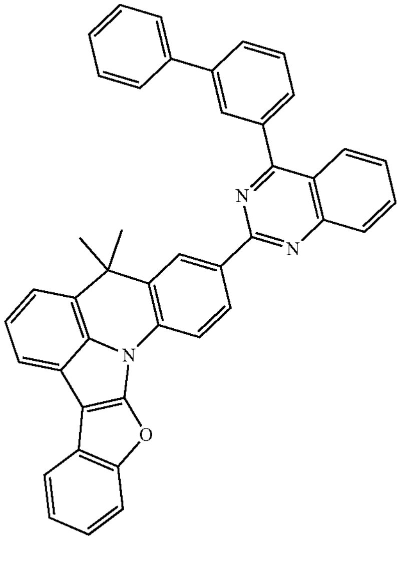

-continued
HAC33
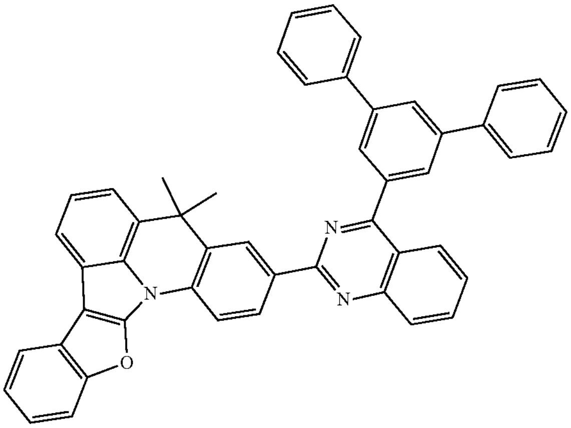
HAC34
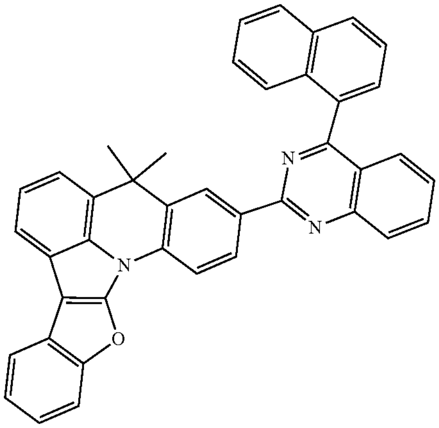
HAC35
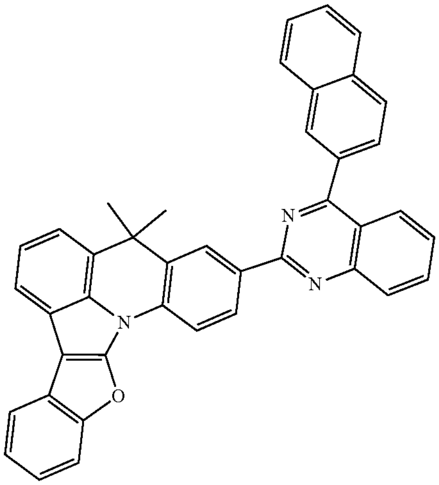
-continued
HAC36
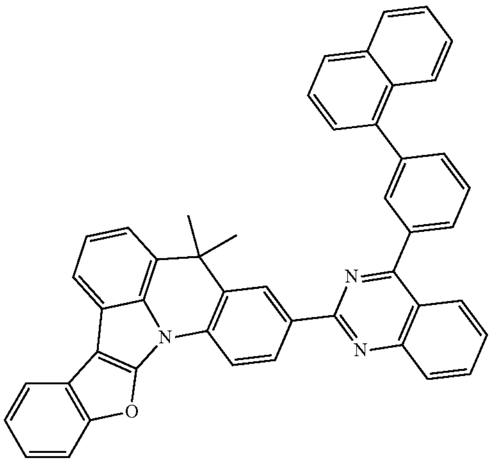
HAC37
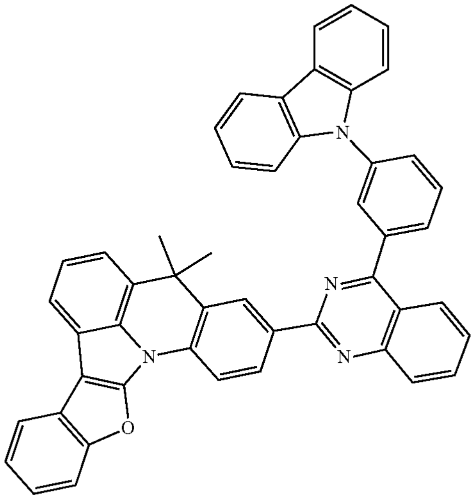
HAC38
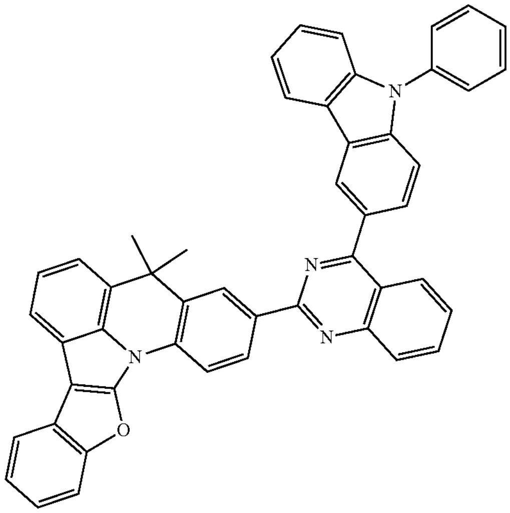

-continued
HAC39
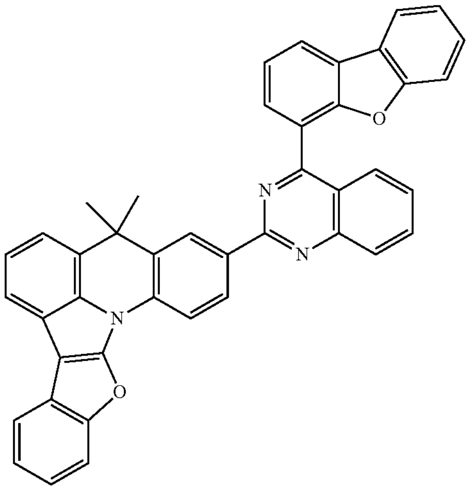
HAC40
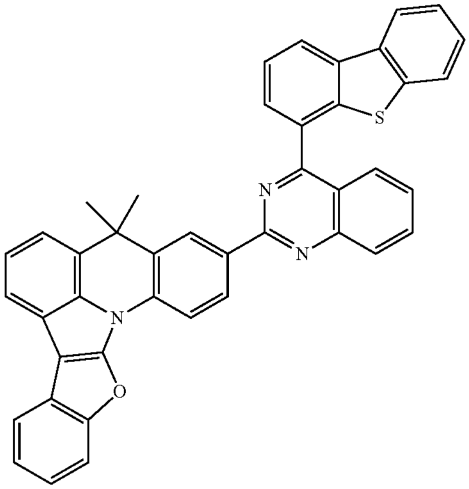
HAC41
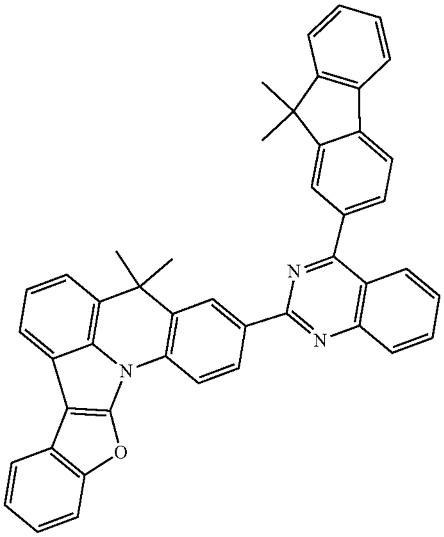
-continued
HAC42
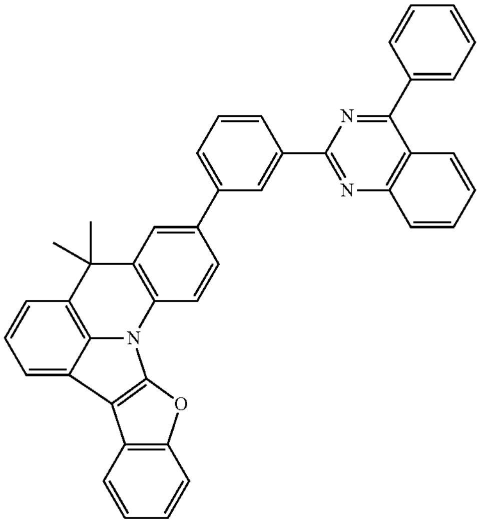
HAC43
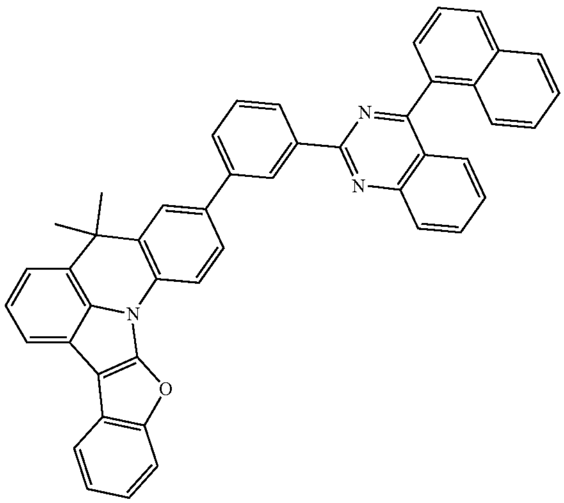
HAC44
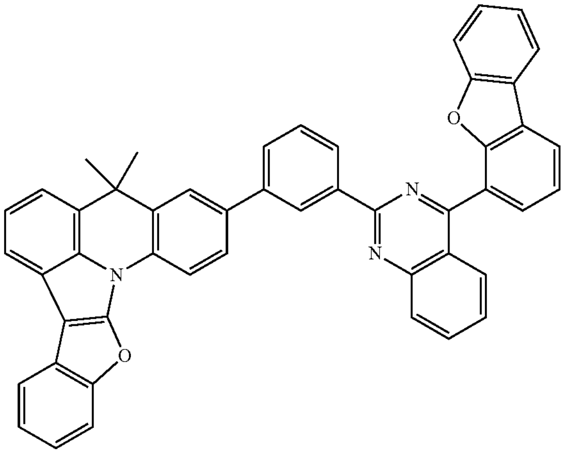

-continued
HAC45
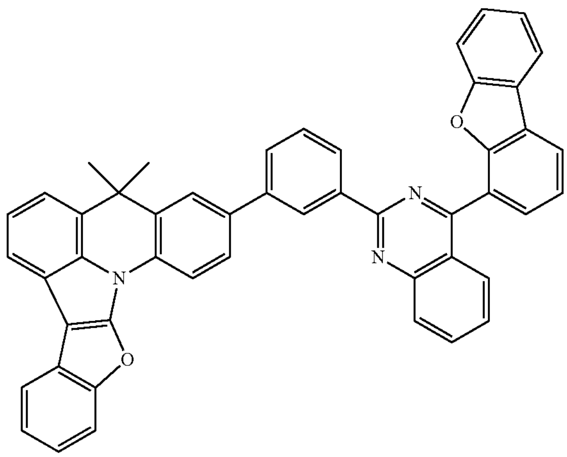
HAC46
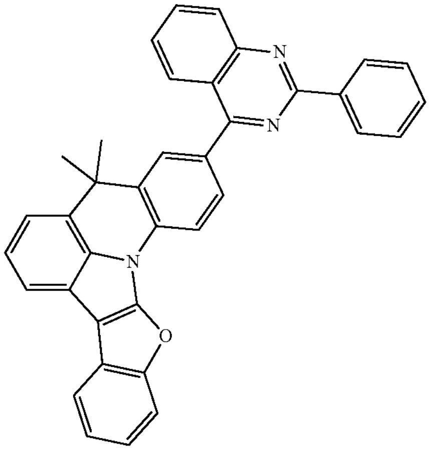
HAC47
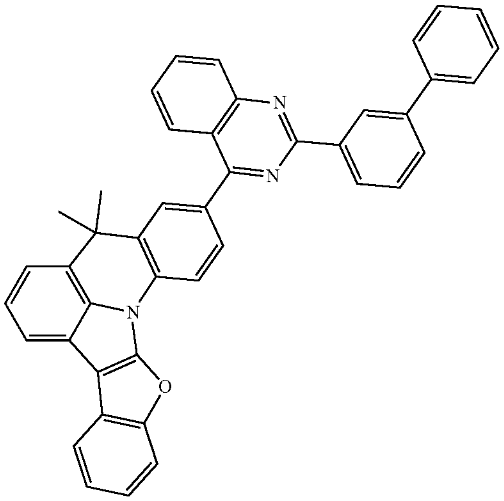
-continued
HAC48
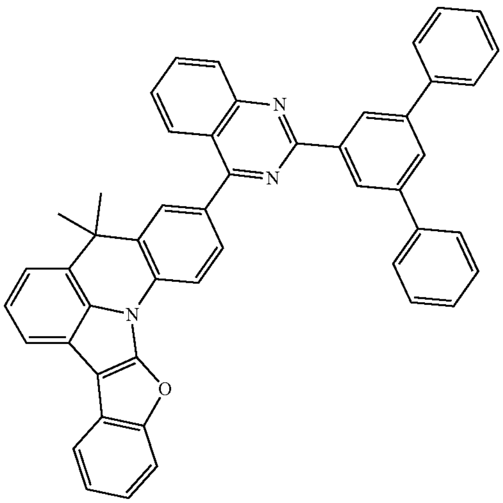
HAC49
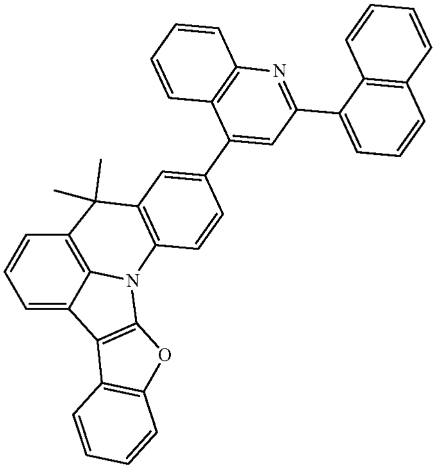
HAC50
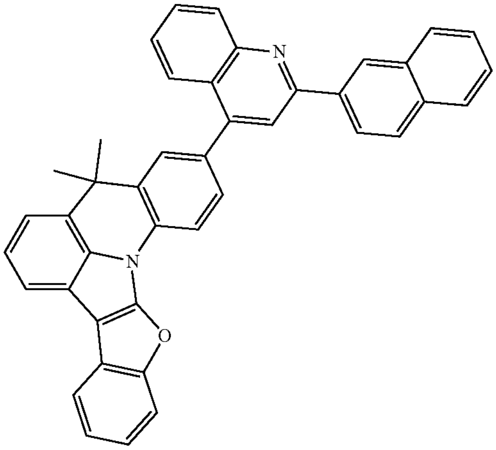

-continued
HAC51
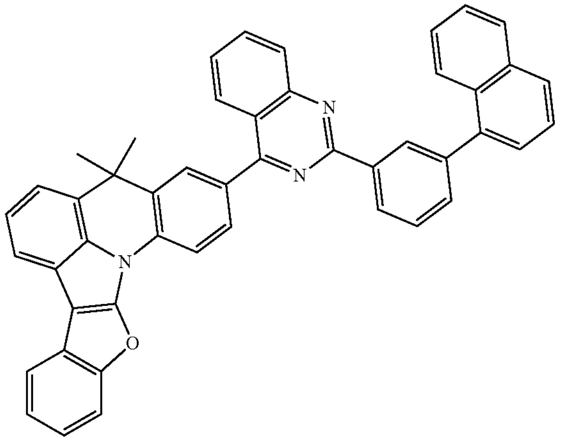
HAC52
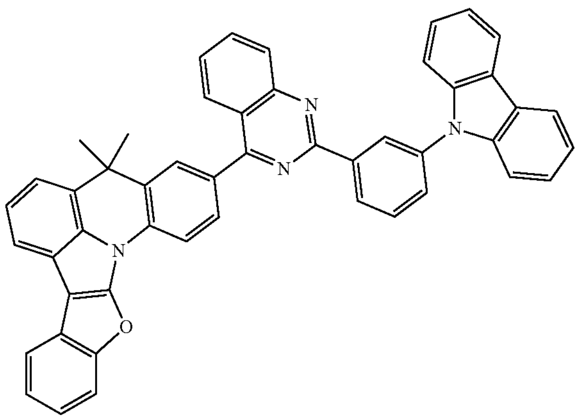
HAC53
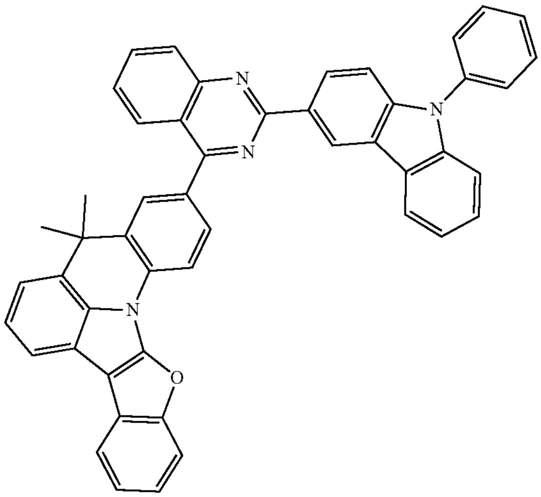
-continued
HAC54
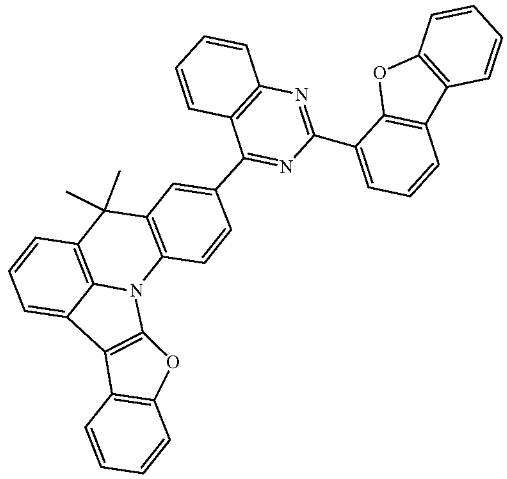
HAC55
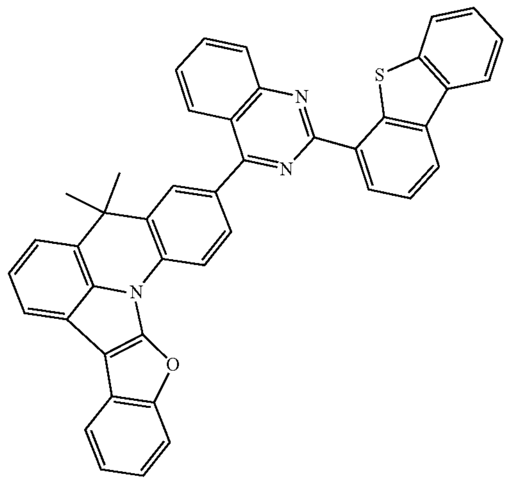
HAC56
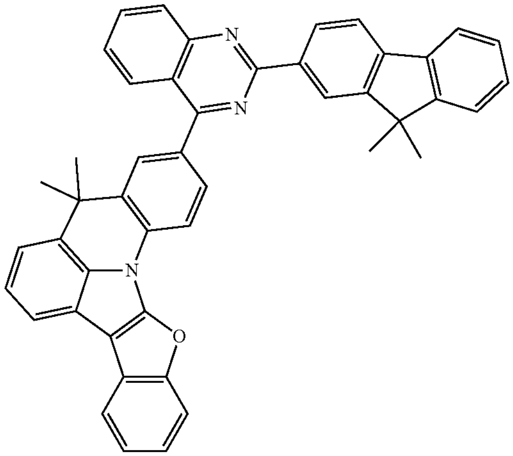

-continued
HAC57
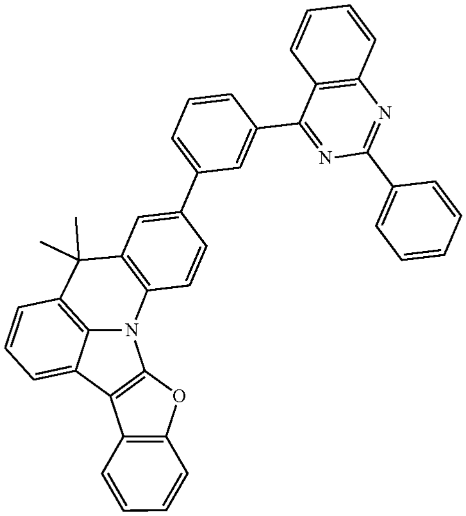
HAC58
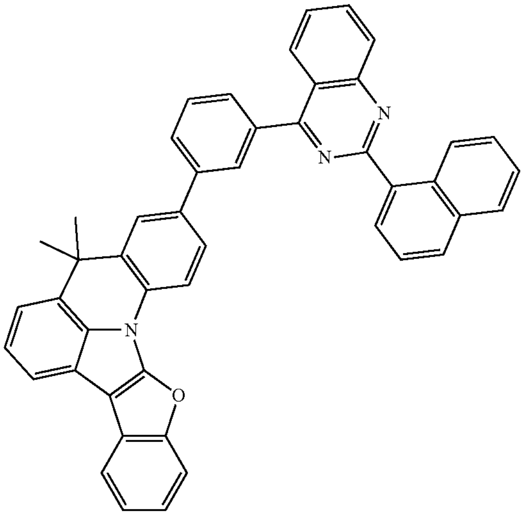
HAC59
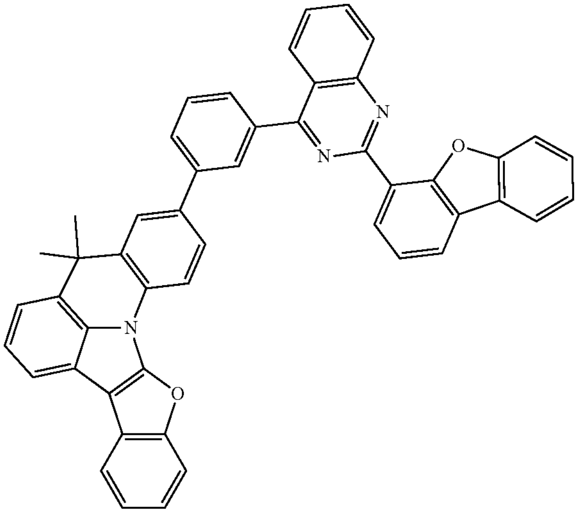
-continued
HAC60
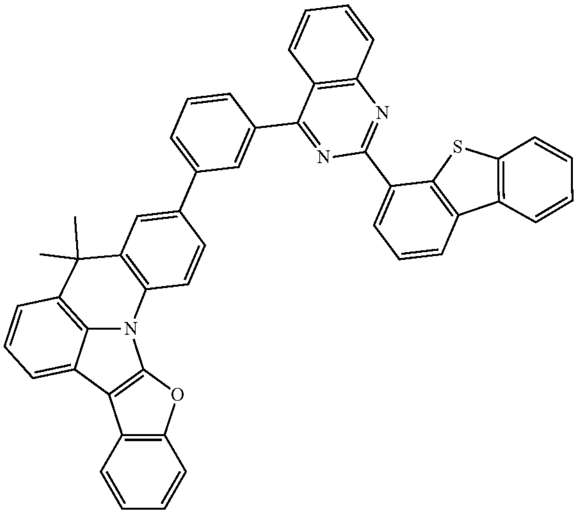
HAC61
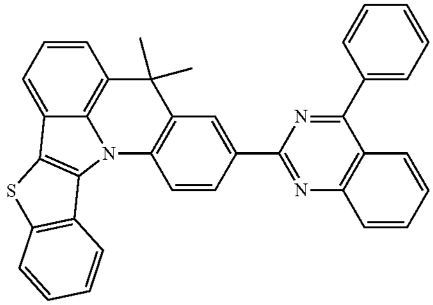
HAC62
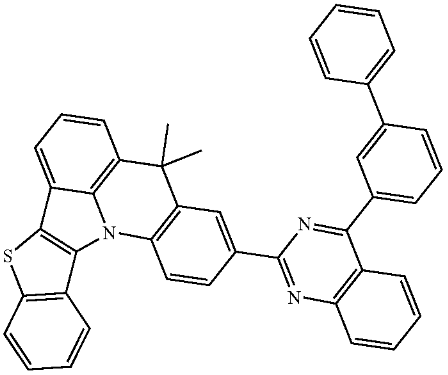
HAC63
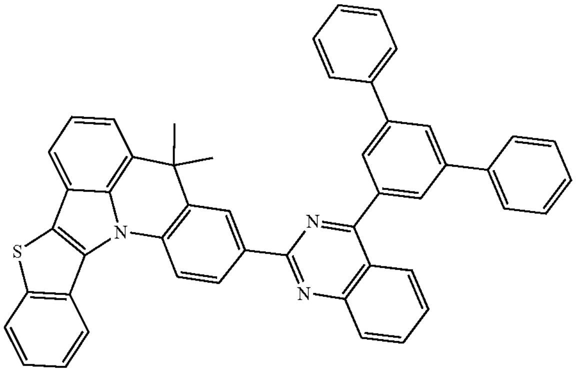

-continued
HAC64
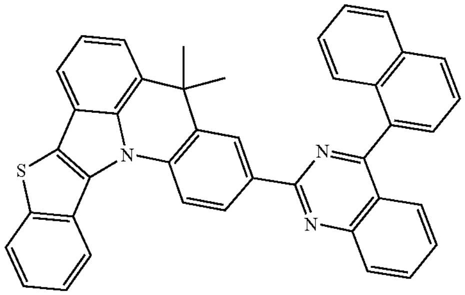
HAC65
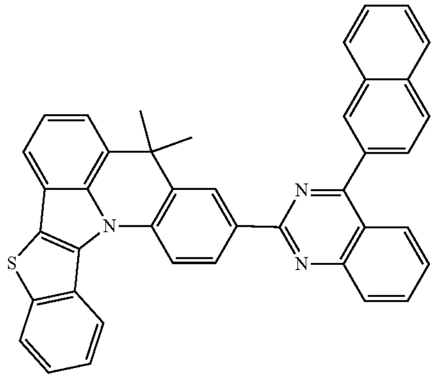
HAC66
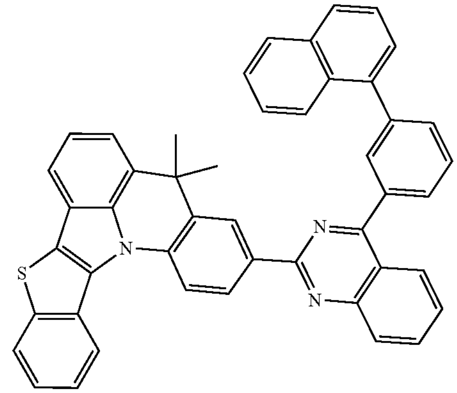
HAC67
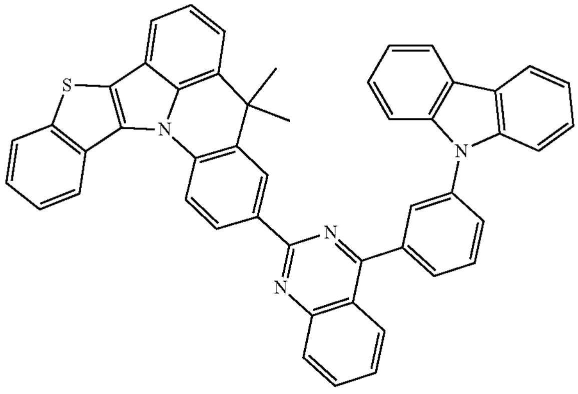
-continued
HAC68
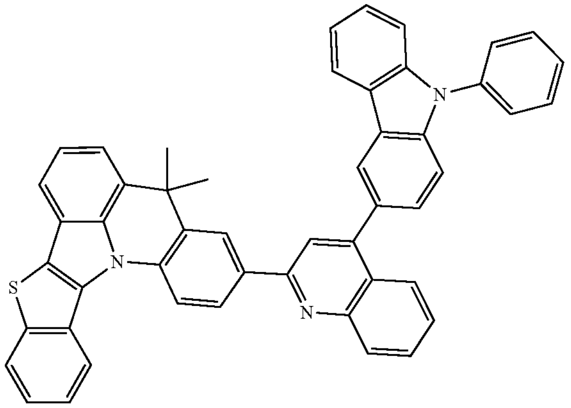
HAC69
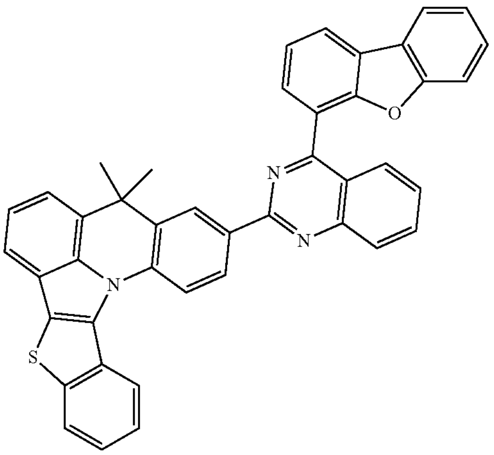
HAC70
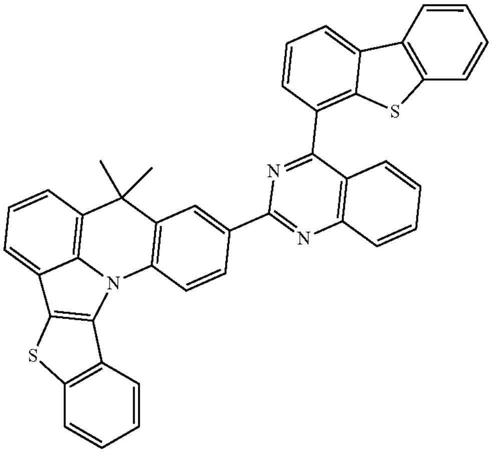

-continued
HAC71
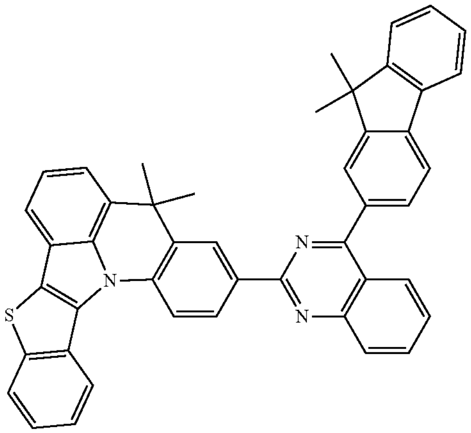
HAC72
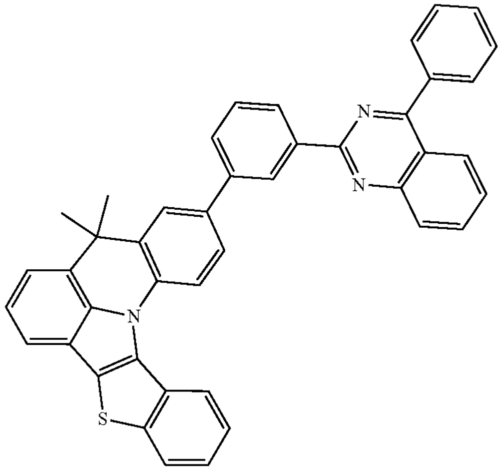
HAC73
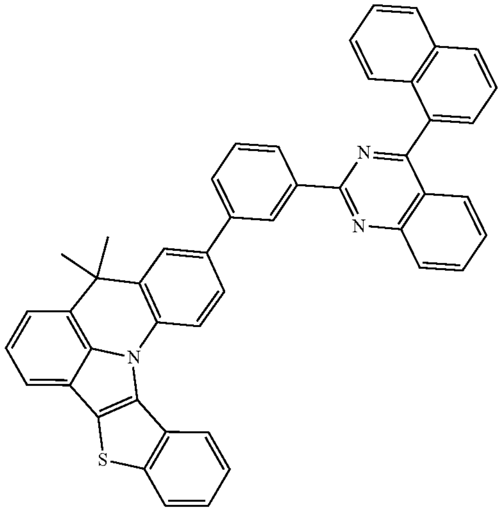
-continued
HAC74
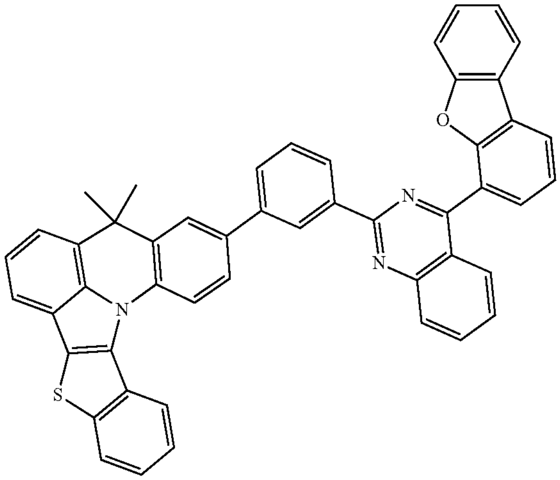
HAC75
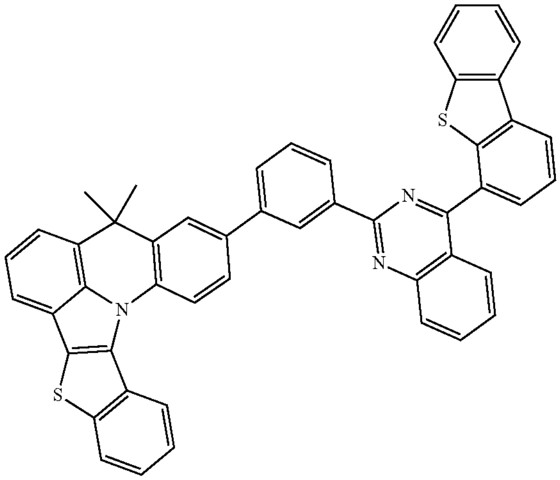
HAC76
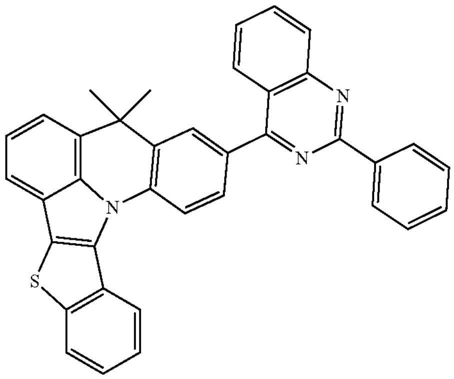

-continued
HAC77
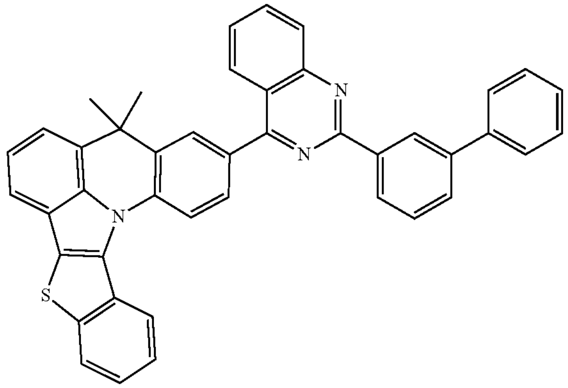
HAC78
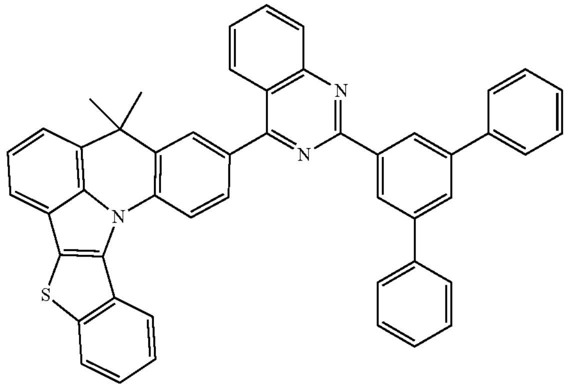
HAC79
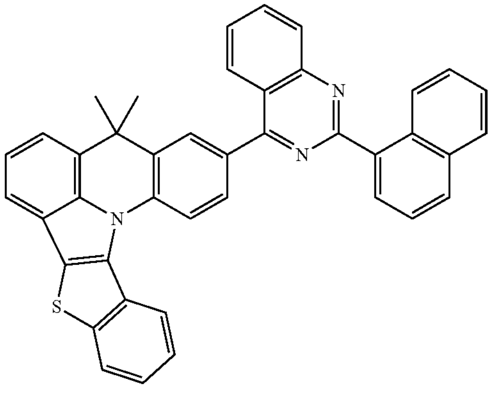
-continued
HAC80
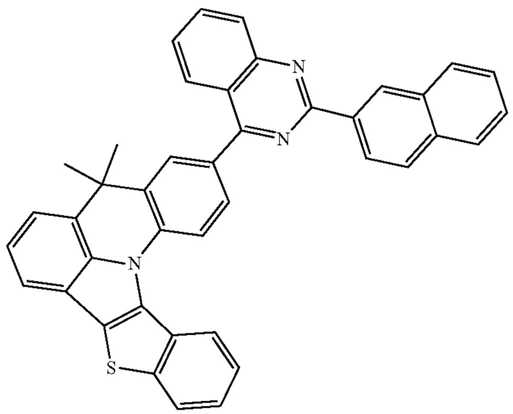
HAC81
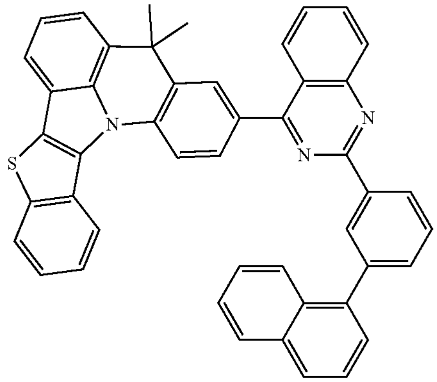
HAC82
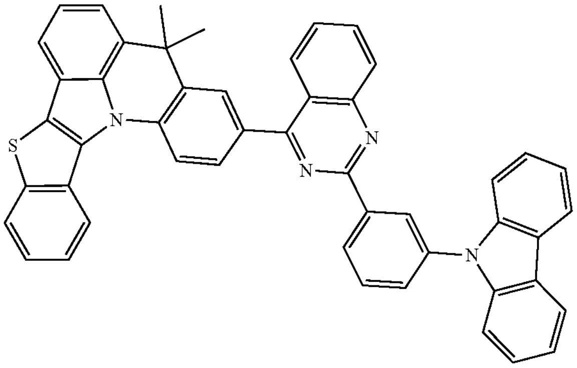
HAC83
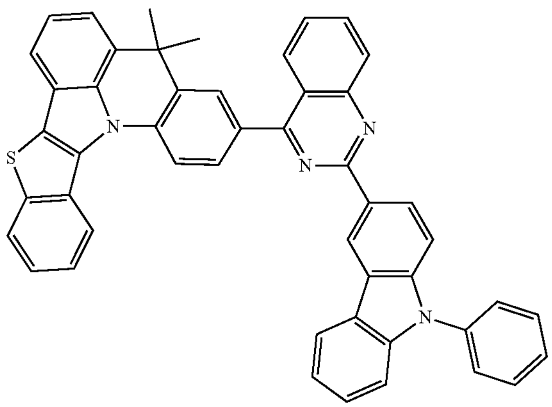

-continued
HAC84
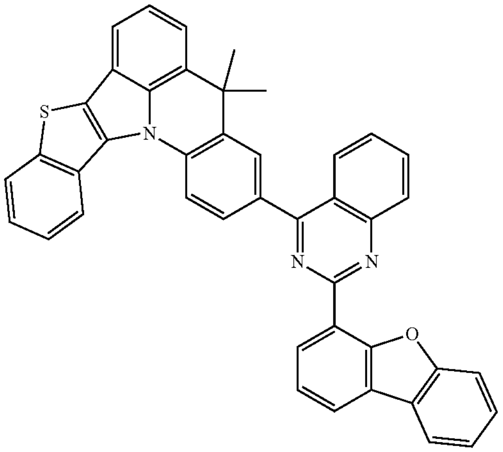
HAC85
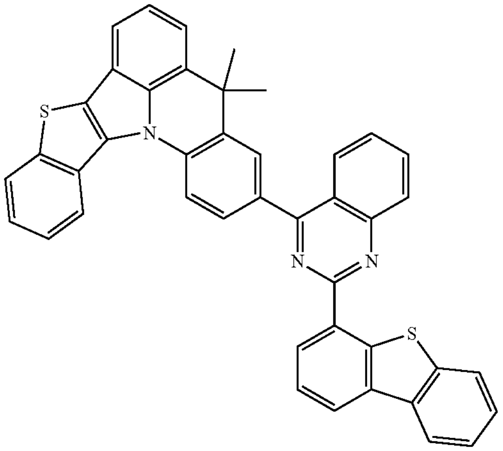
HAC86
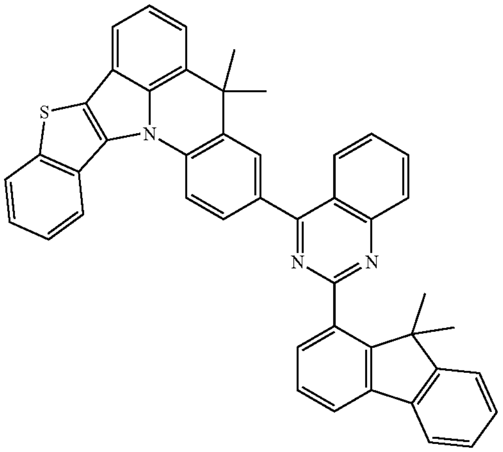
-continued
HAC87
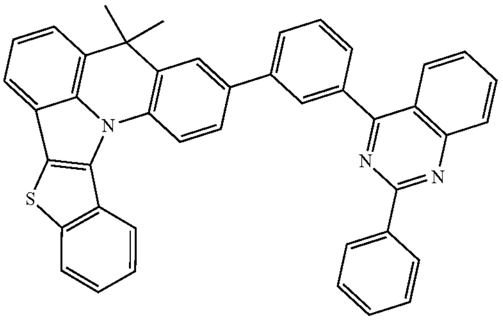
HAC88
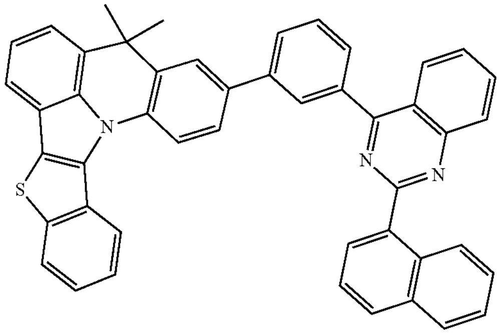
HAC89
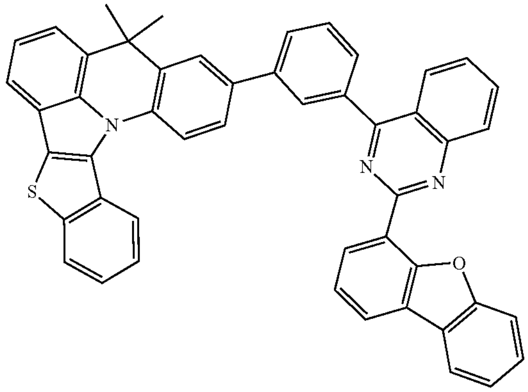
HAC90
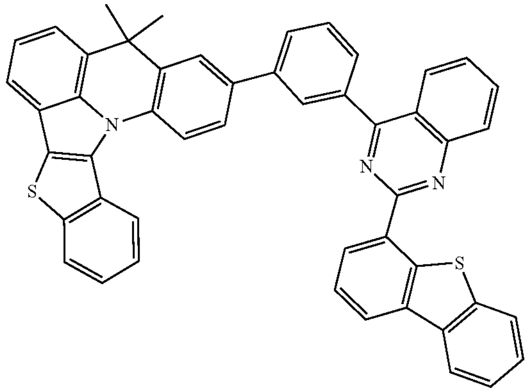

-continued
HAC91
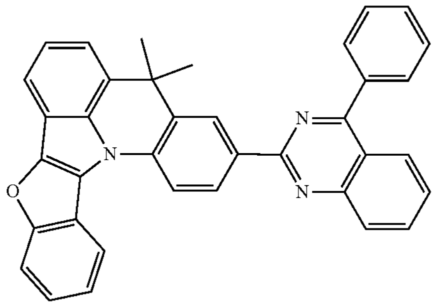
HAC92
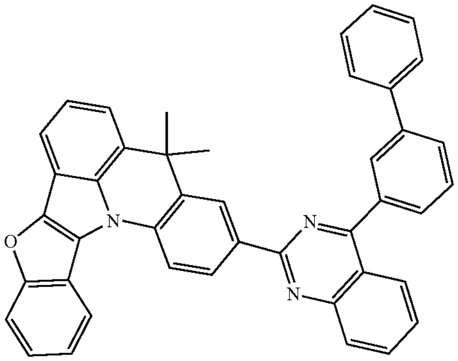
HAC93
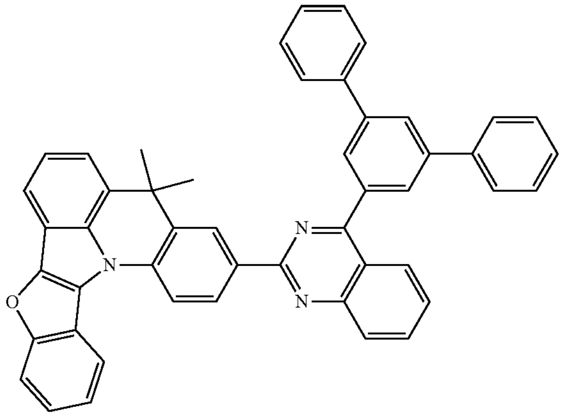
HAC94
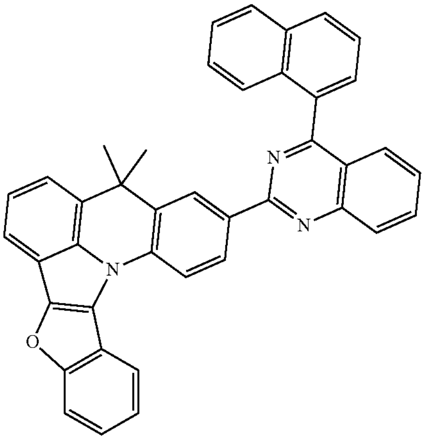
-continued
HAC95
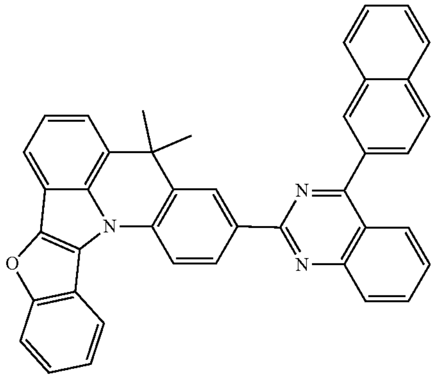
HAC96
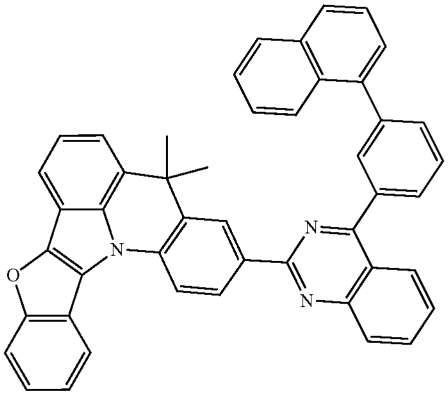
HAC97
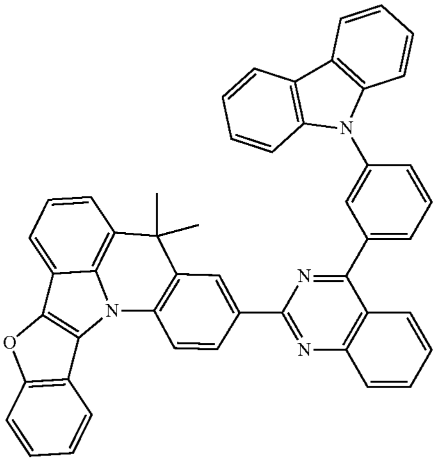

-continued
HAC98
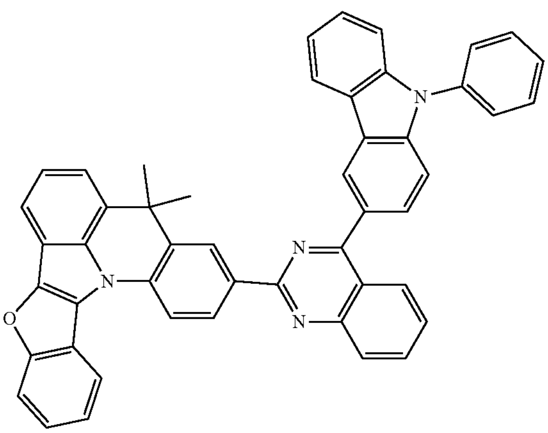
HAC99
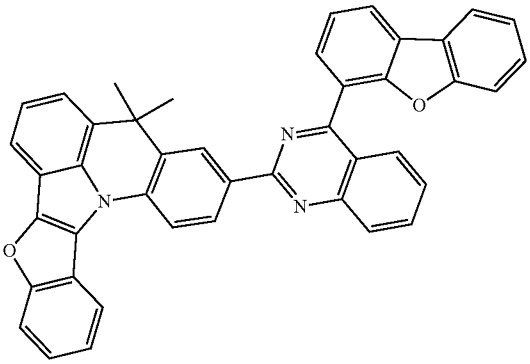
HAC100
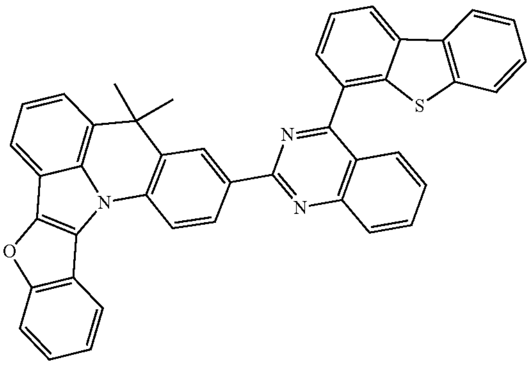
-continued
HAC101
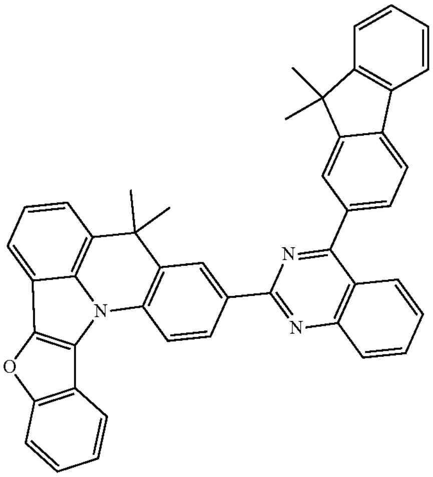
HAC102
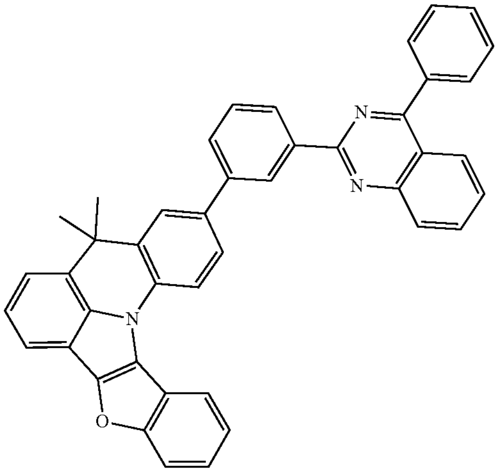
HAC103
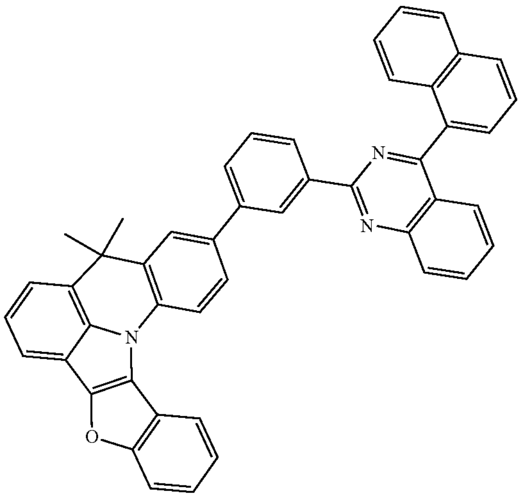

-continued
HAC104
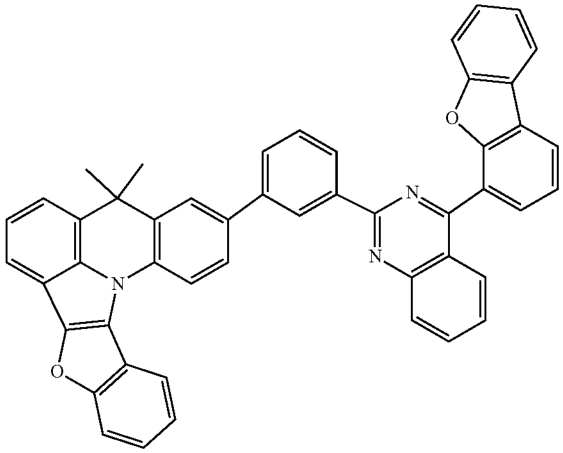
HAC105
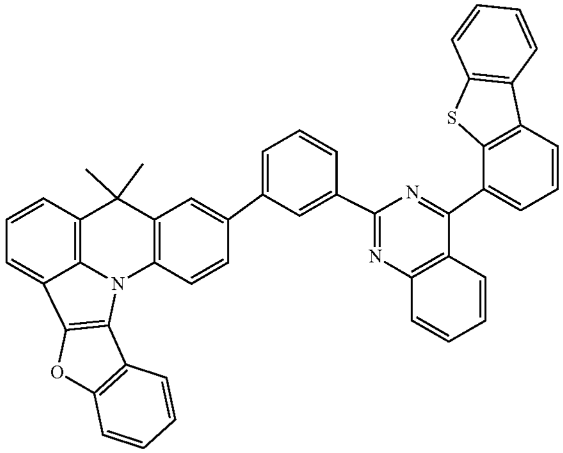
HAC106
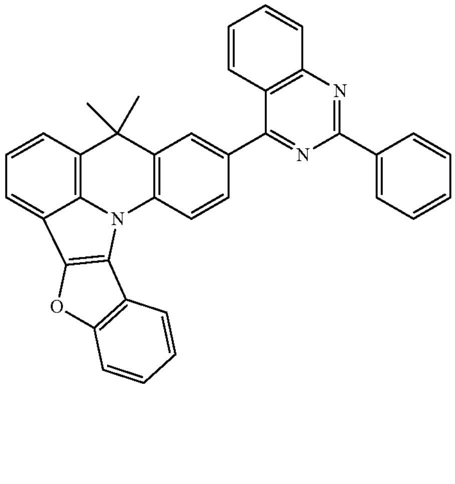
-continued
HAC107
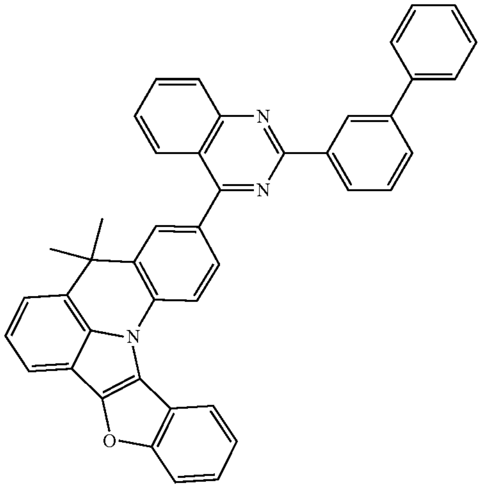
HAC108
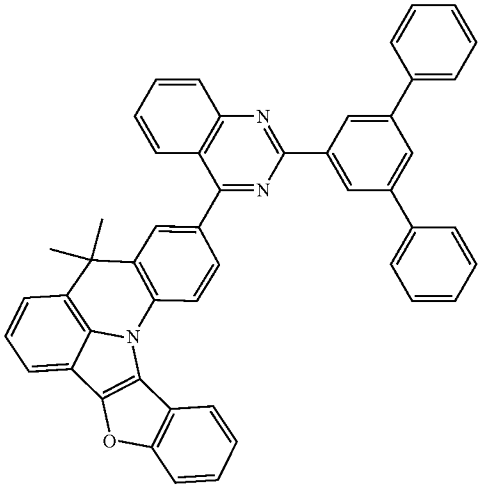
HAC109
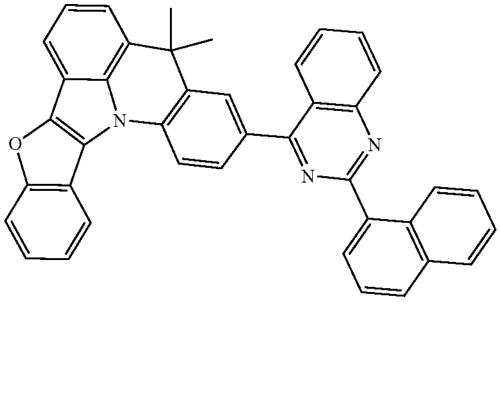

-continued
HAC110
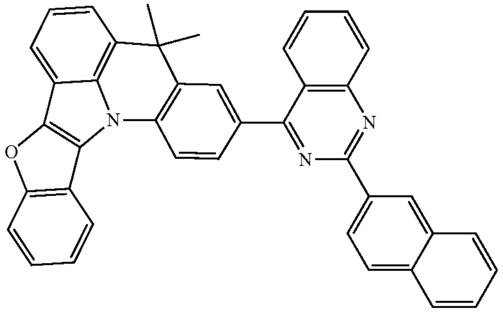
HAC111
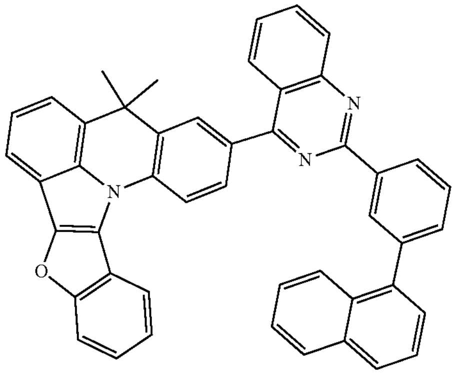
HAC112
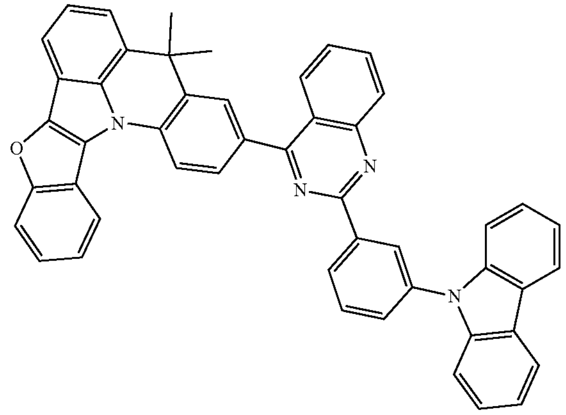
HAC113
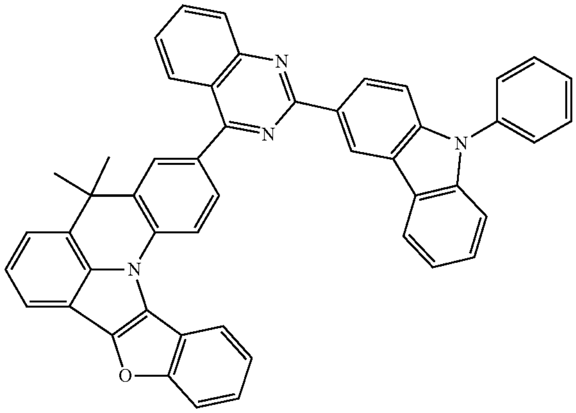
-continued
HAC114
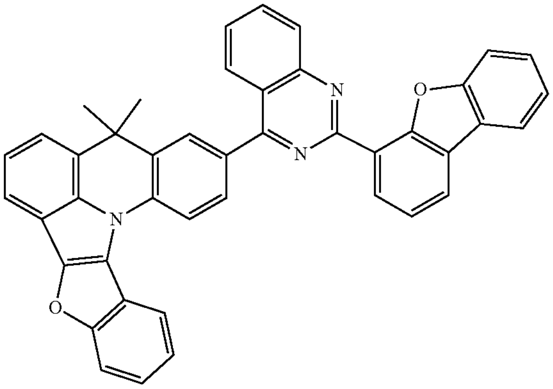
HAC115
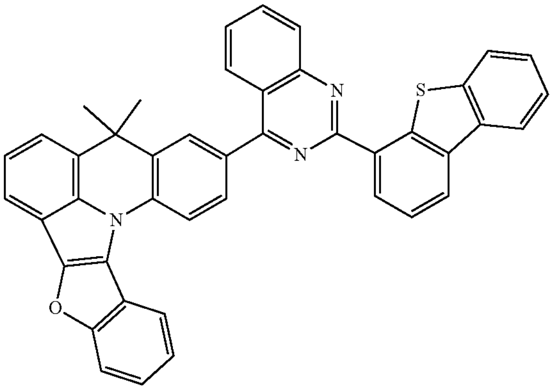
HAC116
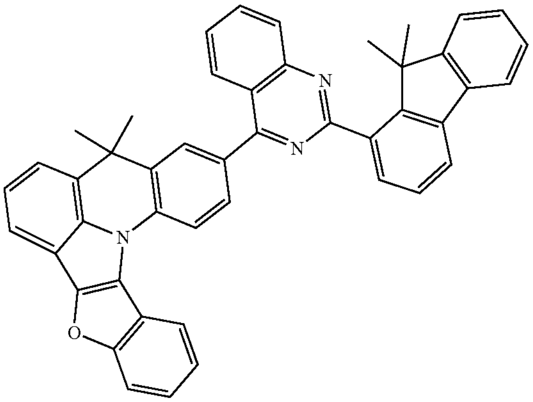
HAC117
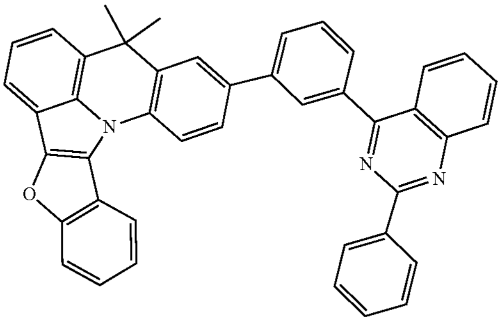

-continued
HAC118
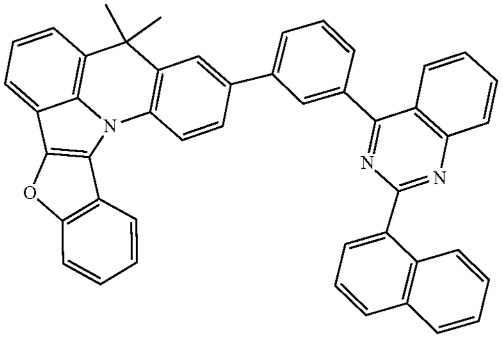
HAC119
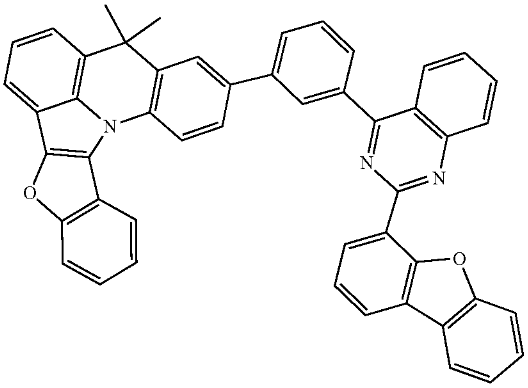
HAC120
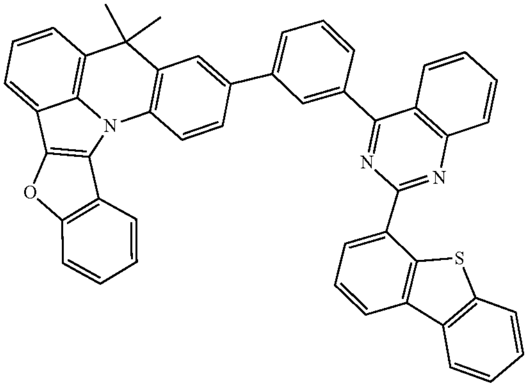
HAC121
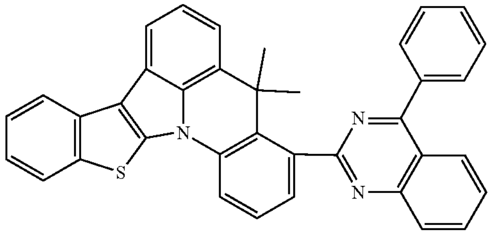
-continued
HAC122
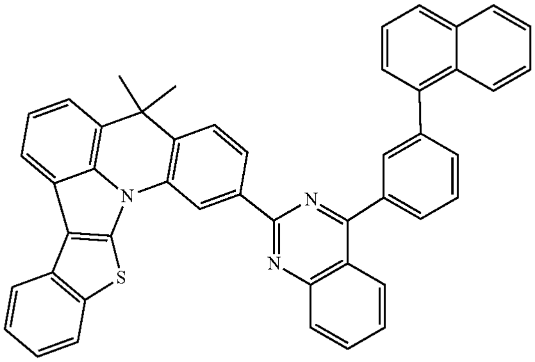
HAC123
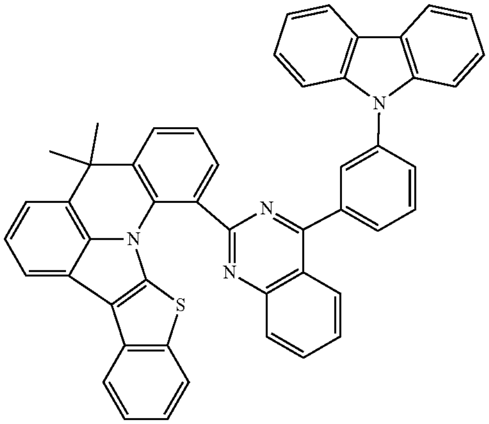
HAC124
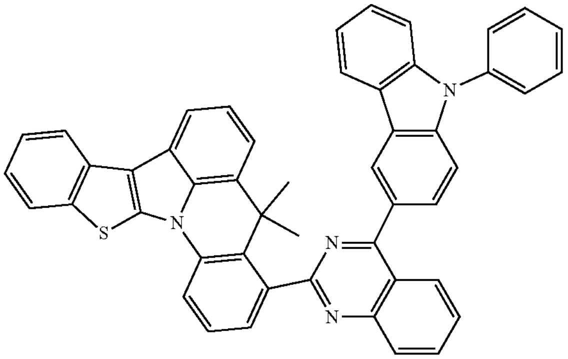
HAC125
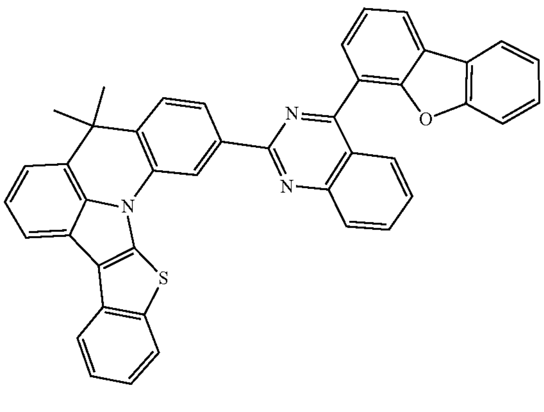

-continued
HAC126
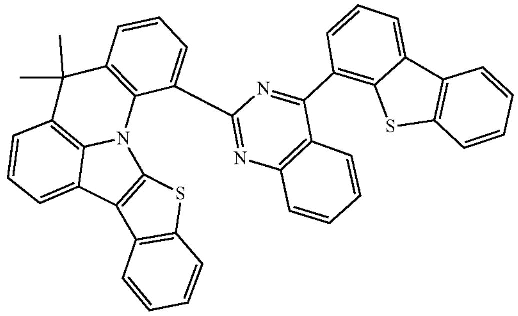
HAC127
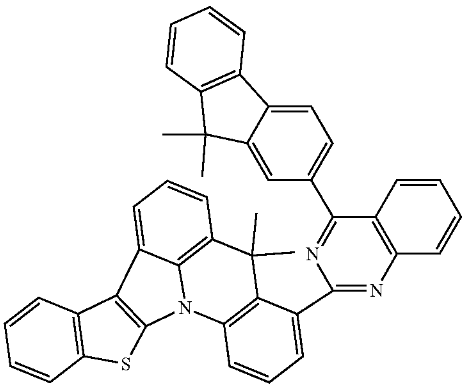
HAC128
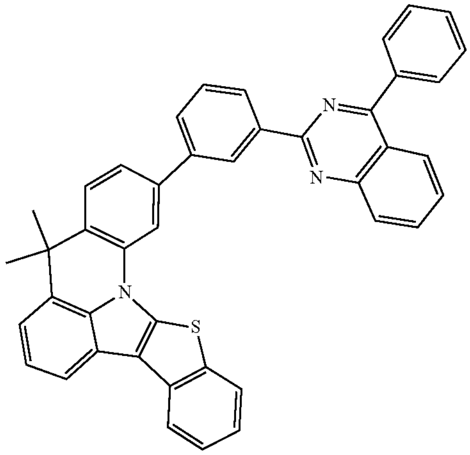
-continued
HAC129
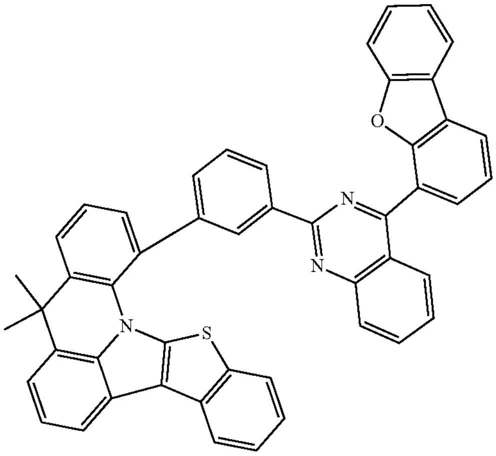
HAC130
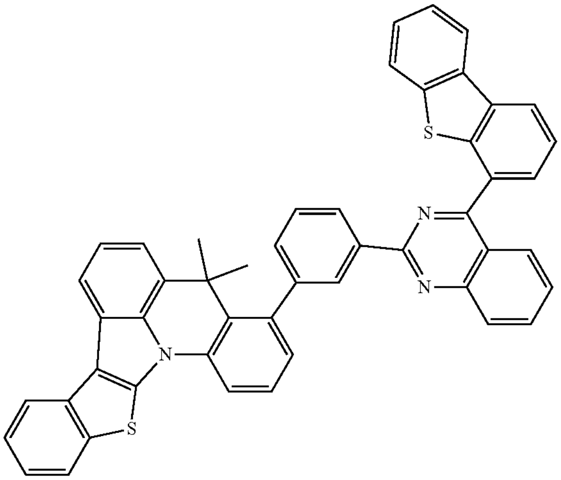
HAC131
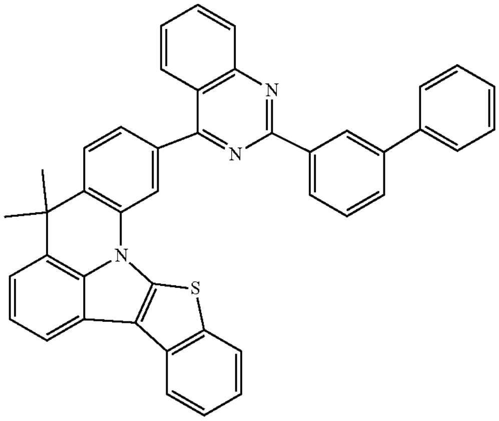

HAC132
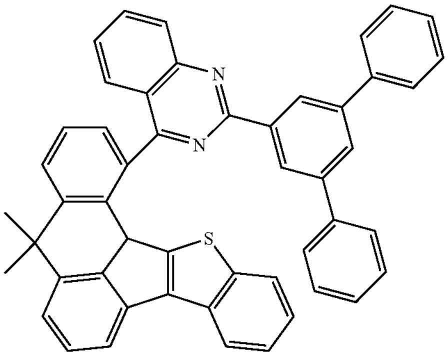
HAC133
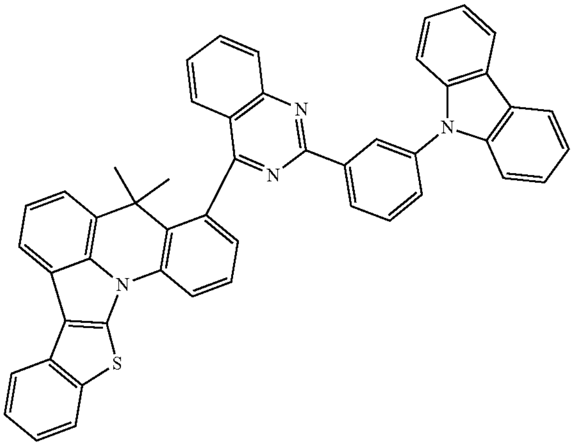
HAC134
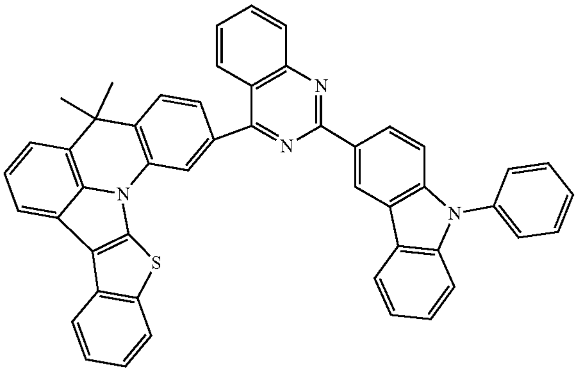
HAC135
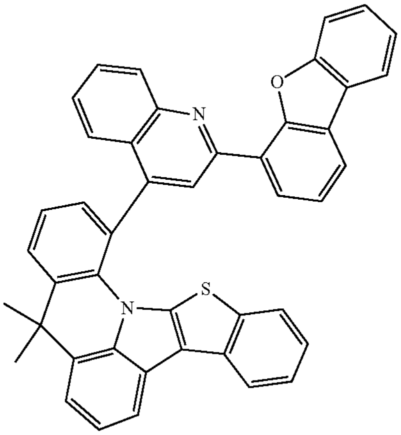
HAC136
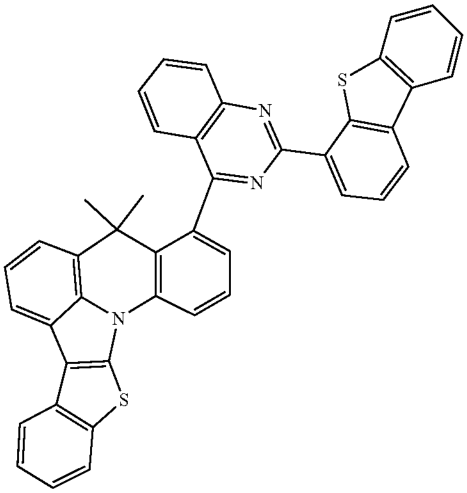
HAC137
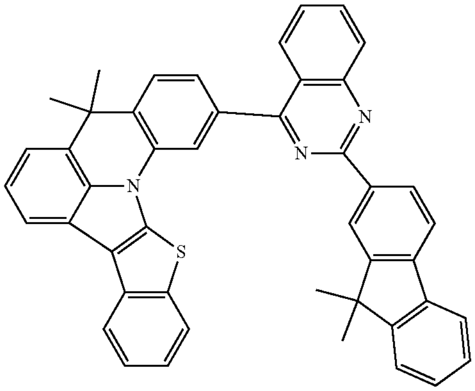
HAC138
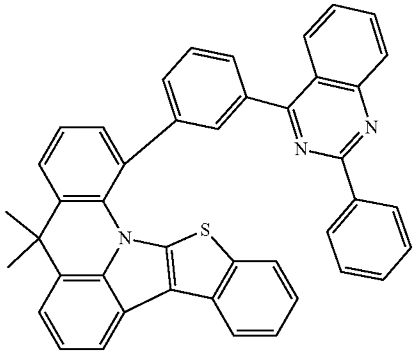

-continued
HAC139
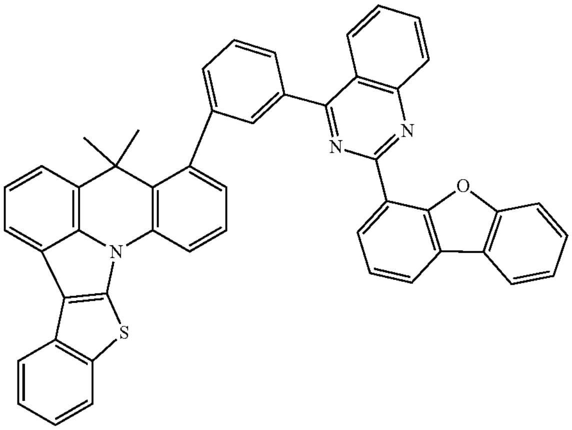
HAC140
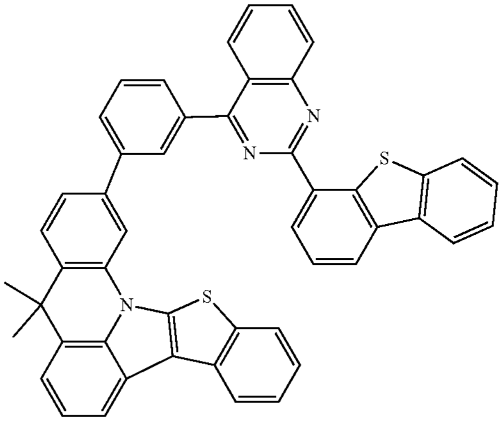
HAC141
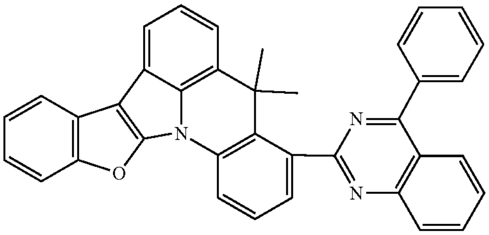
HAC142
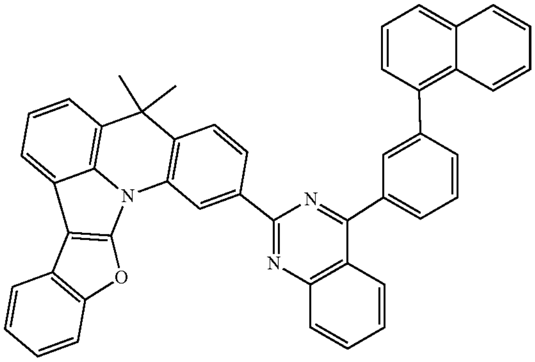
-continued
HAC143
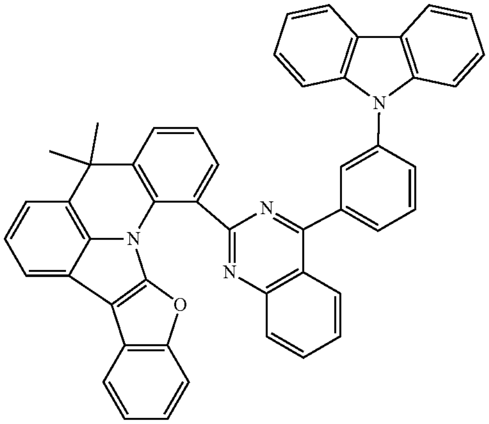
HAC144
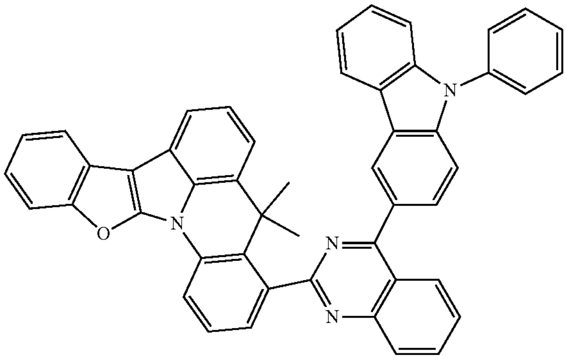
HAC145
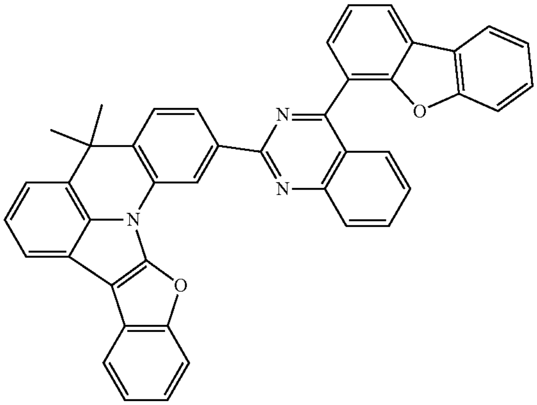
HAC146
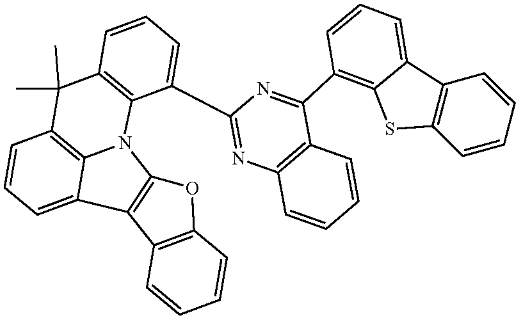

-continued
HAC147
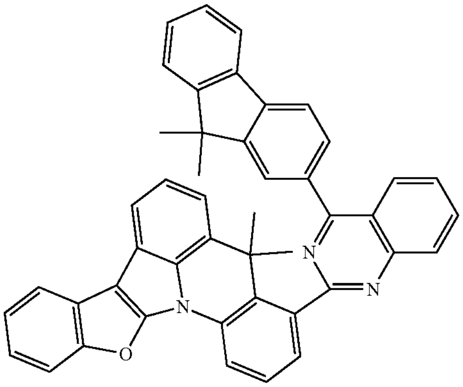
HAC148
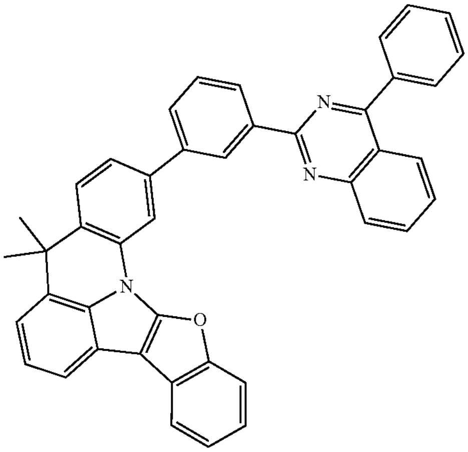
HAC149
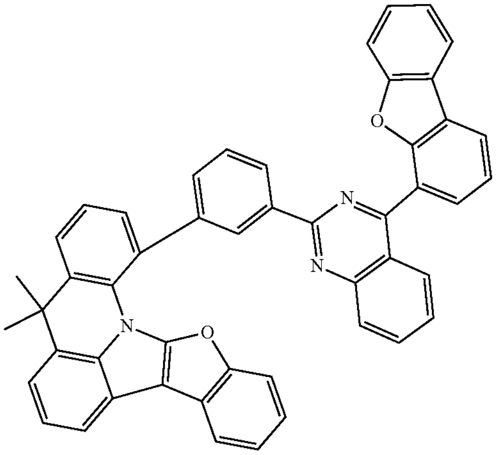
-continued
HAC150
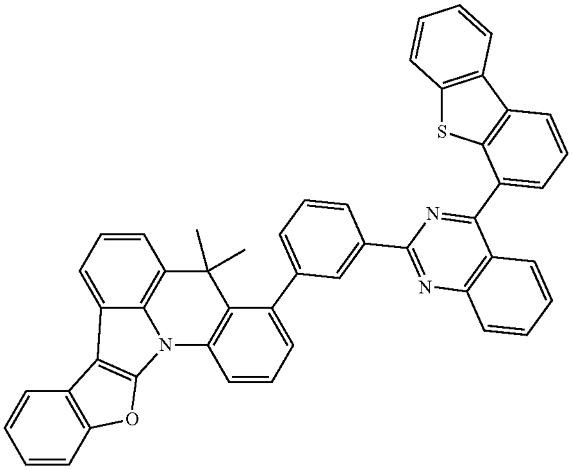
HAC151
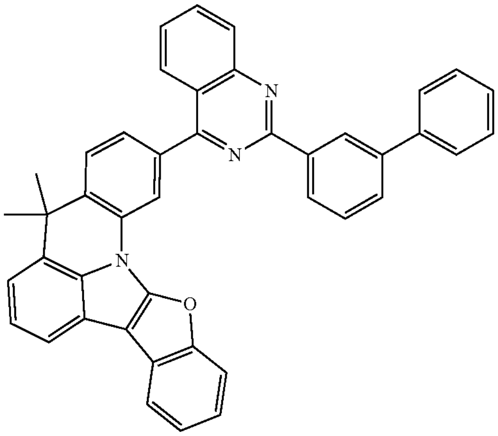
HAC152
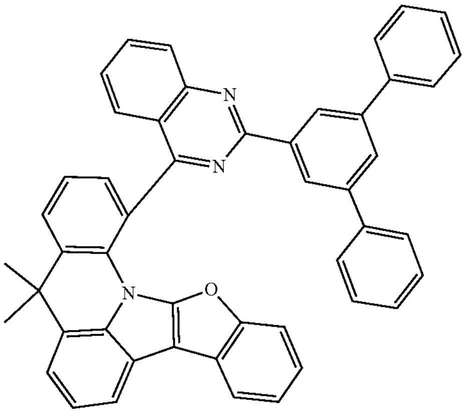

-continued
HAC153
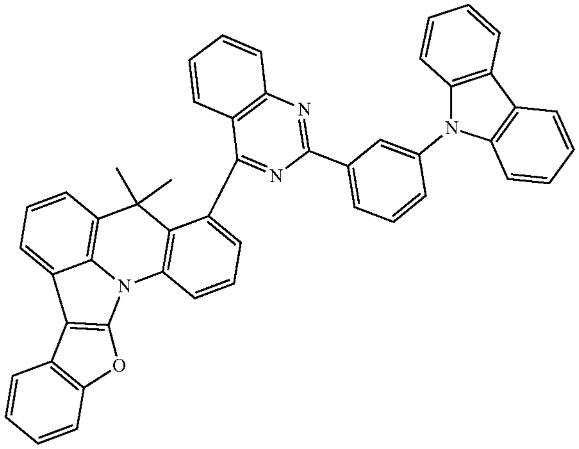
HAC154
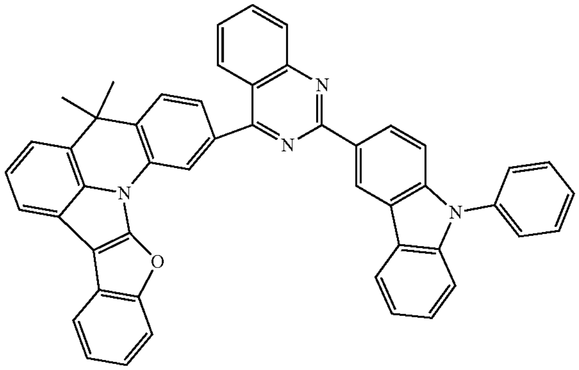
HAC155
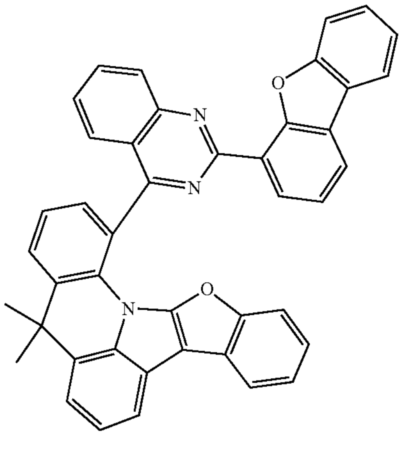
-continued
HAC156
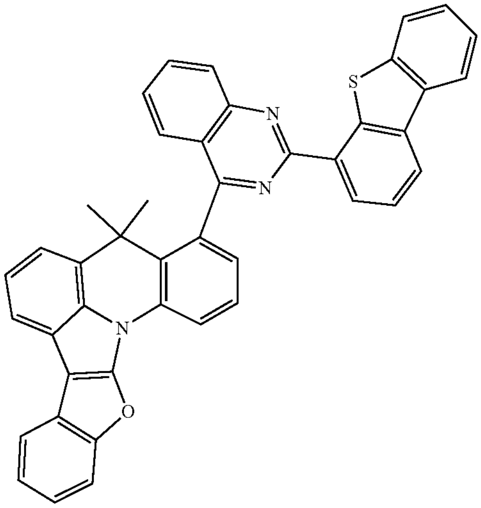
HAC157
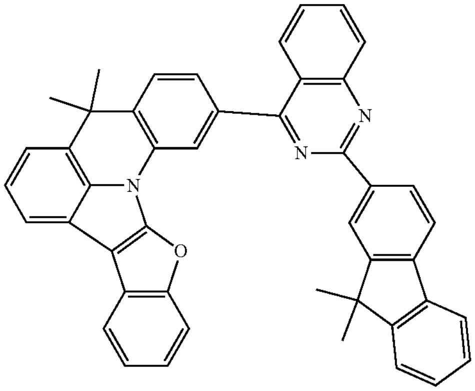
HAC158
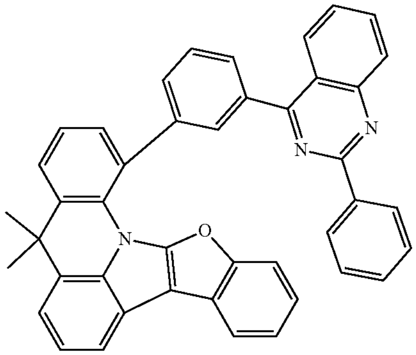

-continued
HAC159
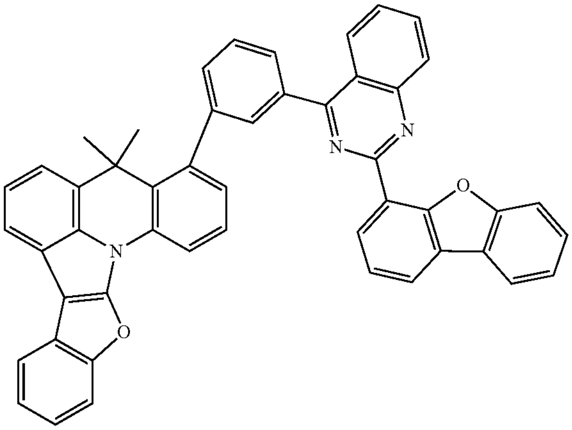
HAC160
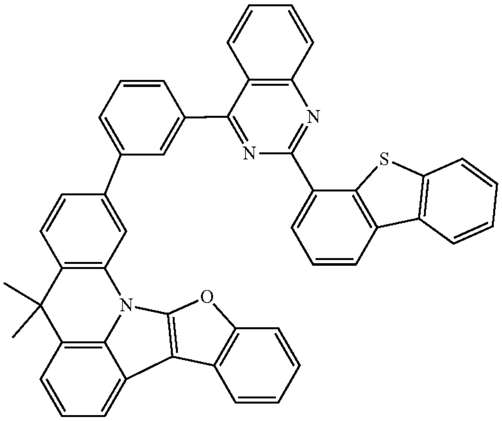
HAC161
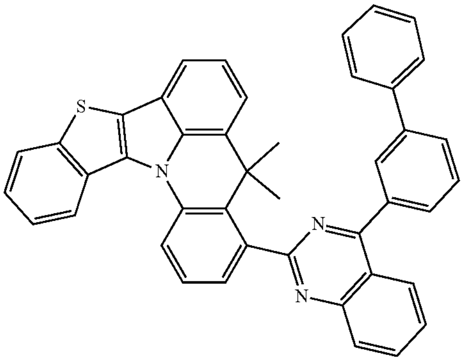
HAC162
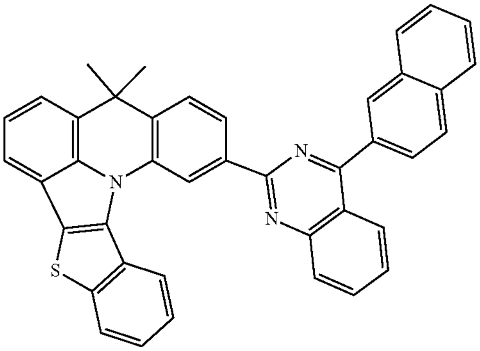
-continued
HAC163
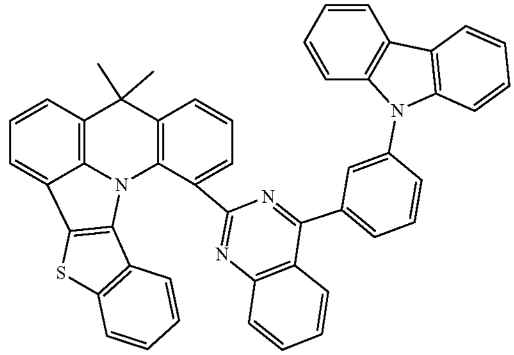
HAC164
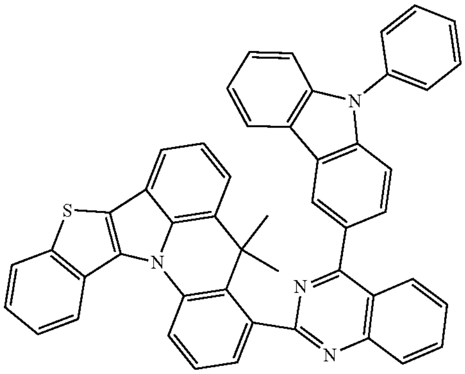
.
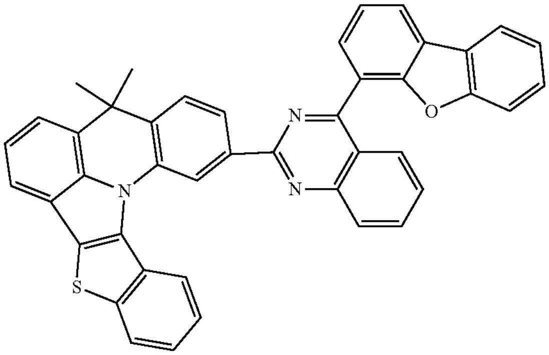
HAC166
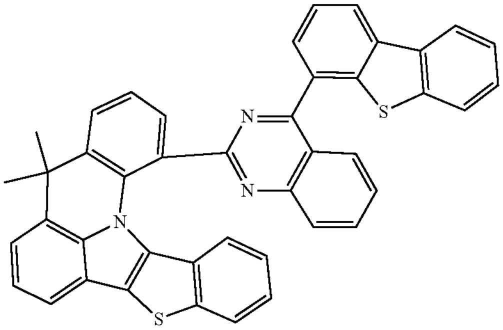

-continued
HAC167
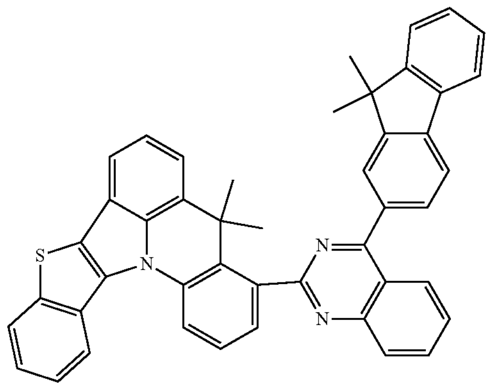
HAC168
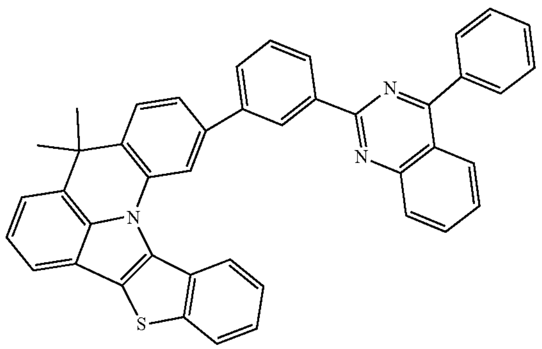
HAC169
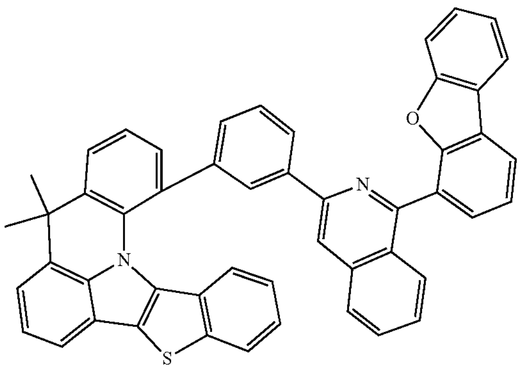
HAC170
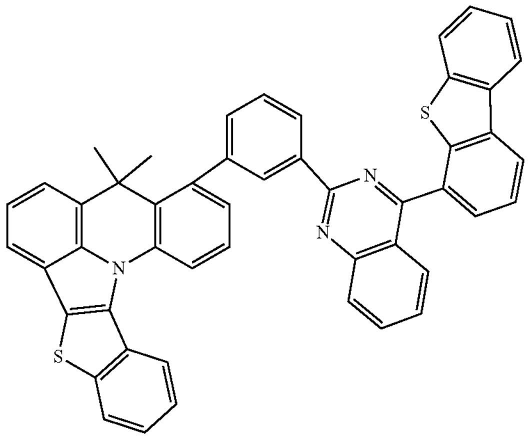
-continued
HAC171
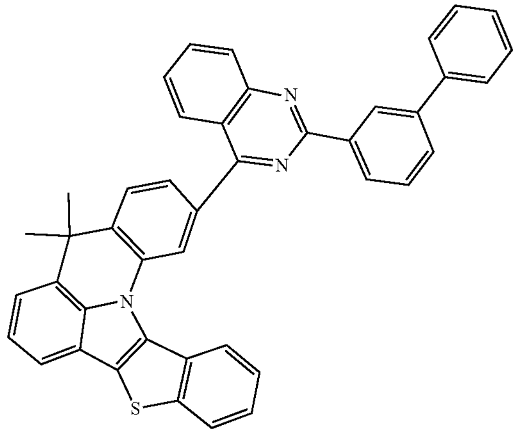
HAC172
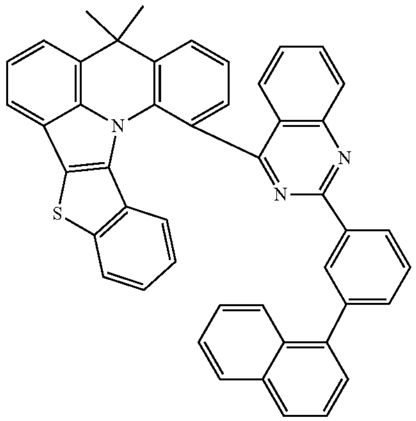
HAC173
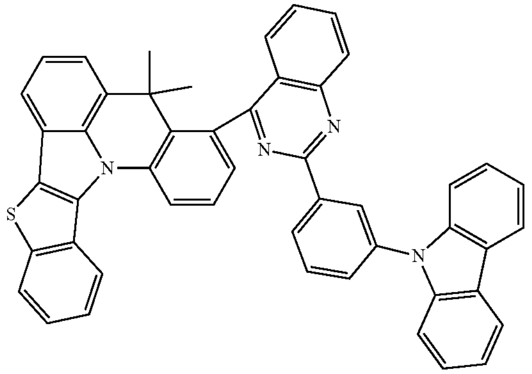

-continued
HAC174
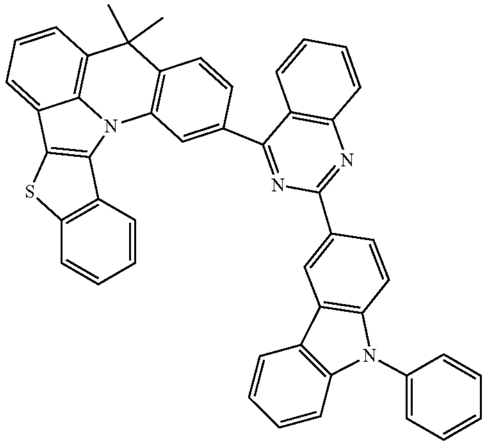
HAC175
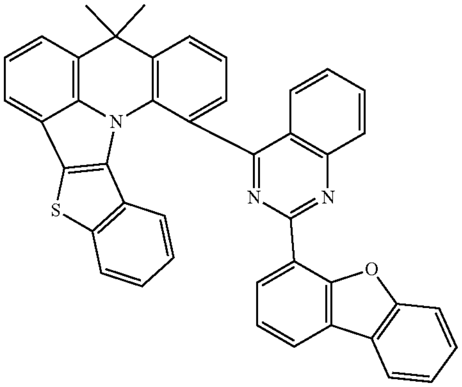
HAC176
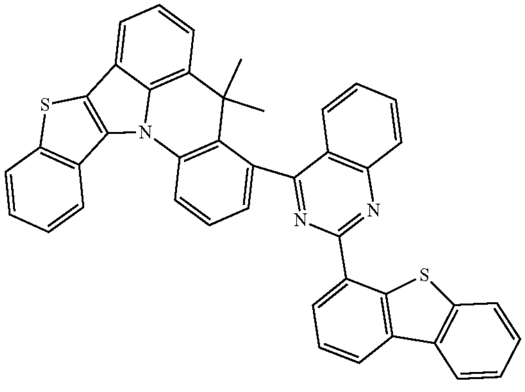
HAC177
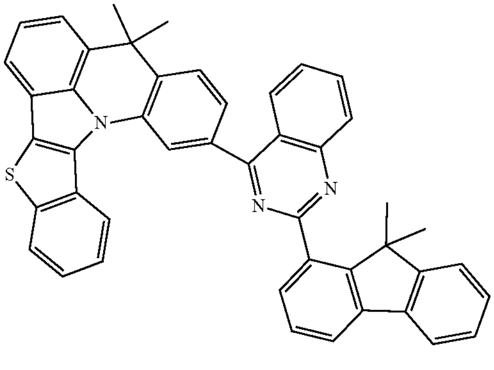
-continued
HAC178
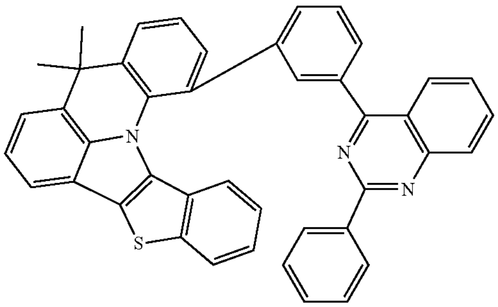
HAC179
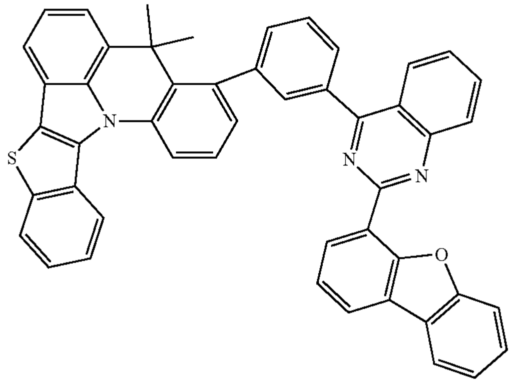
HAC180
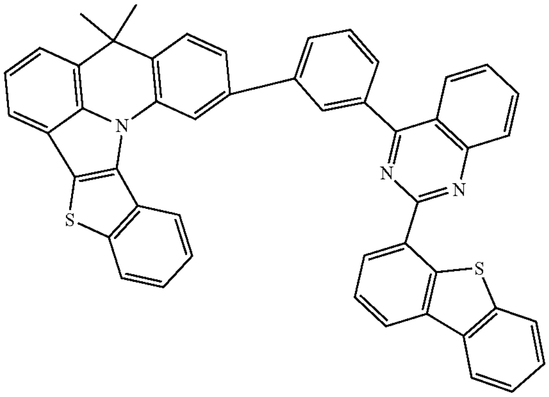
HAC181
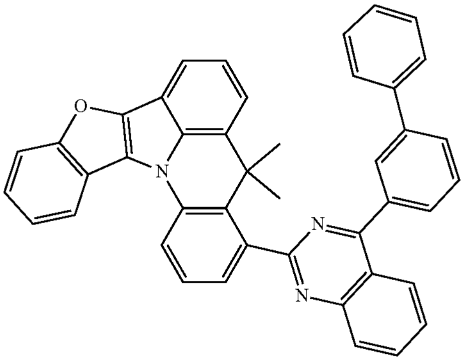

-continued
HAC182
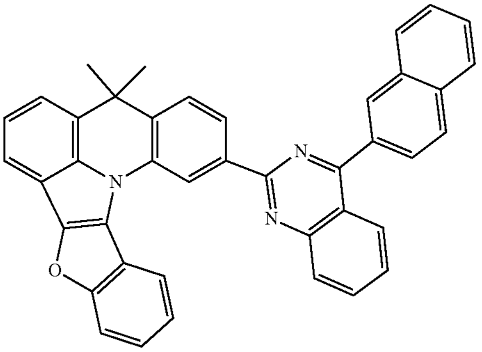
HAC183
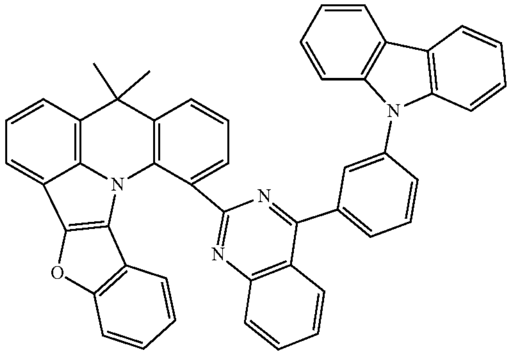
HAC184
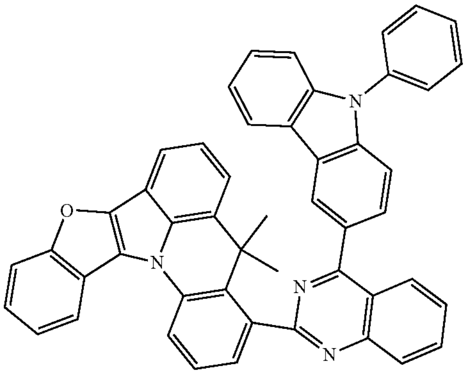
HAC185
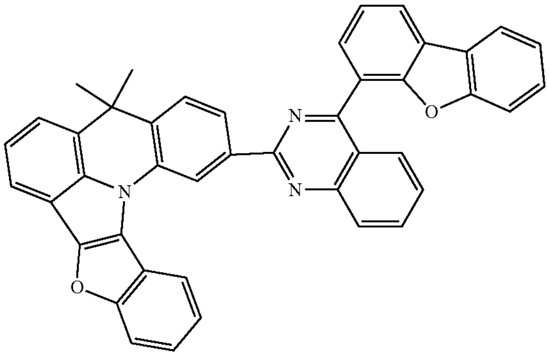
-continued
HAC186
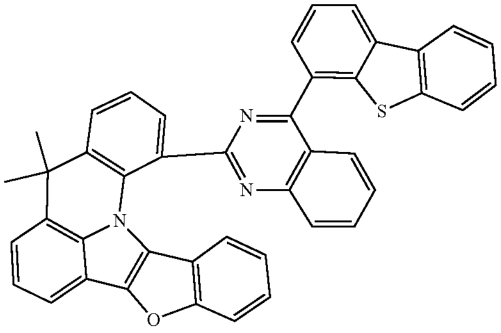
HAC187
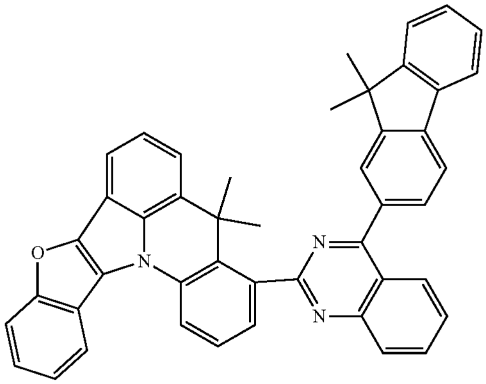
HAC188
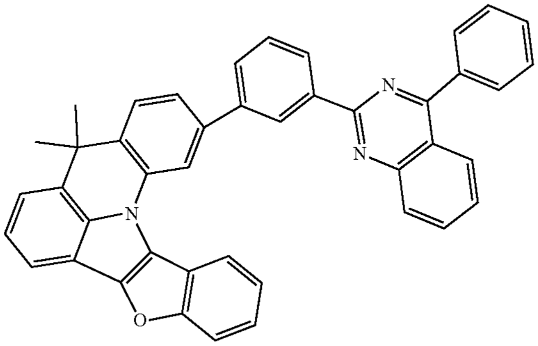
HAC189
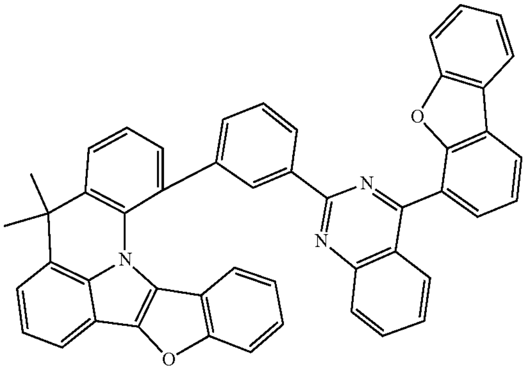

-continued
HAC190
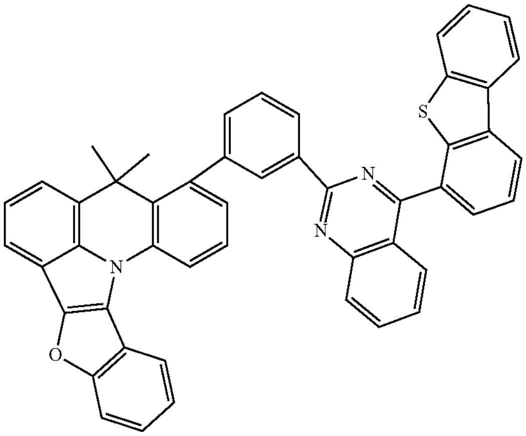
HAC191
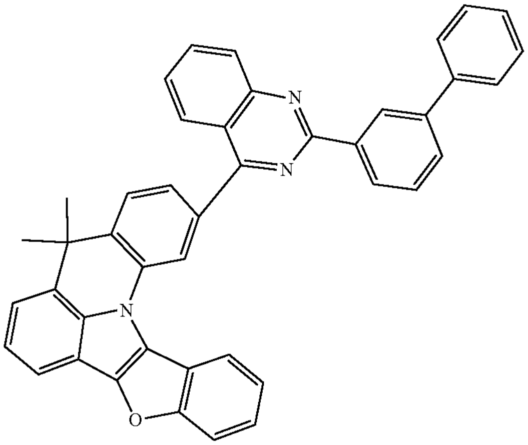
HAC192
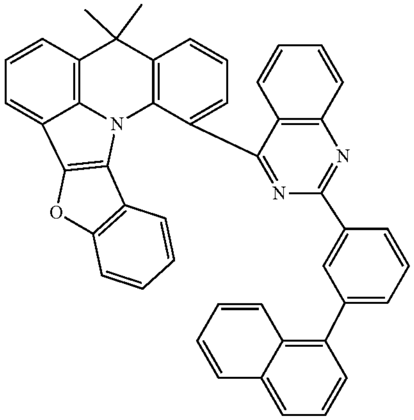
-continued
HAC193
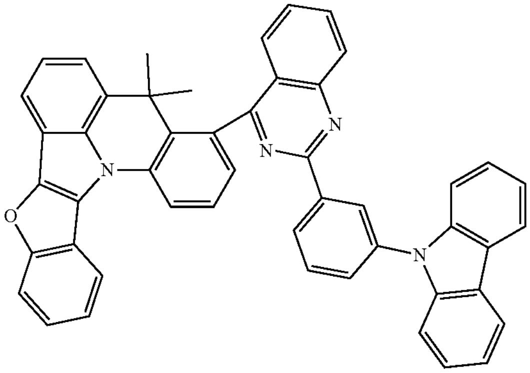
HAC194
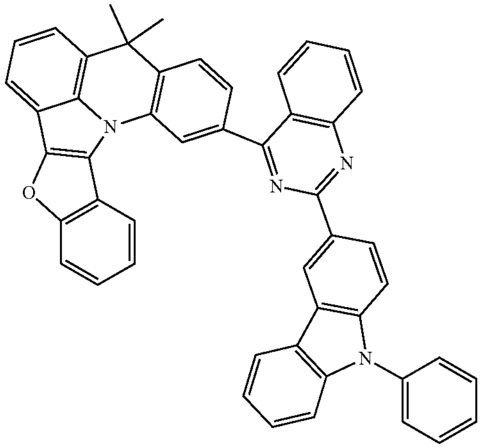
HAC195
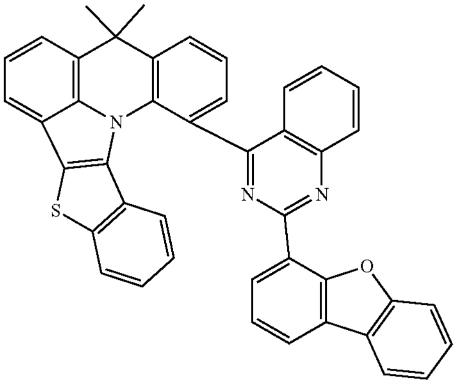

-continued

HAC196

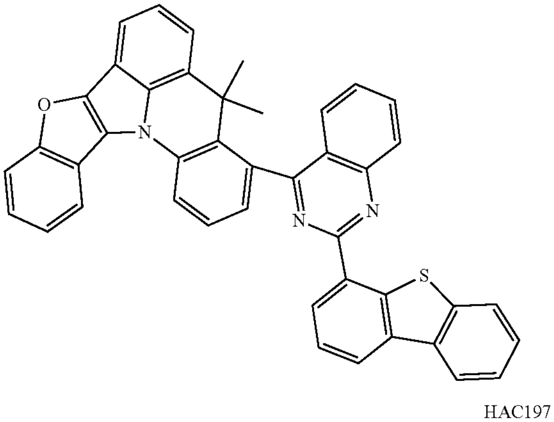

HAC197

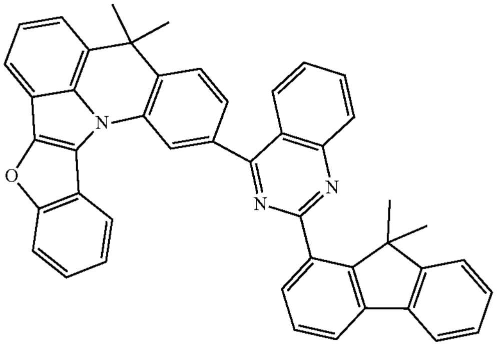

HAC198

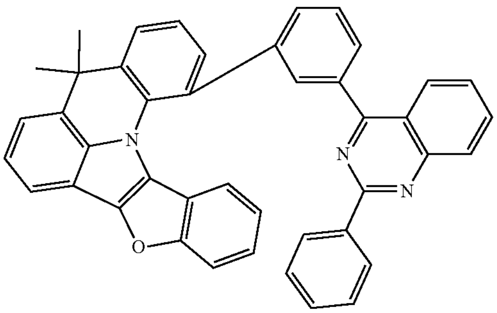

HAC199

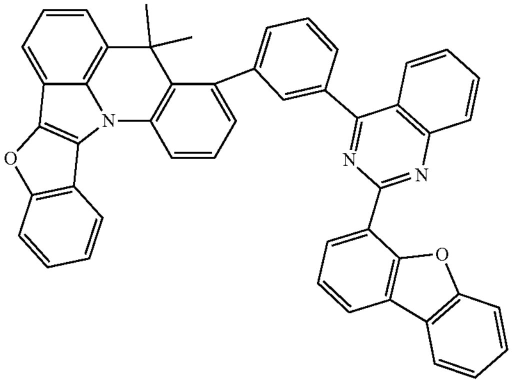

-continued

HAC200

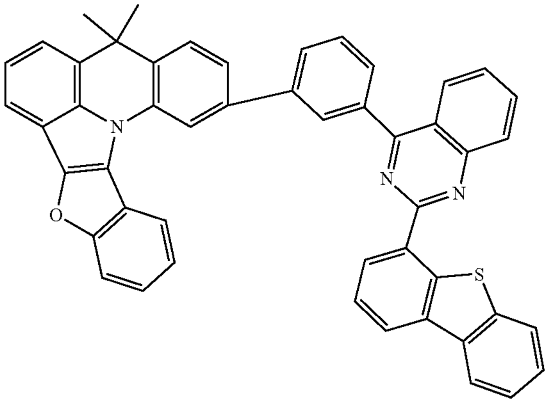

One or more of the hydrogen atoms comprised in HAC1 to HAC200 may be substituted with deuterium or tritium.

An example of manufacturing an organic light emitting element according to embodiments of the present disclosure are described below in detail with reference to embodiments thereof, but embodiments of the present disclosure are not limited to the following embodiments.

Example of Preparing the Compound

The organic compound represented by Chemical Formula 1 may be prepared by preparing the final compound according to synthesis methods below.

1. Synthesis of Intermediate

Reaction Scheme 1

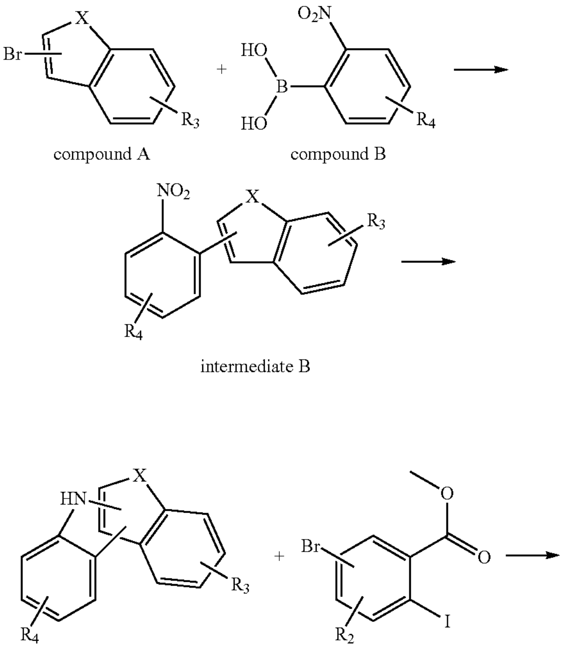

compound A compound B intermediate B intermediate C compound C

-continued

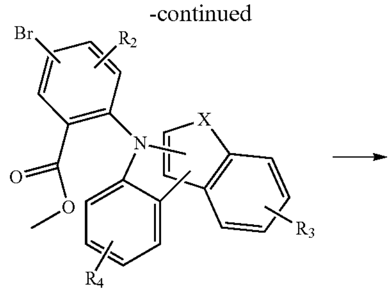

intermediate D

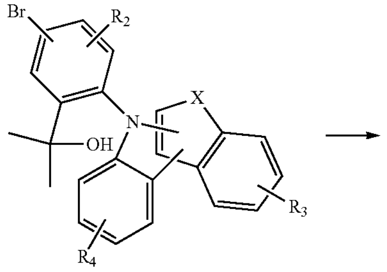

intermediate E

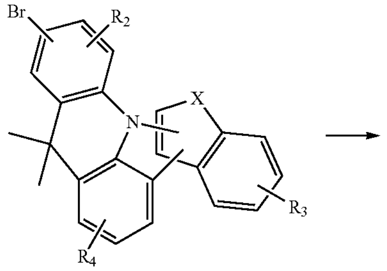

intermediate F

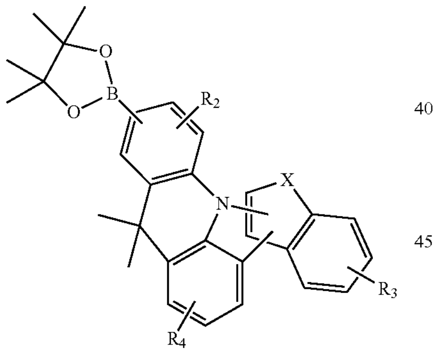

intermediate G (1) Synthesis of Intermediate B

A compound A (1.0 eq.), a compound B (1.2 eq.) Tetrakis (triphenylphosphine)palladium(0) (0.02 eq.), toluene, ethanol, and 4M $K_2CO_3$ (2 eq.) were put into a round-bottom flask and were stirred under reflux for 12 hours. After the reaction was finished, the reaction solution was separated into layers to recover the organic layer, and then filtered through silica gel to remove impurities. The filtered reaction solution was concentrated under reduced pressure to obtain a crude product. The obtained crude material was subjected to column separation, obtaining an intermediate B in a yield of 72%.

(2) Synthesis of Intermediate C

An intermediate B (1 eq), Triphenylphosphine (2.5 eq.), and dichlorobenzene were put into a round-bottom flask and was stirred under reflux for 8 hours. After the reaction was finished, the reaction solution was concentrated under reduced pressure and washed with methanol, obtaining intermediate C in a yield of 61%.

(3) Synthesis of Intermediate D

A compound C (1 eq.), intermediate C (1.1 eq.), Copper (0.2 eq.), $K_2CO_3$ (1.5 eq.), and Nitrobenzene were put in a round-bottom flask and was stirred under reflux for 24 hours. After the reaction is finished, the reaction solution was cooled, washed with EA(Ethyl acetate)/$H_2O$, and the organic layer was recovered by layer separation, and then concentrated under reduced pressure, obtaining a crude material. The obtained crude material was subjected to column separation, obtaining an intermediate D in a yield of 63%.

(4) Synthesis of Intermediate E

An intermediate D (1 eq.) and anhydrous THF were put into a round-bottom flask and was stirred under a nitrogen atmosphere. Methyl magnesium bromide (2.4 eq.) was diluted in 100 ml of anhydrous THF to the reaction solution, slowly added dropwise, and stirred for 6 hours. After the reaction is finished, 10% $NH_4Cl$ aqueous solution was added to the reaction solution, stirred for 1 hour, and then separated by EA to recover the organic layer and distilled under reduced pressure, obtaining an intermediate E in a yield of 70%.

(5) Synthesis of Intermediate F

An intermediate E (1 eq.), hydrochloric acid (1.5 eq.), and acetic acid were put into a round-bottom flask and were stirred, heated under reflux for 2 hours. After the reaction was finished, the reaction solution was poured into distilled water, and then the precipitated crystals were filtered. The filtrate was dissolved in MC (methylene chloride), dried with $MgSO_4$, and reprecipitated using the MC and ethanol, obtaining an intermediate F in a yield of 85%.

(6) Synthesis of Intermediate G

An intermediate F (1 eq.), bis(pinacolato)diboron (1.5 eq.), 1,1'-Bis(diphenylphosphino) ferrocene]dichloropalladium(II) (0.02 eq.), KOAc (potassium acetate) (2 eq.), and 1,4-dioxane were put into a round-bottom flask. The reaction solution was increased in temperature and were stirred under reflux for 12 hours. After the reaction was finished, the reaction solution was cooled to room temperature and filtered with celite filter and then the celite filter was washed with $CHCl_3$(Chloroform). The filtrate was distilled under reduced pressure and was recrystallized with EA, obtaining an intermediate G in a yield of 72%.

2. Synthesis of Product

Reaction Scheme 2

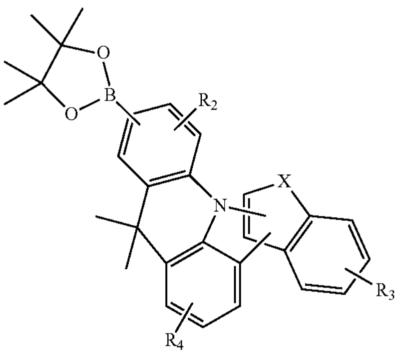

+ intermediate G

-continued

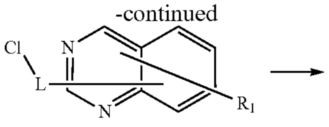

compound H

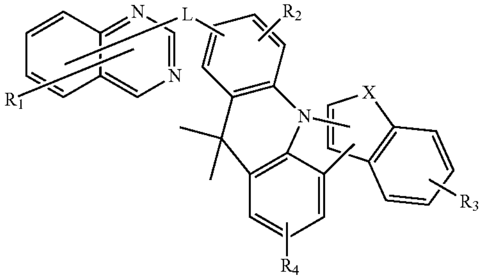

Product

A compound H (halogen compound, 1.0 eq.), intermediate G (1.2 eq.) Tetrakis(triphenylphosphine)palladium(0) (0.02 eq.), and 4M $K_2CO_3$(Potassium carbonate) (2 eq.) were put into a round-bottom flask, and added Toluene and Ethanol as solvent, and then was stirred under reflux for 12 hours. After the reaction was finished, the reaction solution was filtered to obtain a crude material. The obtained crude material was subjected to column separation, obtaining Product in a yield of 70%.

Manufacturing Evaluation of Organic Light Emitting Element

1. Comparison Example 1

An anode, a hole injection layer 50 nm, a hole transport layer 1000 nm, a light emitting layer 250 nm, an electron transport layer 300 nm, an electron injection layer 20 nm, and a cathode 1000 nm were formed on a substrate to manufacture an organic light emitting element having a mono structure as shown in Table 1 below. All the properties of the organic light emitting element manufactured in the disclosure were evaluated at room temperature using a constant current source and a photometer.

TABLE 1

| Components | Materials |
|---|---|
| anode | ITO (Indium tin oxide) |
| hole injection layer | HI1 |
| hole transport layer | HT1 |
| light emitting layer | EM1, EM2, EM3 (EM1:EM2 = 5:5, EM3 = 3 wt %) |

TABLE 1-continued

| Components | Materials |
|---|---|
| electron transport layer | ET1 |
| electron injection layer | LiF |
| cathode | Al |

The compounds used in the comparative example 1 are as follows.

HI1

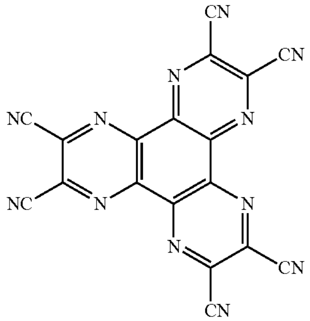

HT1

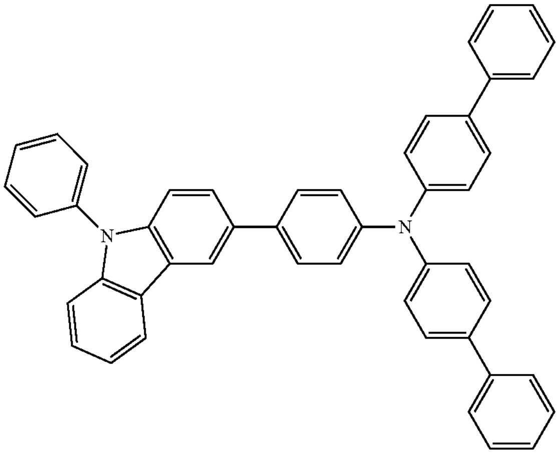

EM1

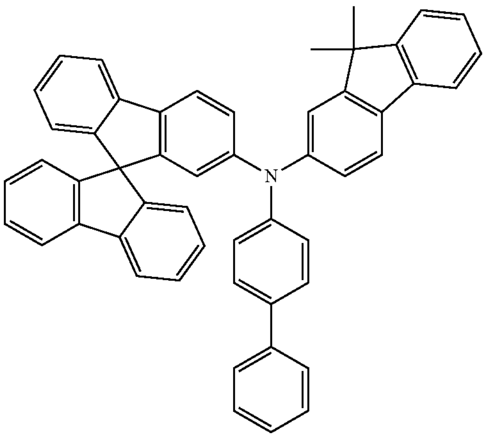

-continued

EM2

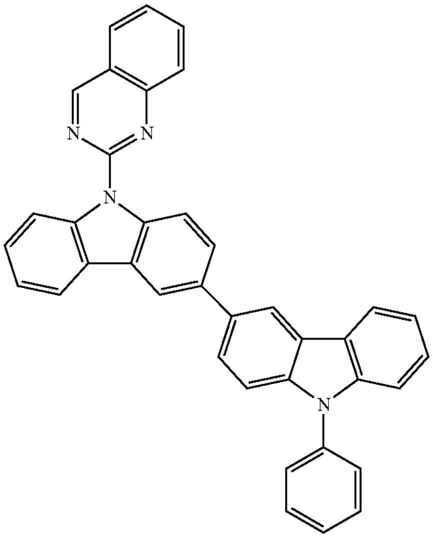

EM3

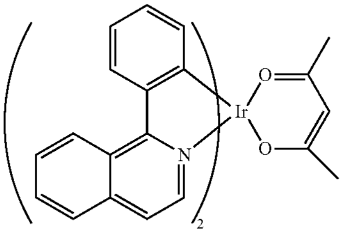

ET1

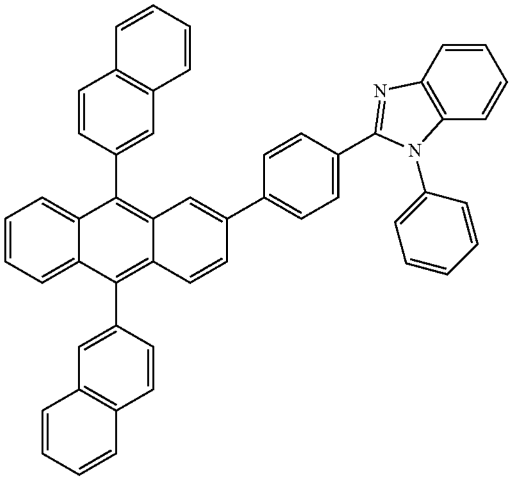

2. Embodiments 1 to 29

The organic light emitting element was manufactured in the same manner as in comparative example 1 except that the materials shown in Table 2 below were used instead of EM2 of the light emitting layer.

TABLE 2

| | light emitting layer material | voltage difference (ΔV) | efficiency (embodiment/ comparative example 1, %) | lifespan (embodiment/ comparative example 1, %) |
|---|---|---|---|---|
| comparative example 1 | EM2 | — | — | — |
| embodiment 1 | HAC1 | −0.13 | 109% | 123% |
| embodiment 2 | HAC2 | −0.13 | 106% | 119% |
| embodiment 3 | HAC4 | −0.13 | 104% | 117% |
| embodiment 4 | HAC8 | −0.14 | 104% | 116% |
| embodiment 5 | HAC9 | −0.14 | 111% | 124% |
| embodiment 6 | HAC10 | −0.13 | 108% | 121% |
| embodiment 7 | HAC11 | −0.15 | 112% | 126% |
| embodiment 8 | HAC12 | −0.15 | 121% | 127% |
| embodiment 9 | HAC31 | −0.14 | 111% | 102% |
| embodiment 10 | HAC32 | −0.15 | 110% | 124% |
| embodiment 11 | HAC33 | −0.15 | 110% | 123% |
| embodiment 12 | HAC38 | −0.14 | 104% | 117% |
| embodiment 13 | HAC39 | −0.13 | 112% | 125% |
| embodiment 14 | HAC40 | −0.13 | 112% | 126% |
| embodiment 15 | HAC42 | −0.17 | 128% | 133% |
| embodiment 16 | HAC44 | −0.17 | 123% | 135% |
| embodiment 17 | HAC61 | −0.12 | 102% | 103% |
| embodiment 18 | HAC62 | −0.12 | 104% | 102% |
| embodiment 19 | HAC67 | −0.12 | 104% | 110% |
| embodiment 20 | HAC69 | −0.12 | 101% | 107% |
| embodiment 21 | HAC72 | −0.12 | 118% | 110% |
| embodiment 22 | HAC87 | −0.10 | 106% | 119% |
| embodiment 23 | HAC89 | −0.10 | 104% | 109% |
| embodiment 24 | HAC91 | −0.14 | 106% | 111% |
| embodiment 25 | HAC92 | −0.14 | 106% | 111% |
| embodiment 26 | HAC99 | −0.14 | 103% | 116% |
| embodiment 27 | HAC101 | −0.14 | 102% | 114% |
| embodiment 28 | HAC102 | −0.14 | 123% | 117% |
| embodiment 29 | HAC117 | −0.11 | 107% | 107% |

Referring to Table 2, it may be seen that the organic light emitting devices comprising a first layer comprising the organic compound according to the embodiments of the present disclosure have better efficiency or lifespan than the organic light emitting element of the comparative example 1.

In Comparative Example 1, a biscarbazole-based compound having the quinazoline as a substituent was used as a host compound for the emission layer. On the other side, the organic compounds used in the embodiments of the present disclosure include the quinazoline applied to the compound of Comparative Example 1 as the substituent, but the organic compounds according to the embodiments of the present disclosure include a core having a structure that is completely different from the comparative example 1 of the biscarbazole-based core.

The organic compounds according to the embodiments of the present disclosure use the quinazoline applied in Comparative Example 1 as the substituent, but the organic compounds include a core having a structure that is completely different from the biscarbazole-based core. Therefore, in the embodiments of the present disclosure, the driving voltage was lowered by up to 0.17V, the efficiency was improved by up to 128%, and the lifespan by up to 135% was improved as compared to Comparative Example 1.

When the organic compound represented by Chemical Formula 1 of the present disclosure is applied to the light emitting layer of the organic light emitting device, it is possible to provide an organic light emitting device having low driving voltage and high efficiency and long lifespan without affecting the light emitting characteristics of the device.

The above description has been presented to enable any person skilled in the art to make and use the technical idea of the present disclosure, and has been provided in the context of a particular application and its requirements. Various modifications, additions and substitutions to the described embodiments will be readily apparent to those skilled in the art, and the general principles defined herein may be applied to other embodiments and applications without departing from the spirit and scope of the present disclosure. The above description and the accompanying drawings provide an example of the technical idea of the present disclosure for illustrative purposes only. That is, the disclosed embodiments are intended to illustrate the scope of the technical idea of the present disclosure. Thus, the scope of the present disclosure is not limited to the embodiments shown, but is to be accorded the widest scope consistent with the claims. The scope of protection of the present disclosure should be construed based on the following claims, and all technical ideas within the scope of equivalents thereof should be construed as being comprised within the scope of the present disclosure.

What is claimed is:

1. An organic compound represented by the following Chemical Formula 1:

[Chemical Formula 1]

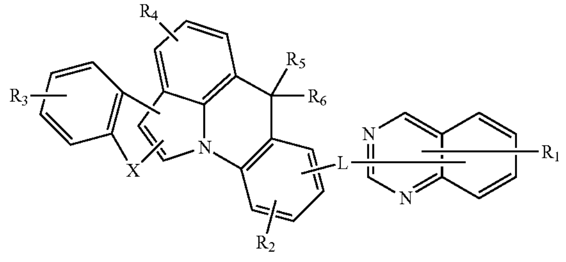

wherein in Chemical Formula 1,

X is O or S, $R_1$ to $R_6$ are each independently selected from the group consisting of a hydrogen; a halogen; a cyano group; a nitro group; a $C_6$-$C_{60}$ aryl group; a fluorenyl group; a $C_2$-$C_{60}$ heterocyclic group containing at least one heteroatom selected from the group consisting of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group, L is selected from the group consisting of a single bond; a $C_6$-$C_{60}$ arylene group; a fluorenylene group; a $C_2$-$C_{60}$ heterocyclic group containing at least one heteroatom selected from the group consisting of O, N, S, Si, and P; and a fused ring group of a $C_3$-$C_{60}$ aliphatic ring and a $C_6$-$C_{60}$ aromatic ring, and the aryl group, the fluorenyl group, the heterocyclic group, the fused ring group, the alkyl group, the alkenyl group, the alkynyl group, the alkoxy group, the aryloxy group, the arylene group and the fluorenylene group may each be further substituted with one or more substituents selected from the group consisting of a nitro group; a cyano group; a halogen; an amino group; a $C_1$-$C_{20}$ alkoxyl group; a $C_1$-$C_{20}$ alkylthio group; a $C_1$-$C_{20}$ alkyl group; a $C_2$-$C_{20}$ alkenyl group; a $C_2$-$C_{20}$ alkynyl group; a $C_6$-$C_{20}$ aryl group; a fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group.

2. The organic compound according to claim 1, wherein the organic compound represented by the Chemical Formula 1 is represented by any one of the following Chemical Formulas 2-1 to 2-4:

[Chemical Formula 2-1]

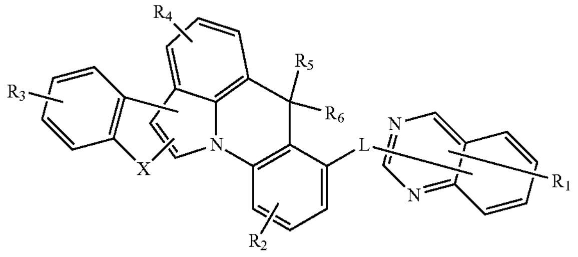

[Chemical Formula 2-2]

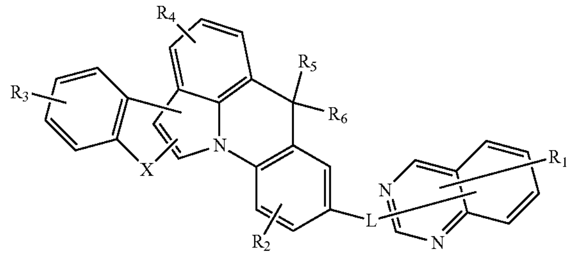

[Chemical Formula 2-3]

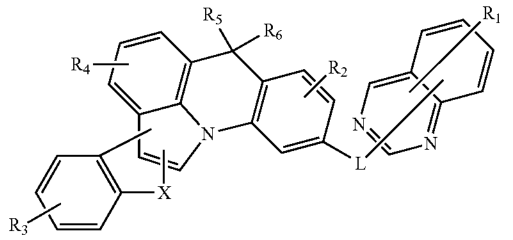

[Chemical Formula 2-4]

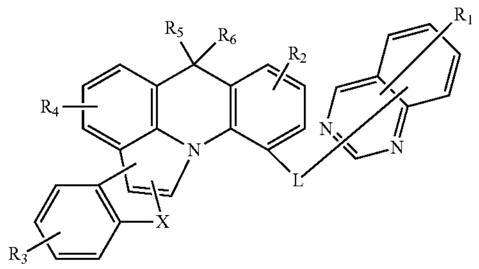

wherein in Chemical Formulas 2-1 to 2-4, X, $R_1$ to $R_6$, and L are the same as defined in Chemical Formula 1.

3. The organic compound according to claim 1, wherein the organic compound represented by the Chemical Formula 1 is represented by any one of the following Chemical Formulas 3-1 to 3-8:

[Chemical Formula 3-1]

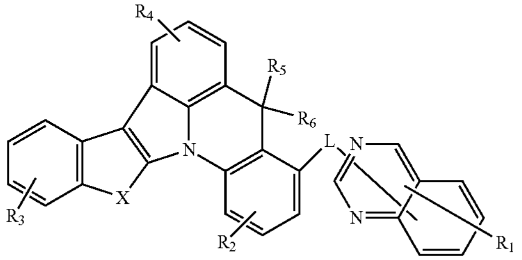

[Chemical Formula 3-2]

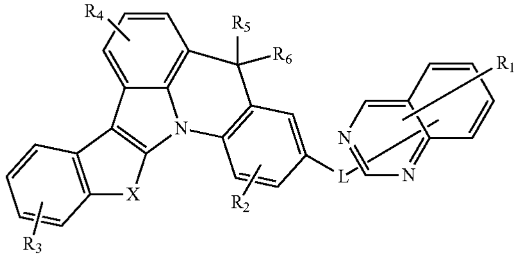

[Chemical Formula 3-3]

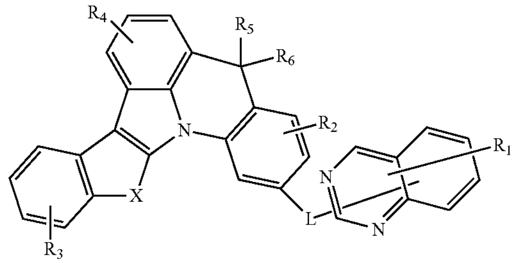

[Chemical Formula 3-4]

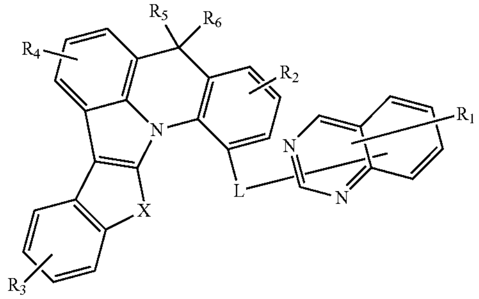

[Chemical Formula 3-5]

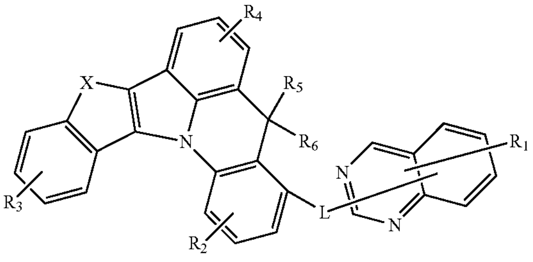

-continued

[Chemical Formula 3-6]

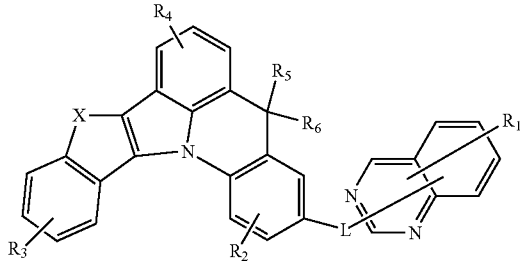

[Chemical Formula 3-7]

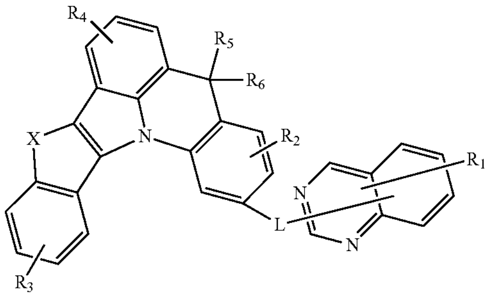

[Chemical Formula 3-8]

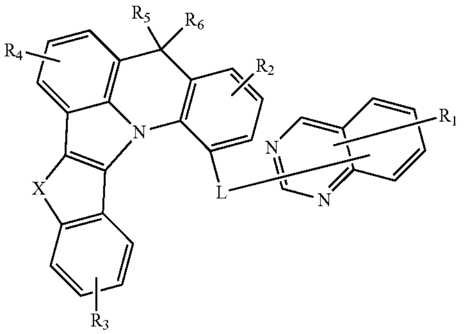

wherein in Chemical Formulas 3-1 to 3-8, X, $R_1$ to $R_6$, and L are the same as defined in Chemical Formula 1.

4. The organic compound according to claim 1, wherein the organic compound represented by the Chemical Formula 1 is one or more of the following organic compounds:

HAC1

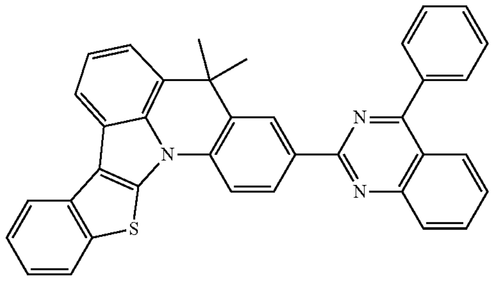

-continued
HAC2
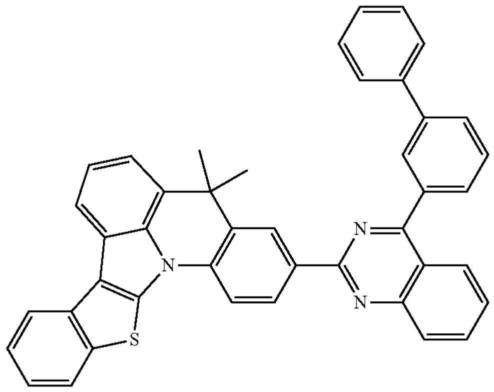
HAC3
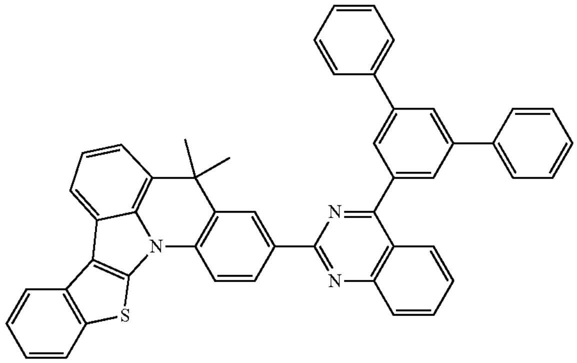
HAC4
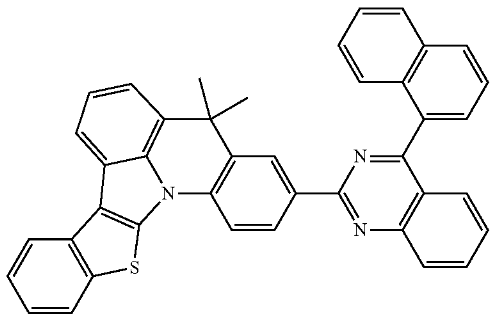
HAC5
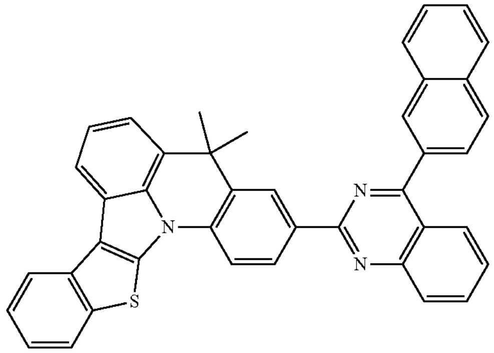
-continued
HAC6
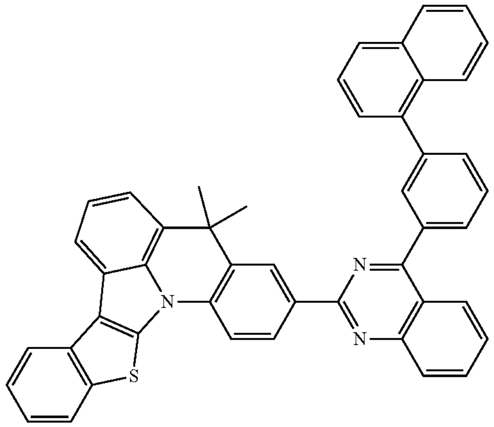
HAC7
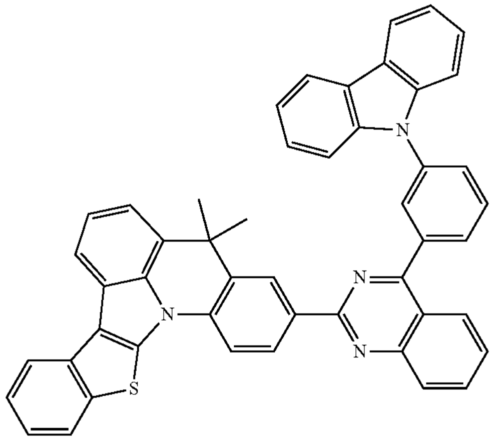
HAC8
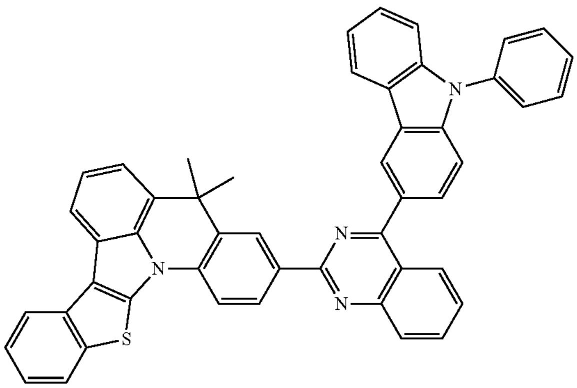

-continued
HAC9
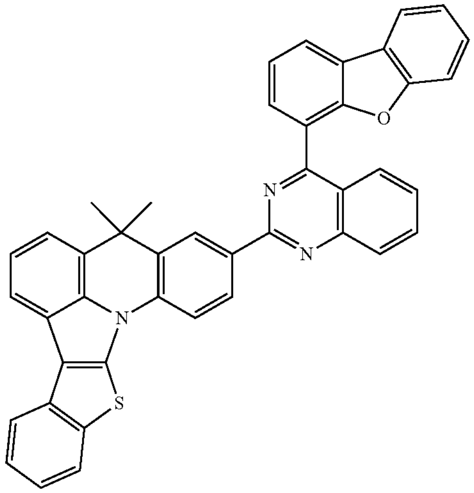
HAC10
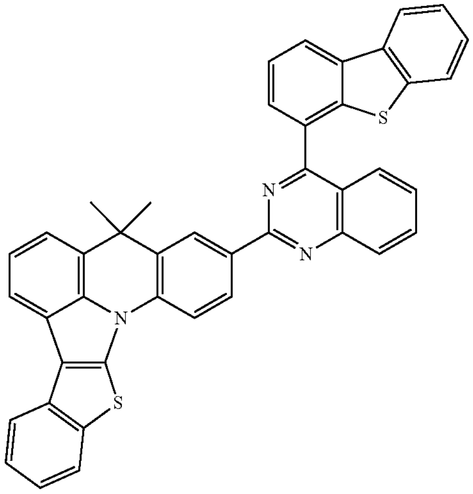
HAC11
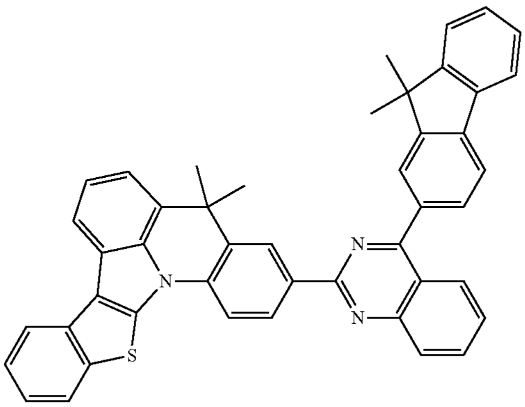
-continued
HAC12
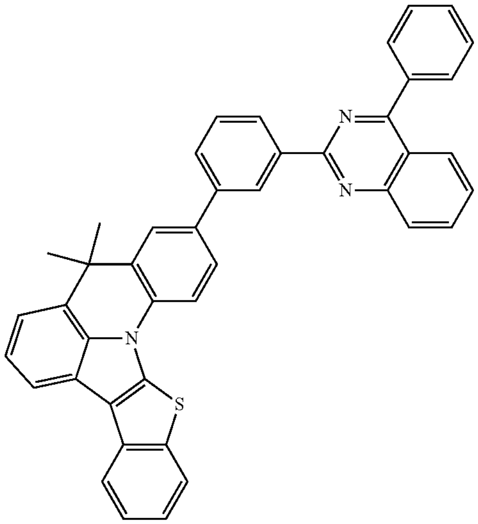
HAC13
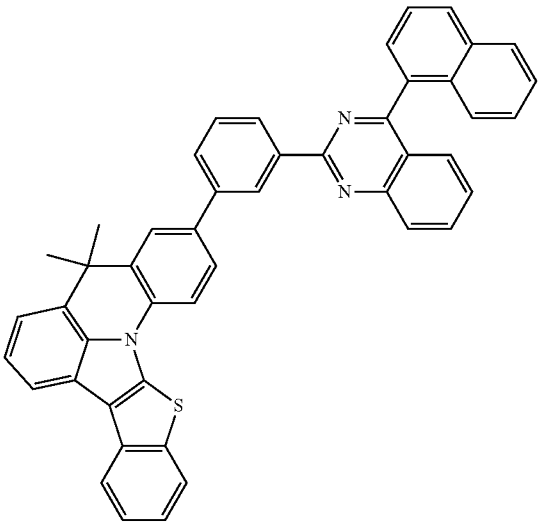
HAC14
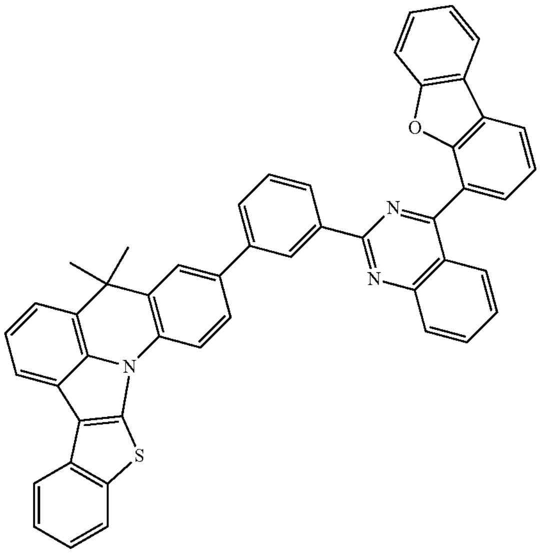

-continued
HAC15
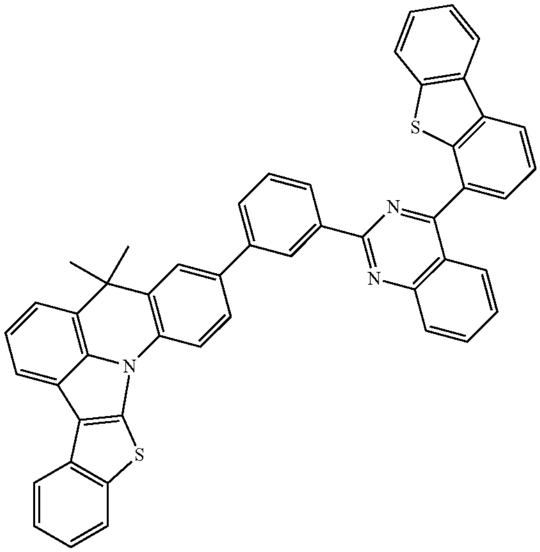
HAC16
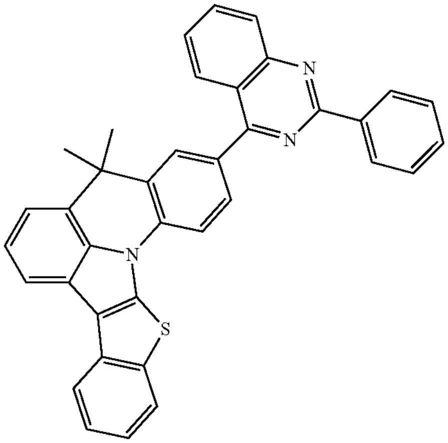
HAC17
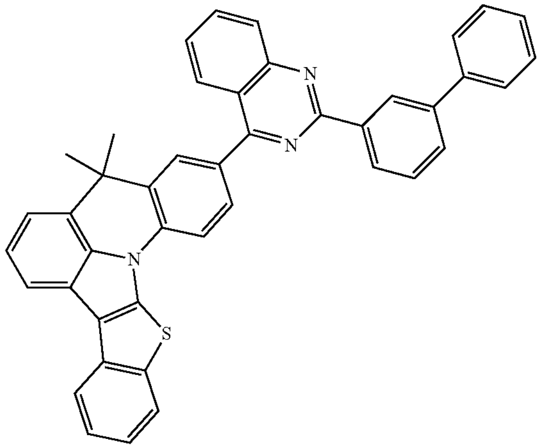
-continued
HAC18
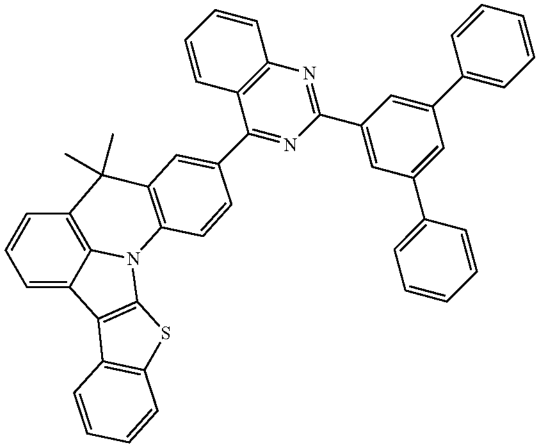
HAC19
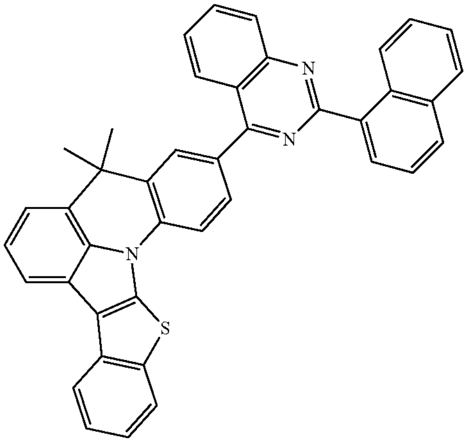
HAC20
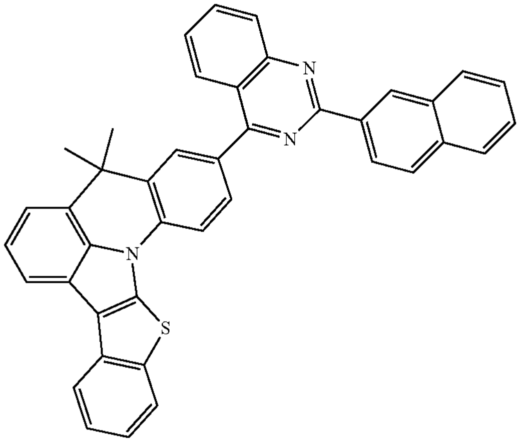

-continued
HAC21
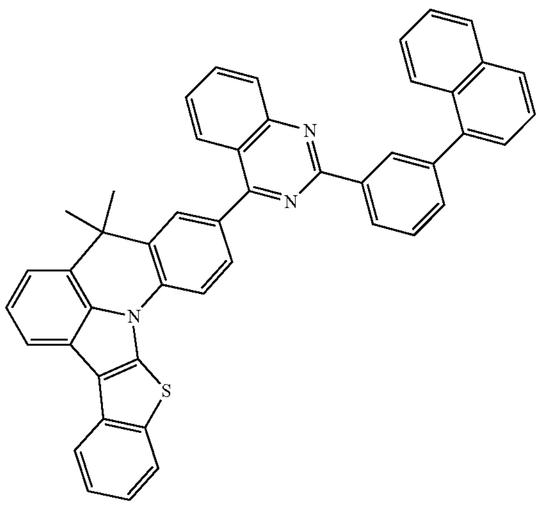
HAC22
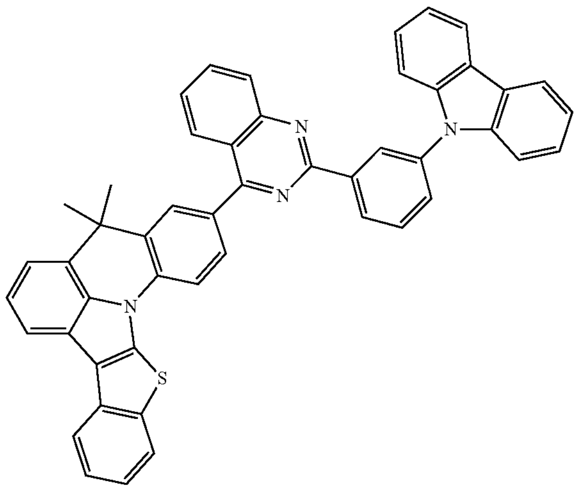
HAC23
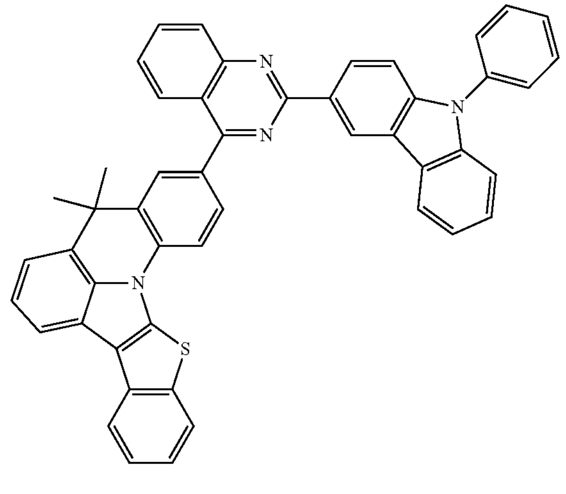
-continued
HAC24
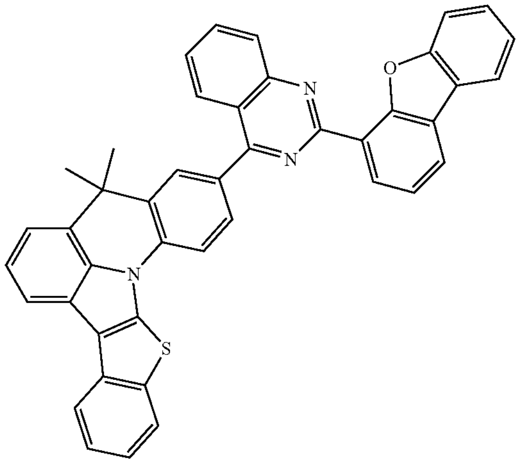
HAC25
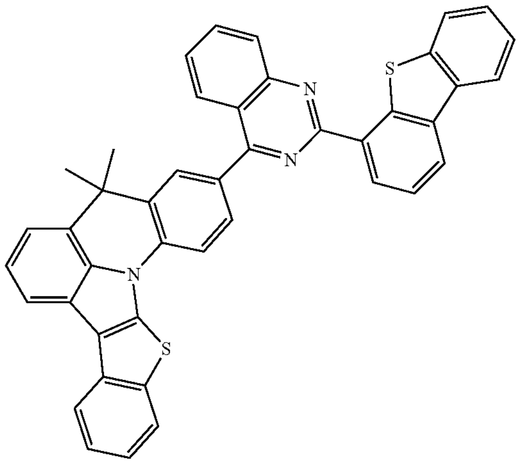
HAC26
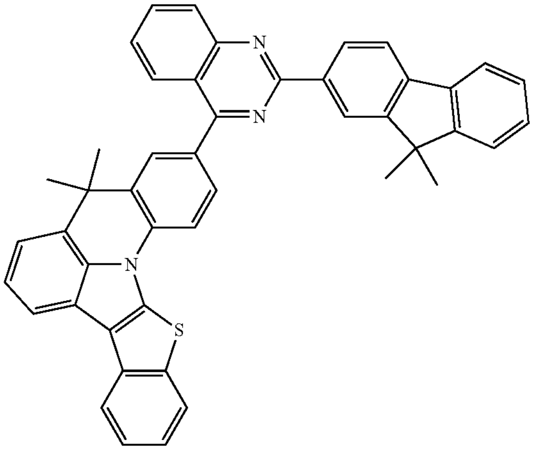

-continued
HAC27
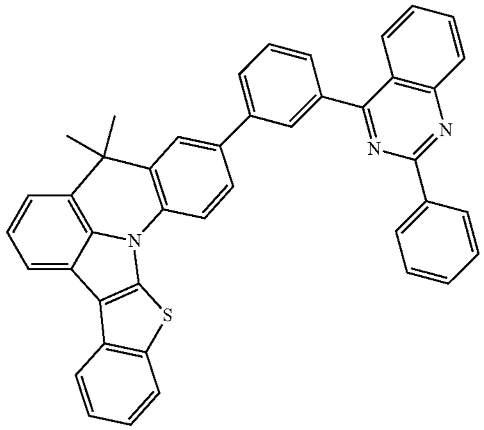
HAC28
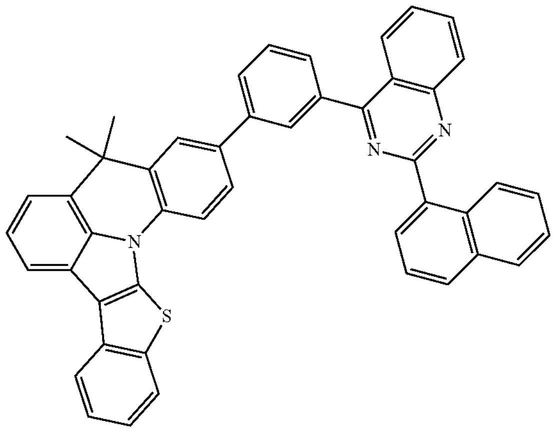
HAC29
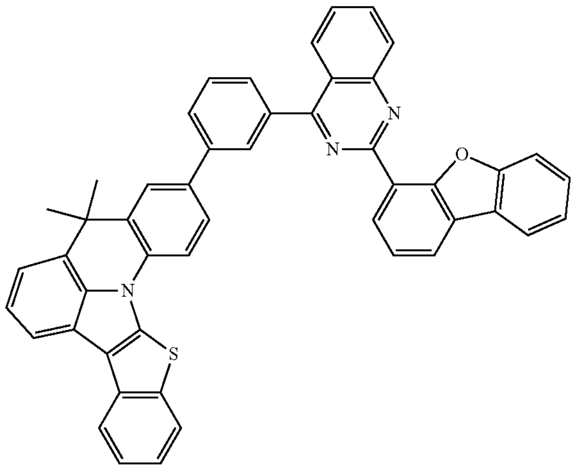
-continued
HAC30
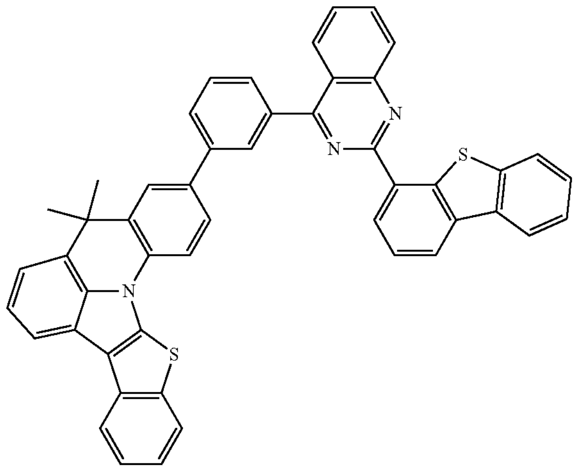
HAC31
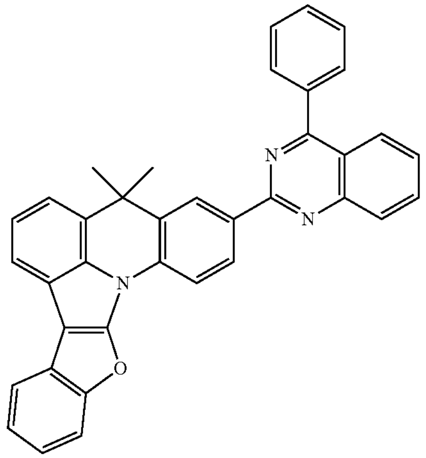
HAC32
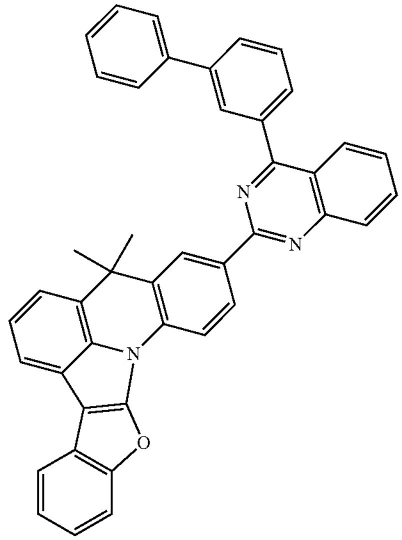

-continued
HAC33
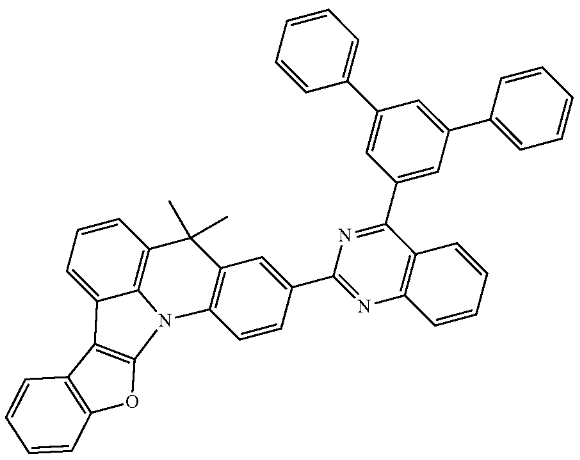
HAC34
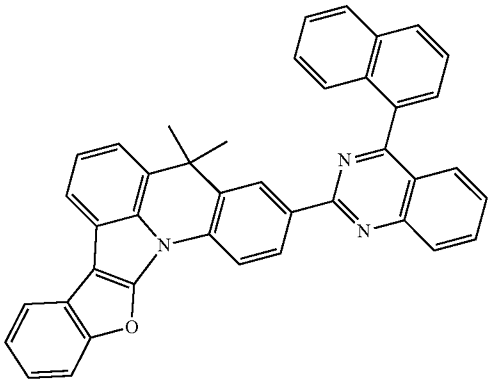
HAC35
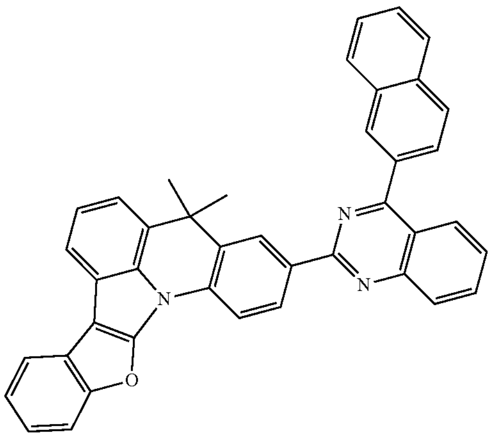
-continued
HAC36
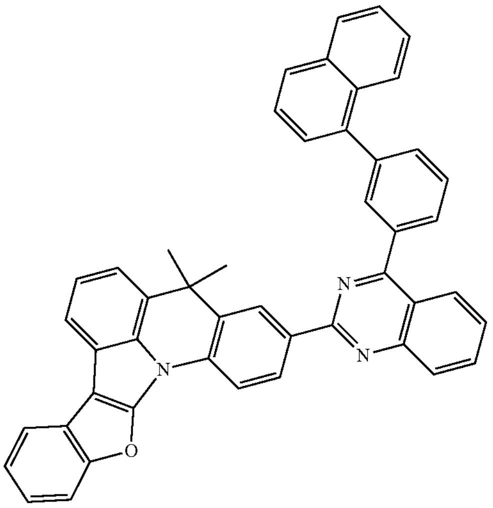
HAC37
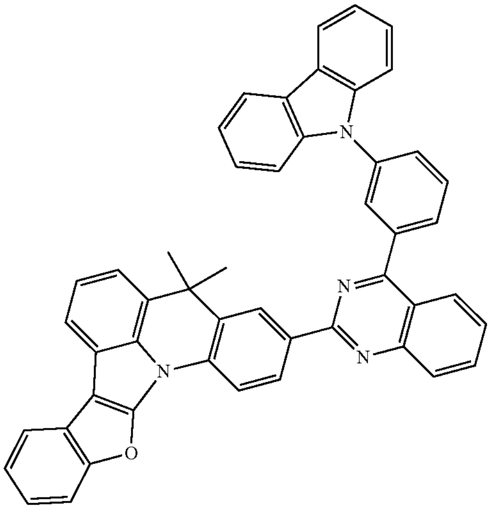
HAC38
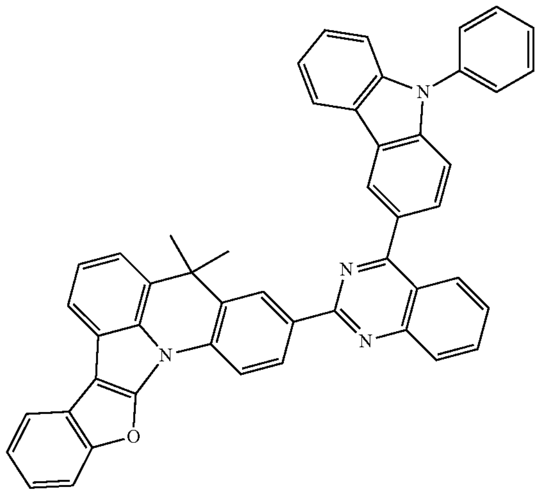

-continued
HAC39
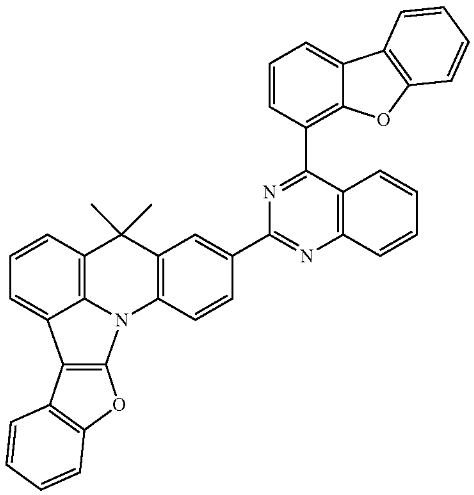
HAC40
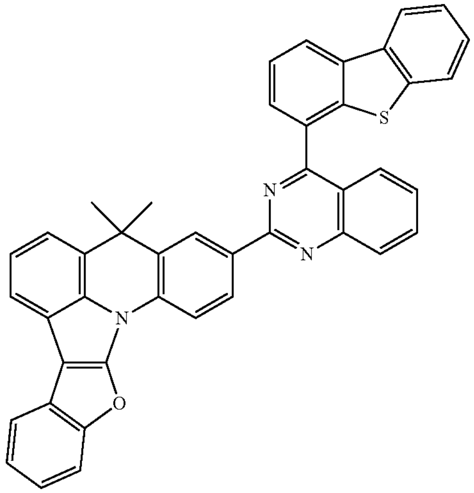
HAC41
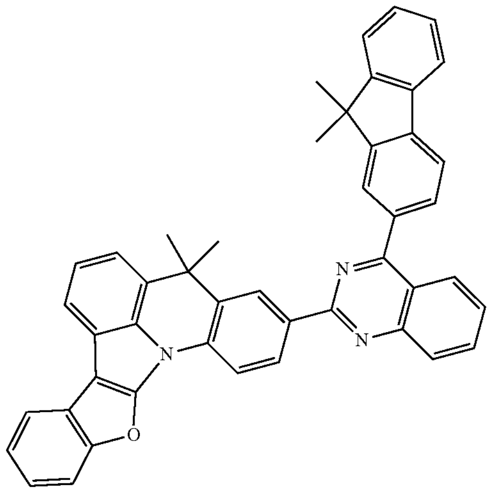
-continued
HAC42
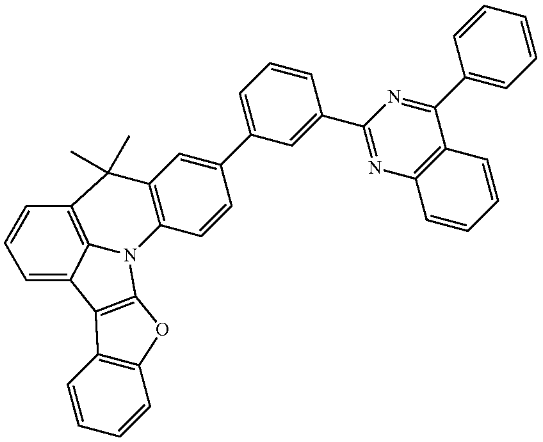
HAC43
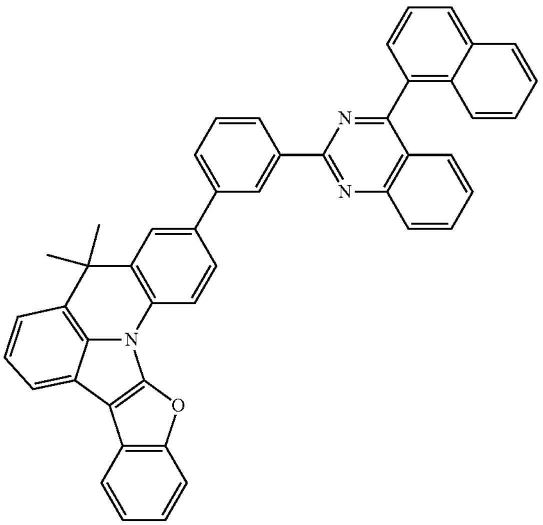
HAC44
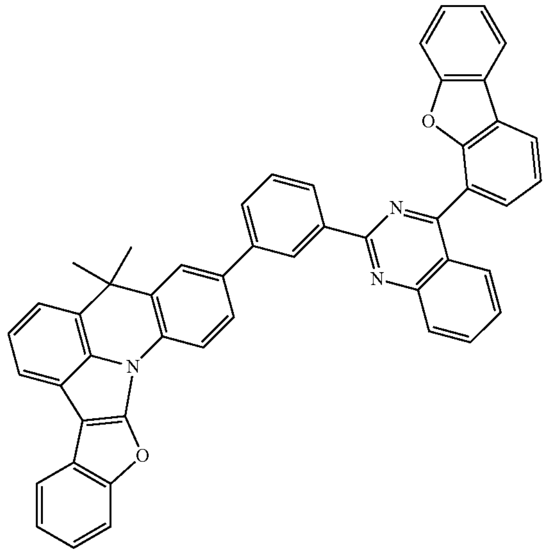

HAC45
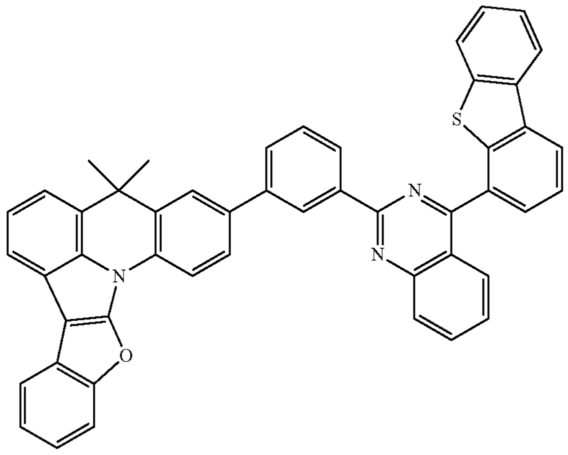
HAC46
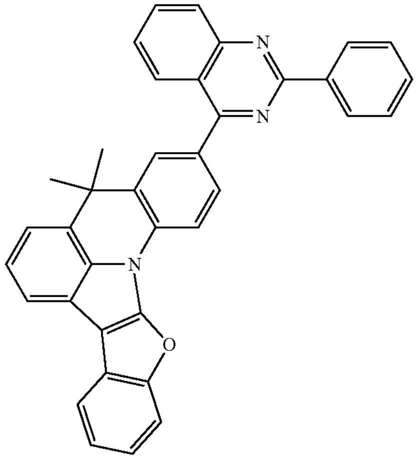
HAC47
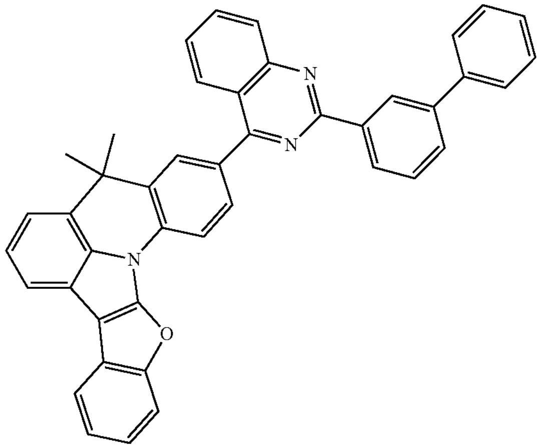
HAC48
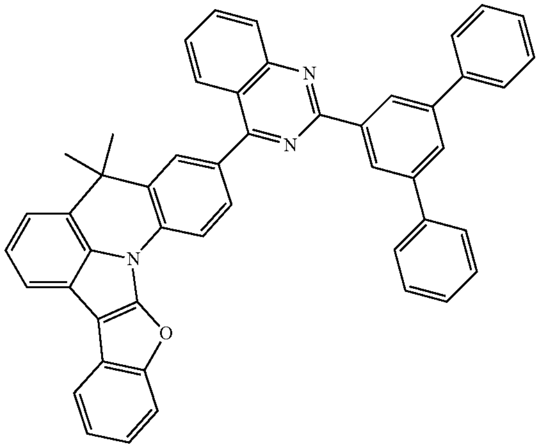
HAC49
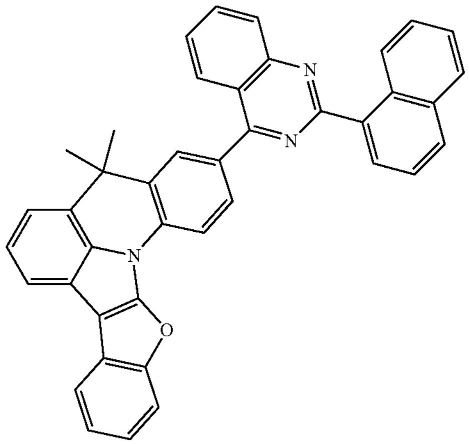
HAC50
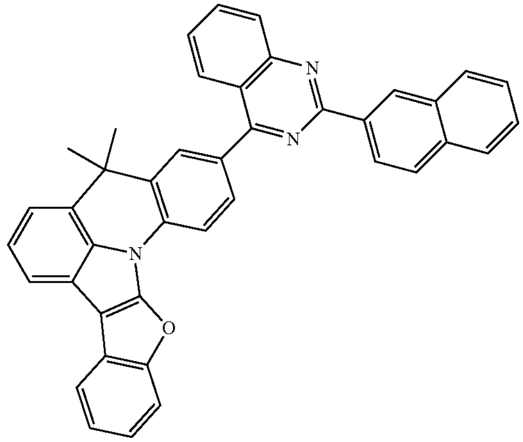

-continued
HAC51
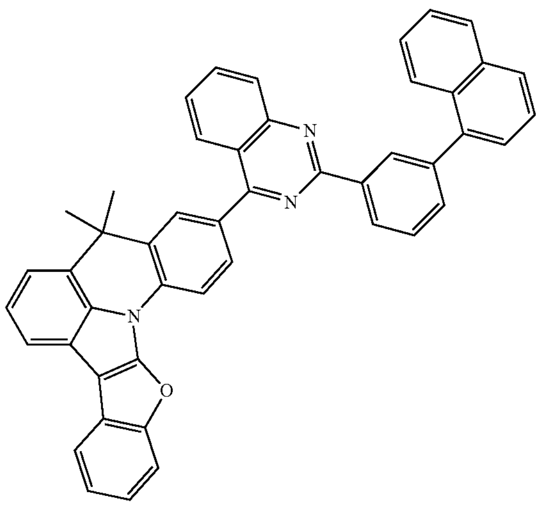
HAC52
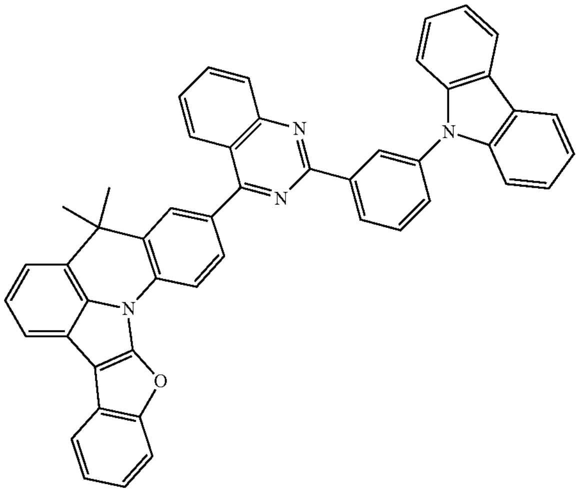
HAC53
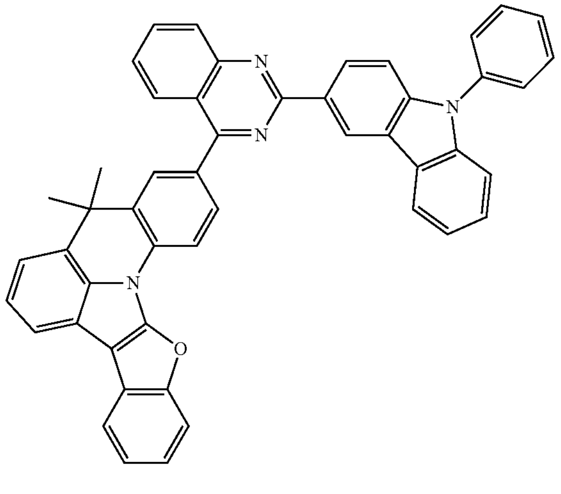
-continued
HAC54
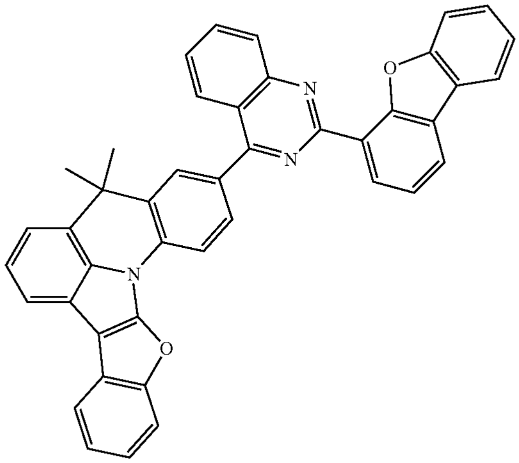
HAC55
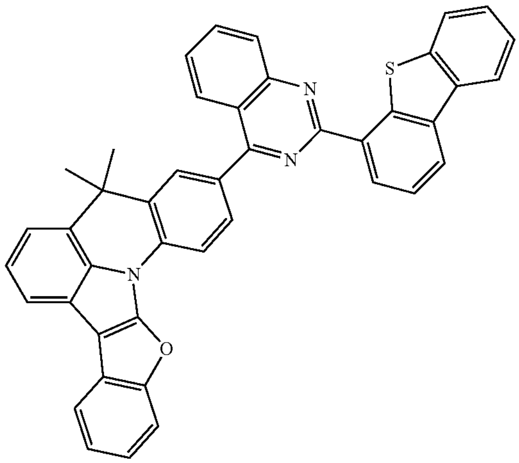
HAC56
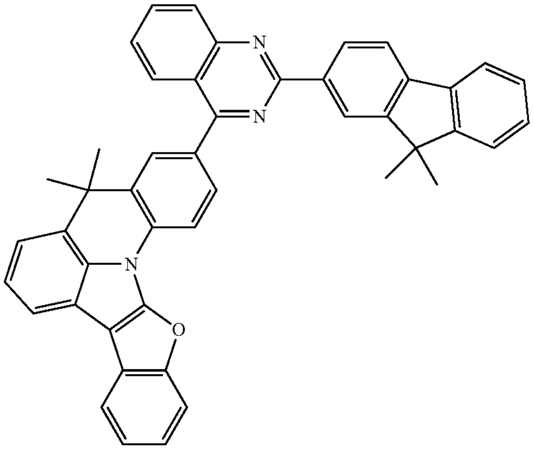

-continued
HAC57
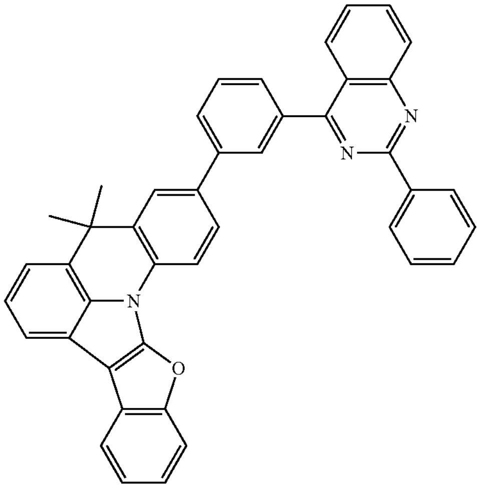
HAC58
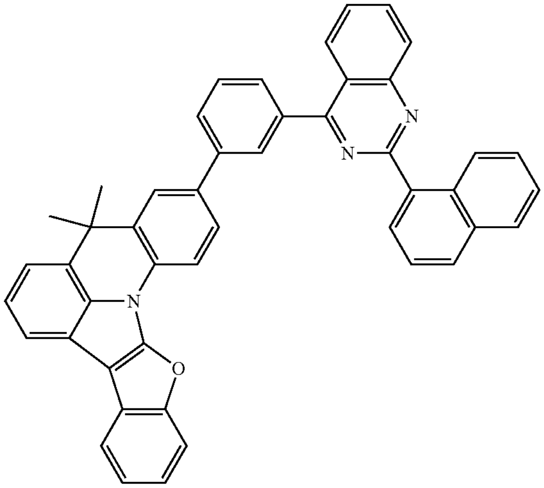
HAC59
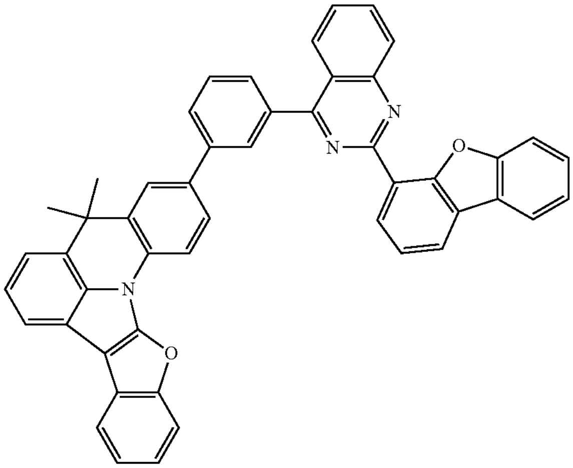
-continued
HAC60
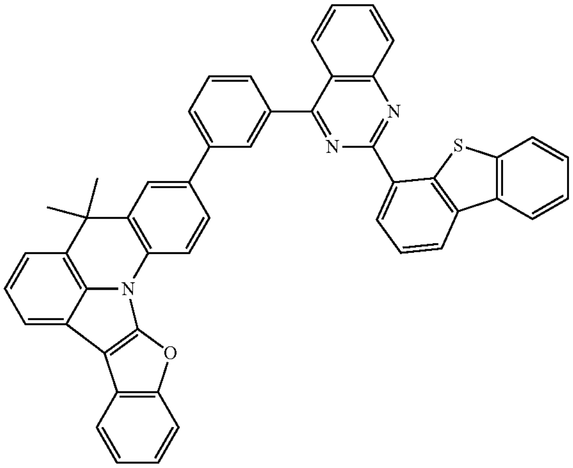
HAC61
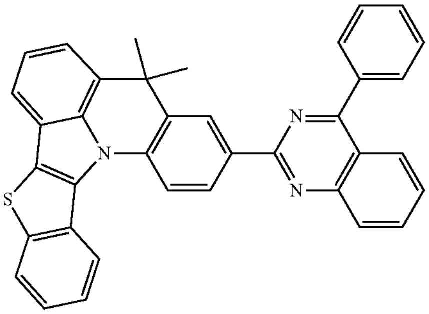
HAC62
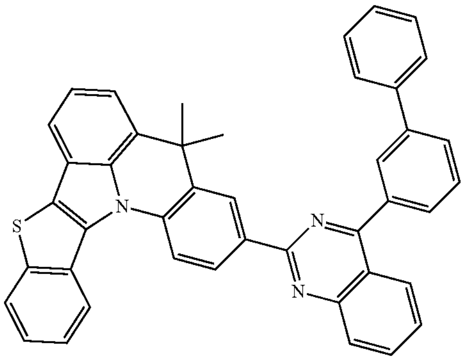
HAC63
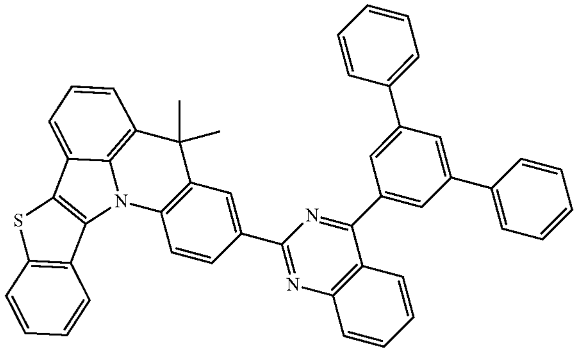

-continued
HAC64
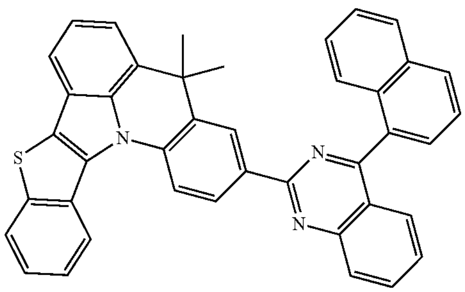
HAC65
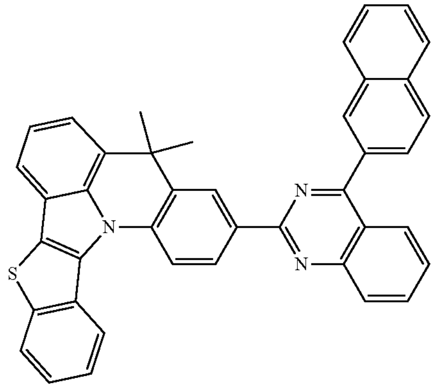
HAC66
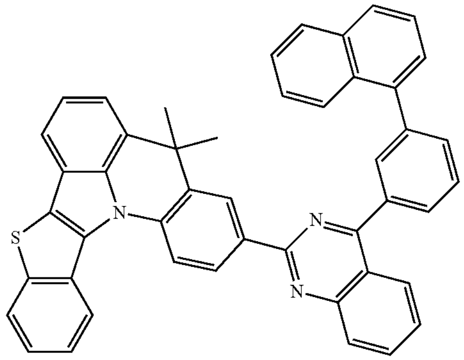
HAC67
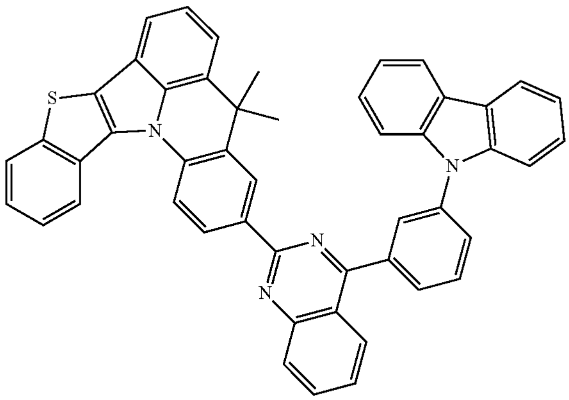
-continued
HAC68
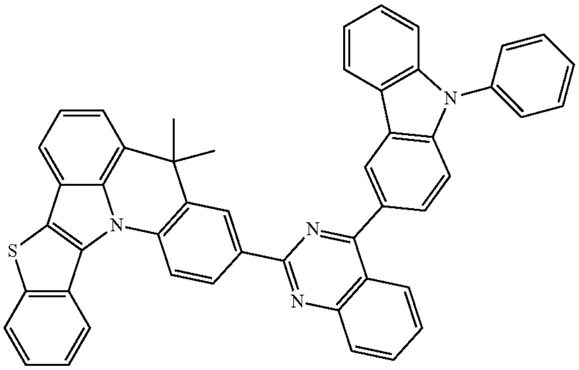
HAC69
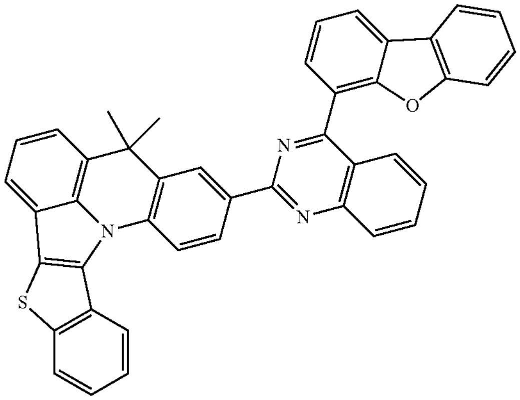
HAC70
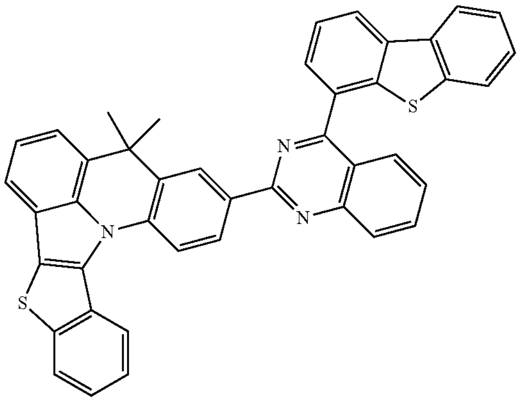

-continued
HAC71
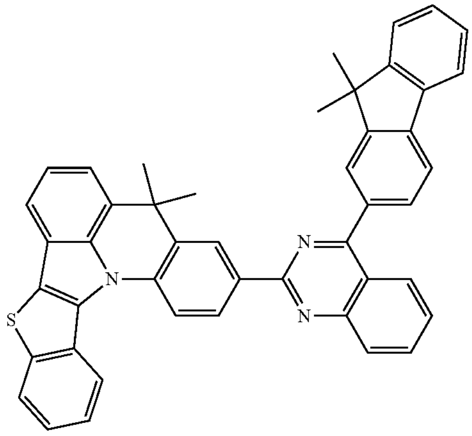
HAC72
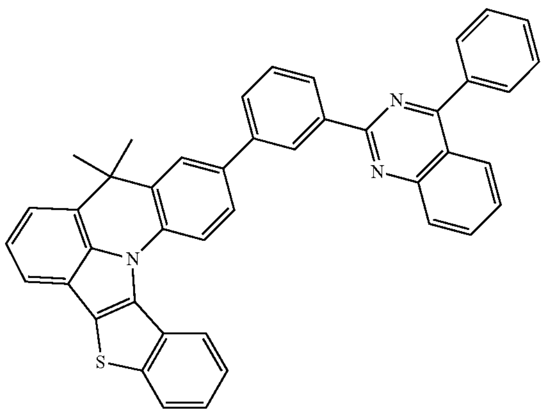
HAC73
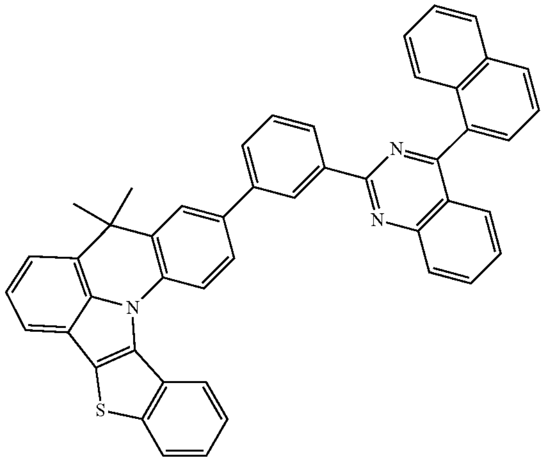
-continued
HAC74
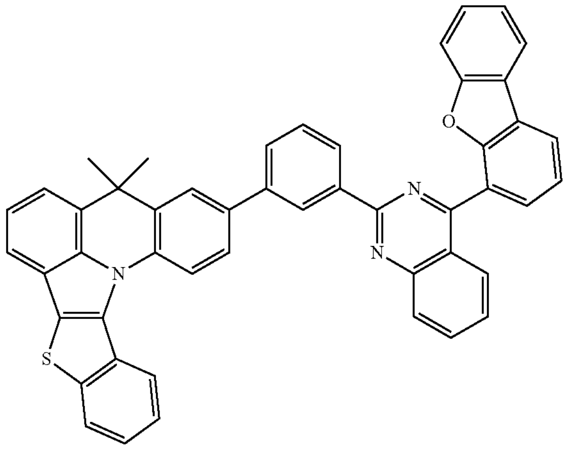
HAC75
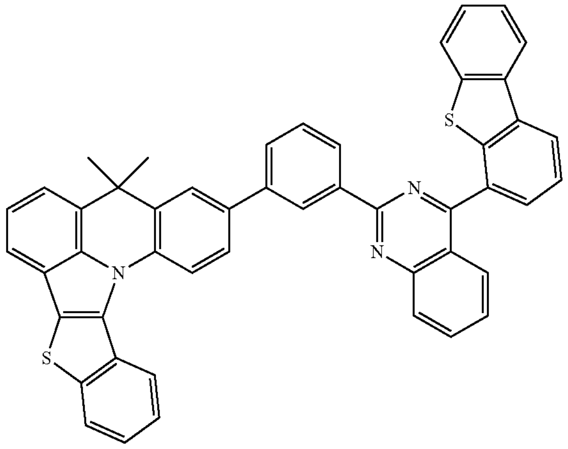
HAC76
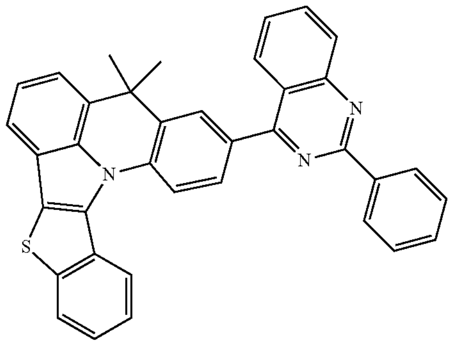

-continued
HAC77
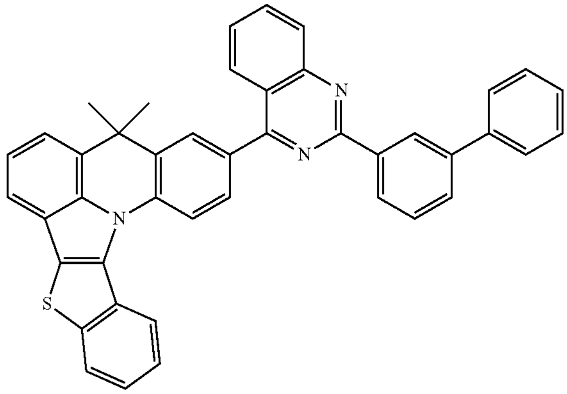
HAC78
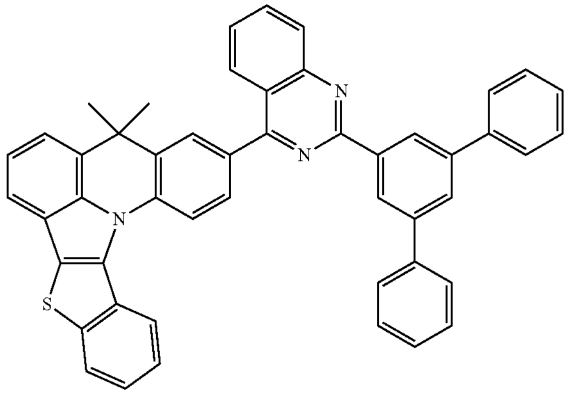
HAC79
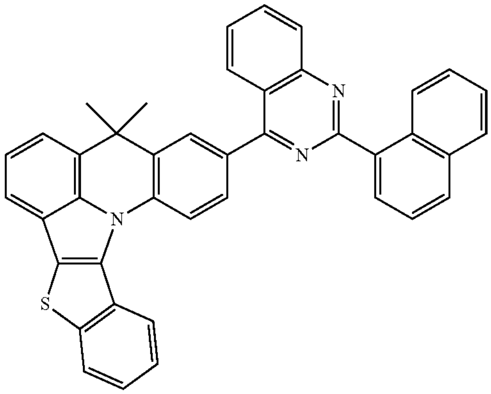
-continued
HAC80
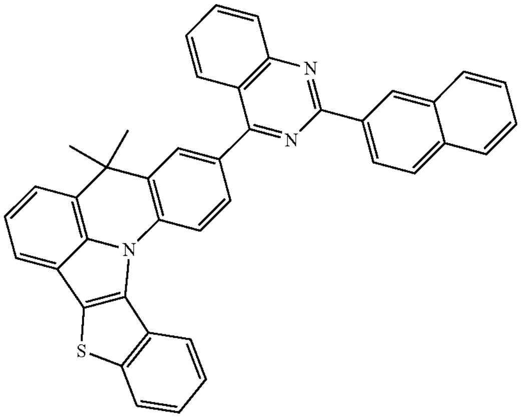
HAC81
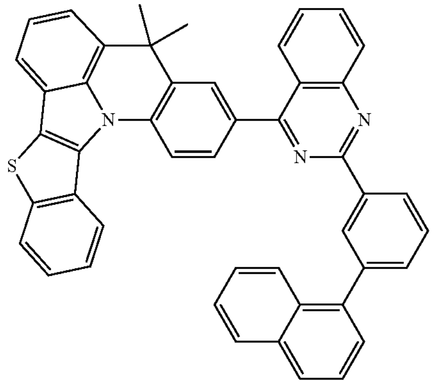
HAC82
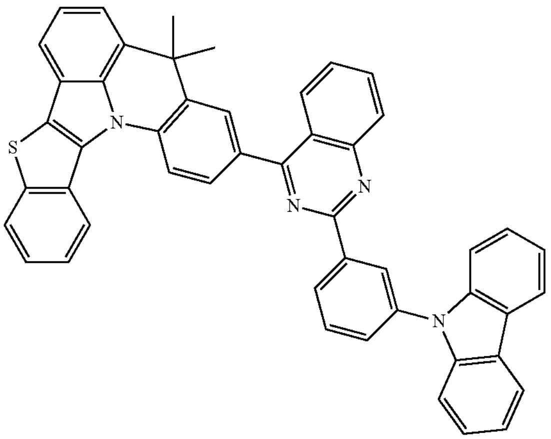

HAC83
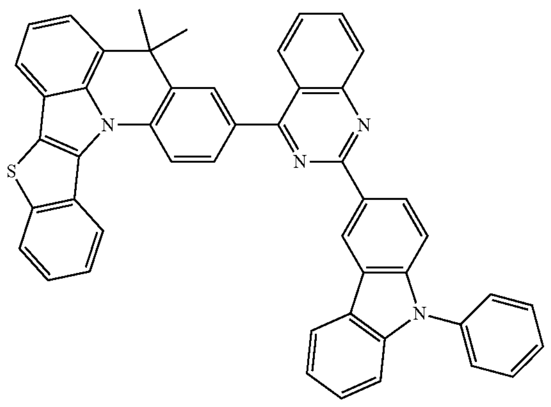
HAC84
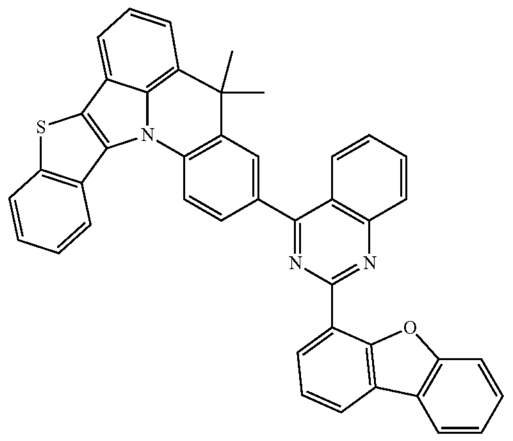
HAC85
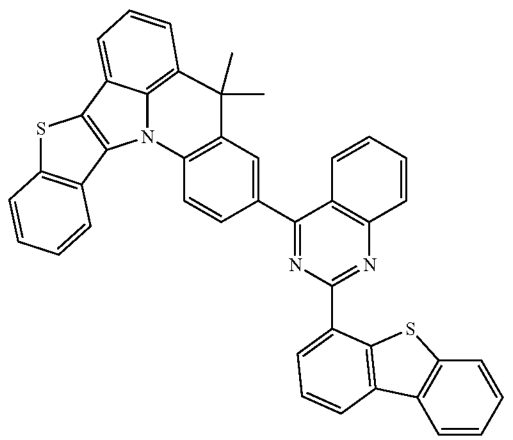
HAC86
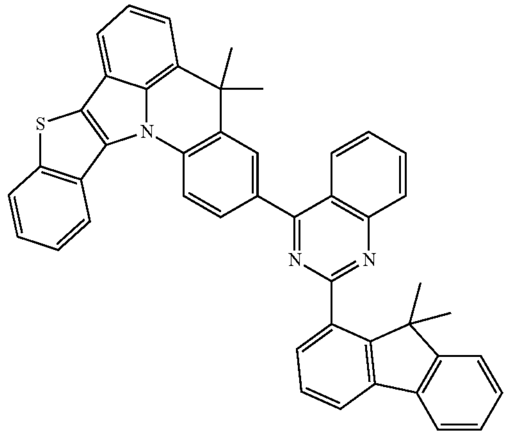
HAC87
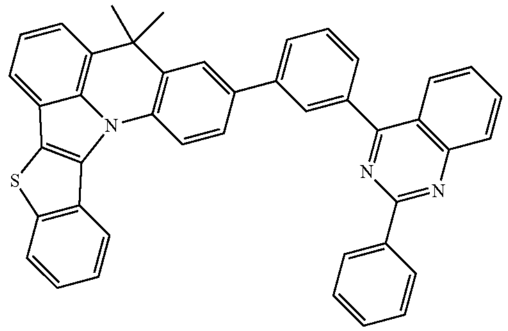
HAC88
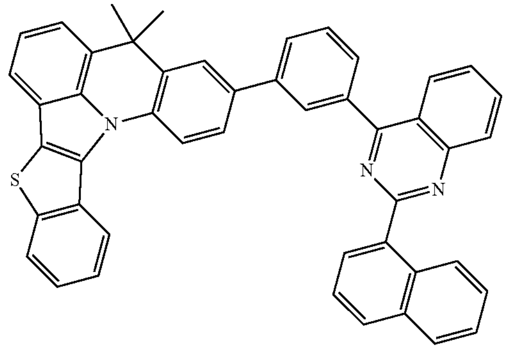
HAC89
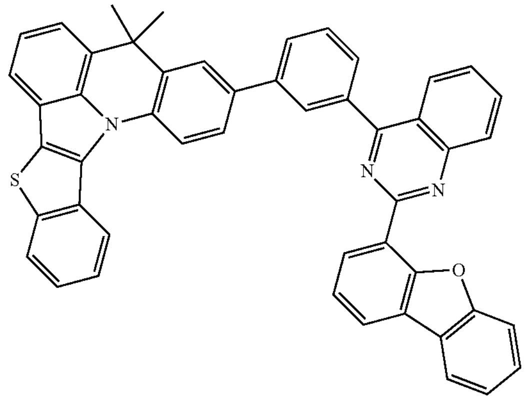

-continued
HAC90
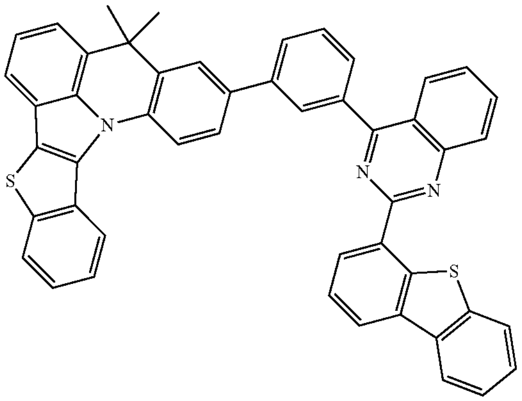
HAC91
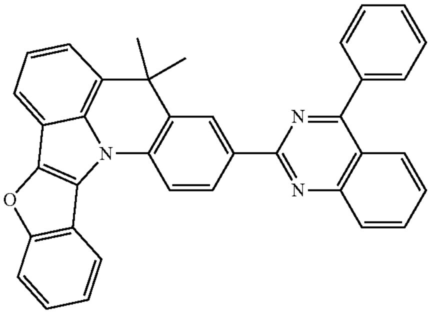
HAC92
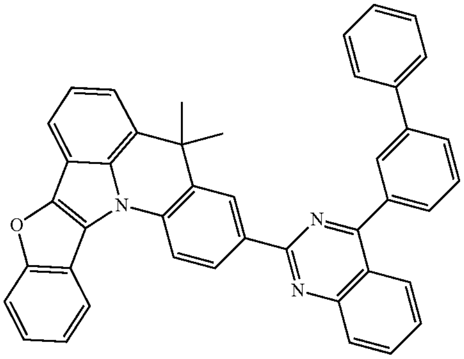
HAC93
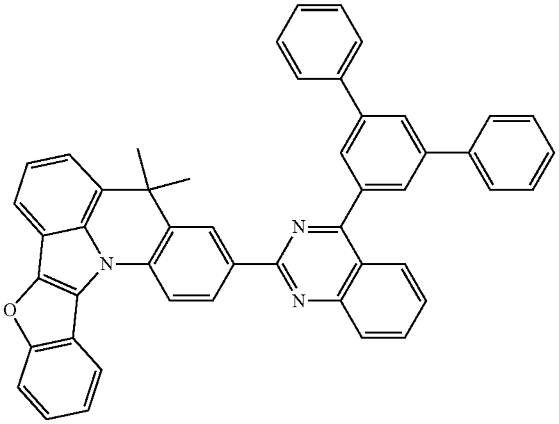
-continued
HAC94
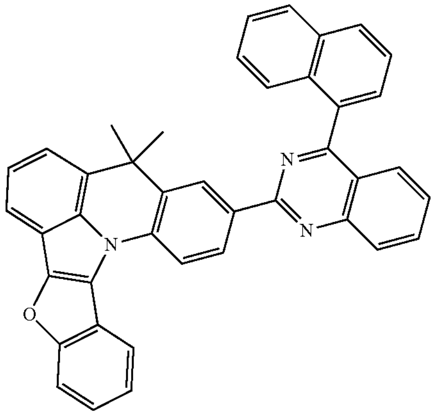
HAC95
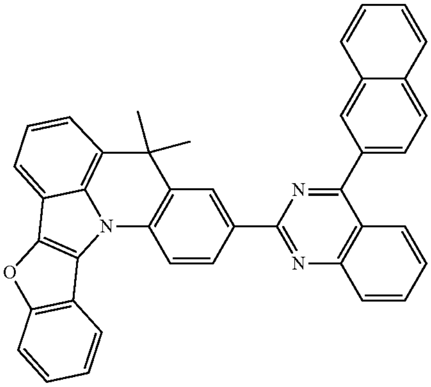
HAC96
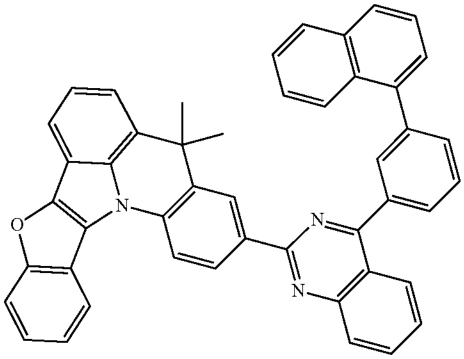
HAC97
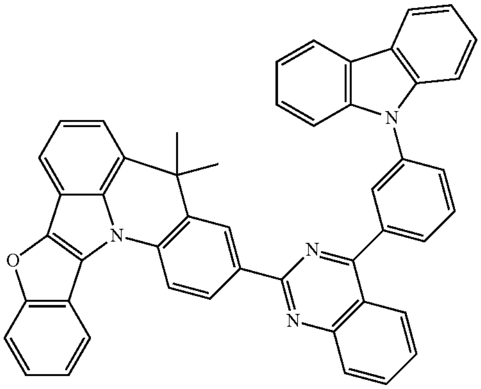

-continued
HAC98
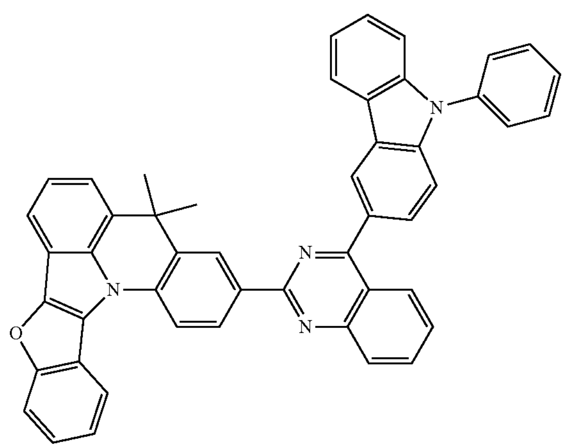
HAC99
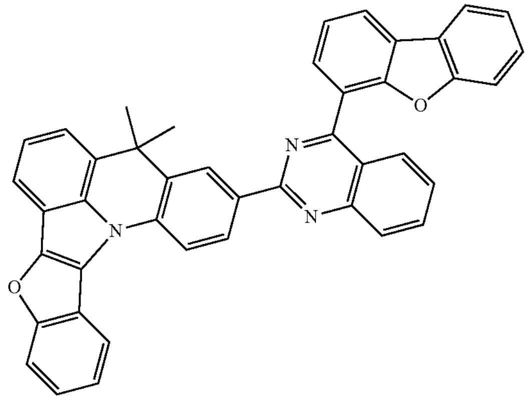
HAC100
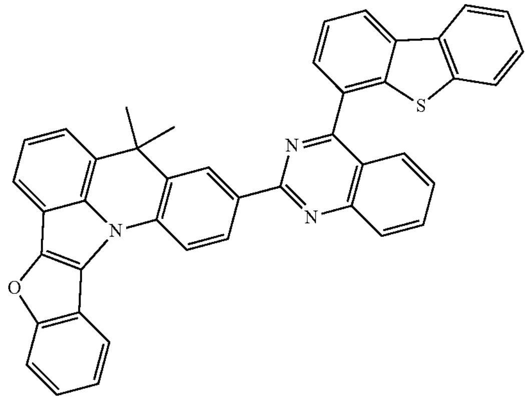
-continued
HAC101
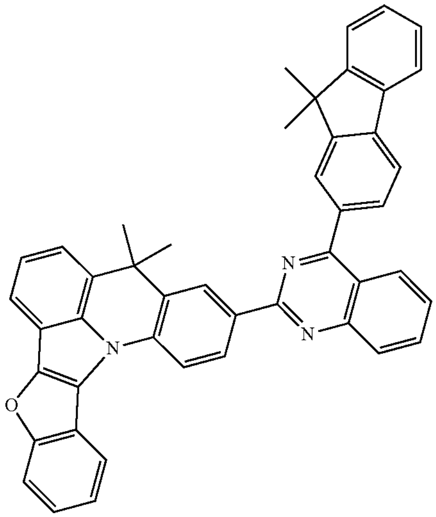
HAC102
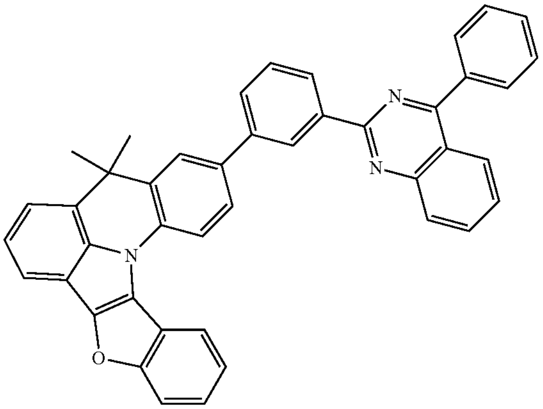
HAC103
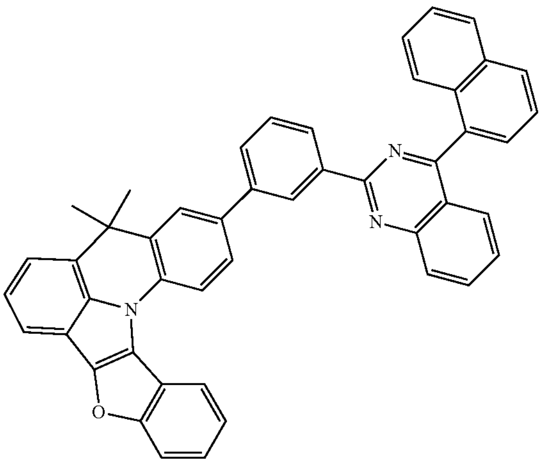

-continued
HAC104
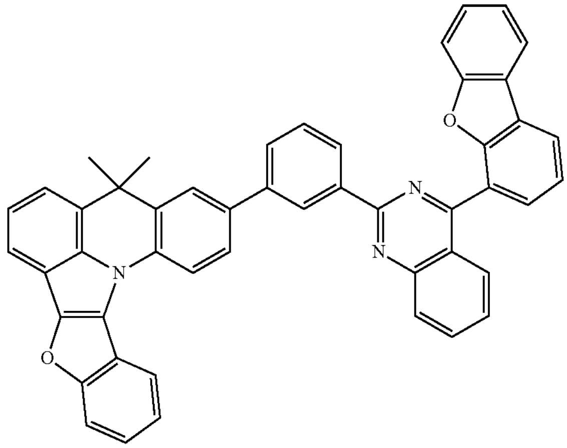
HAC105
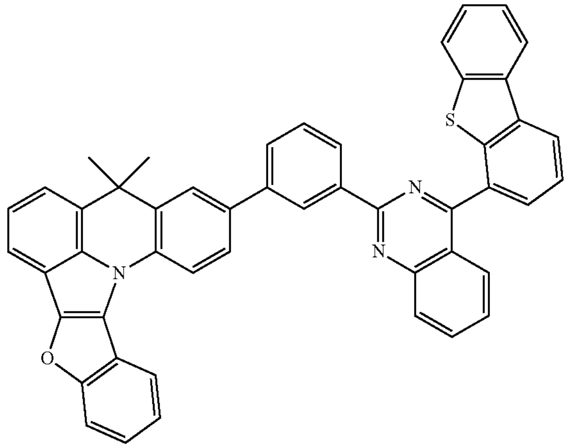
HAC106
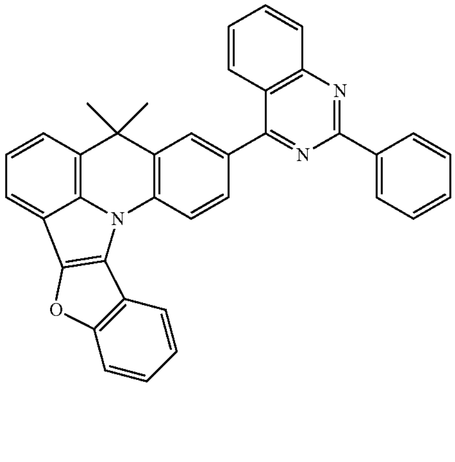
-continued
HAC107
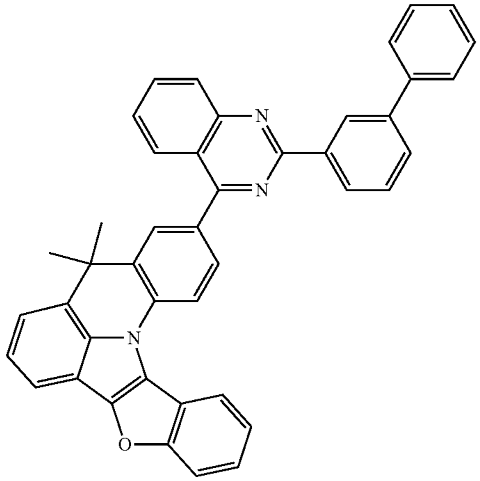
HAC108
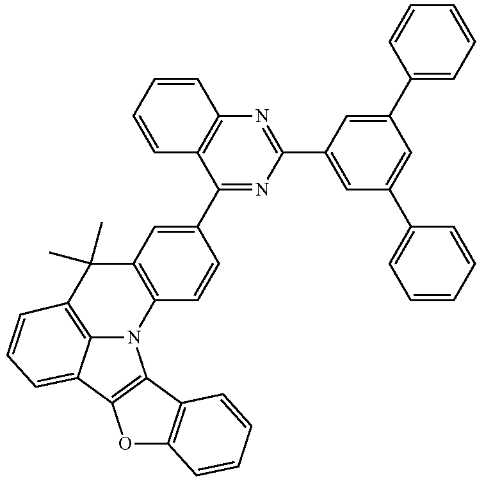
HAC109
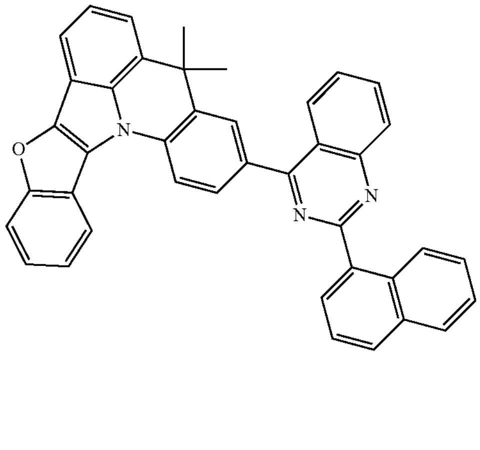

-continued
HAC110
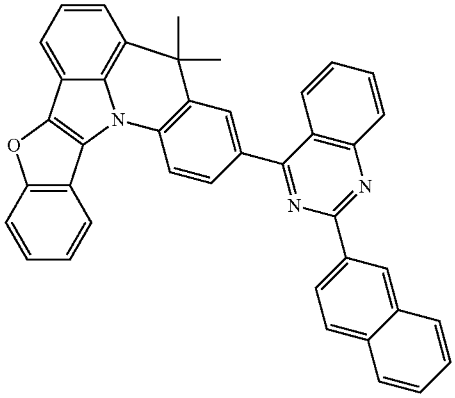
HAC111
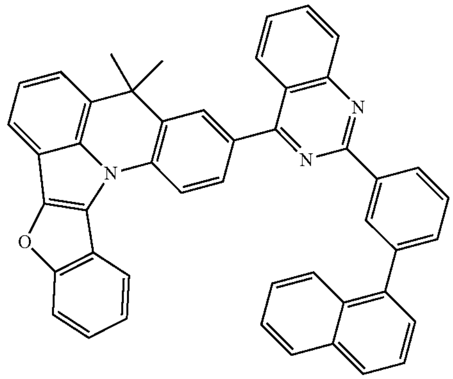
HAC112
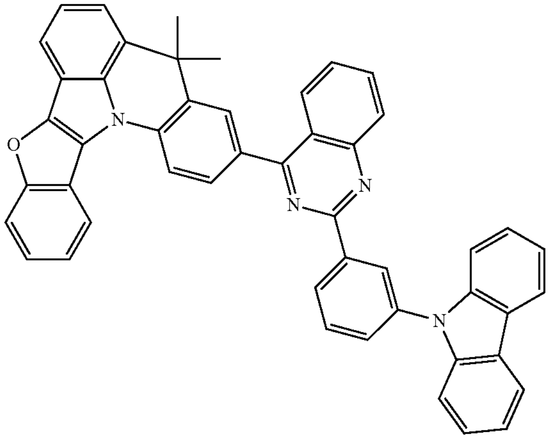
-continued
HAC113
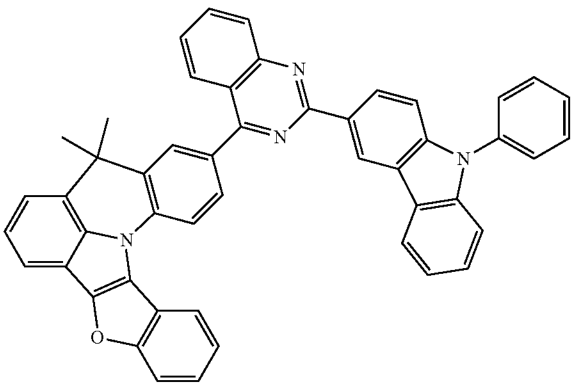
HAC114
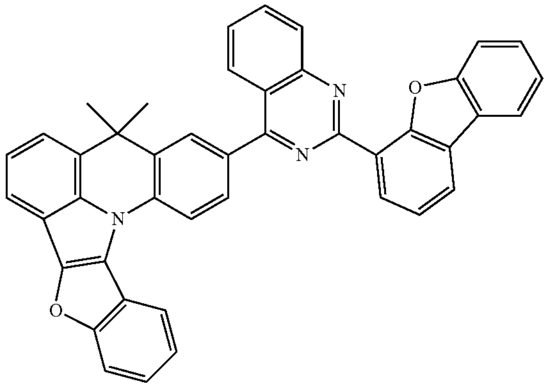
HAC115
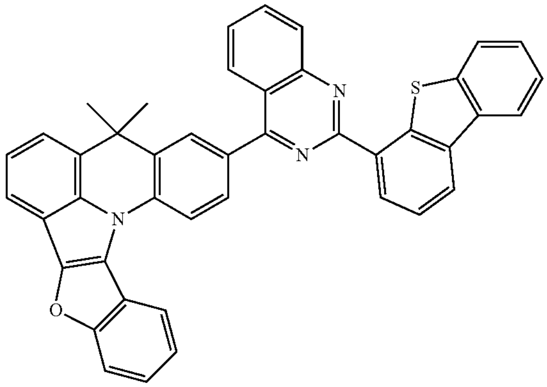
HAC116
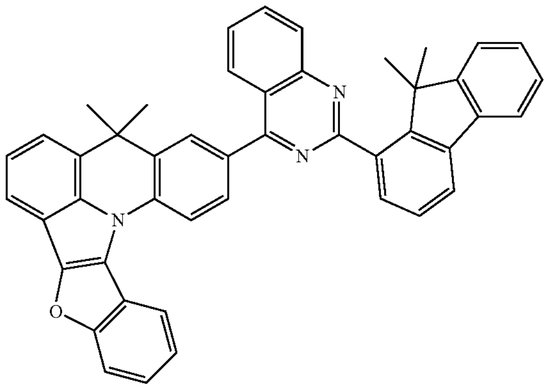

-continued
HAC117
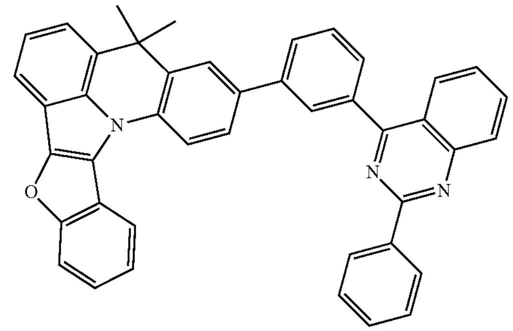
HAC118
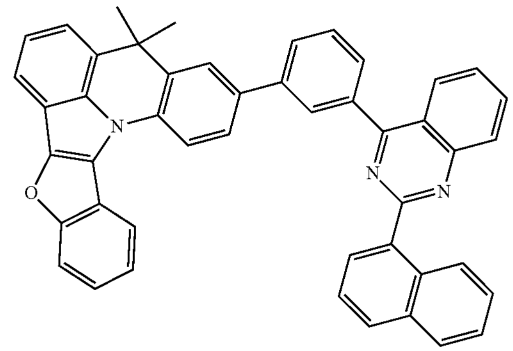
HAC119
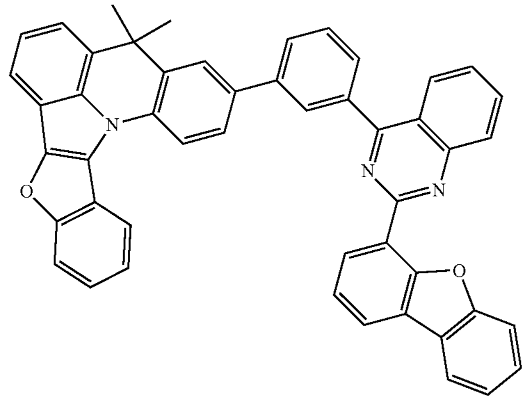
HAC120
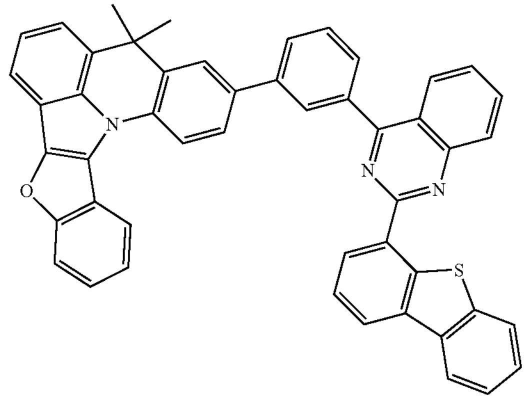
-continued
HAC121
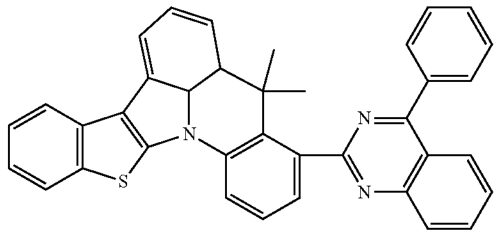
HAC122
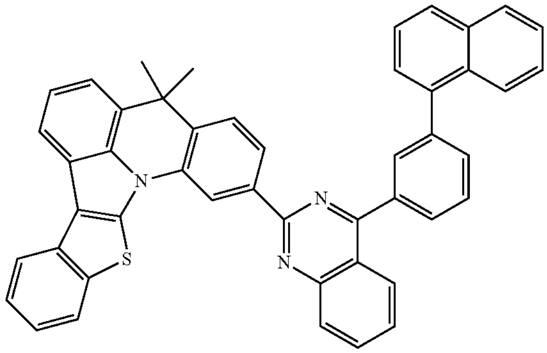
HAC123
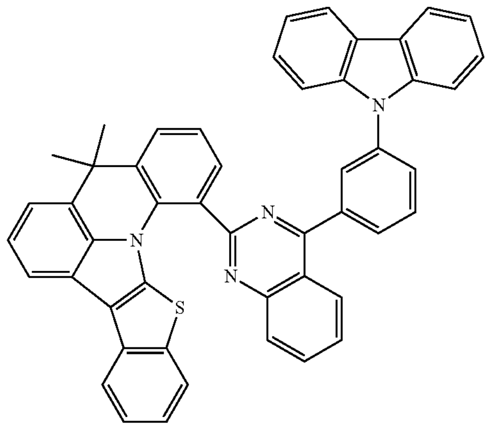
HAC124
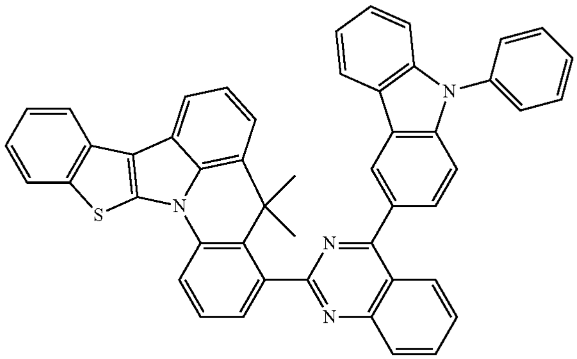

-continued
HAC125
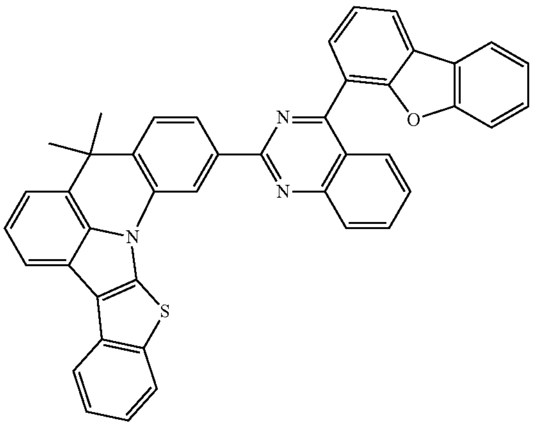
HAC126
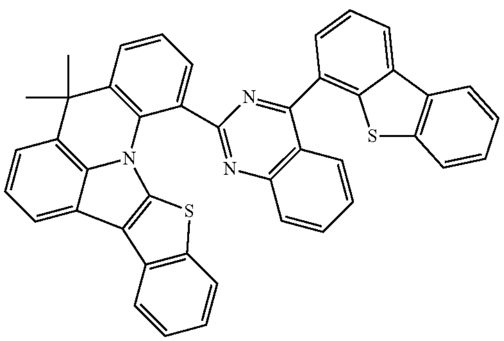
HAC127
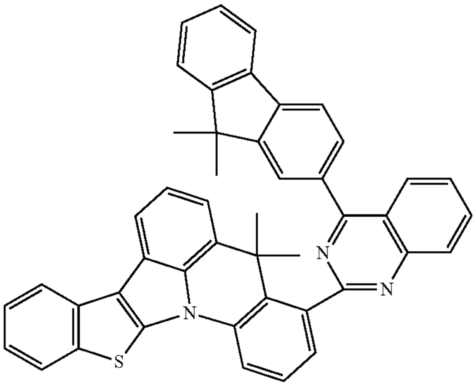
HAC128
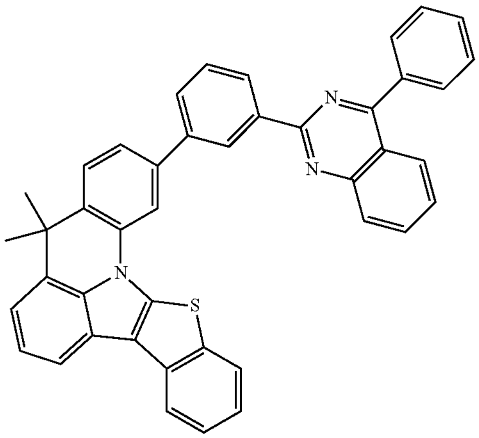
-continued
HAC129
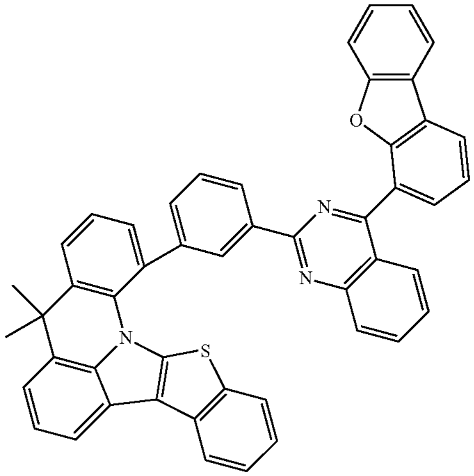
HAC130
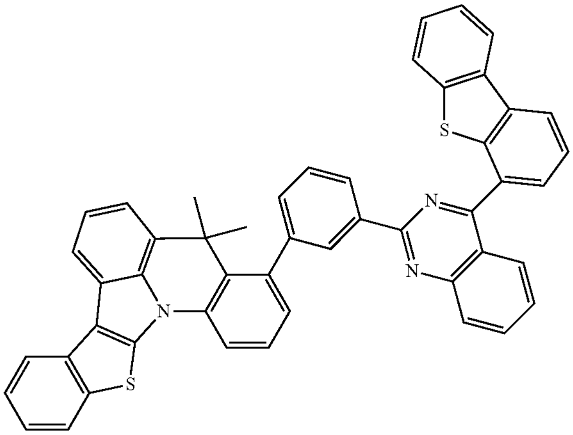
HAC131
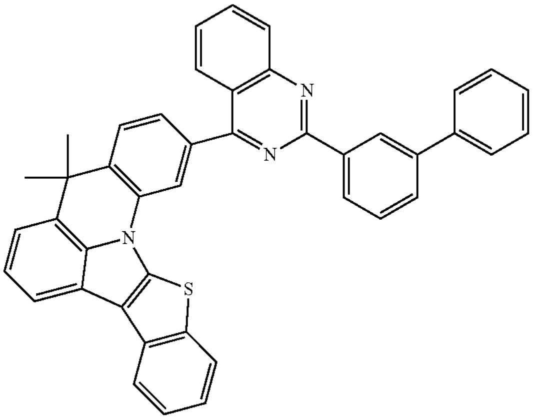

-continued
HAC132
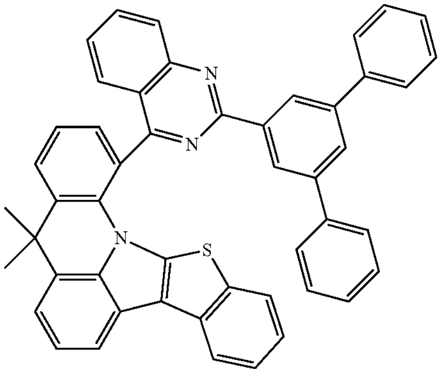
HAC133
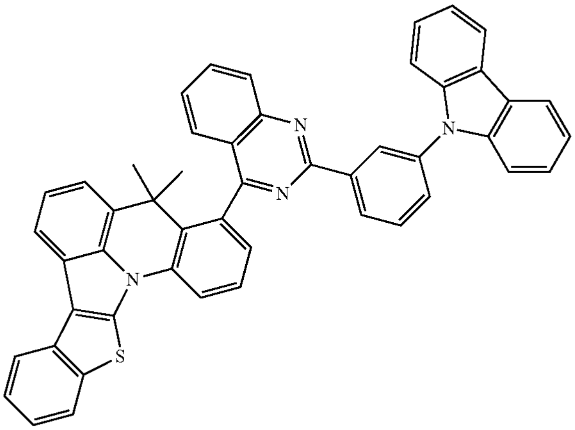
HAC134
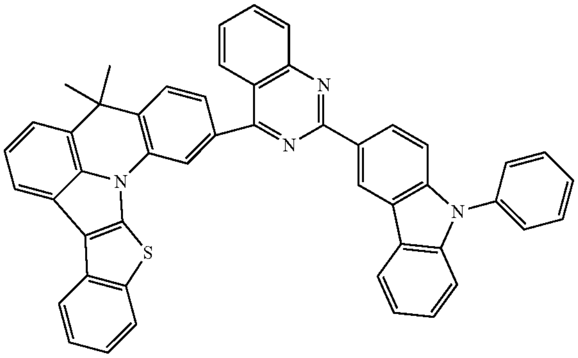
HAC135
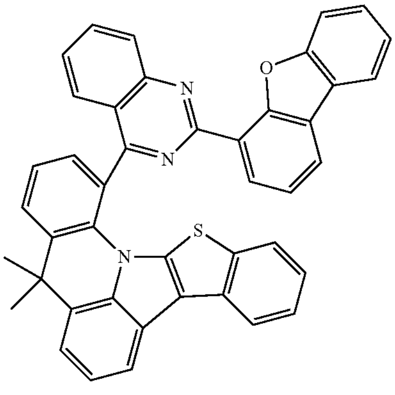
-continued
HAC136
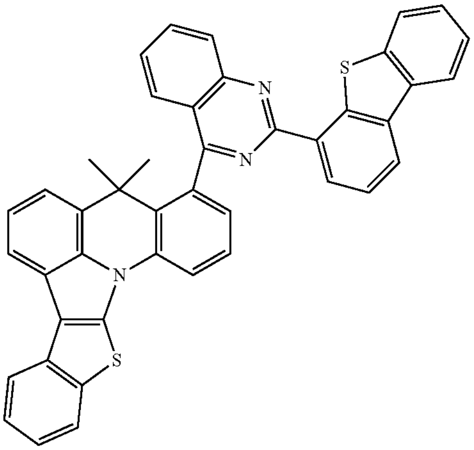
HAC137
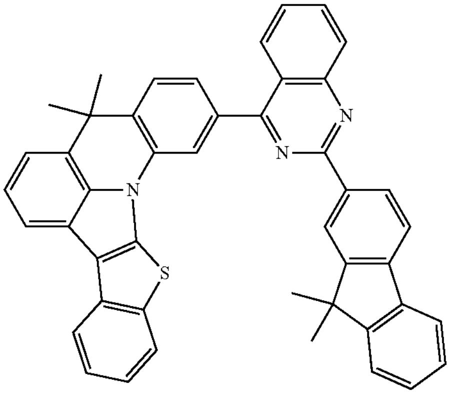
HAC138
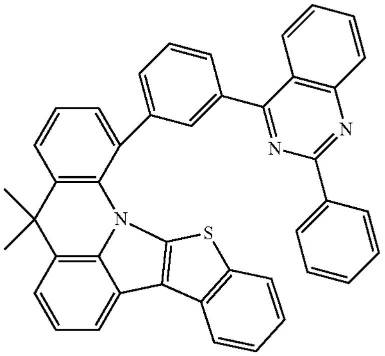
HAC139
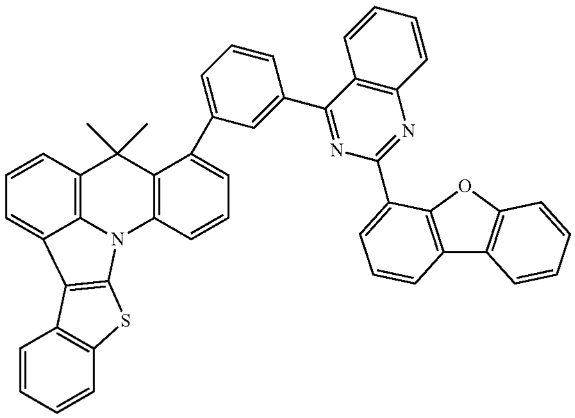

-continued
HAC140
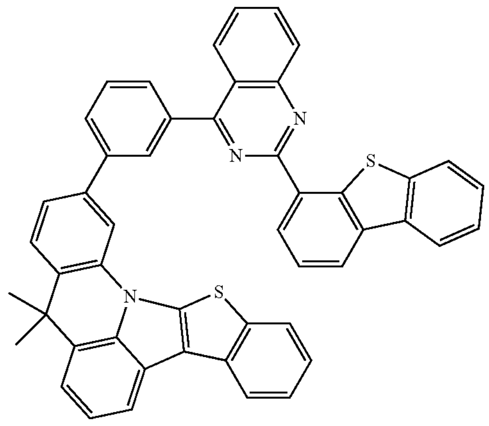
HAC141
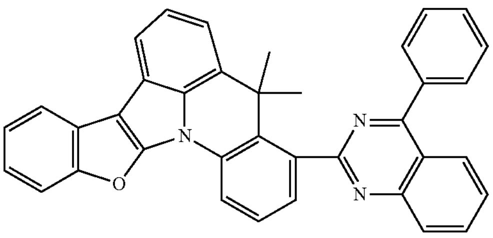
HAC142
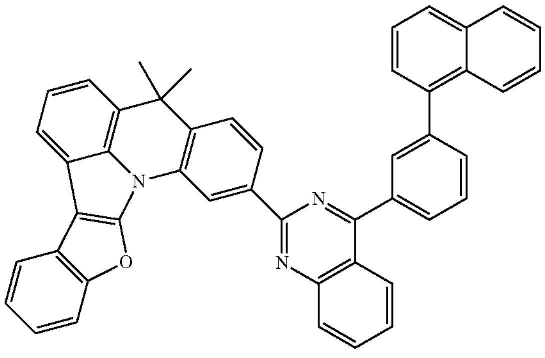
HAC143
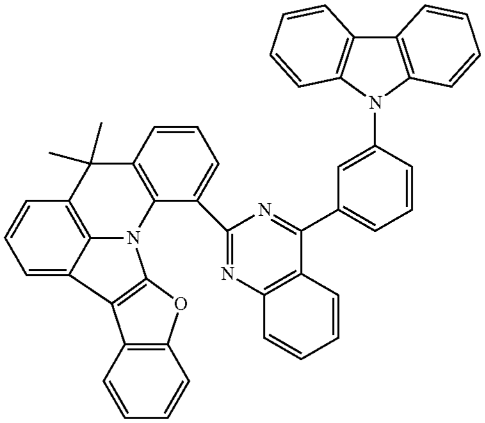
-continued
HAC144
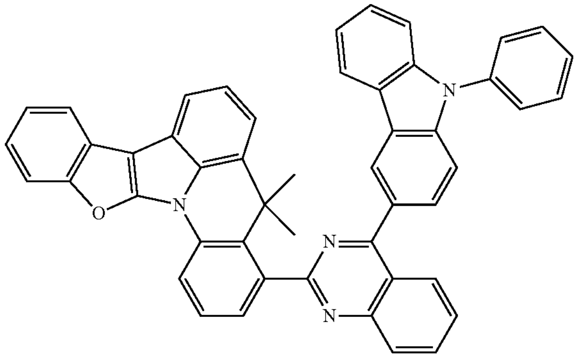
HAC145
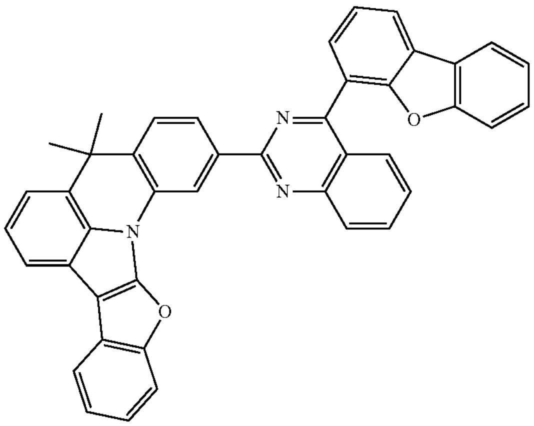
HAC146
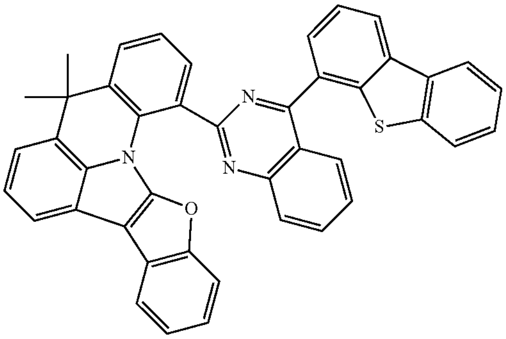
HAC147
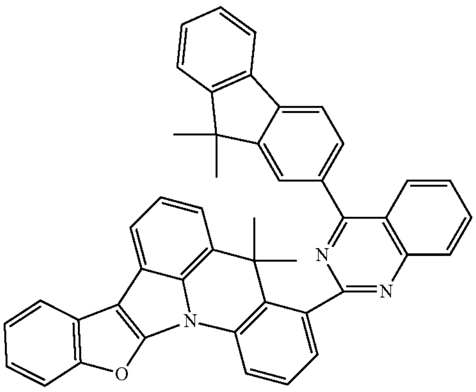

-continued
HAC148
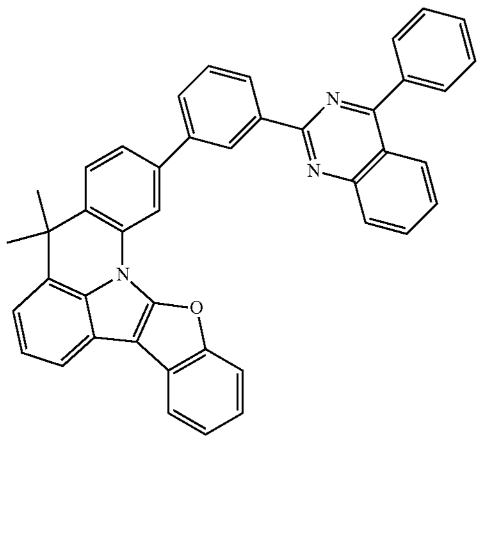
HAC149
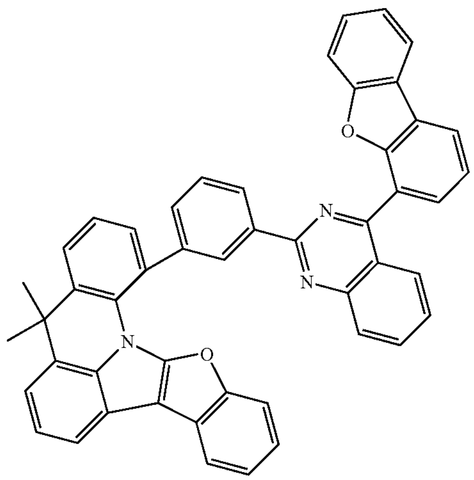
HAC150
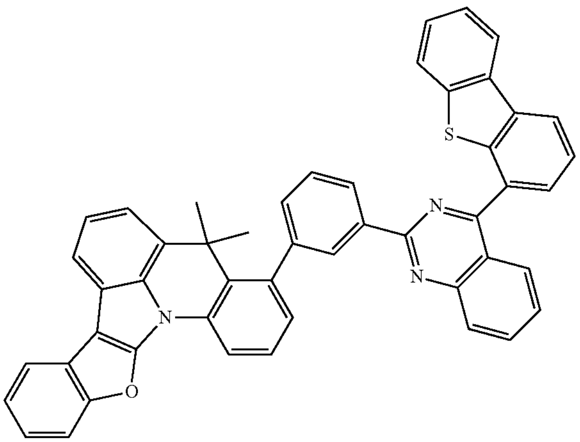
-continued
HAC151
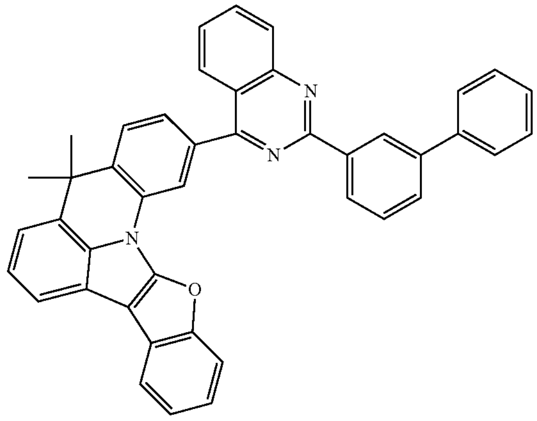
HAC152
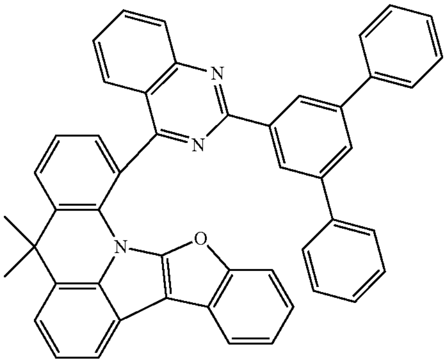
HAC153
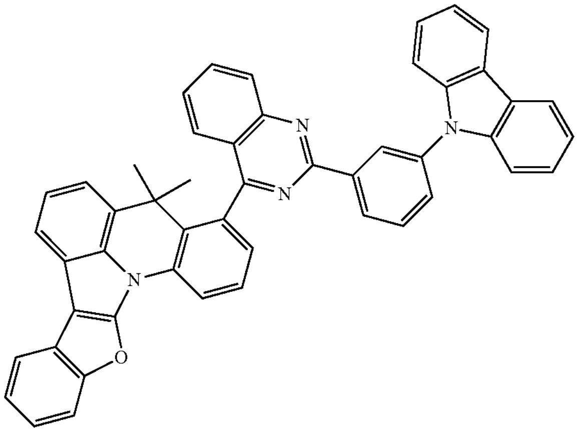

-continued
HAC154
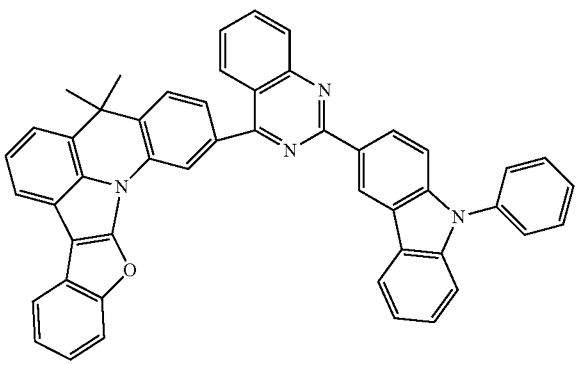
HAC155
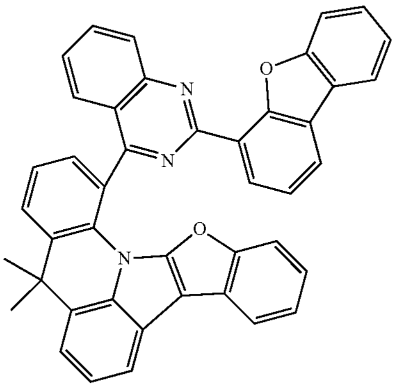
HAC156
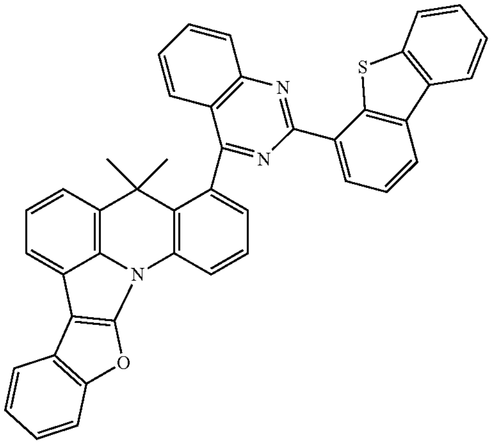
HAC157
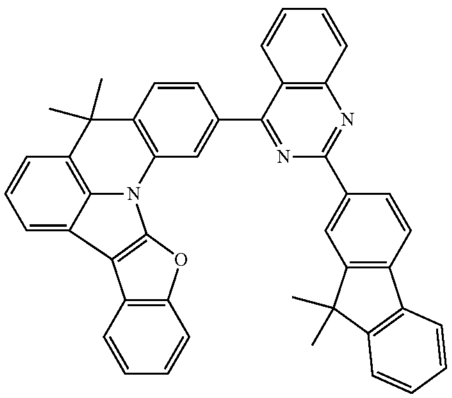
-continued
HAC158
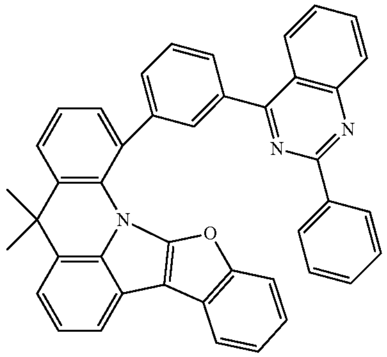
HAC159
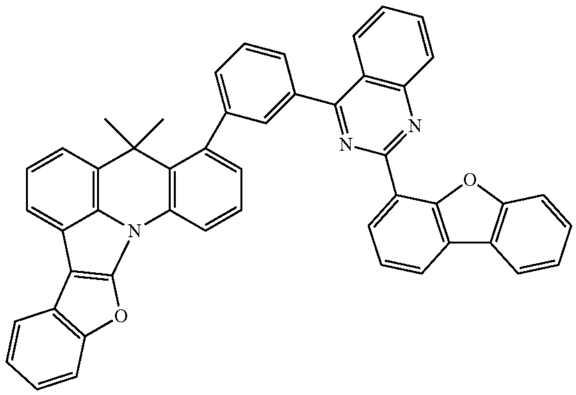
HAC160
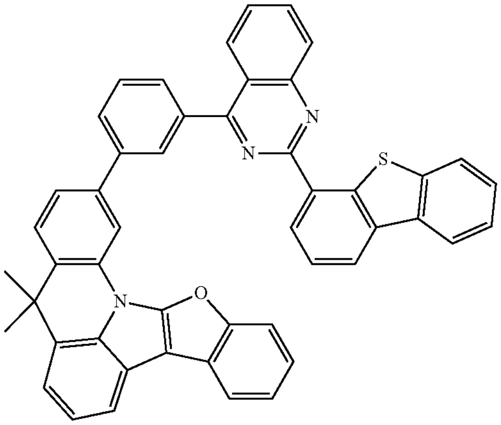
HAC161
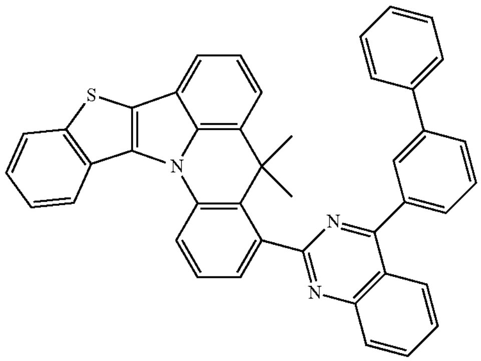

-continued
HAC162
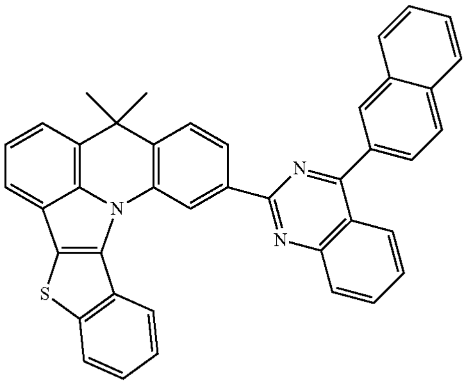
HAC163
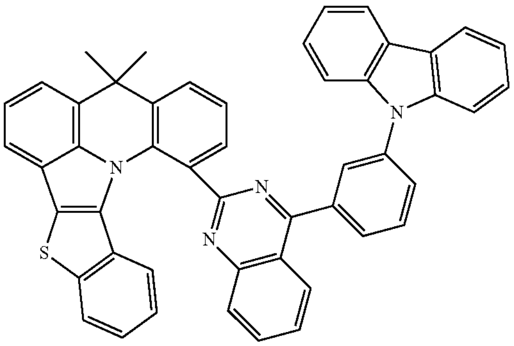
HAC164
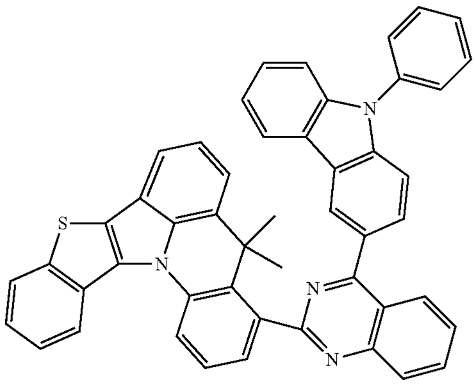
HAC165
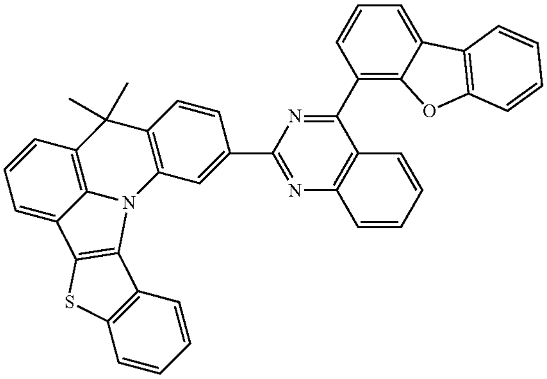
-continued
HAC166
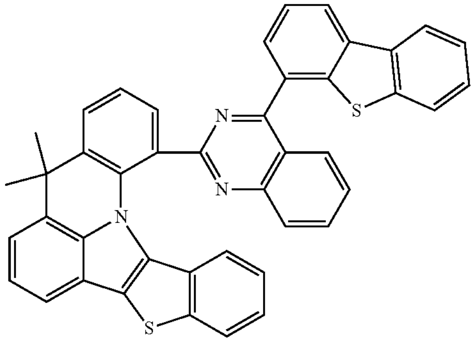
HAC167
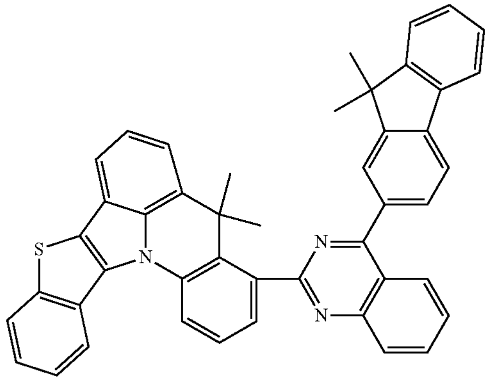
HAC168
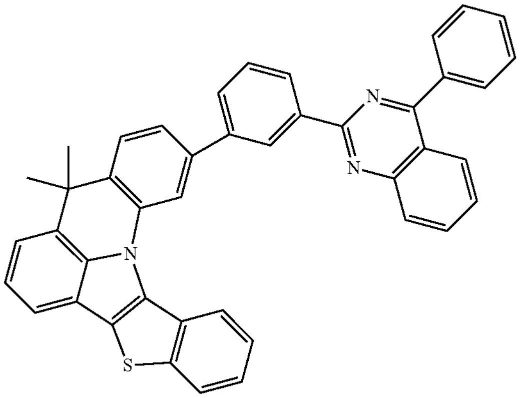
HAC169
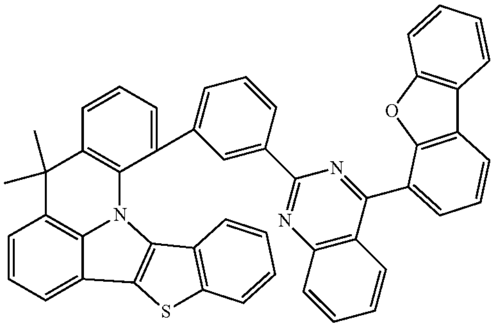

-continued
HAC170
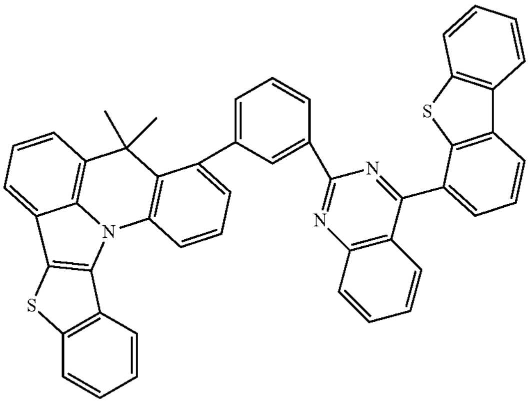
HAC171
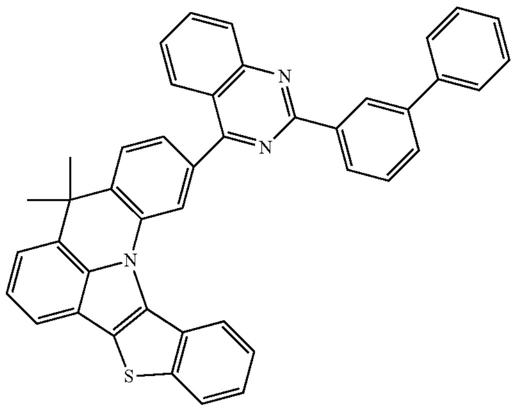
HAC172
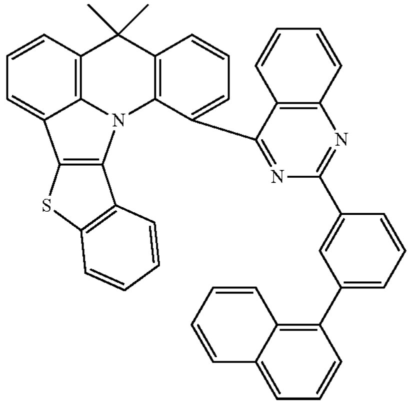
-continued
HAC173
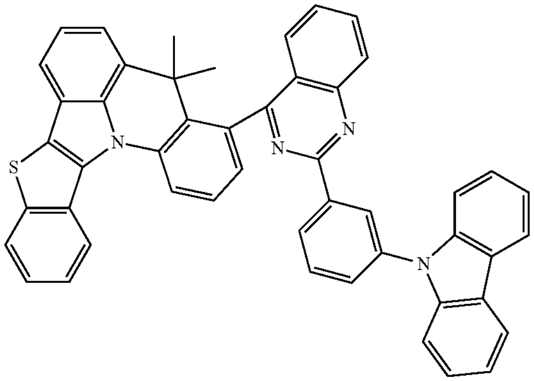
HAC174
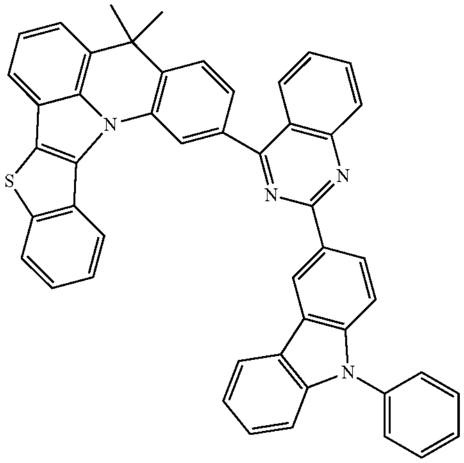
HAC175
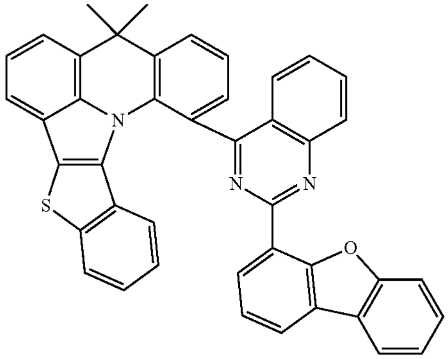

-continued
HAC176
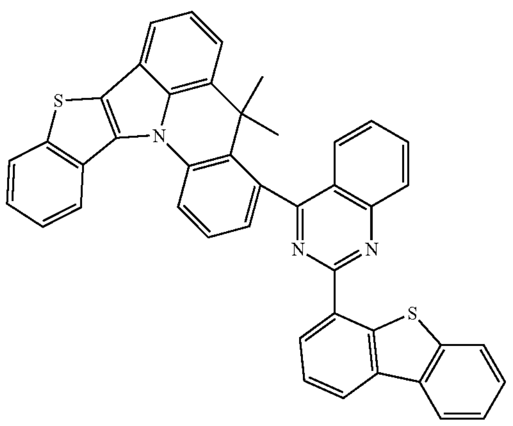
HAC177
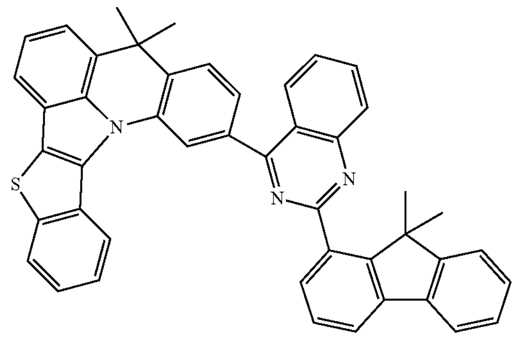
HAC178
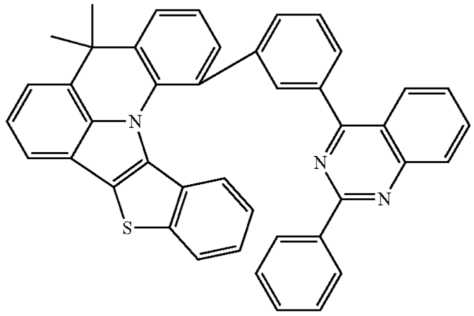
HAC179
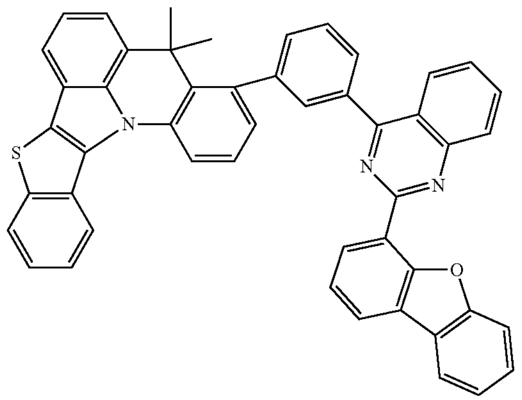
-continued
HAC180
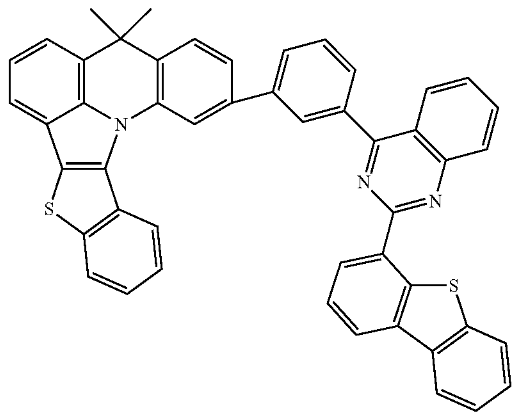
HAC181
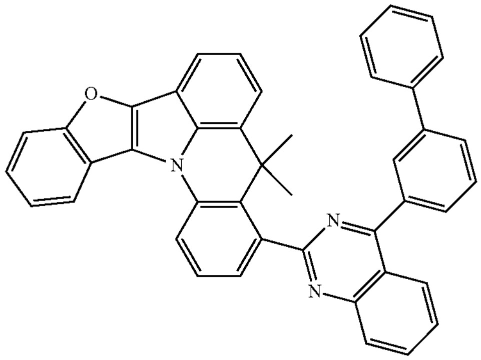
HAC182
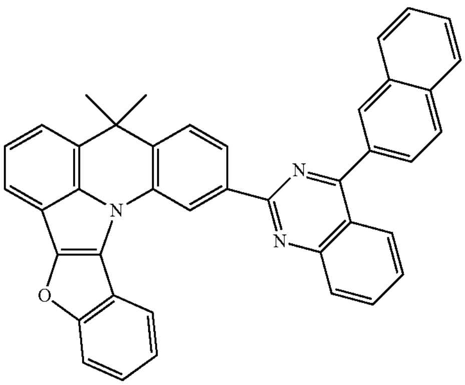
HAC183
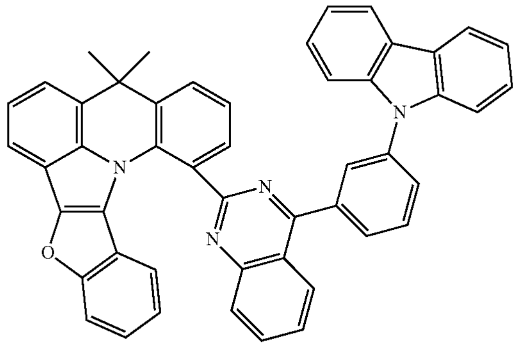

-continued
HAC184
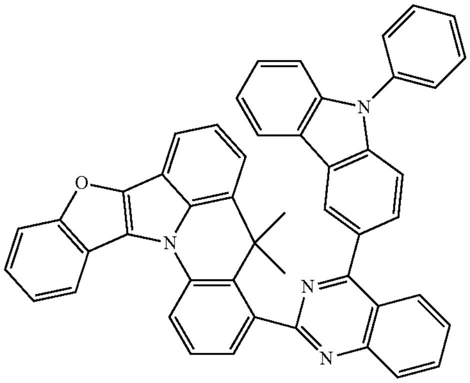
HAC185
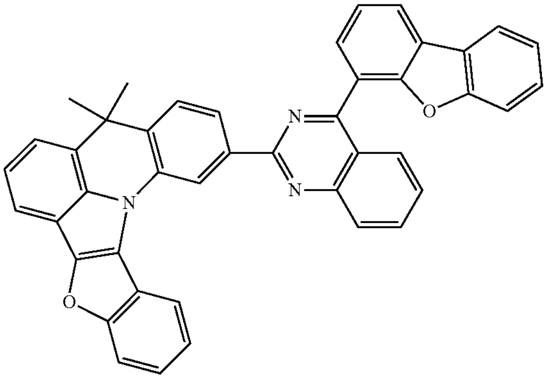
HAC186
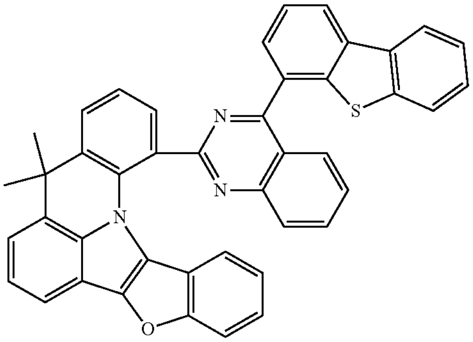
HAC187
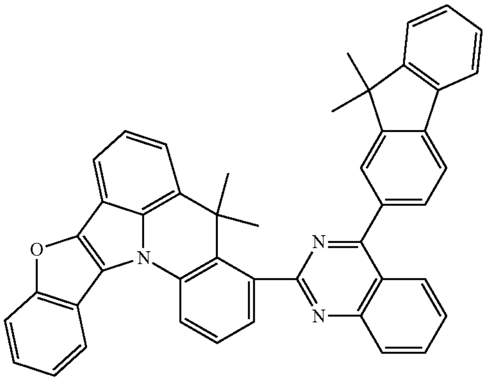
-continued
HAC188
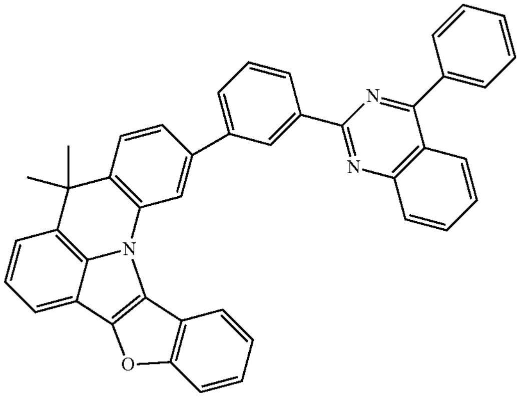
HAC189
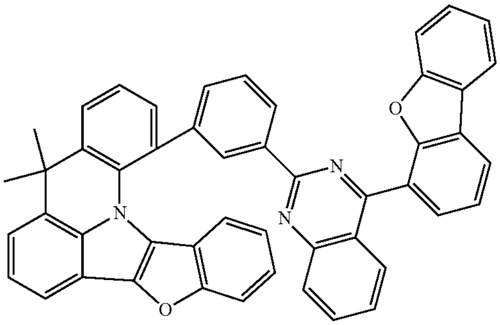
HAC190
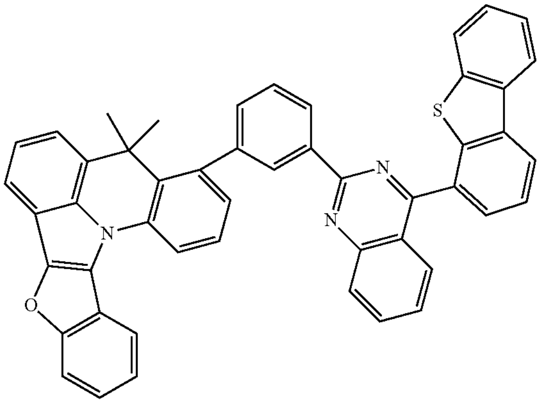
HAC191
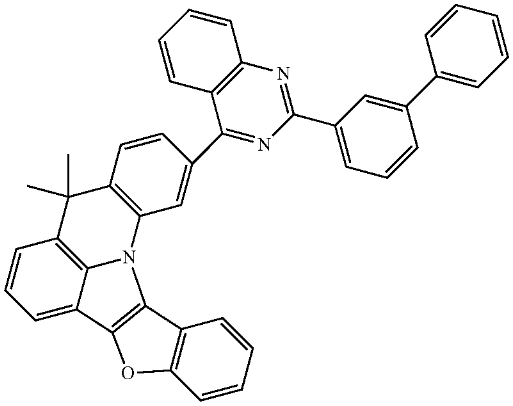

-continued
HAC192
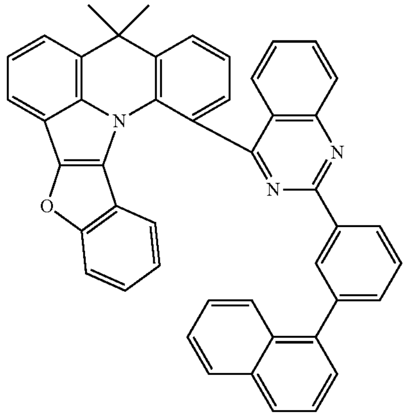
HAC193
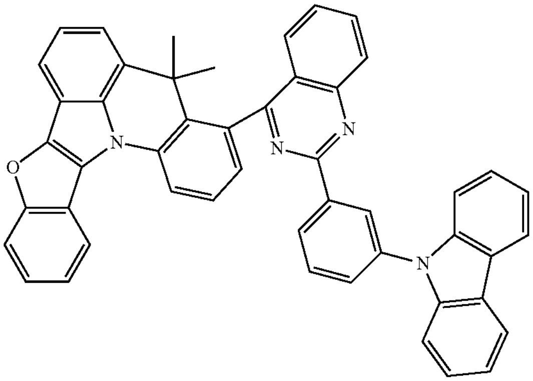
HAC194
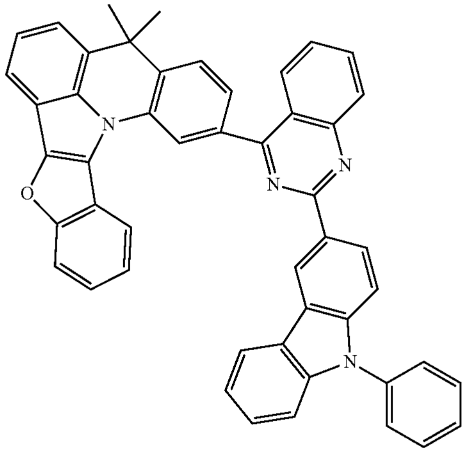
HAC195
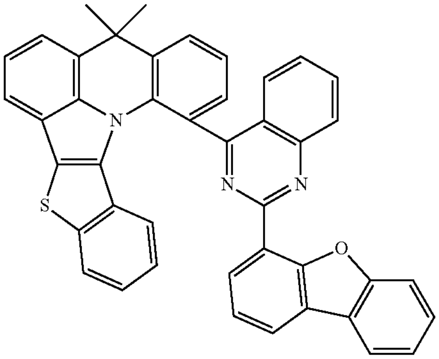
-continued
HAC196
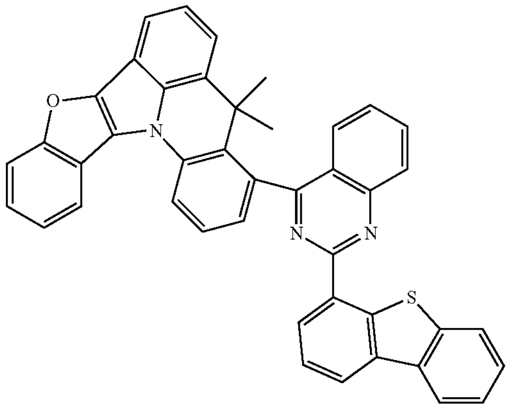
HAC197
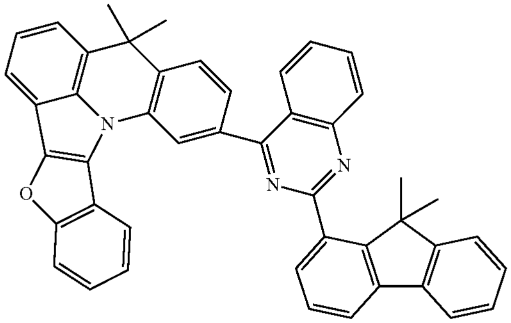
HAC198
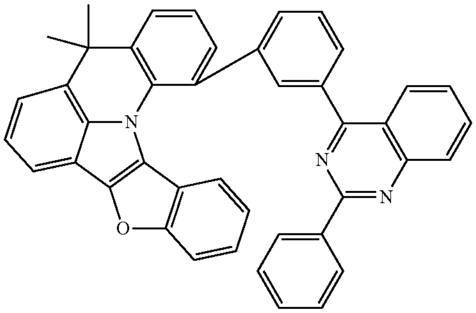
HAC199
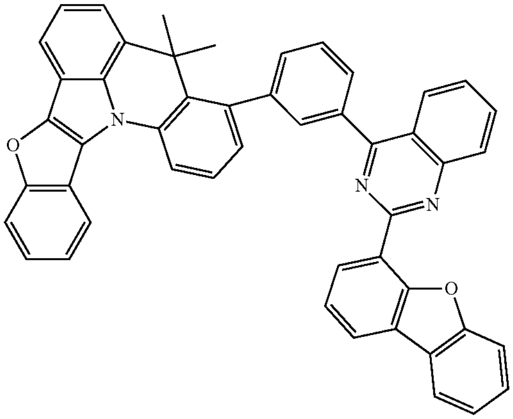

-continued

HAC200

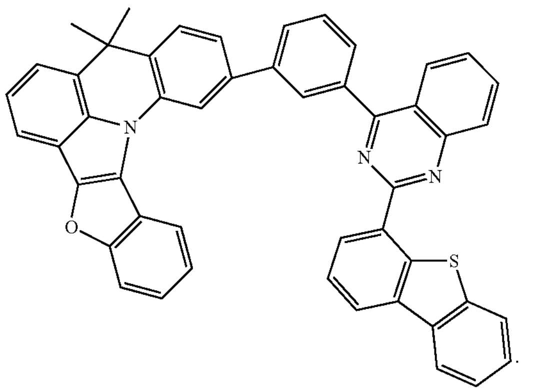

5. An organic light emitting element comprising:

a first electrode;

a second electrode; and an organic material layer positioned between the first electrode and the second electrode, and wherein the organic material layer comprises an organic compound represented by the following Chemical Formula 1:

[Chemical Formula 1]

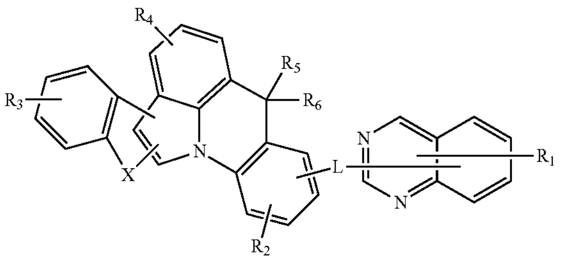

wherein in Chemical Formula 1,

X is O or S, $R_1$ to $R_6$ are each independently selected from the group consisting of a hydrogen; a halogen; a cyano group; a nitro group; a $C_6$-$C_{60}$ aryl group; a fluorenyl group; a $C_2$-$C_{60}$ heterocyclic group containing at least one heteroatom selected from the group consisting of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group, L is selected from the group consisting of a single bond; a $C_6$-$C_{60}$ arylene group; a fluorenylene group; a $C_2$-$C_{60}$ heterocyclic group containing at least one heteroatom selected from the group consisting of O, N, S, Si, and P; and a fused ring group of a $C_3$-$C_{60}$ aliphatic ring and a $C_6$-$C_{60}$ aromatic ring, and the aryl group, the fluorenyl group, the heterocyclic group, the fused ring group, the alkyl group, the alkenyl group, the alkynyl group, the alkoxy group, the aryloxy group, the arylene group and the fluorenylene group may be each further substituted with one or more substituents selected from the group consisting of a nitro group; a cyano group; a halogen; an amino group; a $C_1$-$C_{20}$ alkoxyl group; a $C_1$-$C_{20}$ alkylthio group; a $C_1$-$C_{20}$ alkyl group; a $C_2$-$C_{20}$ alkenyl group; a $C_2$-$C_{20}$ alkynyl group; a $C_6$-$C_{20}$ aryl group; a fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group.

6. The organic light emitting element according to claim 5, wherein the organic compound represented by the Chemical Formula 1 is represented by any one of the following Chemical Formulas 2-1 to 2-4:

[Chemical Formula 2-1]

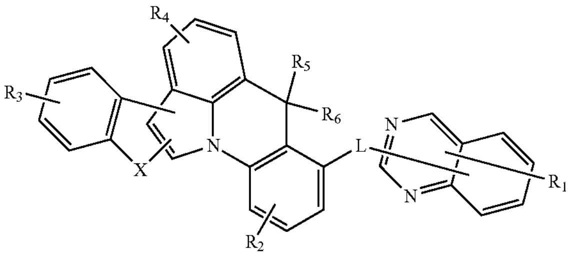

[Chemical Formula 2-2]

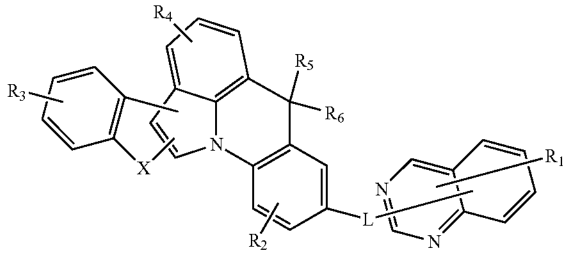

[Chemical Formula 2-3]

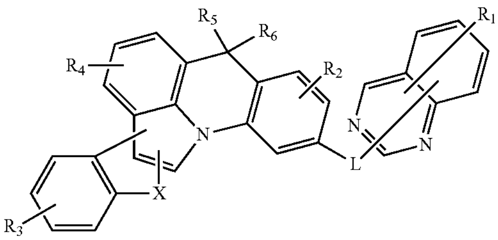

[Chemical Formula 2-4]

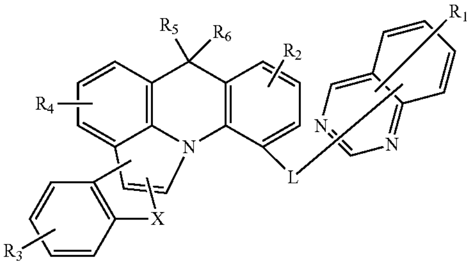

wherein in Chemical Formulas 2-1 to 2-4, X, $R_1$ to $R_6$, and L are the same as defined in Chemical Formula 1.

7. The organic light emitting element according to claim 5, wherein the organic compound represented by the Chemical Formula 1 is represented by any one of the following Chemical Formulas 3-1 to 3-8:

-continued

[Chemical Formula 3-1]

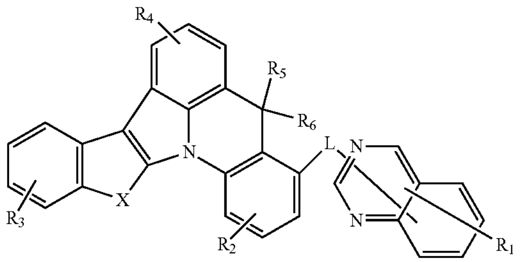

[Chemical Formula 3-2]

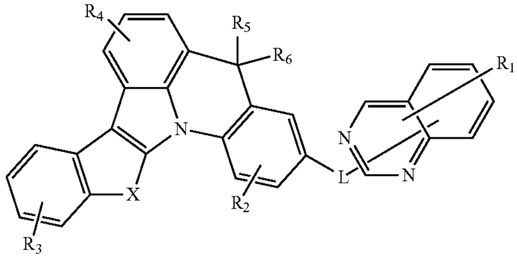

[Chemical Formula 3-3]

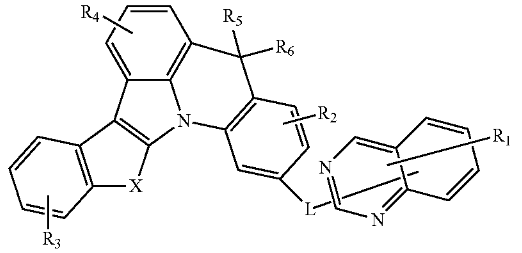

[Chemical Formula 3-4]

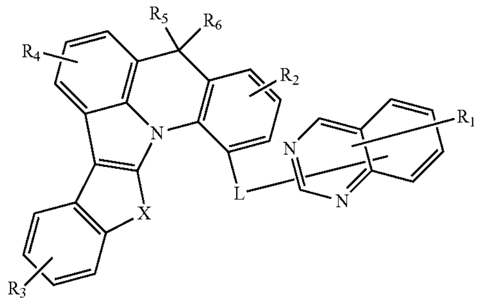

[Chemical Formula 3-5]

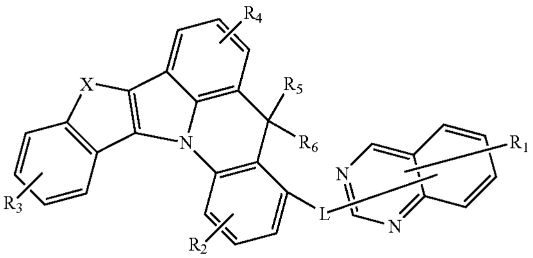

[Chemical Formula 3-6]

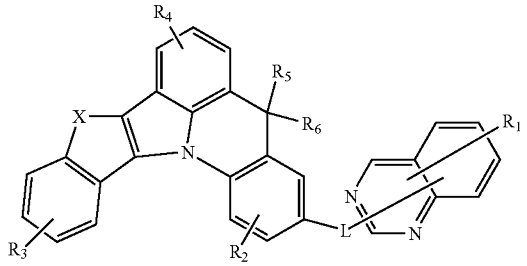

[Chemical Formula 3-7]

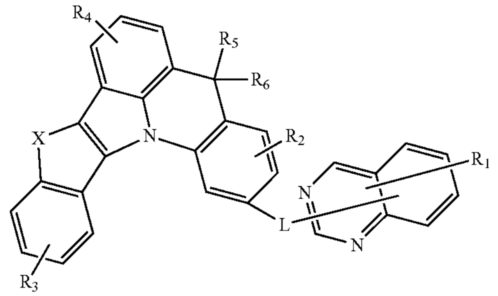

[Chemical Formula 3-8]

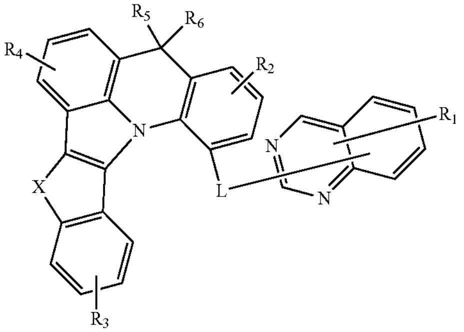

wherein in Chemical Formulas 3-1 to 3-8, X, $R_1$ to $R_6$, and L are the same as defined in Chemical Formula 1.

8. The organic light emitting element according to claim 5, wherein the organic compound represented by the Chemical Formula 1 is one or more of the following organic compounds:

HAC1

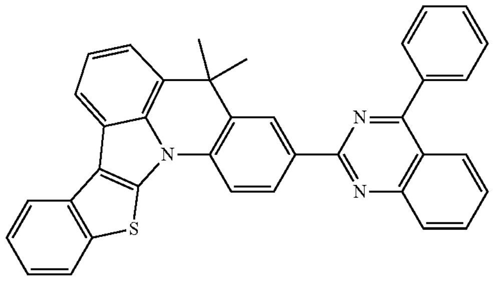

-continued
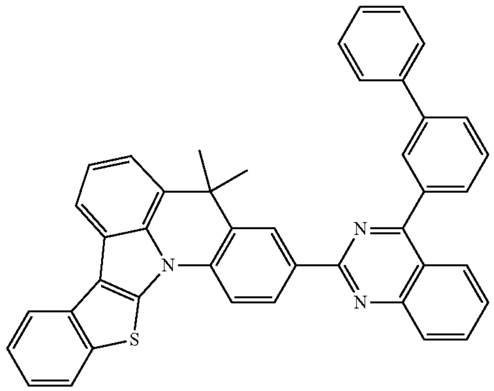
HAC2
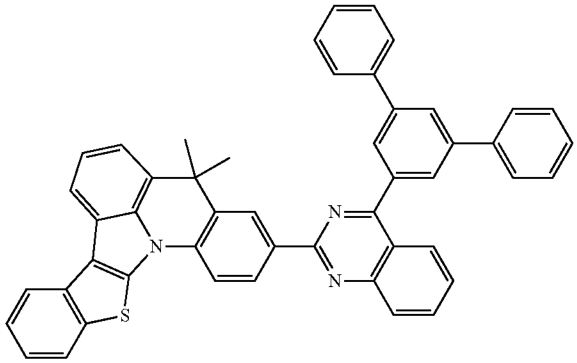
HAC3
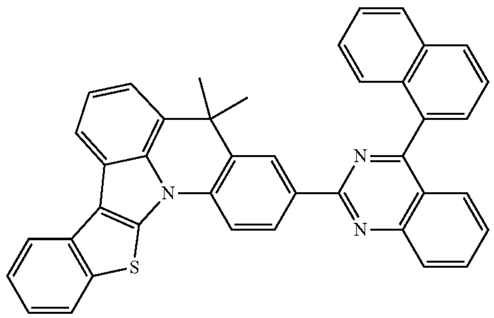
HAC4
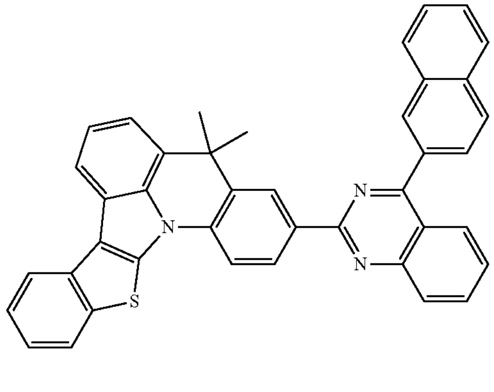
HAC5
-continued
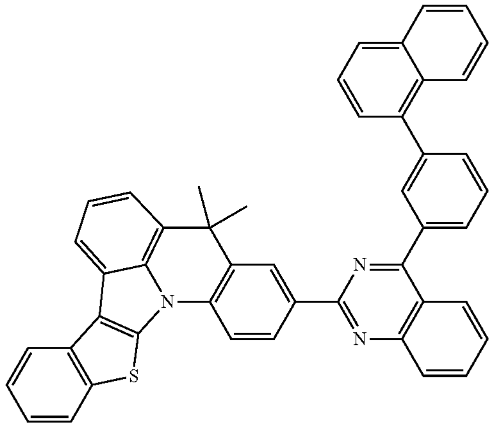
HAC6
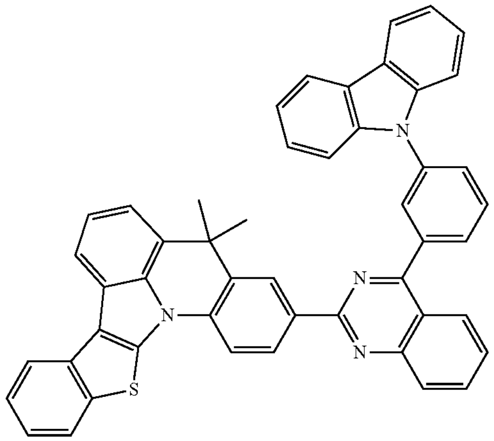
HAC7
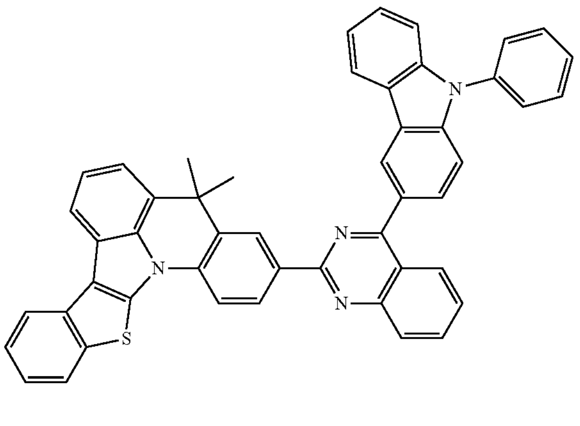
HAC8

-continued
HAC9
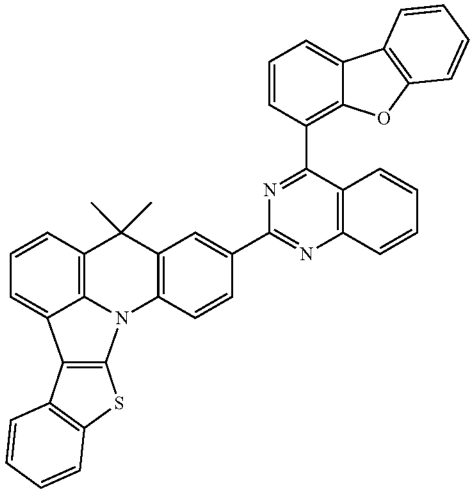
HAC10
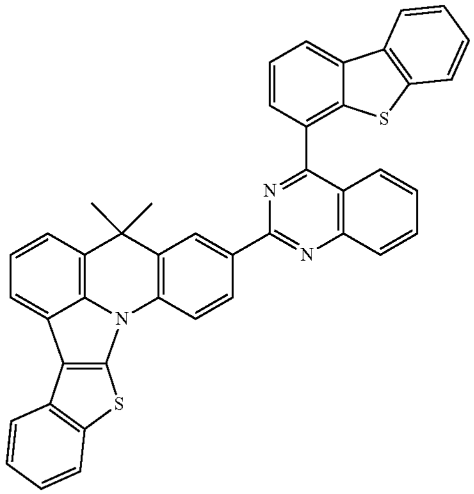
HAC11
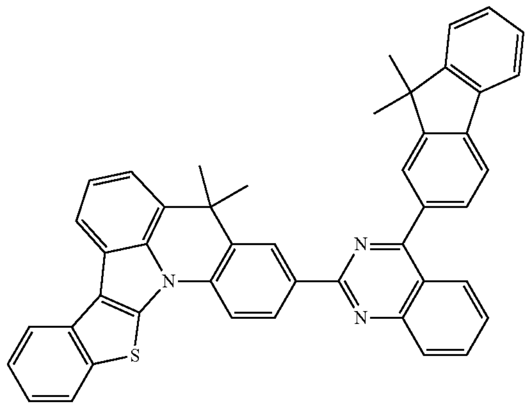
-continued
HAC12
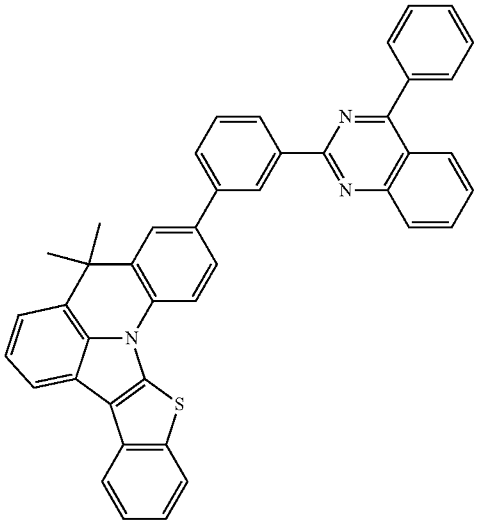
HAC13
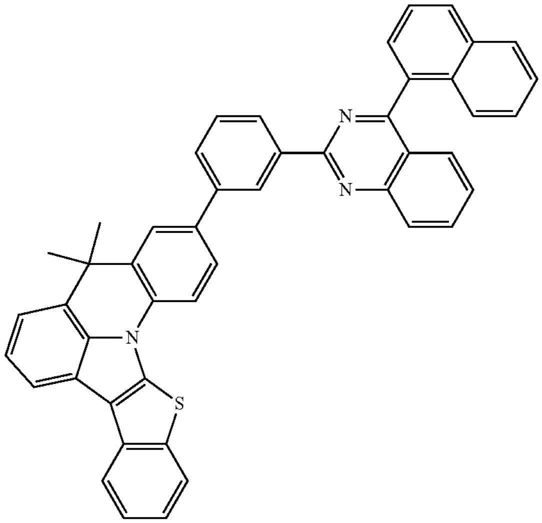
HAC14
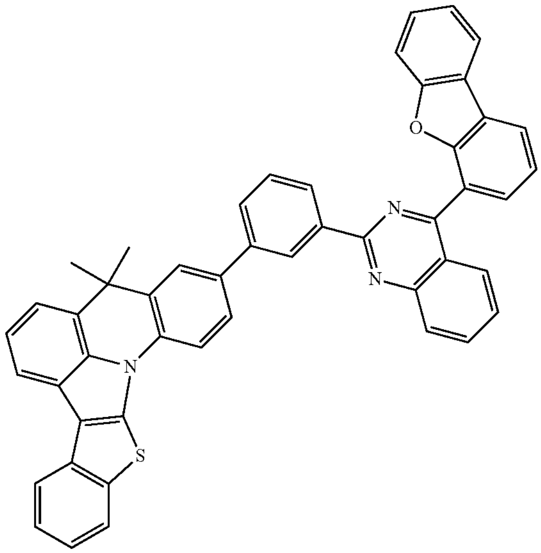

-continued
HAC15
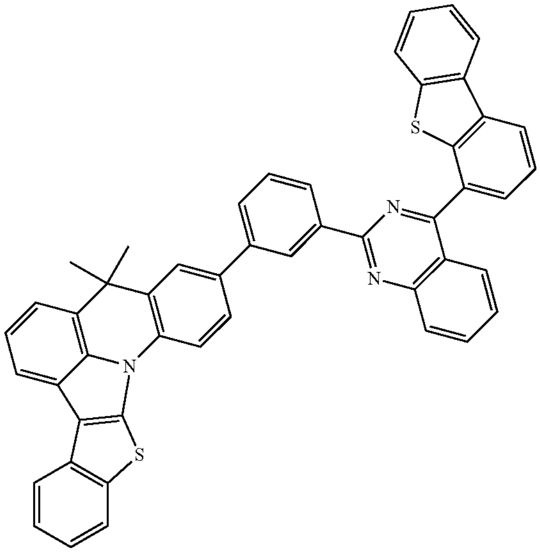
HAC16
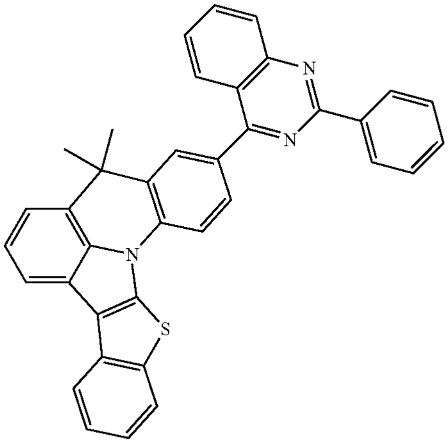
HAC17
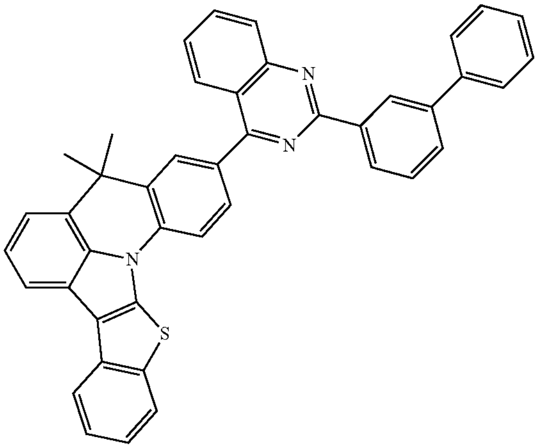
-continued
HAC18
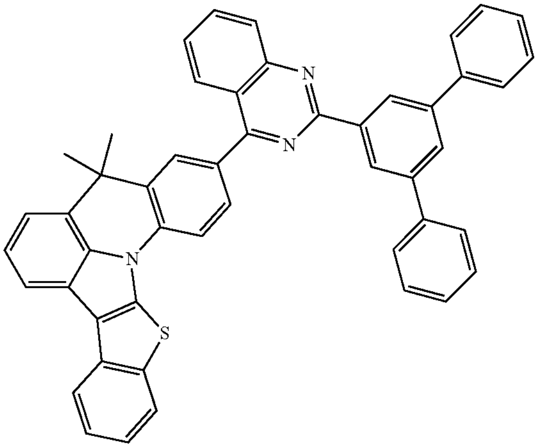
HAC19
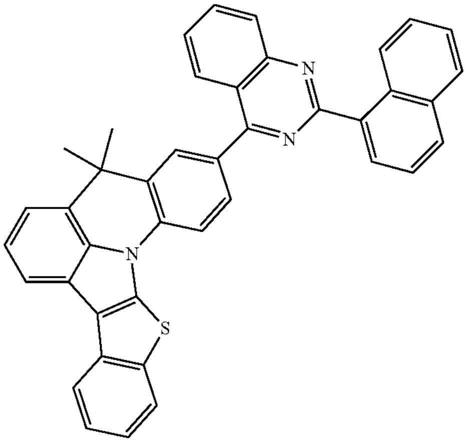
HAC20
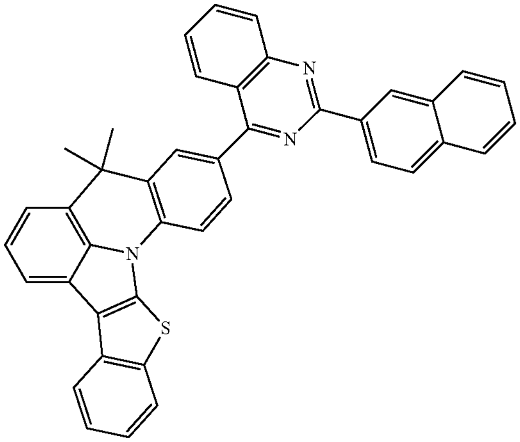

-continued
HAC21
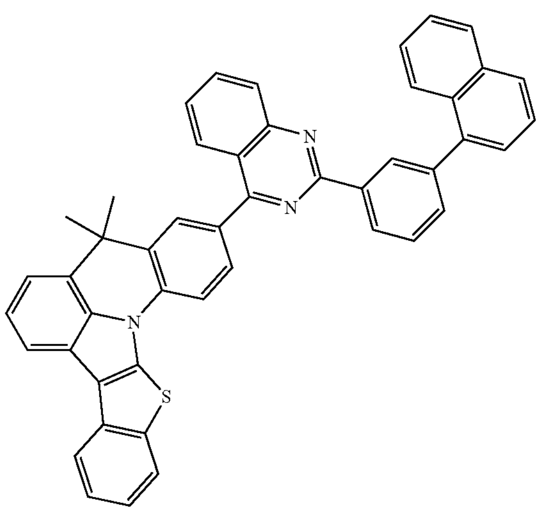
HAC22
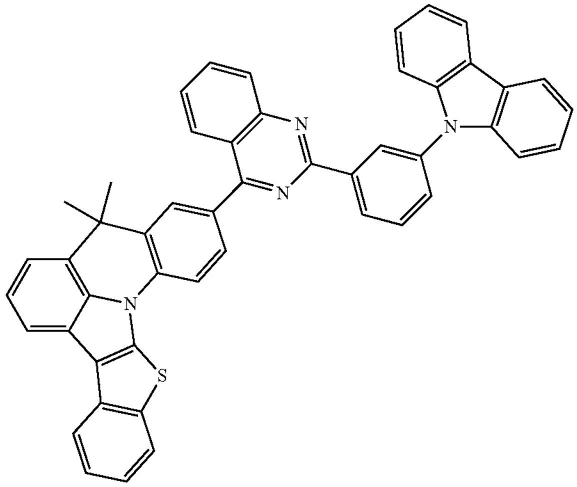
HAC23
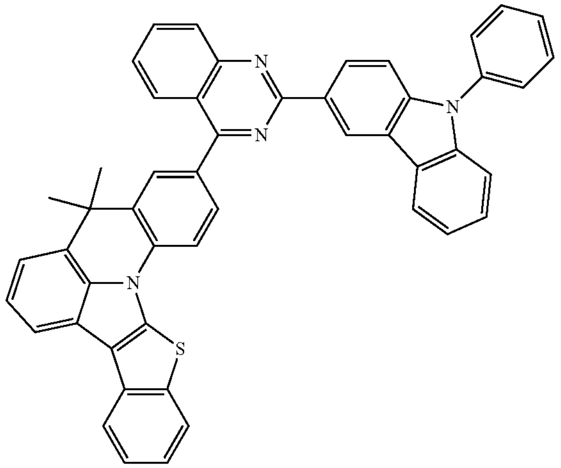
-continued
HAC24
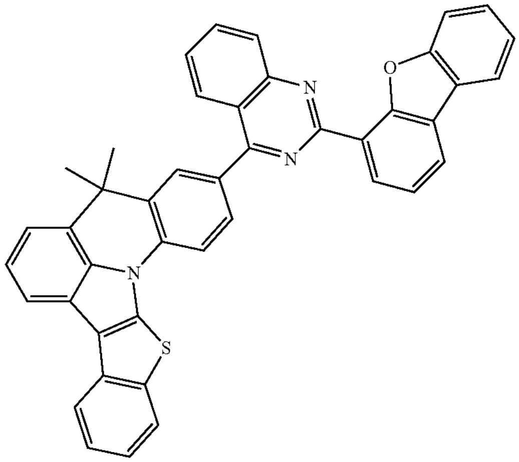
HAC25
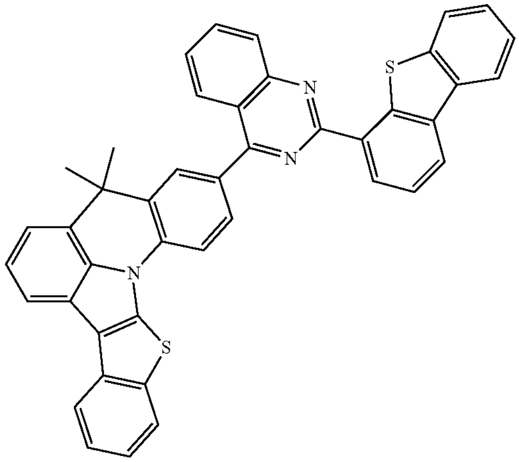
HAC26
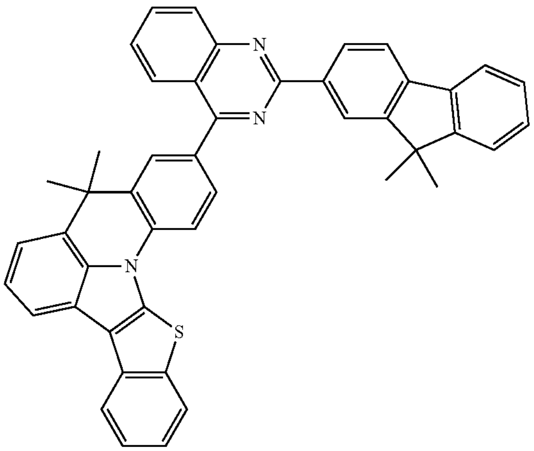

-continued
HAC27
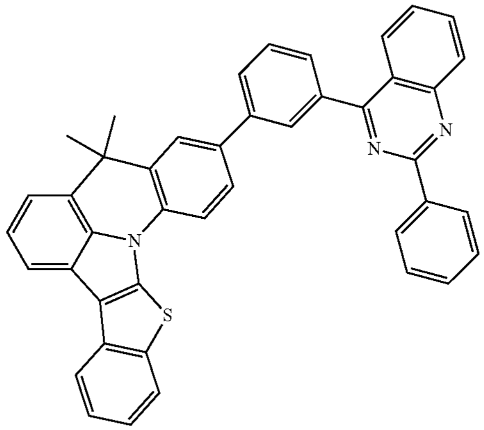
HAC28
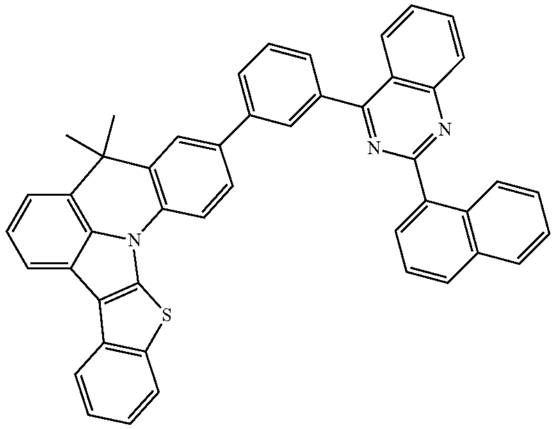
HAC29
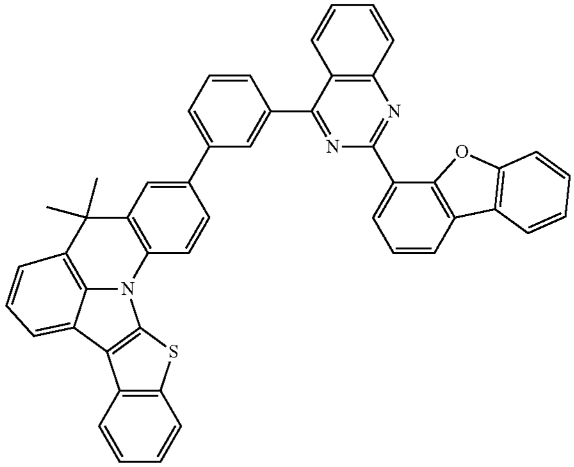
-continued
HAC30
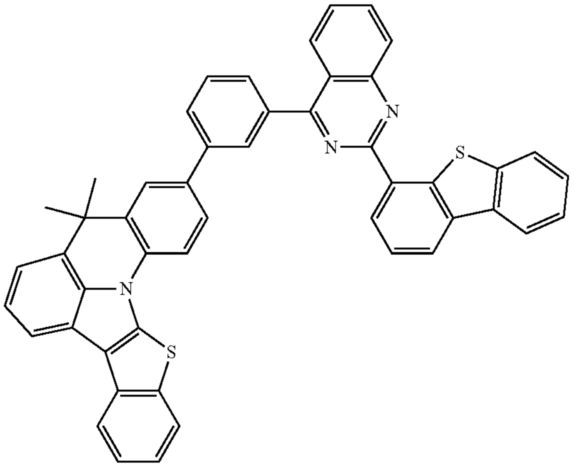
HAC31
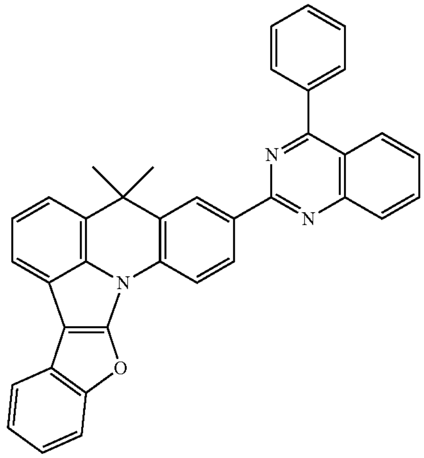
HAC32
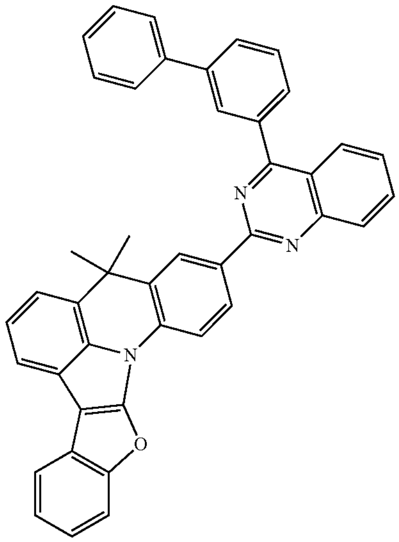

-continued
HAC33
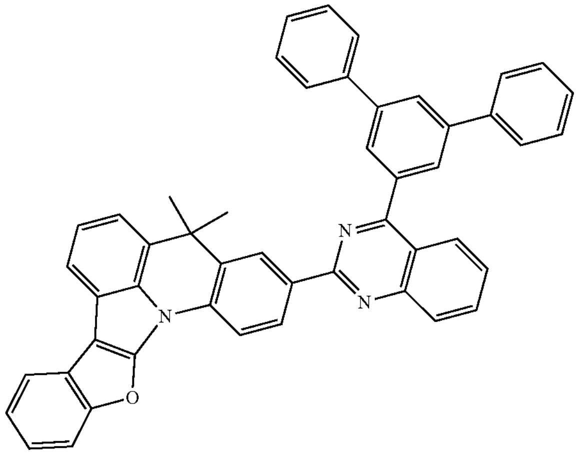
HAC34
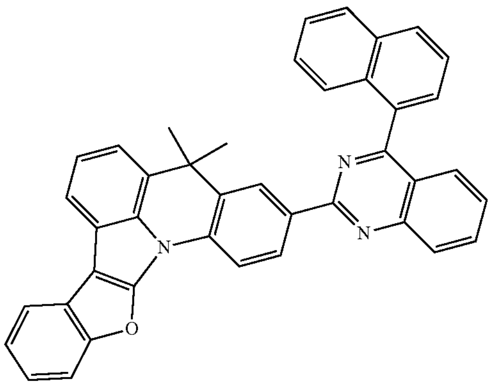
HAC35
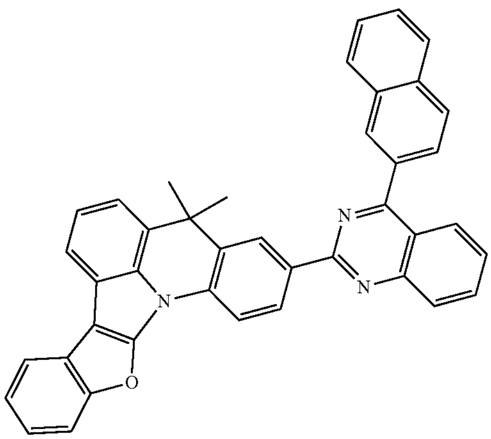
-continued
HAC36
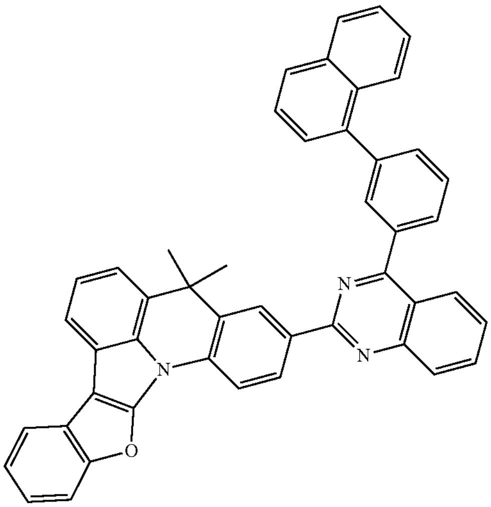
HAC37
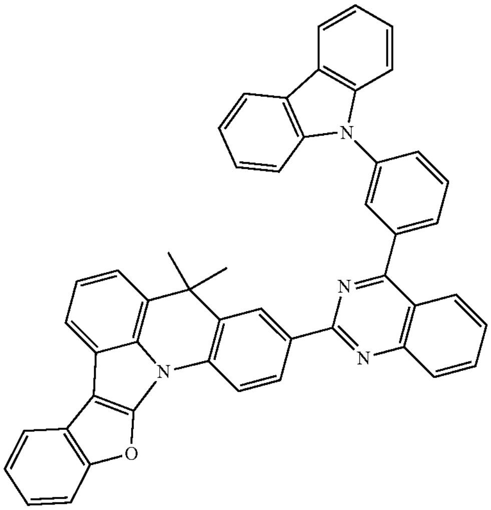
HAC38
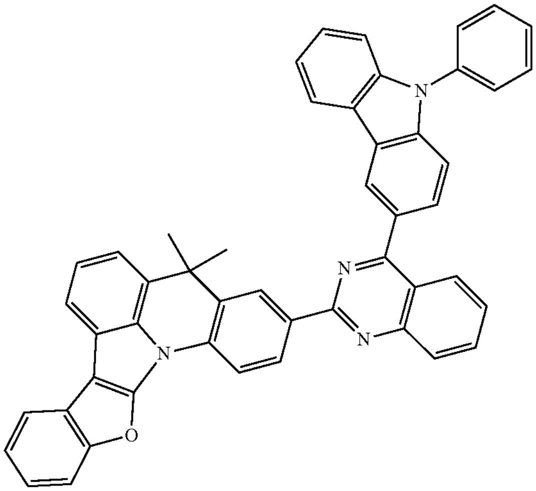

-continued
HAC39
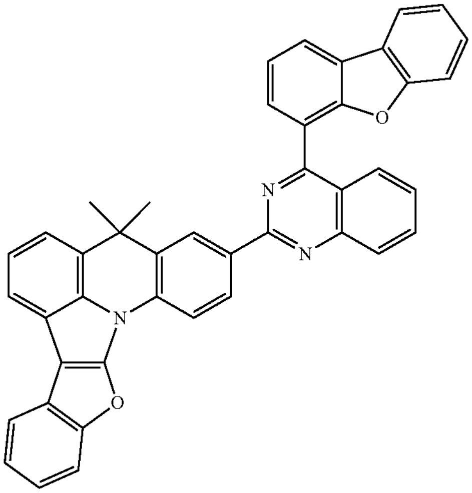
HAC40
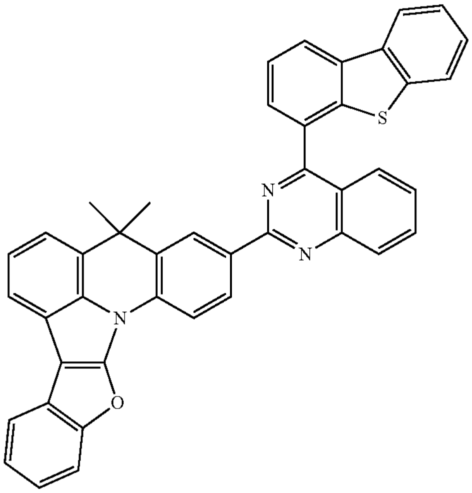
HAC41
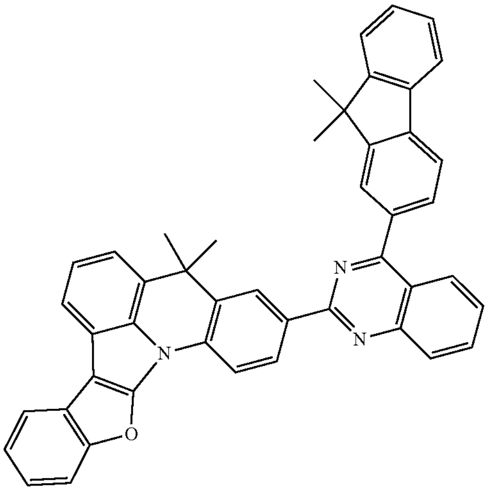
-continued
HAC42
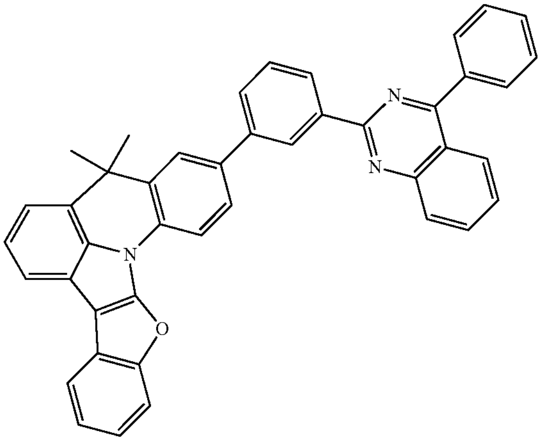
HAC43
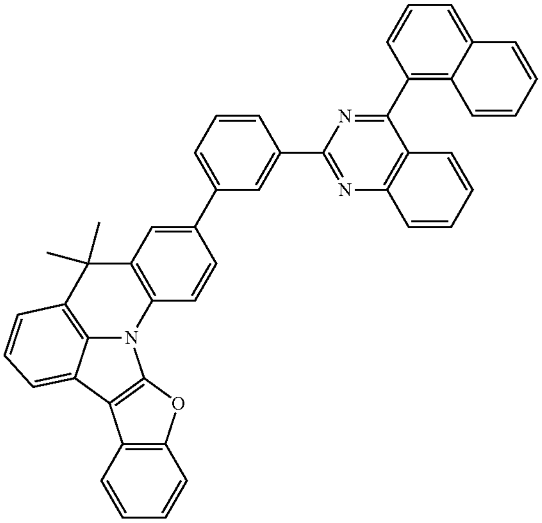
HAC44
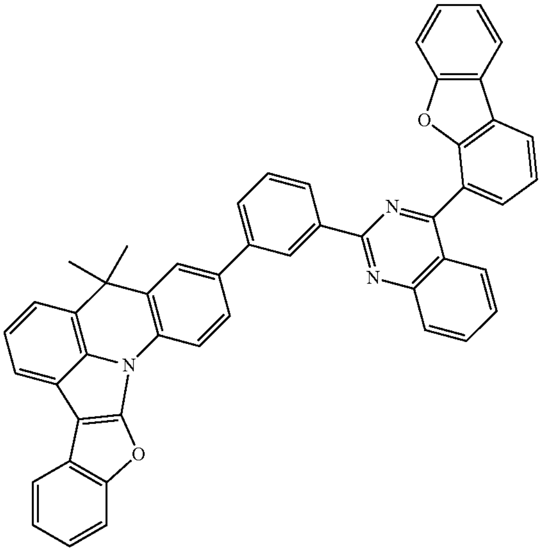

-continued
HAC45
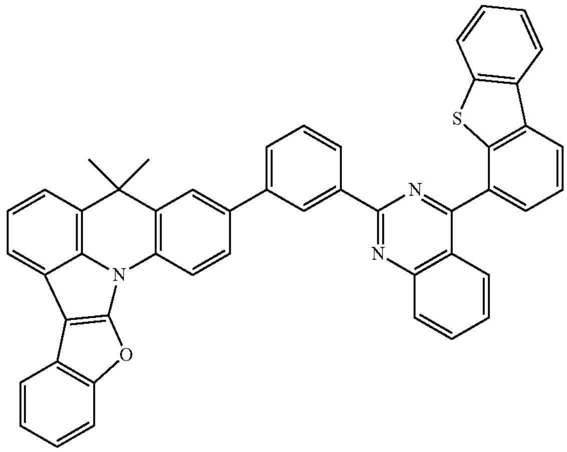
HAC46
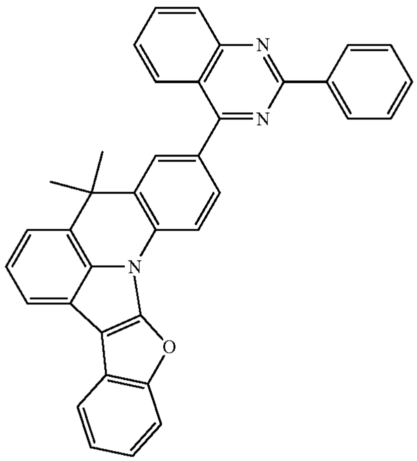
HAC47
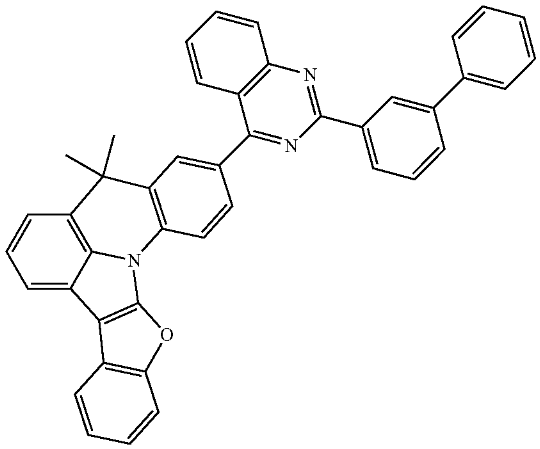
-continued
HAC48
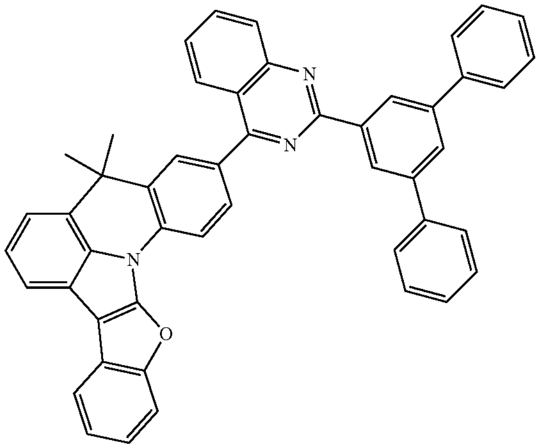
HAC49
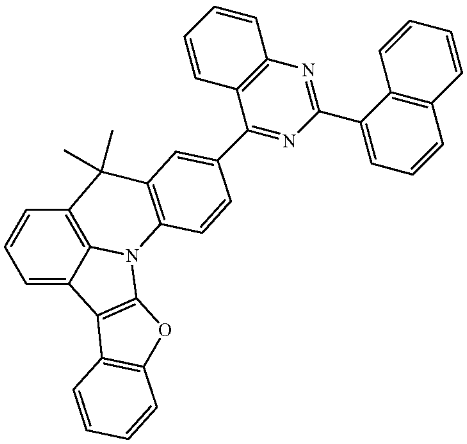
HAC50
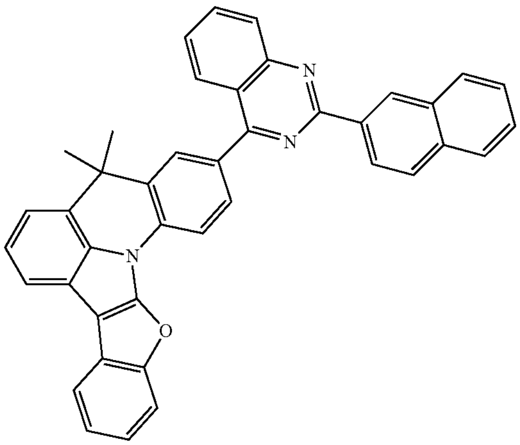

-continued
HAC51
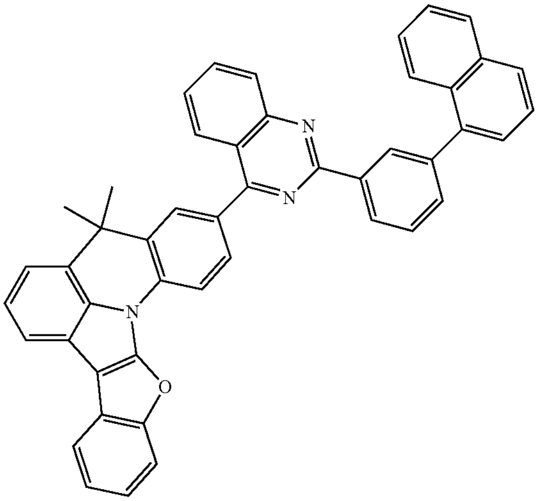
HAC52
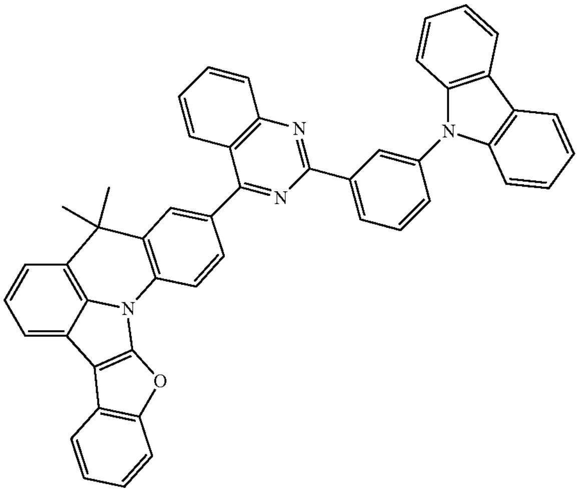
HAC53
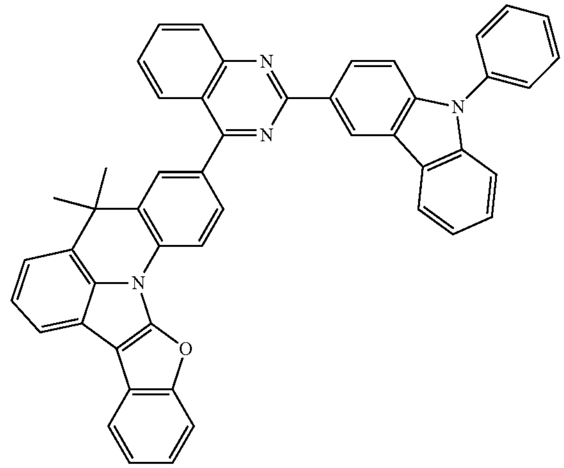
-continued
HAC54
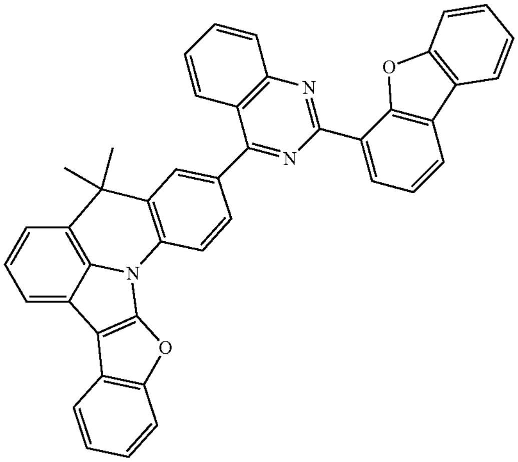
HAC55
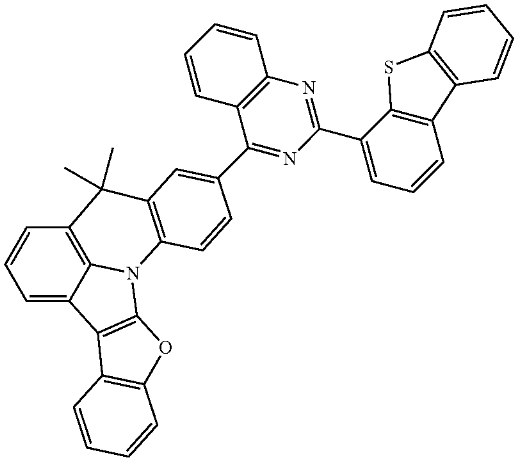
HAC56
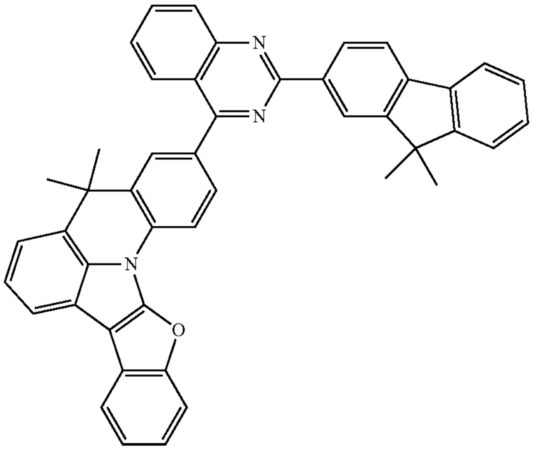

-continued
HAC57
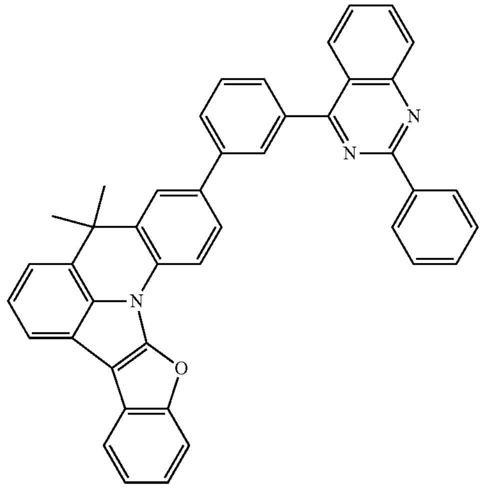
HAC58
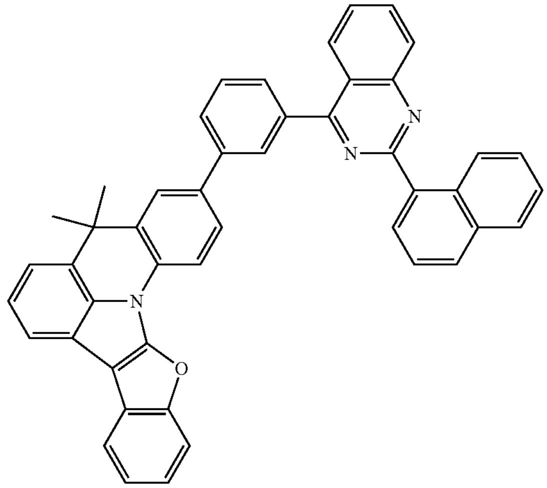
HAC59
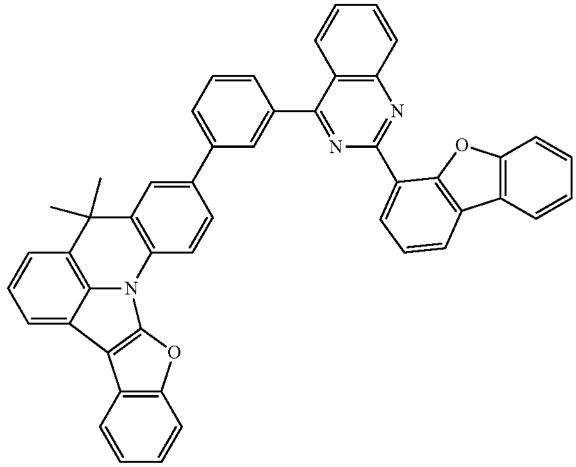
-continued
HAC60
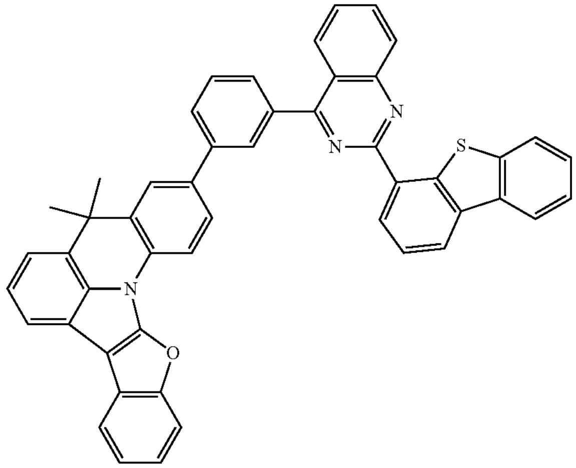
HAC61
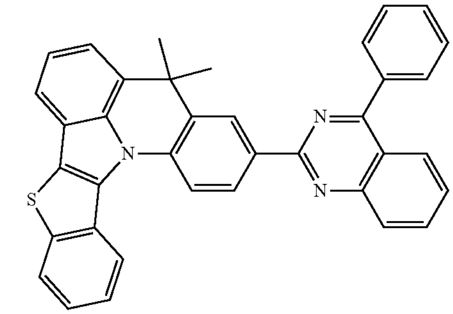
HAC62
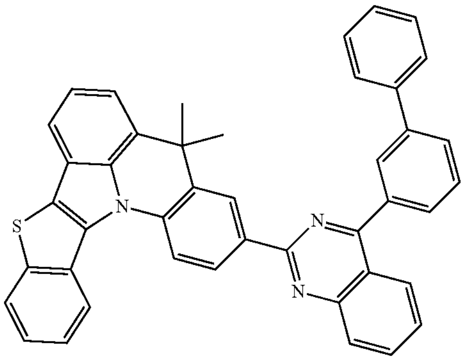
HAC63
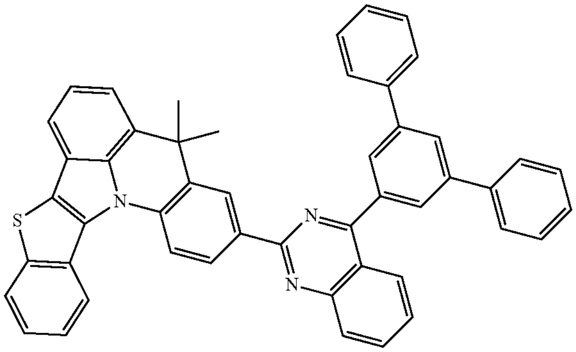

-continued
HAC64
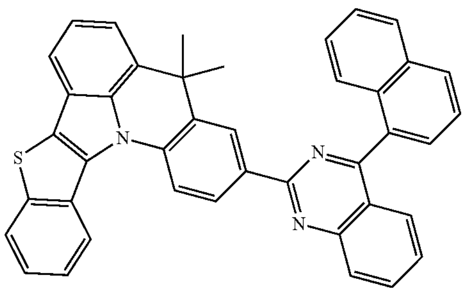
HAC65
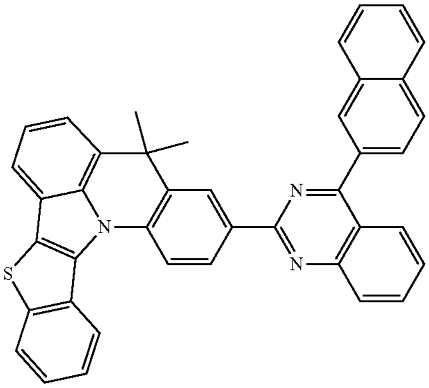
HAC66
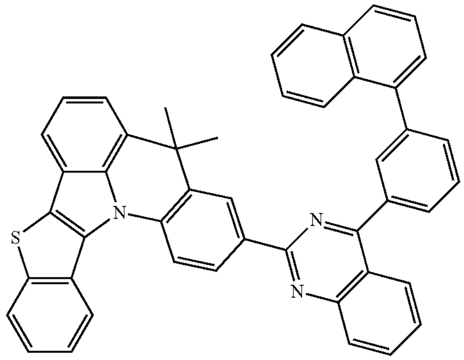
HAC67
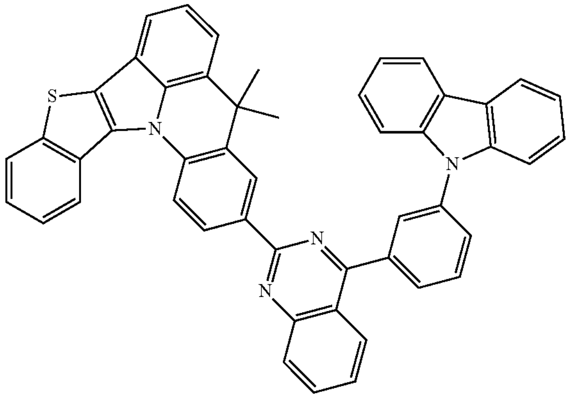
-continued
HAC68
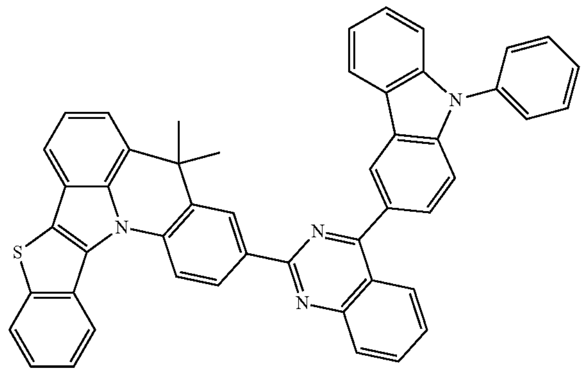
HAC69
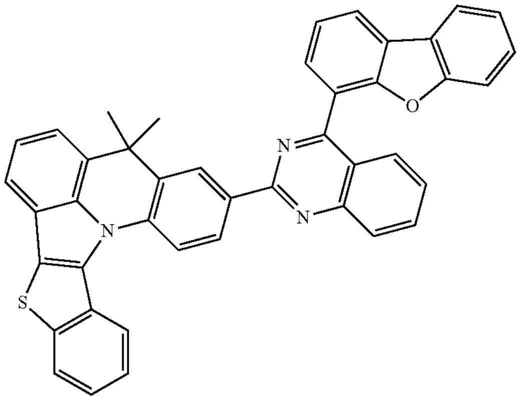
HAC70
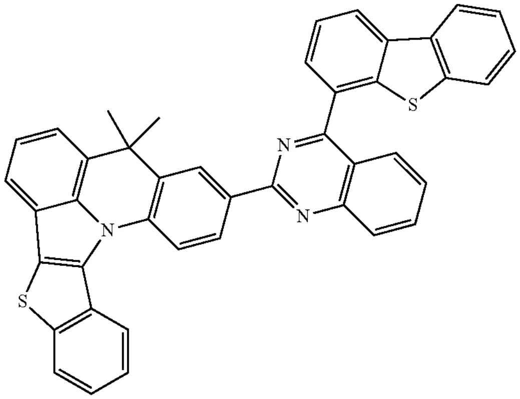

-continued
HAC71
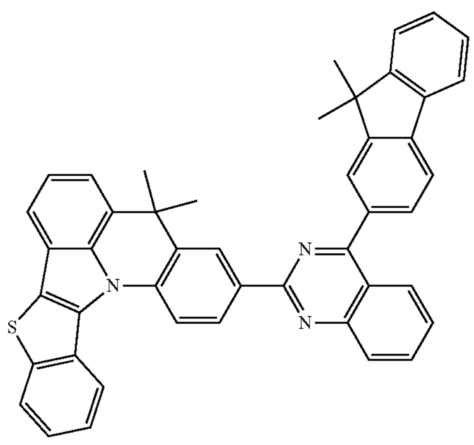
HAC72
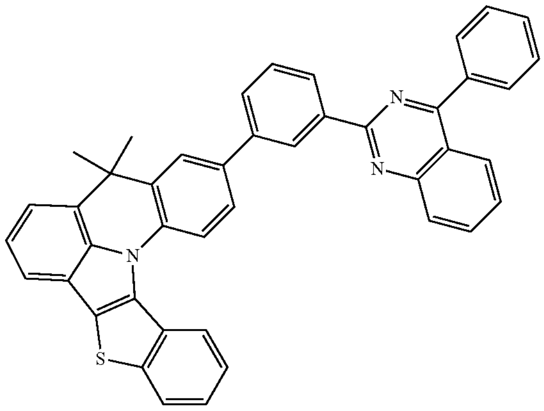
HAC73
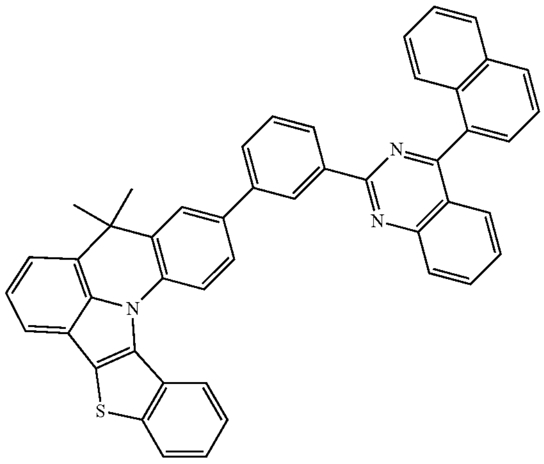
-continued
HAC74
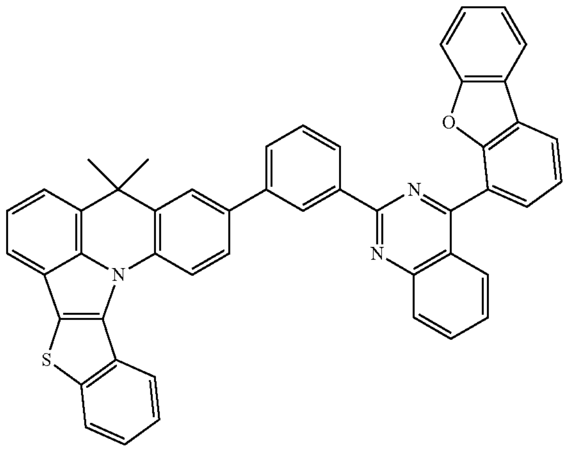
HAC75
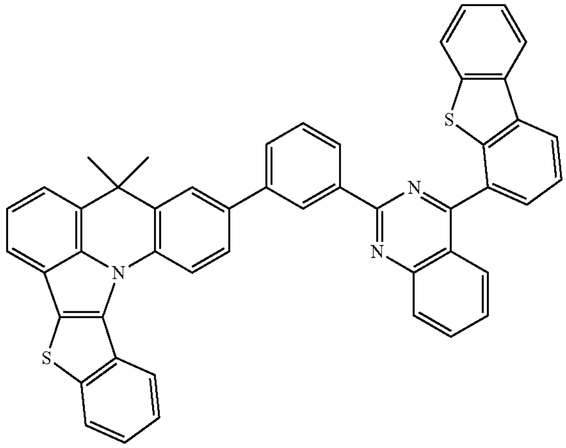
HAC76
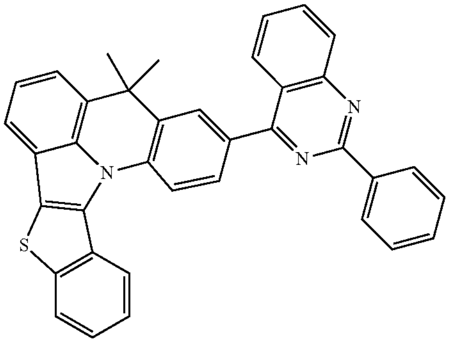

-continued
HAC77
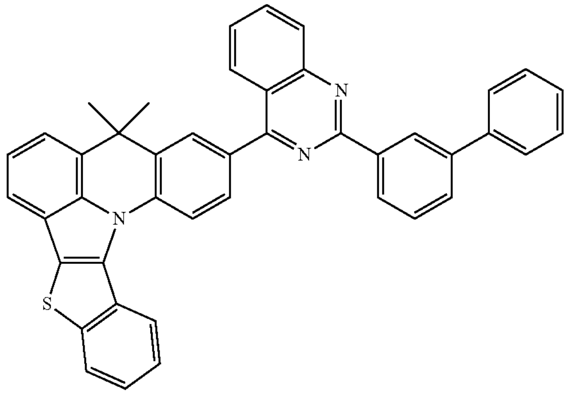
HAC78
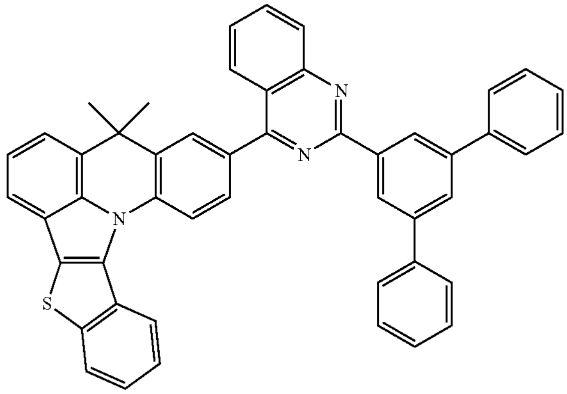
HAC79
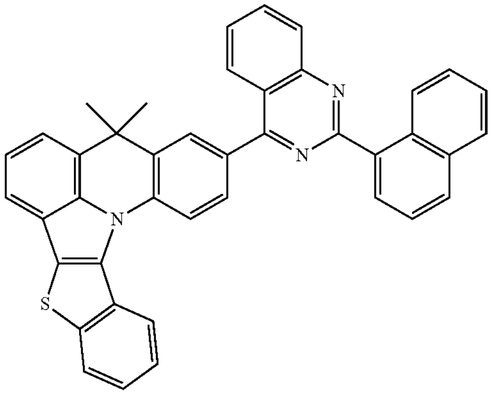
-continued
HAC80
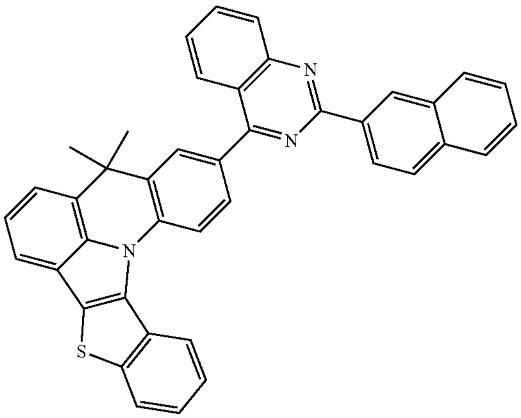
HAC81
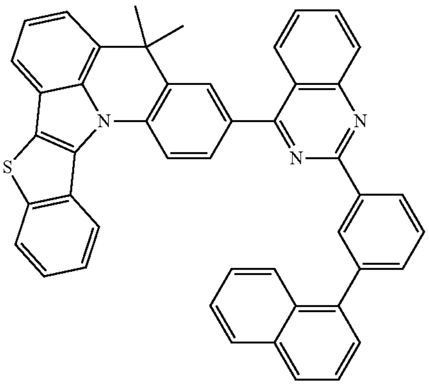
HAC82
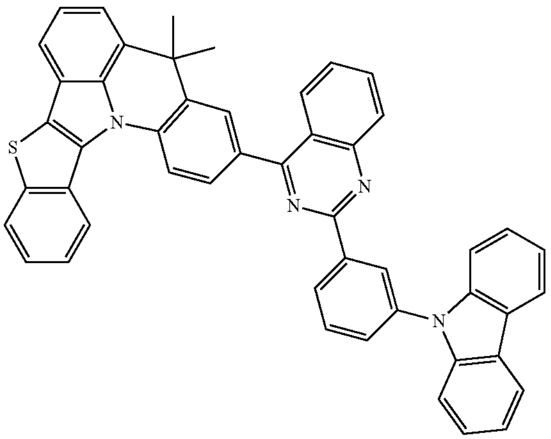

-continued
HAC83
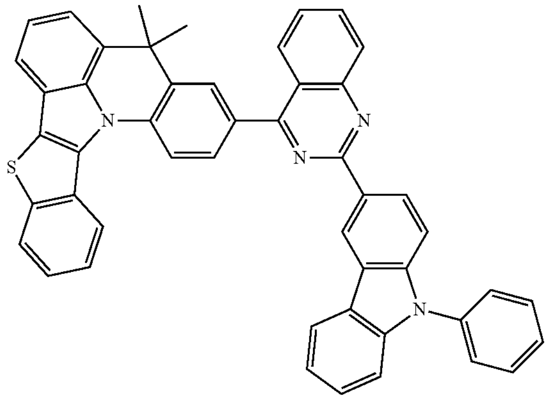
HAC84
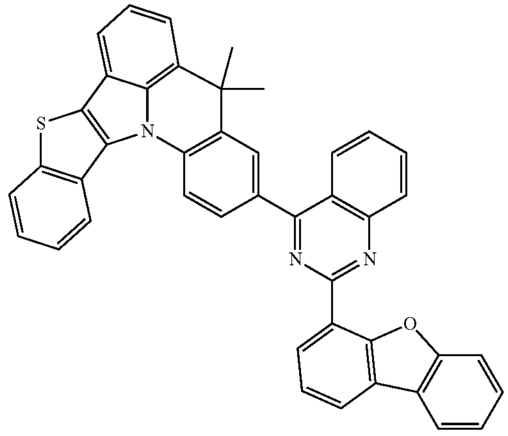
HAC85
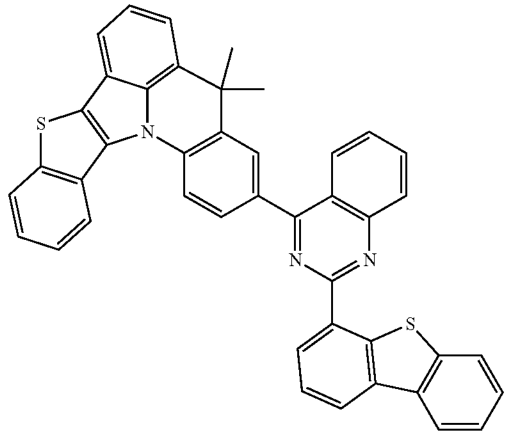
-continued
HAC86
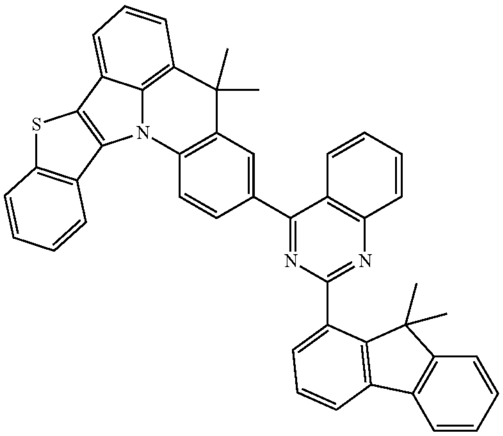
HAC87
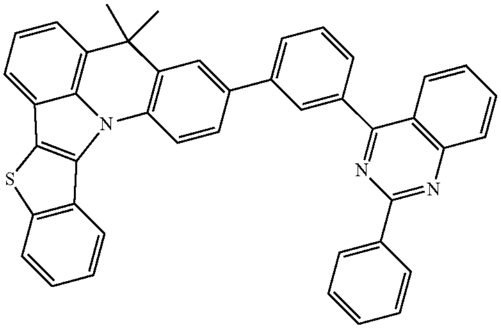
HAC88
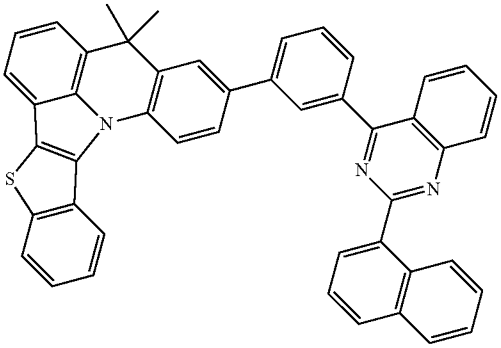
HAC89
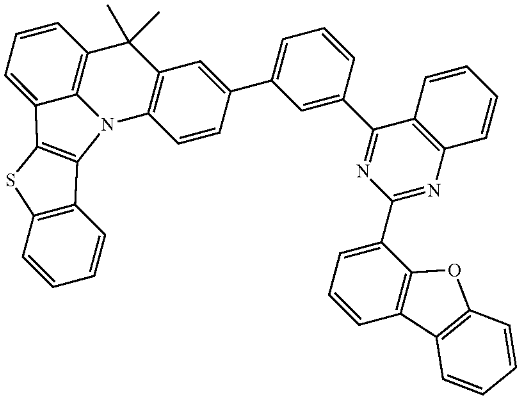

-continued
HAC90
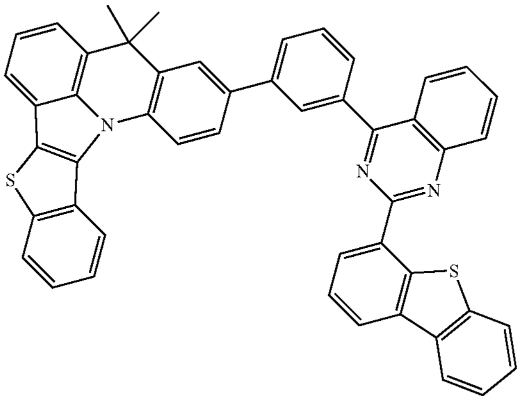
HAC91
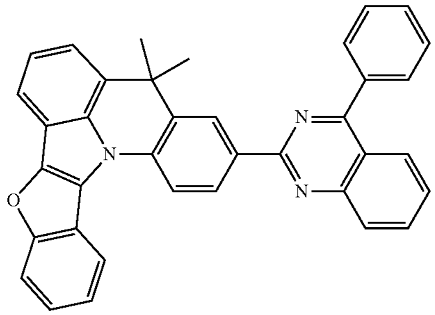
HAC92
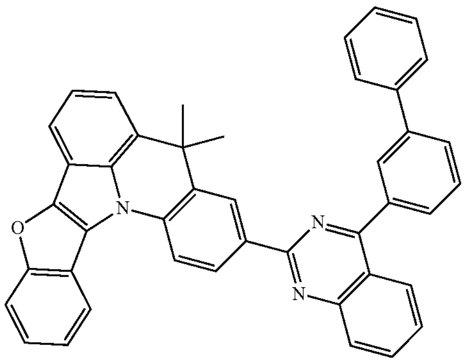
HAC93
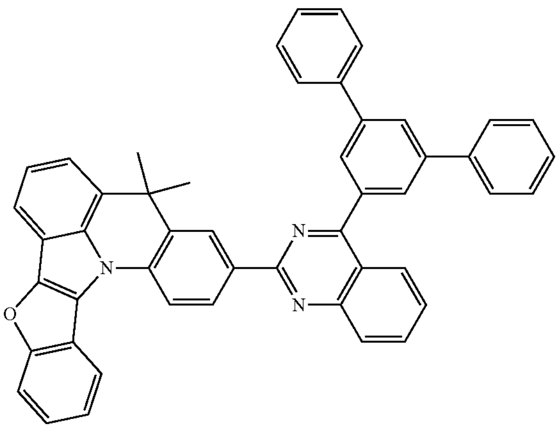
-continued
HAC94
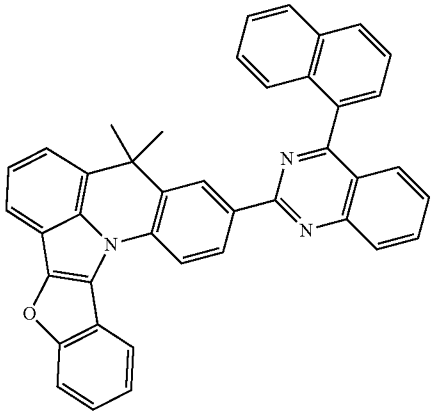
HAC95
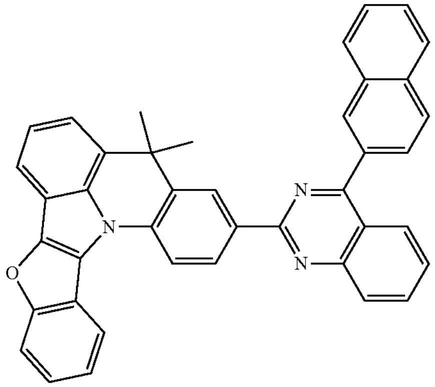
HAC96
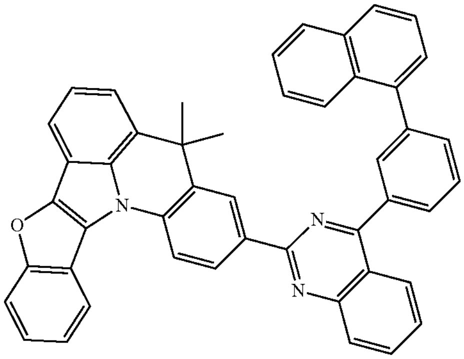
HAC97
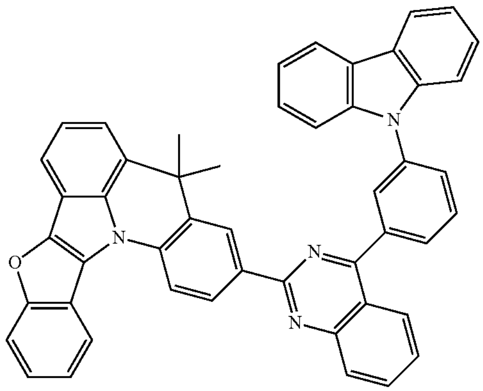

-continued
HAC98
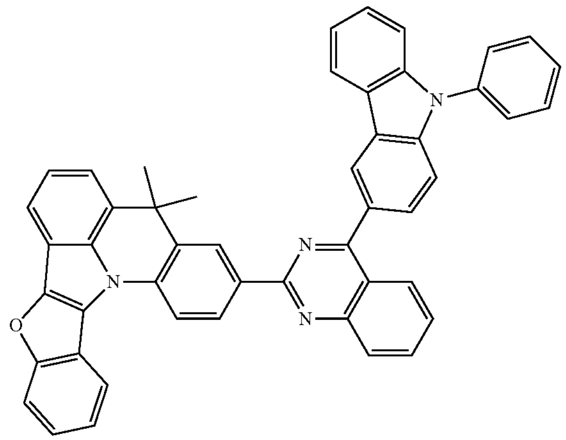
HAC99
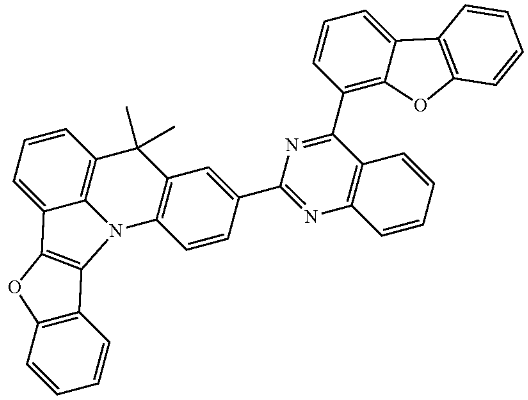
HAC100
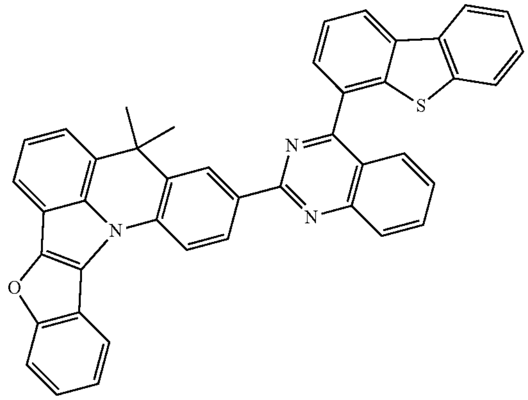
-continued
HAC101
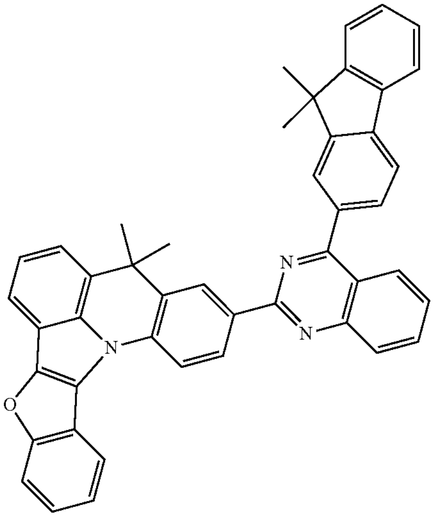
HAC102
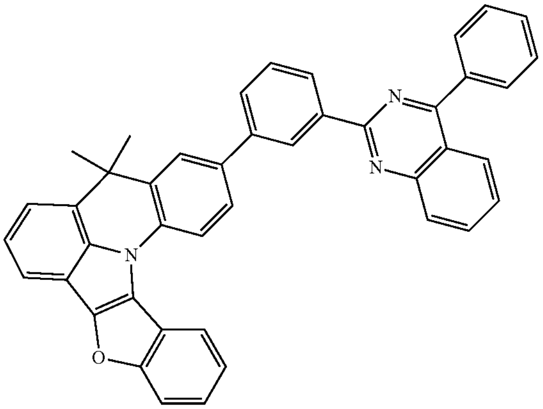
HAC103
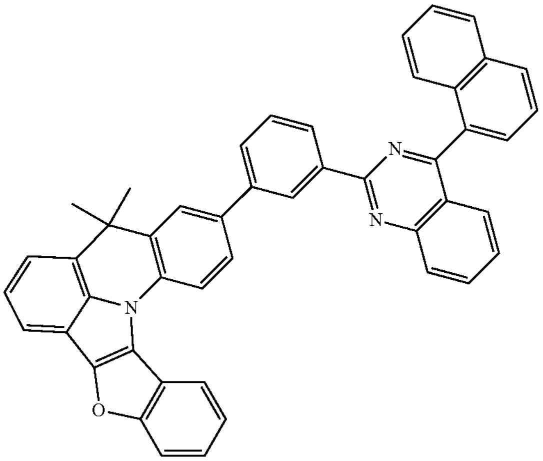

-continued
HAC104
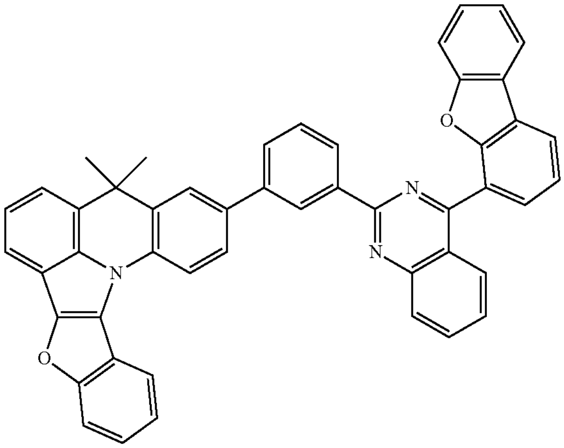
HAC105
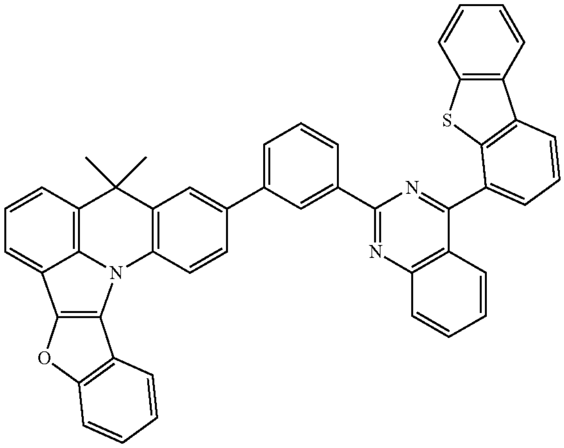
HAC106
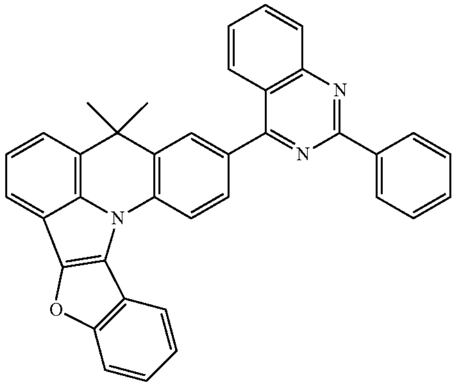
-continued
HAC107
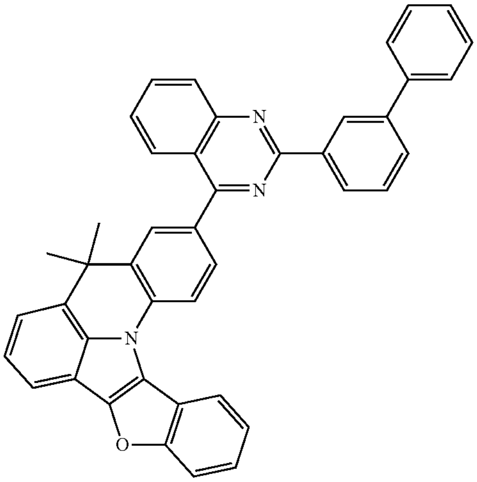
HAC108
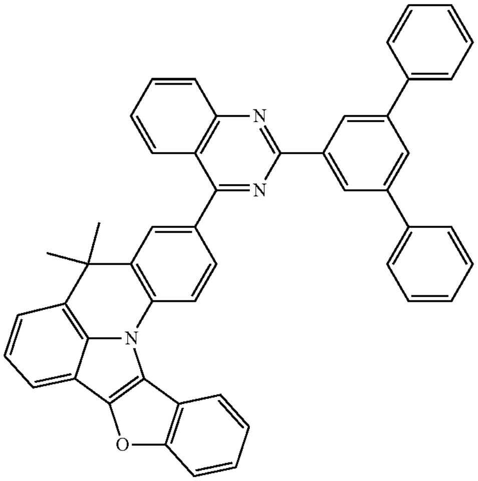
HAC109
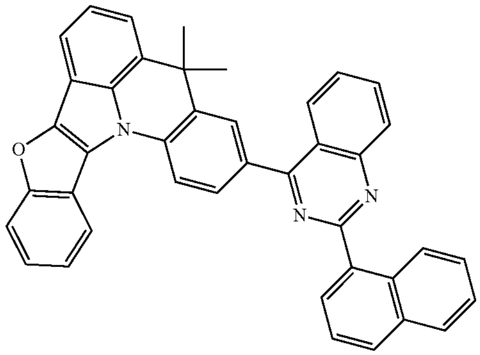

-continued
HAC110
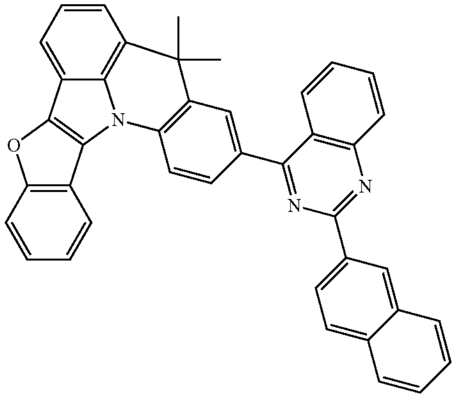
HAC111
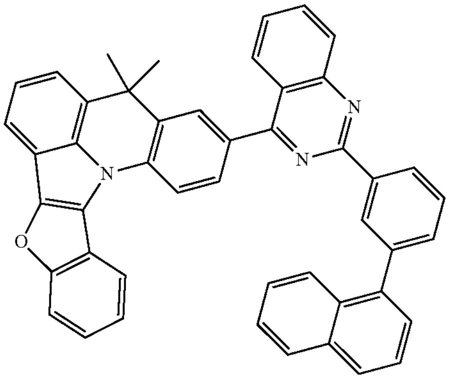
HAC112
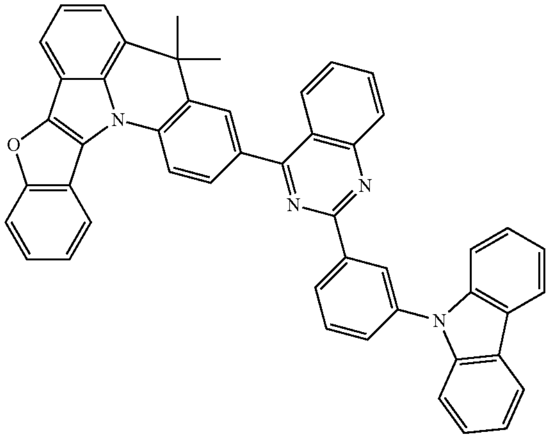
-continued
HAC113
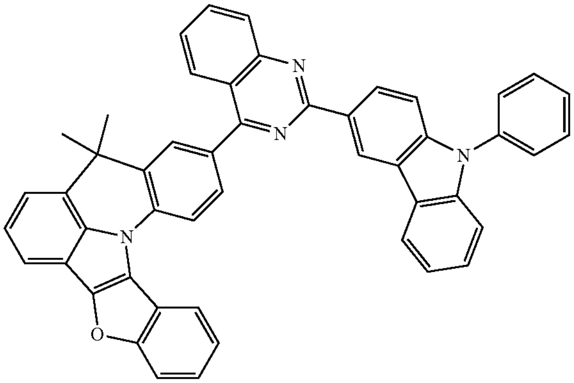
HAC114
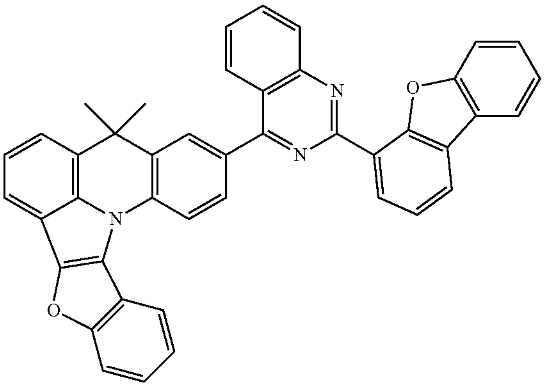
HAC115
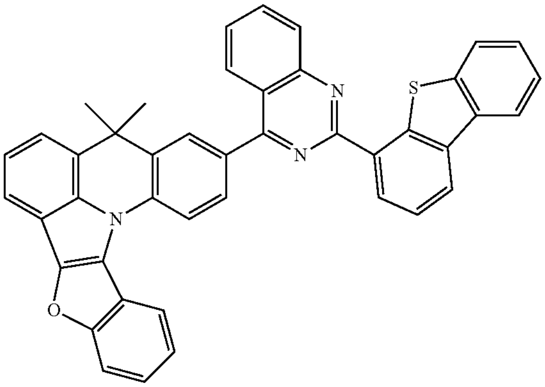
HAC116
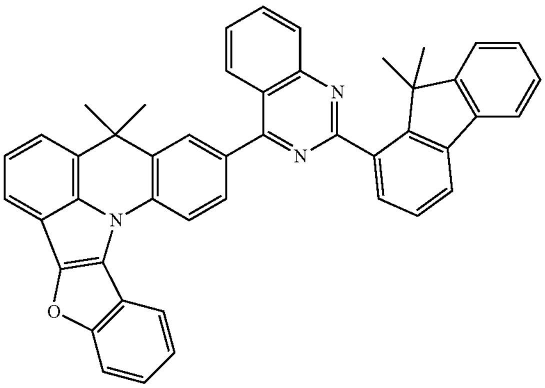

-continued
HAC117
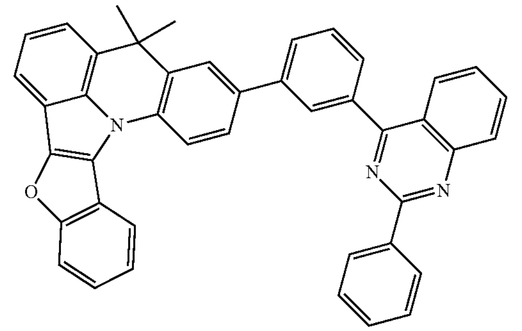
HAC118
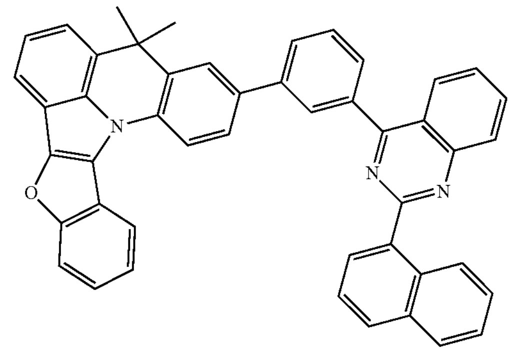
HAC119
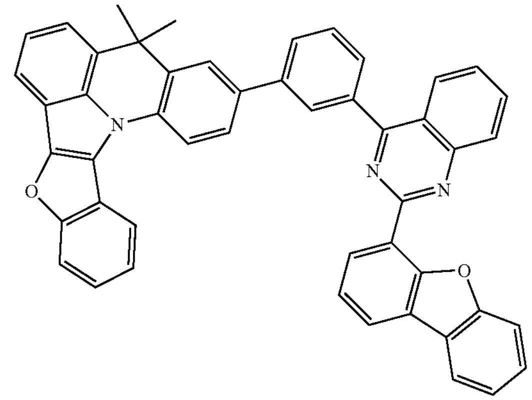
HAC120
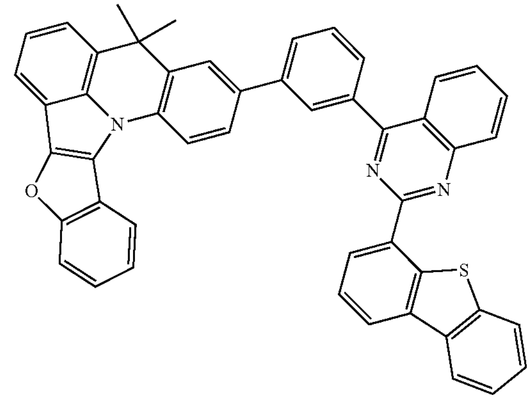
-continued
HAC121
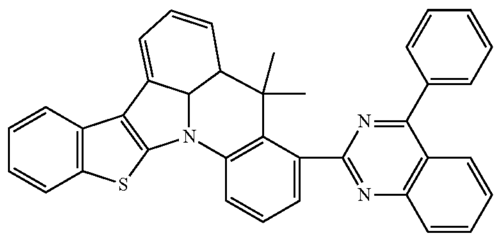
HAC122
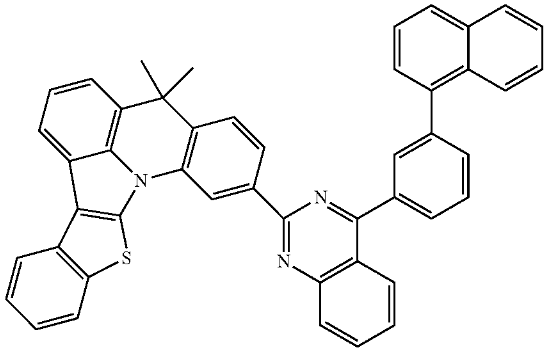
HAC123
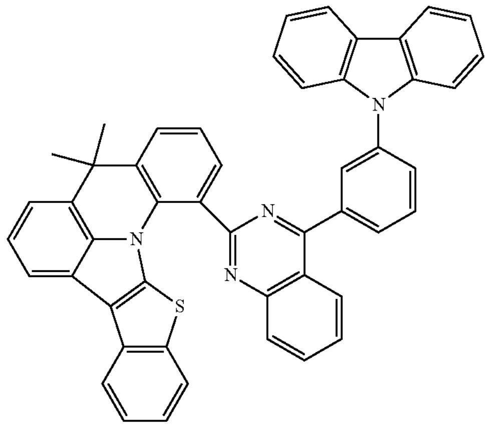
HAC124
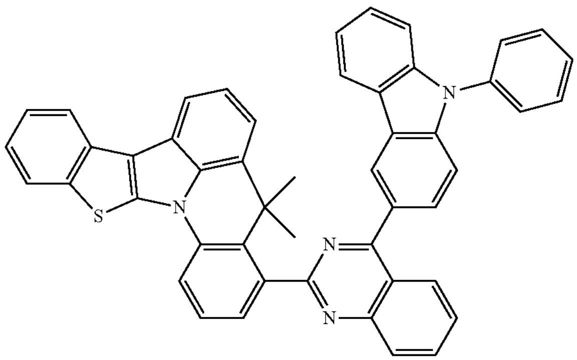

-continued
HAC125
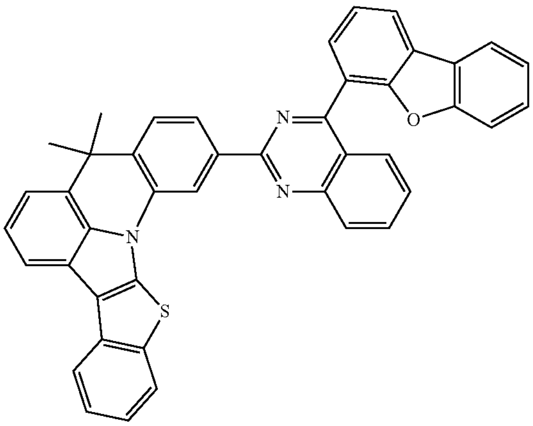
HAC126
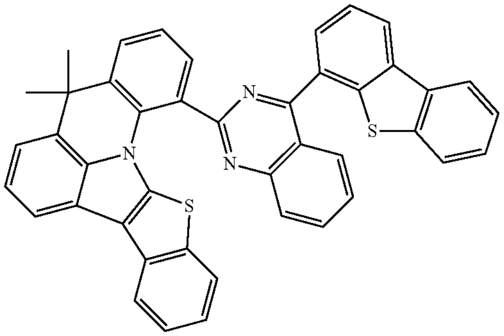
HAC127
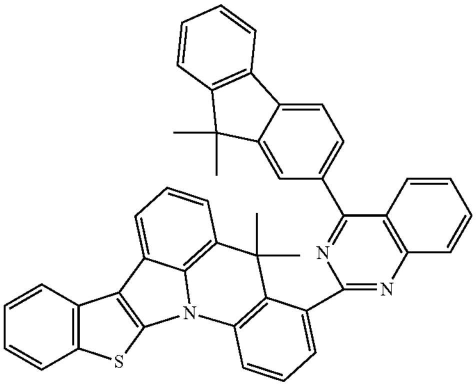
HAC128
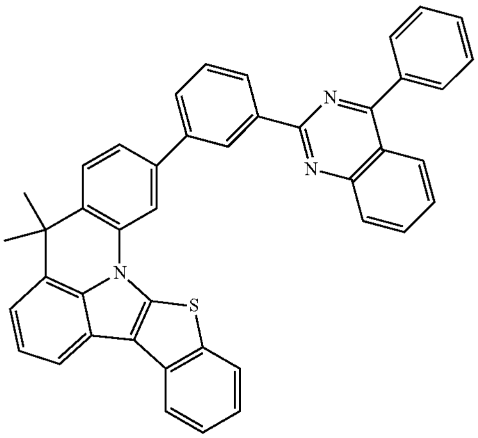
-continued
HAC129
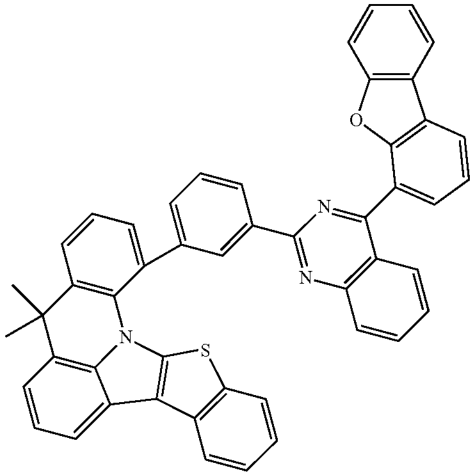
HAC130
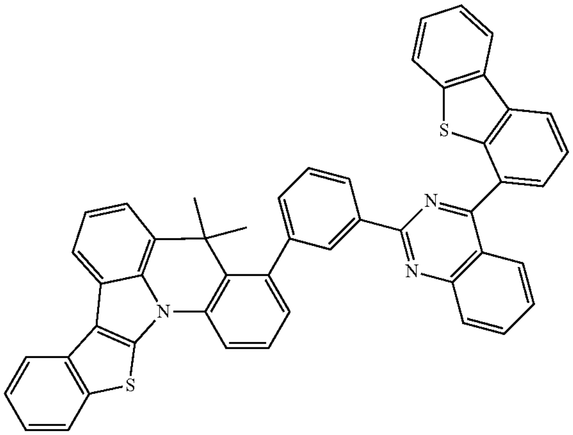
HAC131
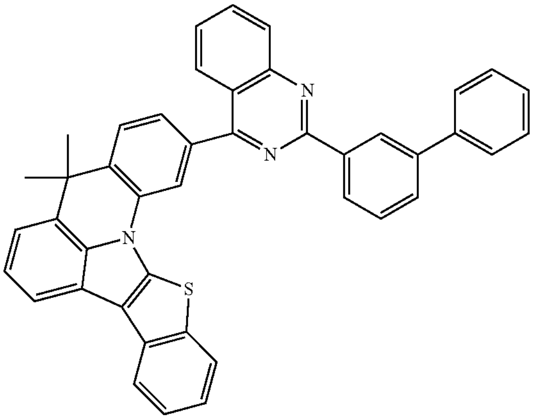

-continued
HAC132
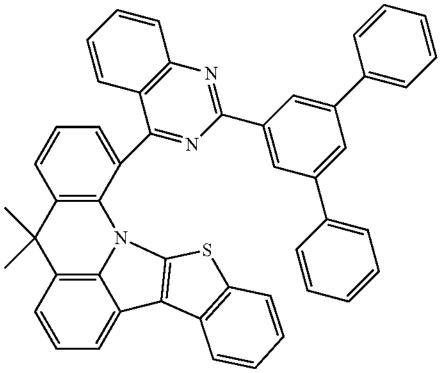
HAC133
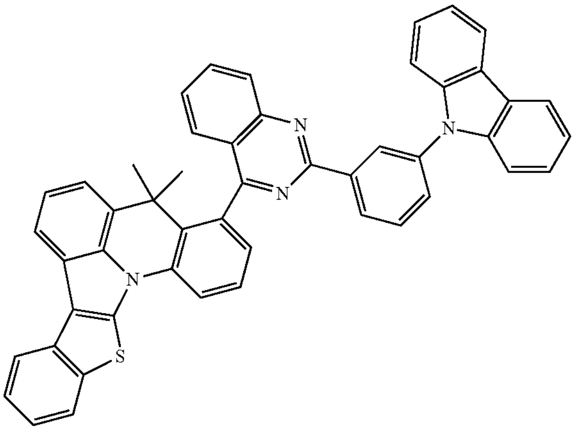
HAC134
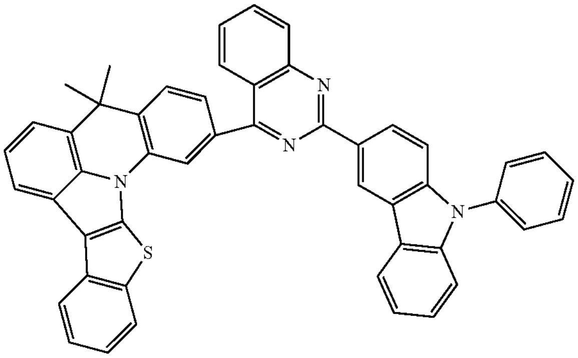
HAC135
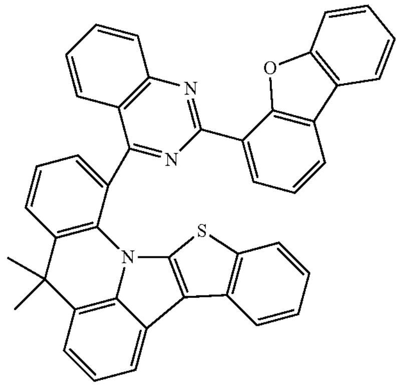
-continued
HAC136
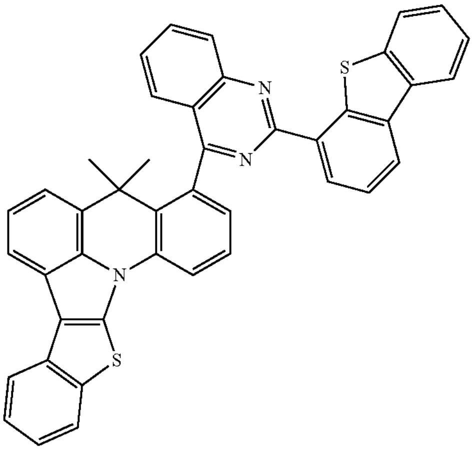
HAC137
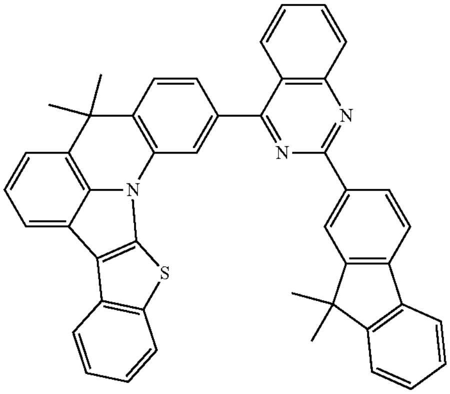
HAC138
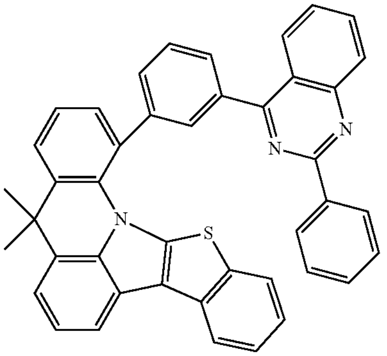
HAC139
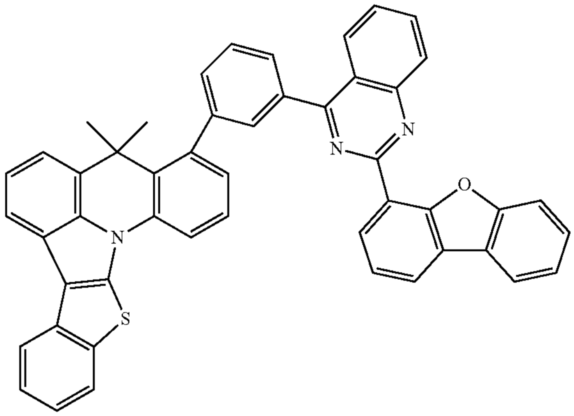

-continued
HAC140
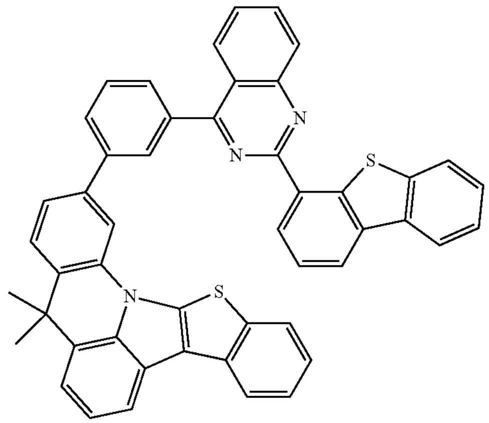
HAC141
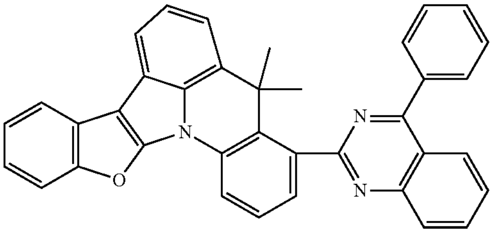
HAC142
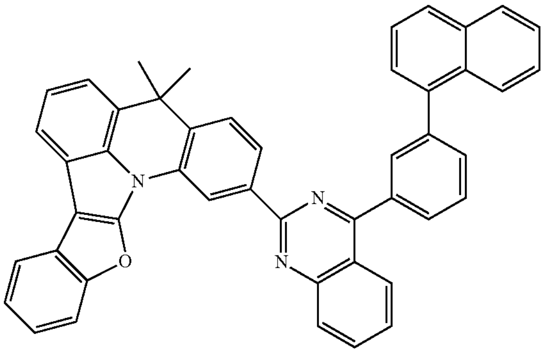
HAC143
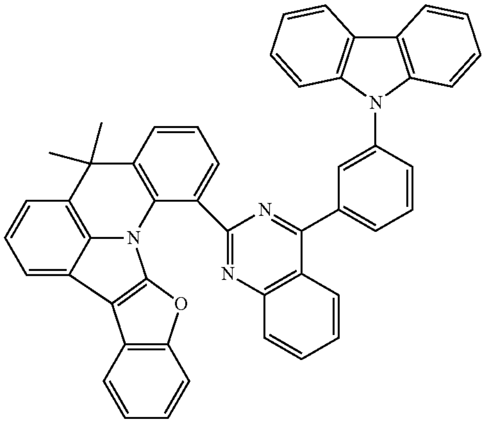
-continued
HAC144
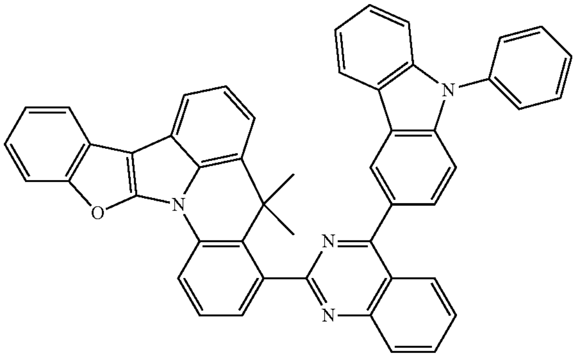
HAC145
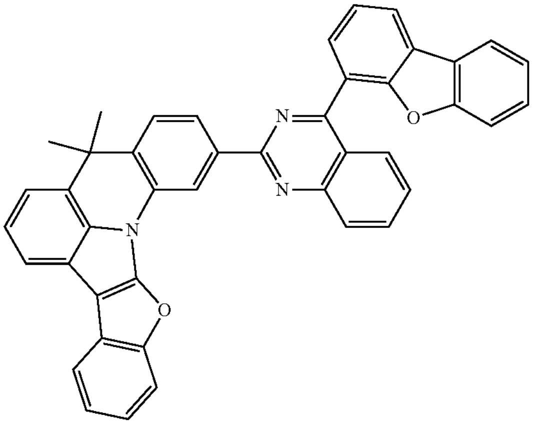
HAC146
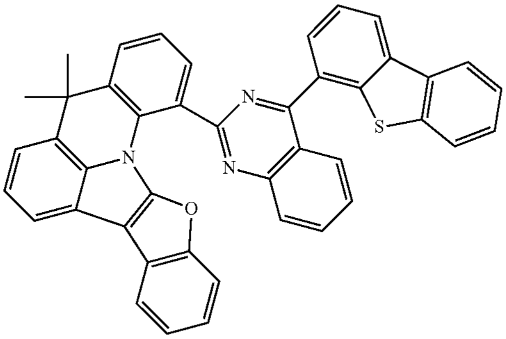
HAC147
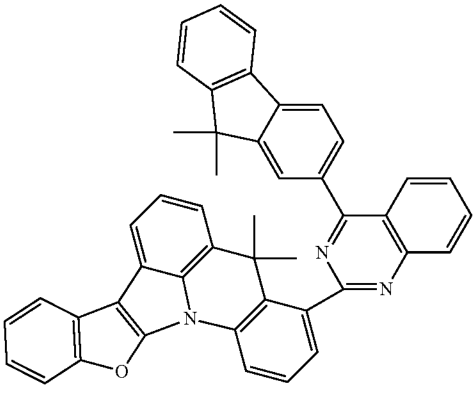

-continued
HAC148
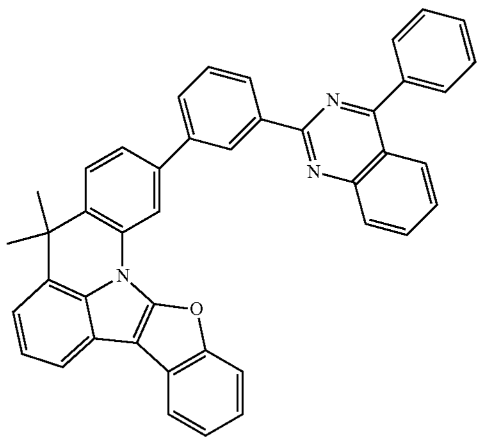
HAC149
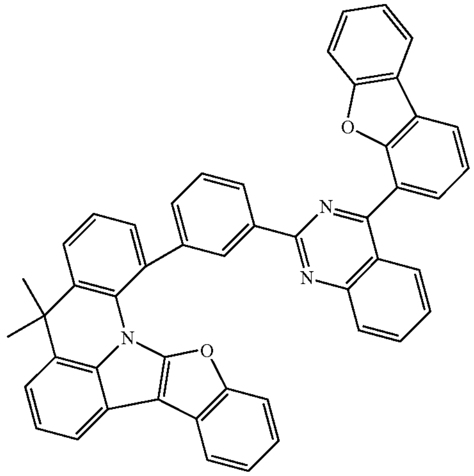
HAC150
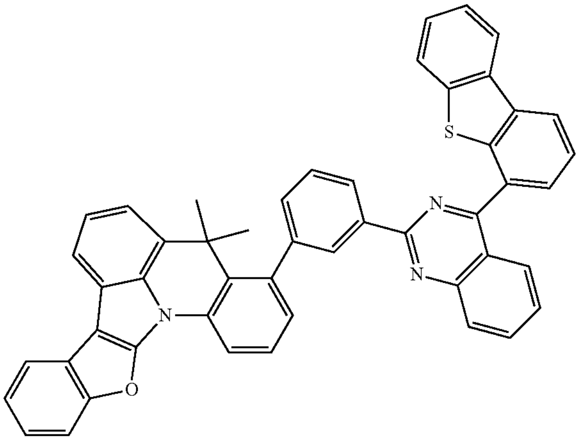
-continued
HAC151
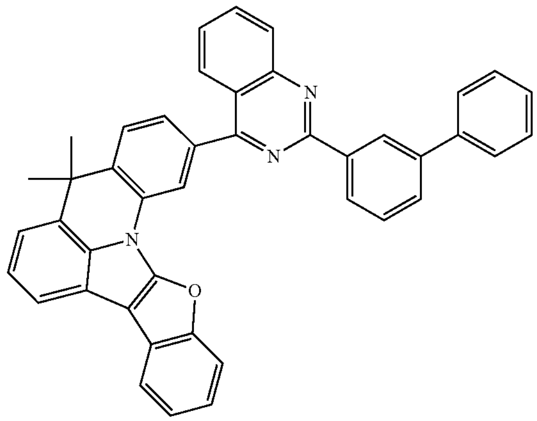
HAC152
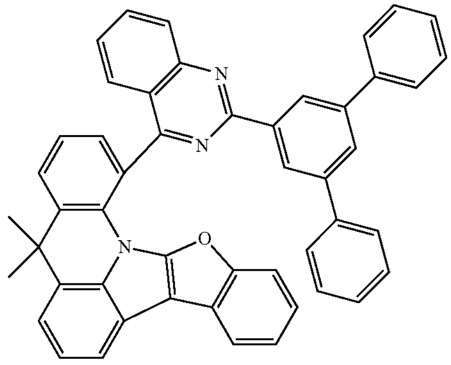
HAC153
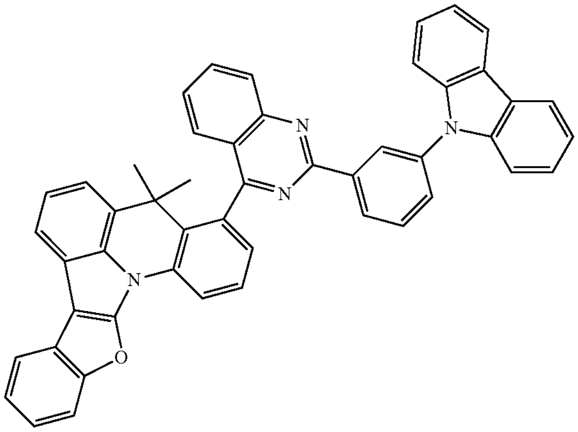

-continued
HAC154
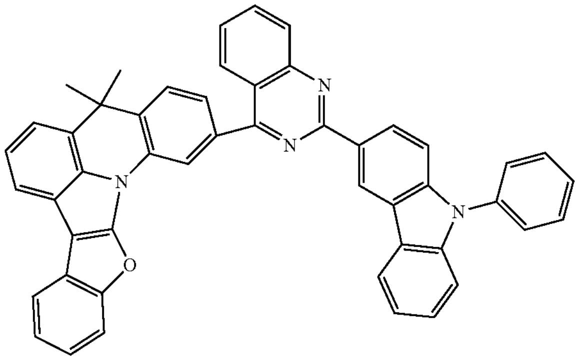
HAC155
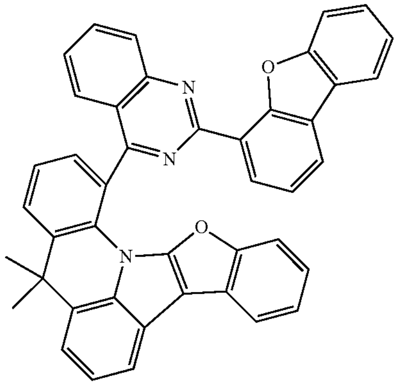
HAC156
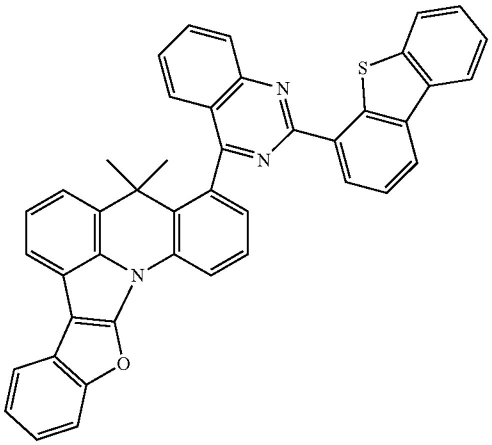
HAC157
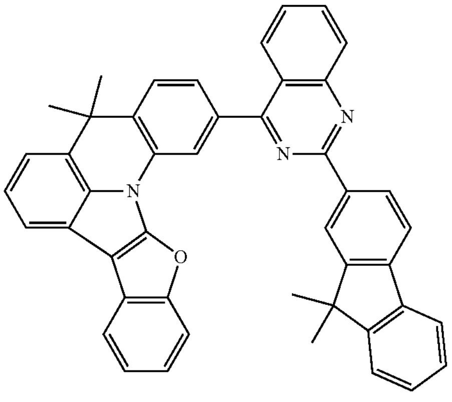
-continued
HAC158
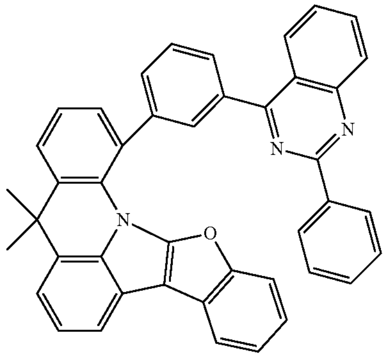
HAC159
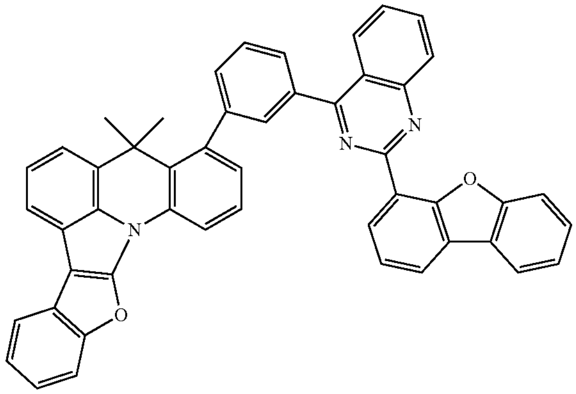
HAC160
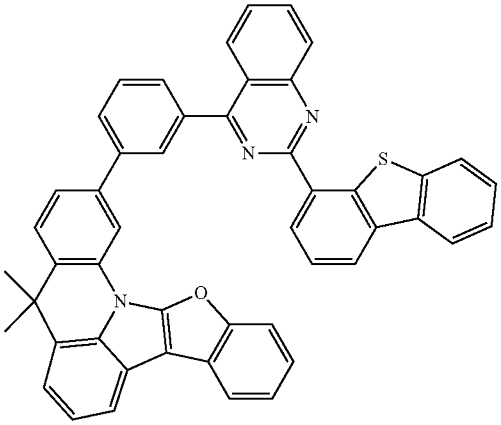
HAC161
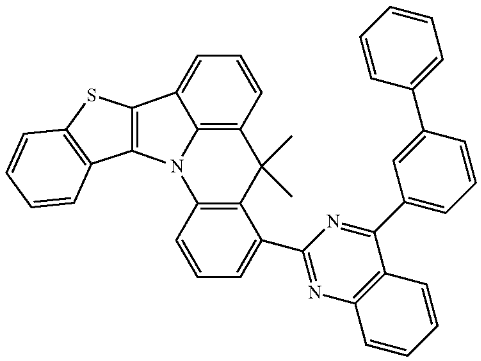

-continued
HAC162
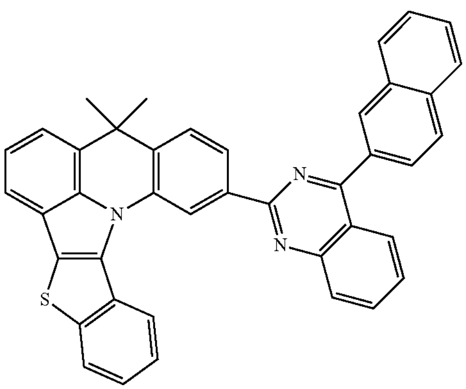
HAC163
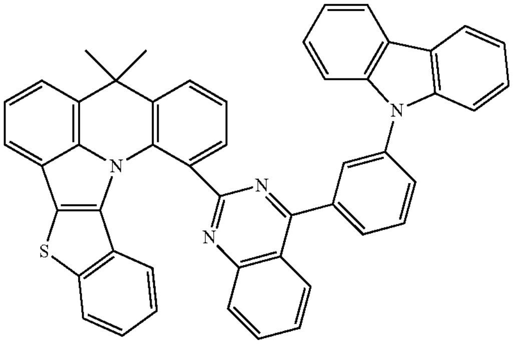
HAC164
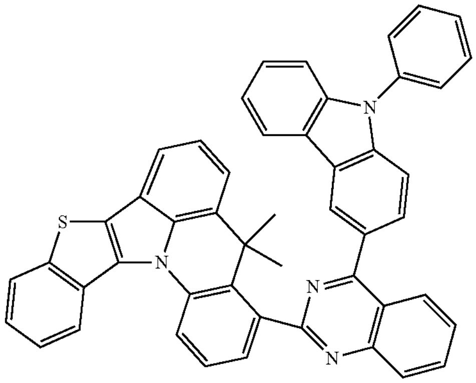
HAC165
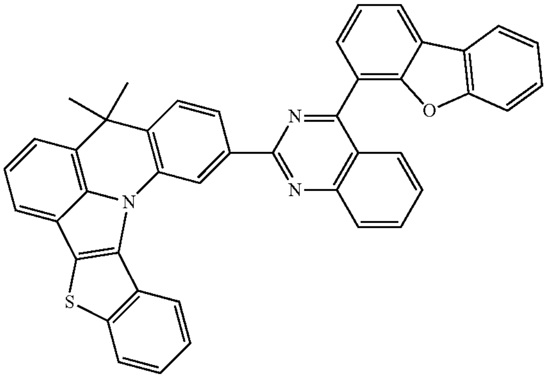
-continued
HAC166
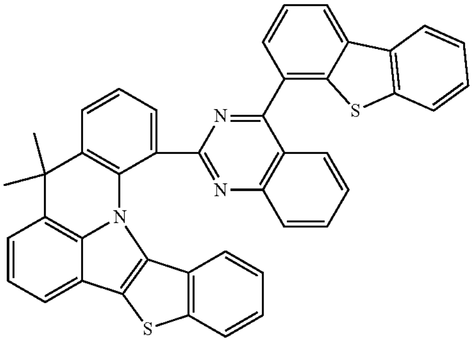
HAC167
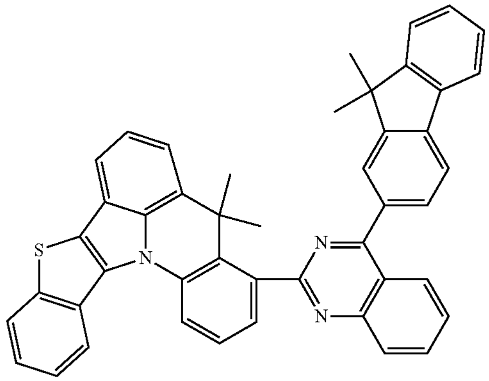
HAC168
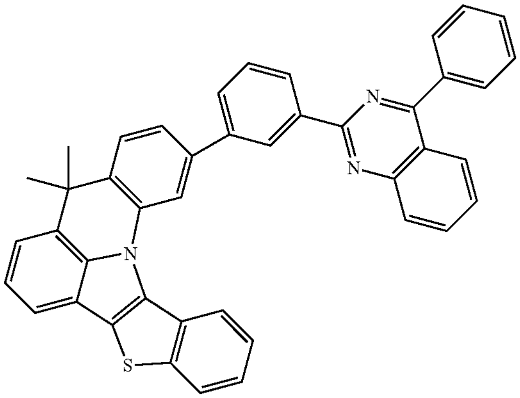
HAC169
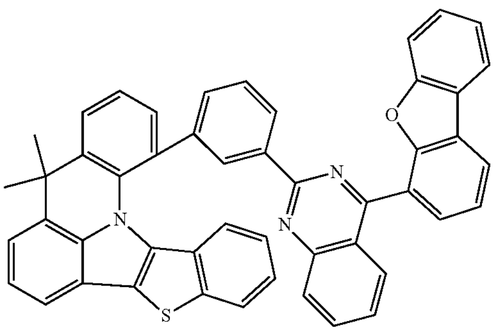

-continued
HAC170
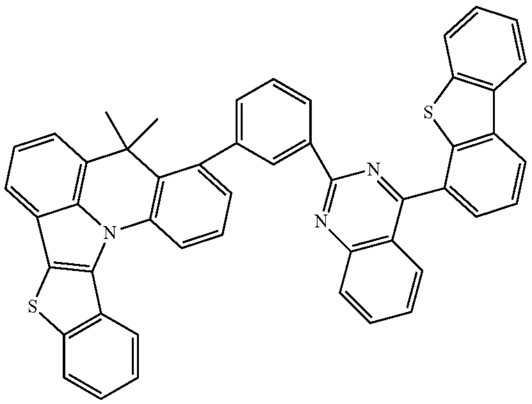
HAC171
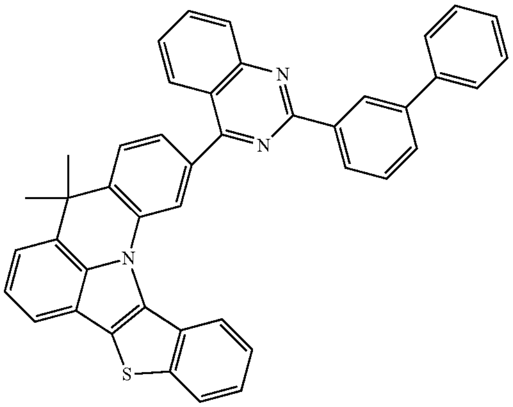
HAC172
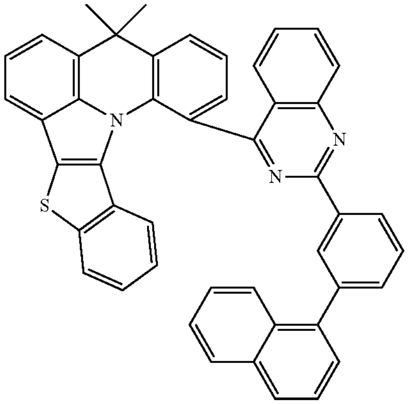
-continued
HAC173
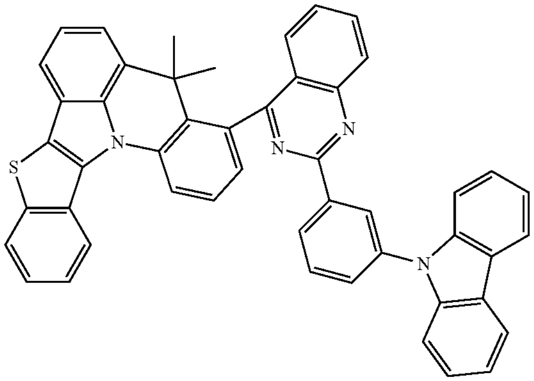
HAC174
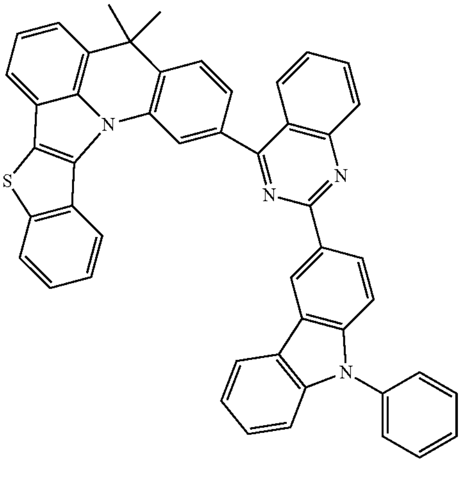
HAC175
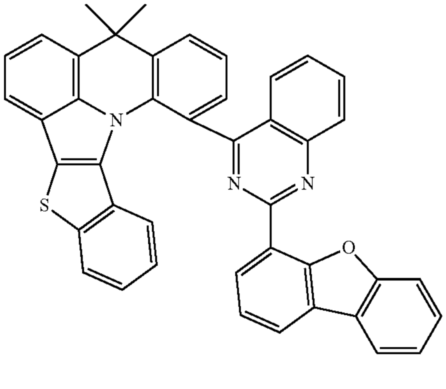

-continued
HAC176
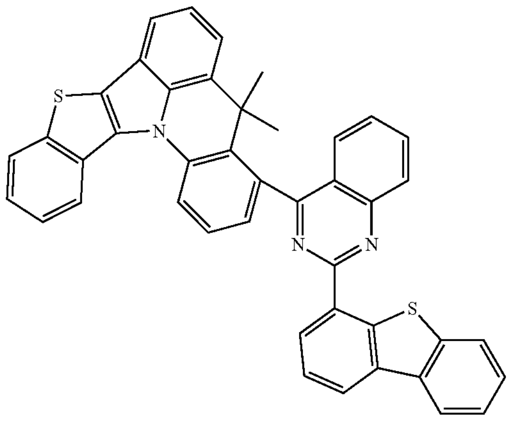
HAC177
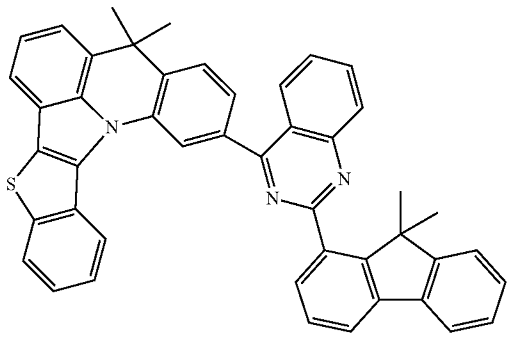
HAC178
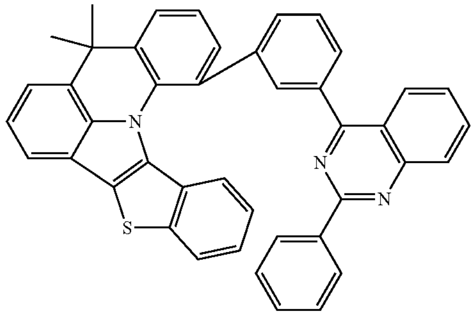
HAC179
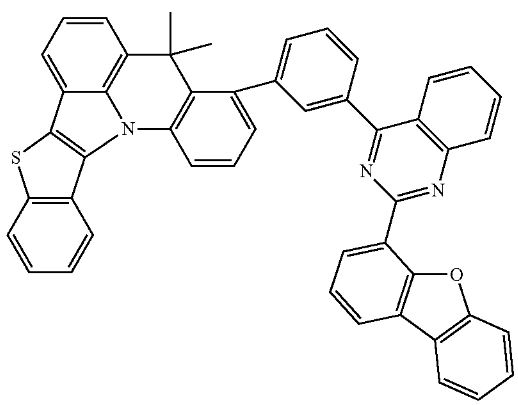
-continued
HAC180
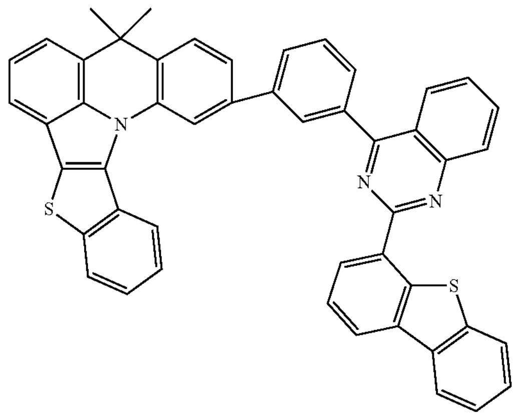
HAC181
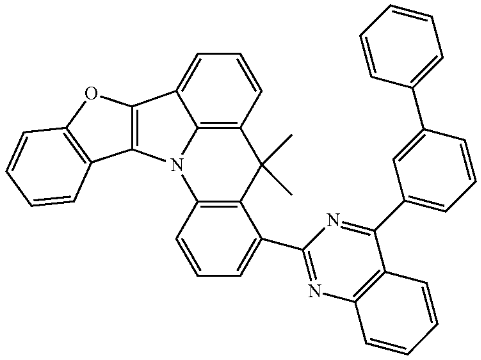
HAC182
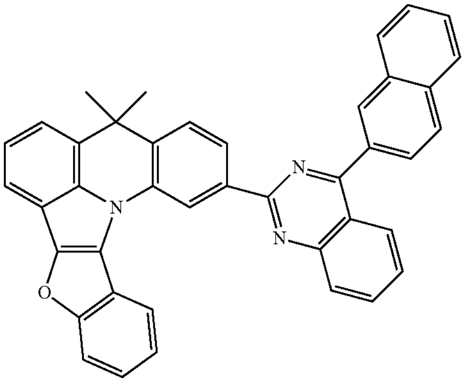
HAC183
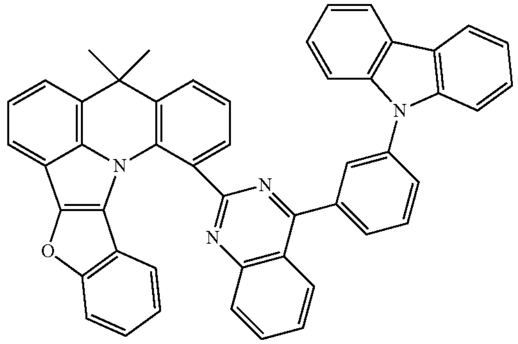

-continued
HAC184
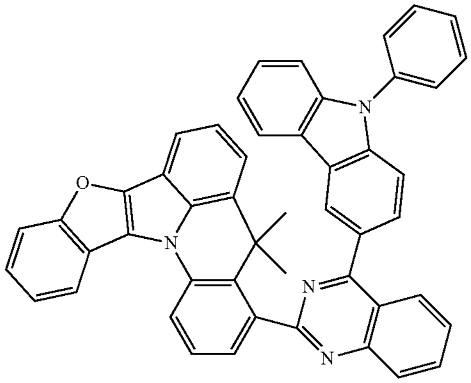
HAC185
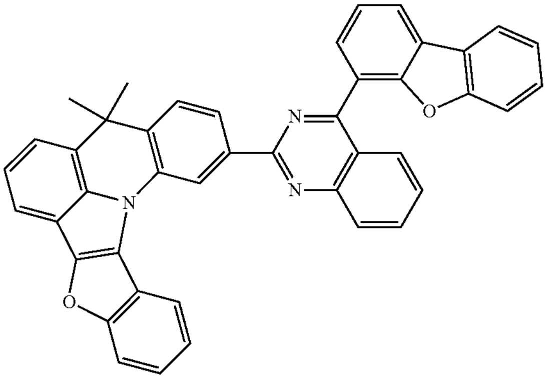
HAC186
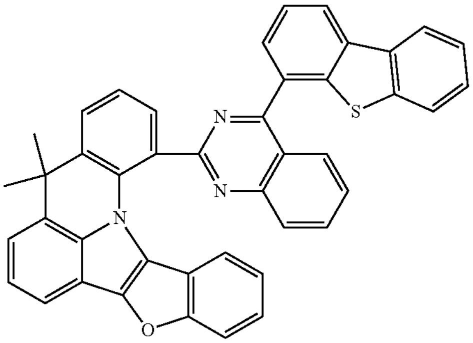
HAC187
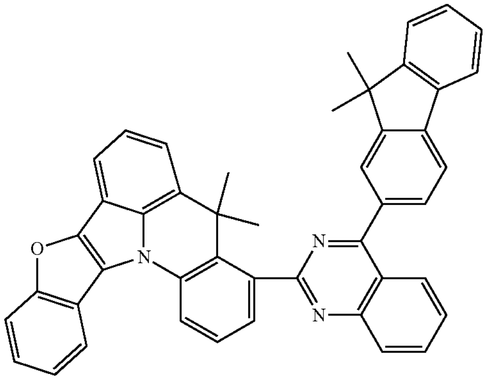
-continued
HAC188
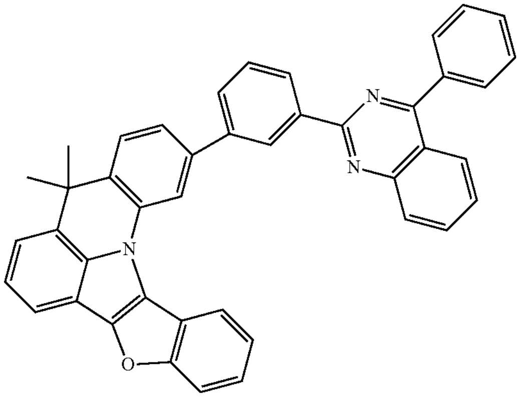
HAC189
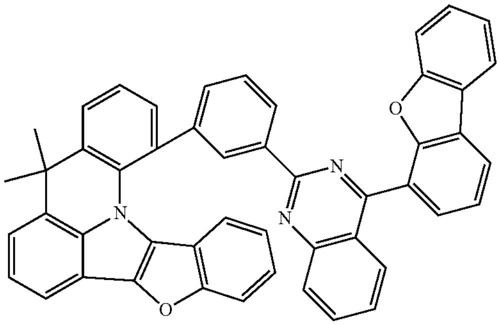
HAC190
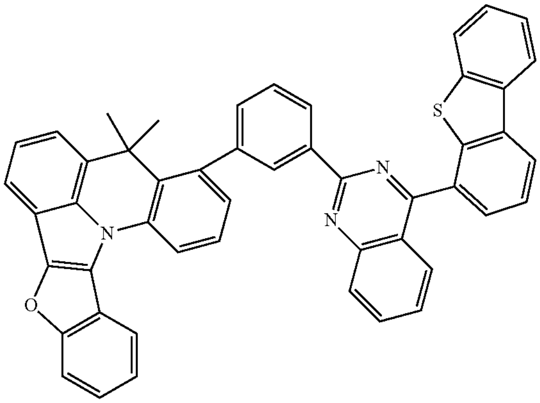
HAC191
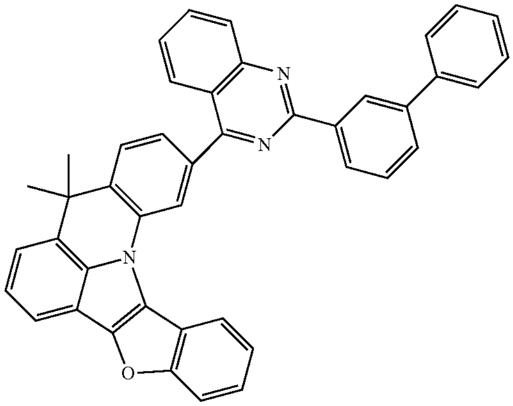

-continued
HAC192
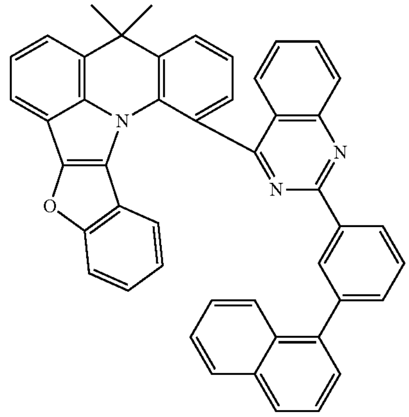
HAC193
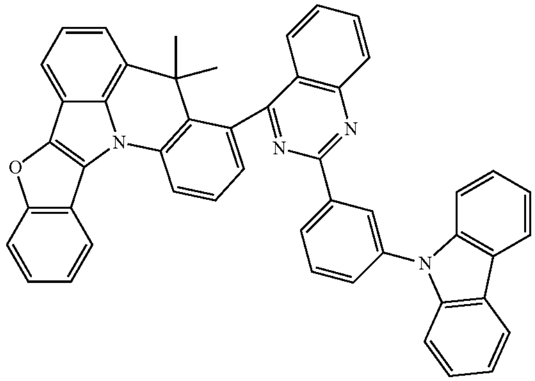
HAC194
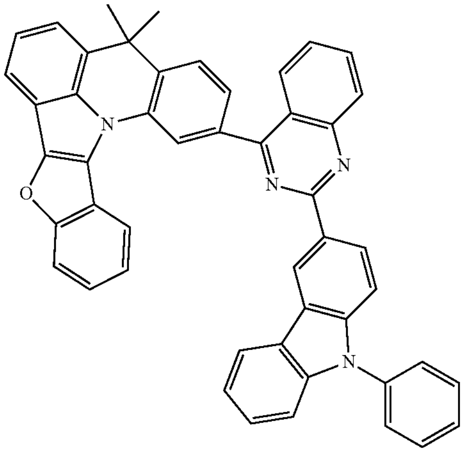
HAC195
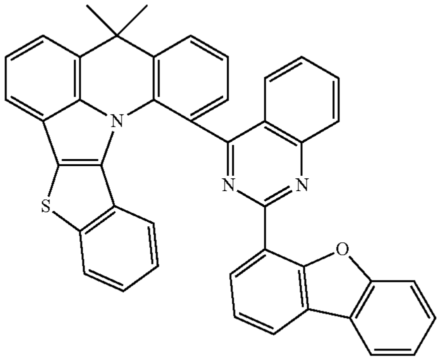
-continued
HAC196
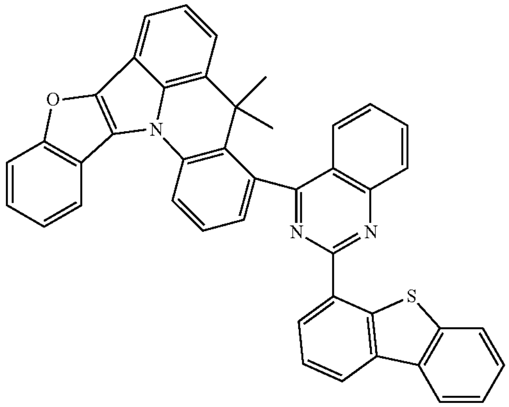
HAC197
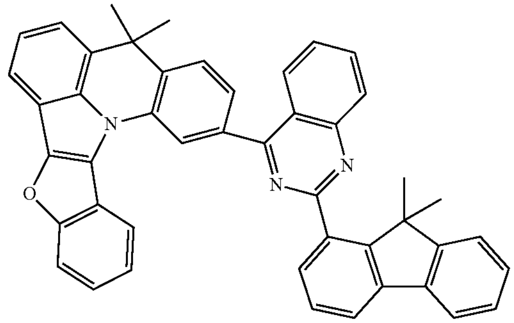
HAC198
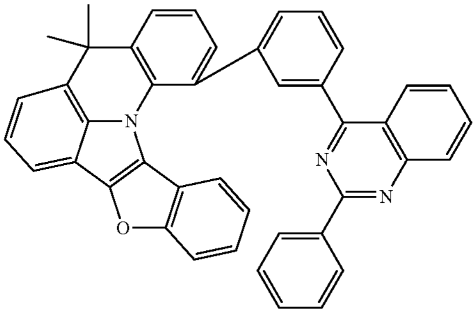
HAC199
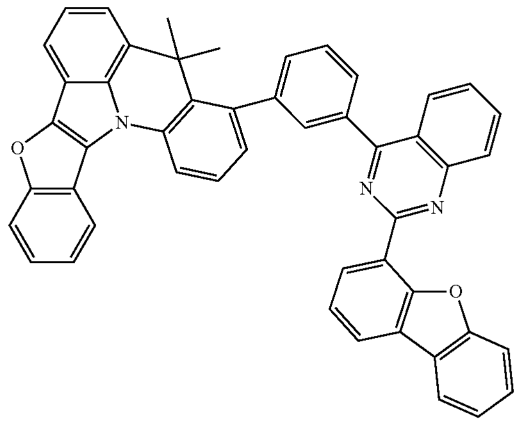

-continued

HAC200

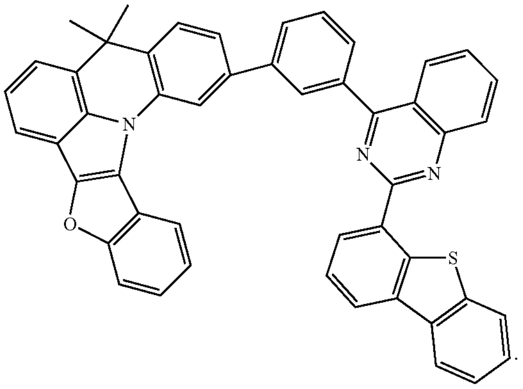

9. The organic light emitting element according to claim 5, wherein the organic material layer comprises a light emitting layer, and wherein the light emitting layer comprises the organic compound.

10. The organic light emitting element according to claim 9, wherein the organic material layer comprises at least one layer of a hole injection layer, a hole transport layer, an electron transport layer and an electron injection layer.

11. The organic light emitting element according to claim 9, wherein the organic compound is a host compound of the light emitting layer.

12. The organic light emitting element according to claim 11, wherein the light emitting layer further comprises a host compound different from the organic compound.

13. The organic light emitting element according to claim 5, wherein the organic material layer comprises a first stack comprising a first light emitting layer and a second stack comprising a second light emitting layer.

14. The organic light emitting element according to claim 13, wherein the first light emitting layer comprises the organic compound.

15. The organic light emitting element according to claim 14, wherein the organic compound is a host compound of the first light emitting layer.

16. The organic light emitting element according to claim 15, wherein the first light emitting layer further comprises a host compound different from the organic compound.

* * * * *